United States Patent
Arathoon et al.

(10) Patent No.: US 12,331,121 B2
(45) Date of Patent: Jun. 17, 2025

(54) EFFLUX PUMP-CANCER ANTIGEN MULTI-SPECIFIC ANTIBODIES AND COMPOSITIONS, REAGENTS, KITS AND METHODS RELATED THERETO

(71) Applicant: William Robert Arathoon Living Trust Dated August 29, 2016, Tiburon, CA (US)

(72) Inventors: William Robert Arathoon, Tiburon, CA (US); Evan Matthew Bishop, San Jose, CA (US); Raffaella Briante, Burlingame, CA (US); Alissa Loren Briggs, San Jose, CA (US); Suchismita Mohanty, Millbrae, CA (US); Paul David Ponath, San Francisco, CA (US); Cindy Tan, San Jose, CA (US); Qianting Zhai, South San Francisco, CA (US)

(73) Assignee: William Robert Arathoon Living Trust Dated August 29, 2016, Tiburon, CA (US)

( * ) Notice: Subject to any disclaimer, the term of this patent is extended or adjusted under 35 U.S.C. 154(b) by 852 days.

(21) Appl. No.: 17/598,737

(22) PCT Filed: Apr. 1, 2020

(86) PCT No.: PCT/US2020/026261
§ 371 (c)(1),
(2) Date: Sep. 27, 2021

(87) PCT Pub. No.: WO2020/206033
PCT Pub. Date: Oct. 8, 2020

(65) Prior Publication Data
US 2022/0204627 A1    Jun. 30, 2022

Related U.S. Application Data

(60) Provisional application No. 62/967,478, filed on Jan. 29, 2020, provisional application No. 62/828,044, filed on Apr. 2, 2019.

(51) Int. Cl.
| | | |
|---|---|---|
| *C07K 16/28* | (2006.01) | |
| *A61K 39/00* | (2006.01) | |
| *A61P 35/00* | (2006.01) | |
| *C07K 16/46* | (2006.01) | |

(52) U.S. Cl.
CPC .......... *C07K 16/2827* (2013.01); *A61P 35/00* (2018.01); *C07K 16/2863* (2013.01); *C07K 16/2896* (2013.01); *C07K 16/468* (2013.01); *A61K 2039/505* (2013.01); *C07K 2317/24* (2013.01); *C07K 2317/31* (2013.01); *C07K 2317/526* (2013.01); *C07K 2317/55* (2013.01); *C07K 2317/565* (2013.01); *C07K 2317/71* (2013.01); *C07K 2317/92* (2013.01)

(58) Field of Classification Search
CPC ............ C07K 16/2827; C07K 16/2863; C07K 16/2896; C07K 16/468; C07K 2317/24; C07K 2317/31; C07K 2317/526; C07K 2317/55; C07K 2317/565; C07K 2317/71; C07K 2317/92; C07K 16/2803; C07K 16/30; C07K 2317/52; C07K 2317/56; A61P 35/00; A61K 2039/505; A61K 2039/545; A61K 39/395; A61K 45/06; C12N 5/0634; C12N 5/0686; C12N 15/8509; C12N 2501/998; C12N 2510/00
See application file for complete search history.

(56) References Cited

U.S. PATENT DOCUMENTS

| | | | | |
|---|---|---|---|---|
| 5,959,084 A | * | 9/1999 | Ring ...................... | C07K 16/30 435/71.1 |
| 9,017,675 B2 | * | 4/2015 | Liu ..................... | C07K 16/2803 424/133.1 |
| 2015/0216970 A1 | * | 8/2015 | Grogan .............. | C07K 16/3046 |

FOREIGN PATENT DOCUMENTS

| | | |
|---|---|---|
| EP | 3243840 | 11/2017 |
| WO | 2006/108070 | 10/2006 |

OTHER PUBLICATIONS

Dondelinger et al. Understanding the significance and implications of anitbody numbering and antigen-binding surface/ residue definition. Front Immunol, 2018, 9: 2278. (Year: 2018).*
Janeway, Immuno Biology The immune system in Health and Disease, 5th edition, 2001, section 7.8. (Year: 2001).*
Lydard et al. Immunology, 2011, in Antibodies: Generation of diversity pp. 76-85. (Year: 2011).*

(Continued)

*Primary Examiner* — Anand U Desai
*Assistant Examiner* — Amber K Faust
(74) *Attorney, Agent, or Firm* — Shweta Chandra; Bozicevic, Field & Francis LLP

(57) ABSTRACT

Provided are multi-specific antibodies that target both a cellular efflux pump and a cancer-associated antigen as well as pharmaceutical compositions, nucleic acids, recombinant expression vectors, cells, and kits that include or encode such multi-specific antibodies. Methods of treating a subject for a cancer that include administering to the subject a multi-specific antibody that targets both a cellular efflux pump and a cancer-associated antigen are also provided. Provided as well are methods of generating the described multi-specific antibodies and reagents related thereto, including genetically modified cell lines useful in the subject methods and methods of making such genetically modified cell lines.

18 Claims, 36 Drawing Sheets
Specification includes a Sequence Listing.

(56) References Cited

OTHER PUBLICATIONS

Desmyter et al. Camelid nanobodies: killing two birds with one stone. Current Opinion in Structural Biology, 2015, 32:1-8. (Year: 2015).*
Lin et al. Improved affinity of a chicken single-chain antibody to avian infectious bronchitis virus by site-directed mutagenesis of complementarity-determinig region H3. African J Biotech, 2011, 10(79): 18294-18302. (Year: 2011).*
Szakács et al. Targeting multidrug resistance in cancer. Nat Rev Drug Discov. Mar. 2006;5(3):219-34. (Year: 2006).*
Iwahashi et al. Specific targeting and killing activities of anti-P-glycoprotein monoclonal antibody MRK16 directed against intrinsically multidrug-resistant human colorectal carcinoma cell lines in the nude mouse model. Cancer Res. Nov. 15, 1993;53(22): 5475-82. (Year: 1993).*
Wang et al. Cetuximab enhanced the efficacy of chemotherapeutic agent in ABCB1/P-glycoprotein-overexpressing cancer cells. Oncotarget. Dec. 1, 2015;6(38):40850-65. (Year: 2015).*
Krah et al. Engineering IgG-Like Bispecific Antibodies—An Overview. Antibodies. 2018; 7(3):28. (Year: 2018).*
Zhang et al. The development of bispecific antibodies and their applications in tumor immune escape. Exp Hematol Oncol 6, 12 (2017). (Year: 2017).*
Krah & Schroter. Generation of human bispecific common light chain antibodies by combining animal immunization and yeast display. Protein Eng Des Sel. Apr. 1, 2017;30(4):291-301. (Year: 2017).*
Klein et al., (2012) "Progress in overcoming the chain association issue in bispecific heterodimeric IgG antibodies", MABS,4(6):653-663.
Gao et al., (2004) "Efficient inhibition of multidrug-resistant human tumors with a recombinant bispecific anti-P-glycoprotein X anti-CD3 diabody", Blood Cancer Journal, 18(3):513-520.
Jackman et al., (2010) "Development of a Two-part Strategy to Identify a Therapeutic Human Bispecific Antibody That Inhibits IgE Receptor Signaling", Journal of Biological Chemistry, 285(27):20850-20859.
Krah et al., (2017) "Generation of human bispecific common light chain antibodies by combining animal immunization and yeast display", Protein Engineering, Design and Selection, 30(4):291-301.
Maurizio Cianfriglia (2013) "The biology of MDR1-P-glycoprotein (MDR1-Pgp) in designing functional antibody drug conjugates (ADCs): the experience of gemtuzumab ozogamicin", Ann Ist Super Sanità, 49(2):150-168.
Shiraiwa et al., (2019) "Engineering a bispecific antibody with a common light chain: Identification and optimization of an anti-CD3 epsilon and anti-GPC3 bispecific antibody, ERY974", Methods, 154:10-20.
Van Blarcom et al., (2017) "Productive common light chain libraries yield diverse panels of high affinity bispecific antibodies", MABS, 10(2):256-268.

* cited by examiner

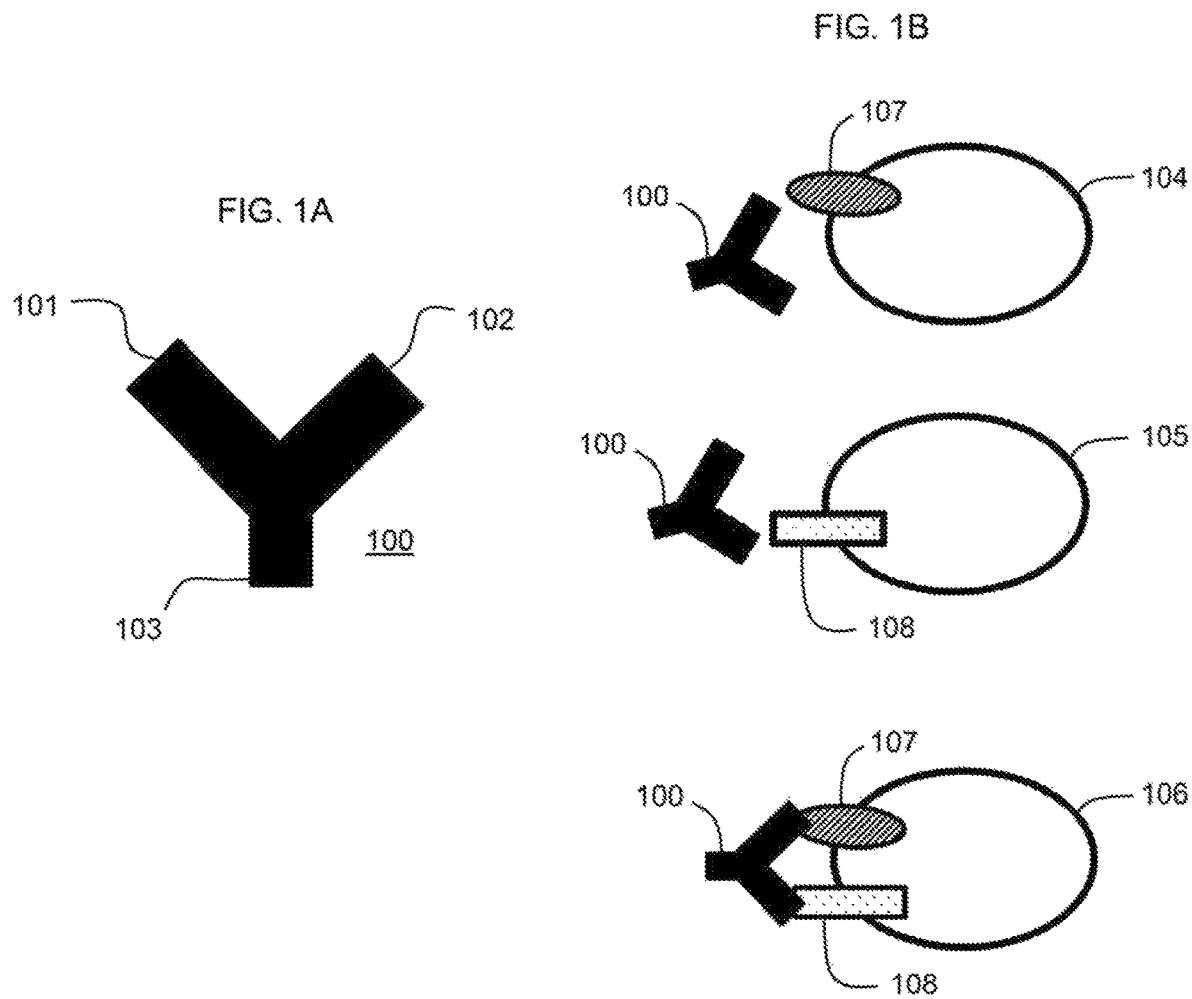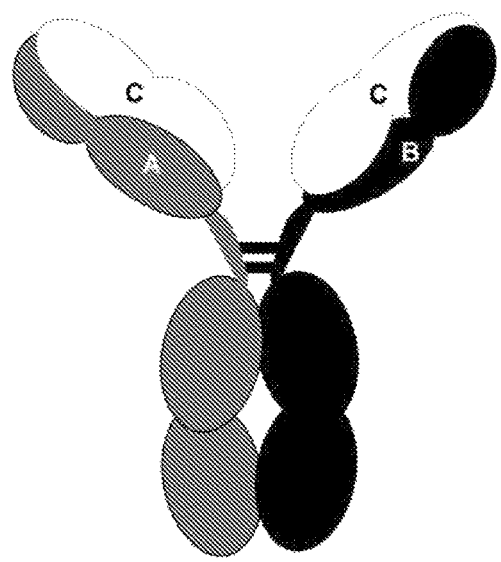

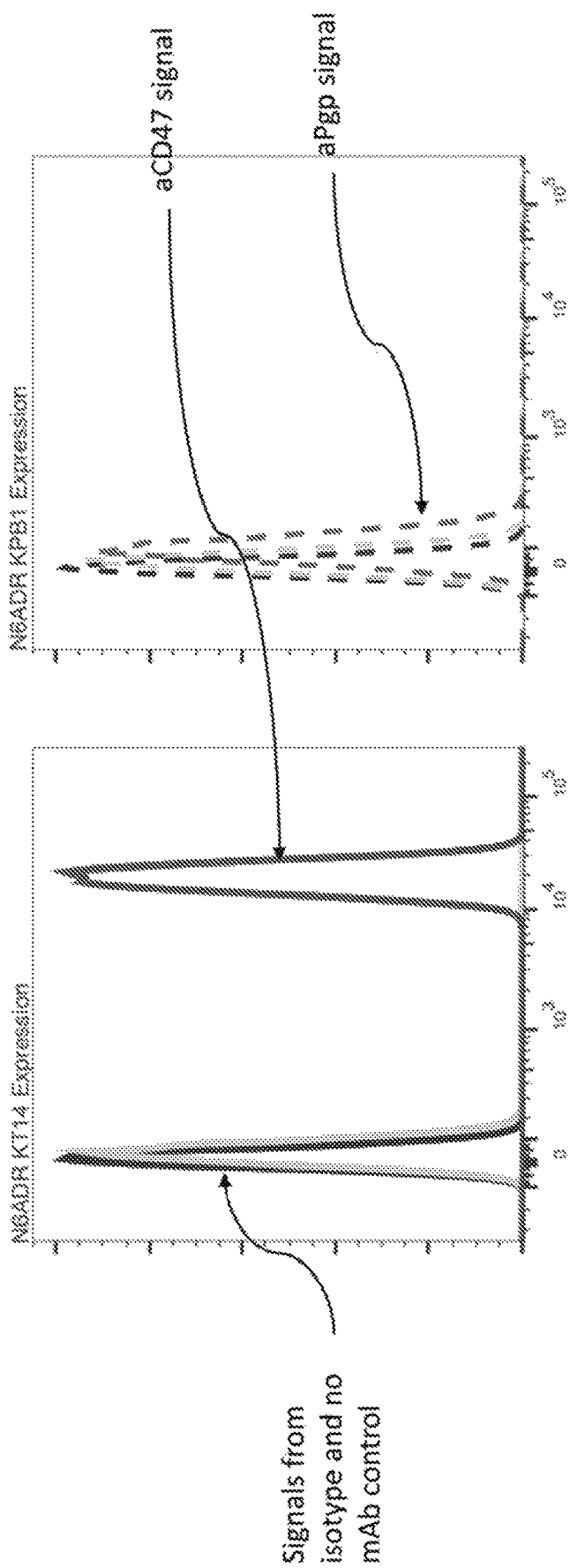

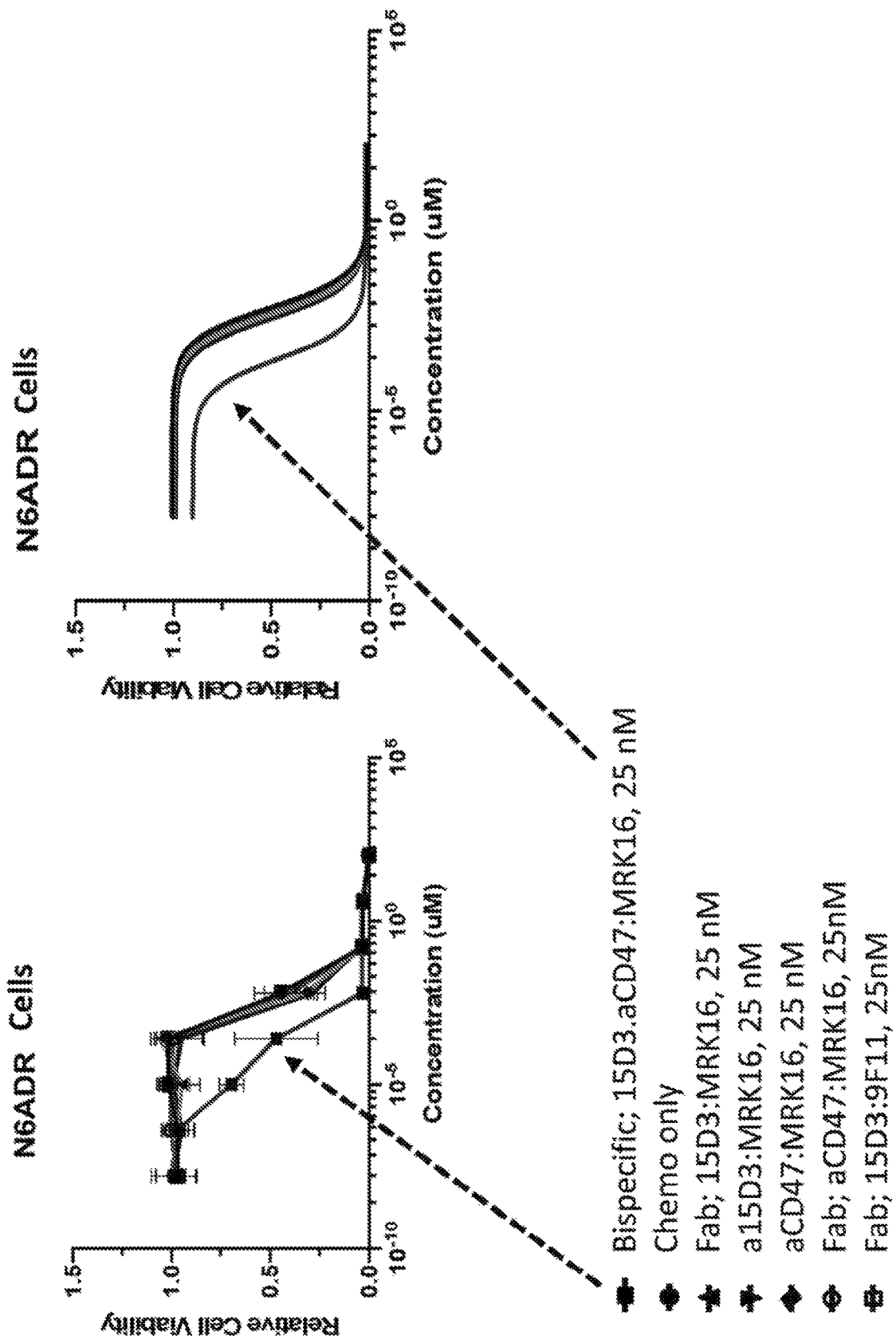

FIG. 8

| Ab | Kd (nM) | Bmax | Killing | Binding (293) | Binding (293 KO CD47) | Binding (293 KO CD47, OX ABCB1) | Binding (293 OX ABCB1) |
|---|---|---|---|---|---|---|---|
| 15D3 IgG1 DD/5F9 IgG1 KK/MRK16 | 144.8 | 1.327 | ++ | + | - | ++ | + |
| 15D3 IgG1 DD/5F9 IgG1 KK/UIC2 | 655.4 | 1.211 | - | - | - | - | - |
| 15D3 IgG1 KK/5F9 IgG1 DD/9F11 | 74.88 | 1.204 | - | - | - | + | + |
| 15D3 IgG1 KK/5F9 IgG1 DD/MRK16 | 200 | 1.097 | + | + | - | ++ | + |
| 15D3 IgG1 DD/5F9 IgG1 DD/UIC2 | 1619 | 1.969 | - | - | - | - | - |
| MM4.17.2 IgG1 DD/5F9 IgG1 KK/9F11 | 44.64 | 1.347 | ± | + | - | ++ | + |
| MM4.17.2 IgG1 DD/5F9 IgG1 KK/MRK16 | 75.21 | 1.109 | ± | + | - | ++ | + |
| MRK16 IgG1 KK/5F9 IgG1 DD/MRK16 | 205.7 | 1.307 | + | - | - | ++ | + |
| MRK16 IgG1 KK/5F9 IgG1 DD/UIC2 | 868.7 | 1.289 | - | - | - | - | - |
| UIC2 IgG1 KK/5F9 IgG1 DD/9F11 | 6.261 | 1.119 | - | ++ | + | + | ± |
| UIC2 IgG1 KK/5F9 IgG1 DD/MRK16 | 53.26 | 1.099 | - | ± | - | - | - |
| UIC2 IgG1 KK/5F9 IgG1 DD/UIC2 | 494.5 | 1.049 | - | ± | - | - | + |

A2780ADR

HeyT30

```
m15D3    evkvvesggglvlvrpggslklscaasgftfsrytmswvrqtpekrlewvatissgggntyy  60
15D3HZ0  evqlvesggglvqpggslrlscaasgftfsrytmswvrqapgkglewvatissgggntyy   60
15D3HZ1  evqlvesggvvvqpggslrlscaasgftfsrytmswvrqapgkglewvatissggggtyy   60
15D3HZ2  evqlvesggvvvqpggslrlscaasgftfsrytmswvrqapgkglewvatissgggstyy   60
         **:;****** ;******.;********************:** * **********:**

m15D3    pdsvkgrftvsrdnamsslylqmsslrsedtalyycarygagdawfaywgqgtlvtvss    119
15D3HZ0  pdsvkgrftvsrdnsknslylqmnslrtedtalyycarygagdawfaywgqgtlvtvss    119
15D3HZ1  pdsvkgrftvsrdnsknslylqmnslrtedtalyycarygagdawfaywgqgtlvtvss    119
15D3HZ2  pdsvkgrftvsrdnsknslylqmnslrtedtalyycarygagdawfaywgqgtlvtvss    119
         **************. .***:**:**:***************************
```

FIG. 23

```
MRK16m     dvlmtqtpvslsvslgdqasiscrassqsivhstgntylewylqkpgqspkliyklsnrf  60
MRK16Hmz0  divmtqtplsspvtlgqpasisqpasiscrassqsivhstgntylewylqkpgqrpgqppriliykisnrf  60
MRK16Hmz1  divmtqtplsspvtlgqpasisqpasiscrassqsivhstggtylewyqqrpgqppriliykisnrf  60
MRK16Hmz2  divmtqtplsspvtlgqpasisqpasiscrassqsivhstgstylewyqqrpgqppriliykisnrf  60
           *:;****  *:***: **************.,***:*******:****.*******

MRK16m     sgvpdrfsgsgsgtdftlkisrveaedlgvyycfgashfprtfggtkleikr  113
MRK16Hmz0  sgvpdrfsgsgagtdftlkisrveaedvgvyycfgashfprtfggtkleikr  113
MRK16Hmz1  sgvpdrfsgsgagtdftlkisrveaedvgvyycfgashfprtfggtkleikr  113
MRK16Hmz2  sgvpdrfsgsgagtdftlkisrveaedvgvyycfgashfprtfggtkleikr  113
           ***********:***************:***********************
```

FIG. 24

| HC1 | HC2 | LC | CD47 ELISA | MDR1 FACS | PDL1 ELISA | EGFR ELISA | EGFR FACS |
|---|---|---|---|---|---|---|---|
| 15D3 hmz | 5F9 (aCD47) | MRK16 hmz | + | + | | | |
| 15D3 | Cetuximab (aEGFR) | 15D3 | | + | | + | |
| 15D3 | Cetuximab (aEGFR) | MRK16 | | + | | ± | |
| MRK16 | Cetuximab (aEGFR) | 15D3 | | + | | + | |
| MRK16 | Cetuximab (aEGFR) | MRK16 | | + | | ± | |
| UIC2 | Cetuximab (aEGFR) | MRK16 | | - | | + | |
| UIC2 | Cetuximab (aEGFR) | 15D3 | | - | | + | |
| 15D3 | Necitumumab (aEGFR) | MRK16 | | + | | - | + |
| 15D3 | Atezolizumab (aPDL1) | MRK16 | | + | + | | |
| 15D3 hmz | Atezolizumab (aPDL1) | MRK16 hmz | | + | + | | |

FIG. 31

EFFLUX PUMP-CANCER ANTIGEN MULTI-SPECIFIC ANTIBODIES AND COMPOSITIONS, REAGENTS, KITS AND METHODS RELATED THERETO

CROSS-REFERENCE TO RELATED APPLICATIONS

This application is a 371 of PCT Application No. US2020/026261, filed Apr. 1, 2020, which claims the benefit of priority to U.S. Provisional Patent Application No. 62/967,478 filed on Jan. 29, 2020 and to U.S. Provisional Patent Application No. 62/828,044 filed on Apr. 2, 2019, which applications are incorporated herein by reference in their entirety.

INCORPORATION BY REFERENCE OF SEQUENCE LISTING PROVIDED AS A TEXT FILE

A Sequence Listing is provided herewith in a text file, "KNJY-002WO_Seq_List_ST25.txt", created on Aug. 5, 2021 and having a size of 143,465 bytes. The contents of the text file are incorporated herein by reference in its entirety.

INTRODUCTION

Drug resistance, a well-known phenomenon that results when diseases become tolerant to pharmaceutical treatments, is a major and increasing challenge in various fields of medicine, including oncology. Some methods of drug resistance are disease-specific, while others, such as drug efflux, which is observed in microbes and human drug-resistant cancers, are evolutionarily conserved. Although many types of cancers are initially susceptible to chemotherapy, over time they can develop resistance through these and other mechanisms, such as DNA mutations and metabolic changes that promote drug inhibition, degradation and enhanced efflux.

Efflux pumps (EP) are proteins expressed by virtually all living cells and have evolved to naturally expel various compounds from the cells. Members of the ATP-binding cassette (ABC) transporter family proteins are examples of EPs that enable drug efflux and are important, well-studied regulators at the plasma membranes of healthy cells. Though a transporter's structure varies from protein to protein (e.g., there are 49 known members of the ABC family in humans), they are all classified by the presence of two distinct domains—a highly conserved nucleotide binding domain and a more variable transmembrane domain. Multidrug resistance protein 1, encoded by the ATP Binding Cassette Subfamily B Member 1 (ABCB1) gene, was the first of these to be identified and has been studied extensively. Normal expression of MDR1 is increased in certain tissues (e.g., colon, liver, and kidney) when these tissues become neoplastic and increased expression in response to treatment with certain chemotherapeutics demonstrates that both intrinsic and extrinsic mechanisms of MDR1 overexpression are at play.

EPs enable cells and tumors to develop resistance to chemotherapeutic agents. Such resistance is frequently associated with enhanced efflux of the treatment molecules from the resistant cells. This chemotherapy resistance is termed multi drug resistance (MDR) when it applies to more than one chemotherapeutic agent. Various small molecule inhibitors have been developed that target and inhibit EPs but none have been successful in the human clinical setting for a variety of reasons among which is their tendency to penetrate into and affect all cells in the body, including healthy cells that employ EPs for efflux of naturally occurring cellular toxins, regardless of the function of the cells or their efflux pumps.

Among cancer patients, where metastatic cancer cell populations have largely been killed and cleared from the patients by use of chemotherapy, it is not uncommon for a drug-resistant cancerous population of cells to emerge and spread without response to renewed treatment with the earlier therapy. In most cases, a different drug with a different mechanism of action is applied until, once again, another emergent population of drug-resistant cells and/or tumor develops.

SUMMARY

Provided are anti-MDR1 antibodies that may be used as multi-specific antibodies that target both MDR1 and a tumor-associated antigen (TAA) as well as pharmaceutical compositions, nucleic acids, recombinant expression vectors, cells, and kits that include or encode such multi-specific antibodies. The multi-specific antibodies include a common variable light (VL) chain that includes an antigen-binding site for MDR1, a first variable heavy (VH) chain that includes an antigen-binding site for MDR1, and a second VH chain that includes an antigen-binding site for the TAA. Methods of treating a subject for a cancer that include administering to the subject a multi-specific antibody that targets both MDR1 and a TAA are also provided. The treating may involve administering the multi-specific antibody alone or administering the multi-specific antibody and a chemotherapeutic agent. Provided as well are methods of generating the described multi-specific antibodies and reagents related thereto, including genetically modified cell lines useful in the subject methods and methods of making such genetically modified cell lines.

The bispecific antibodies provided herein bind to cancer cells expressing both MDR1 and the TAA while showing reduced binding to non-cancer cells expressing MDR1 and/or the TAA. In other words, the bispecific antibodies provided herein bind with low affinity to (1) cells expressing TAA where MDR1 expression is low or absent and (2) cells expressing MDR1 where TAA expression is low or absent, and with high affinity to cancer cells that express at least one or both MDR1 and CD47 at relatively high levels, i.e., levels higher than normal cells.

Also disclosed herein are anti-MDR1 antibodies that have reduced affinity for MDR1 as compared to the anti-MDR1 antibody 15D3 and anti-CD47 antibodies that have reduced affinity for CD47 as compared to the anti-CD47 antibody 5F9. These antibodies find use in treatment of cancer in a subject when co-administered and to increase chemosensitivity of cancer cells to chemotherapy.

BRIEF DESCRIPTION OF THE FIGURES

FIG. 1A provides a schematic depiction of an embodiment of a multi-specific antibody of the present disclosure as described herein.

FIG. 1B provides a schematic depiction showing binding of the embodiment of a multi-specific antibody depicted in FIG. 1A to cells expressing one or both of the targets to which the multi-specific antibody is targeted.

FIG. 2 provides a schematic of a bispecific monoclonal antibody as described herein.

FIG. 3A-3F provide FACS analysis of binding of labeled monoclonal antibodies against Pgp and CD47 (also referred to in some instances as "KT14") on various cell lines, including naïve and recombinant cell lines expressing the targets as indicated.

FIG. 5 demonstrates that in spite of the decreased affinity of the bispecific antibody for each individual target, the bispecific antibody enhances chemosensitivity of naïve 293T cells and Adriamycin resistant N6ADR cells.

FIG. 6A-6C provide re-representations of the data provided in FIG. 5, including side-by-side fitted curves of the naïve 293T cell and N6ADR cell data (FIG. 6A) and side-by-side depictions of the raw (left) and fitted (right) data for naïve 293T cells (FIG. 6B) and N6ADR cells (FIG. 6C).

FIG. 8 provides a table showing binding and target cell killing of antibody light and heavy chain combinations tested, as described in the Examples section.

FIG. 23 shows alignment of humanized 15D3 VH chain sequences, 15D3HZ0 (SEQ ID NO: 16), 15D3HZ1 (SEQ ID NO:11), and 15D3HZ2 (SEQ ID NO:12) with m15D3 (SEQ ID NO: 10).

FIG. 24 shows alignment of humanized MRK16 chain sequences, MRK16Hmz0 (SEQ ID NO: 103), MRK16Hmz1 (SEQ ID NO:104), MRK16Hmz2 (SEQ ID NO:105) with MRK16m (SEQ ID NO:102).

FIG. 31 provides a summary of binding of the indicated antibodies to CD47 measured by ELISA, to MDR1 measured by FACS, to PD-L1 measured by ELISA, and to EGFR, measured by ELISA or FACS.

DEFINITIONS

Figure 3A:
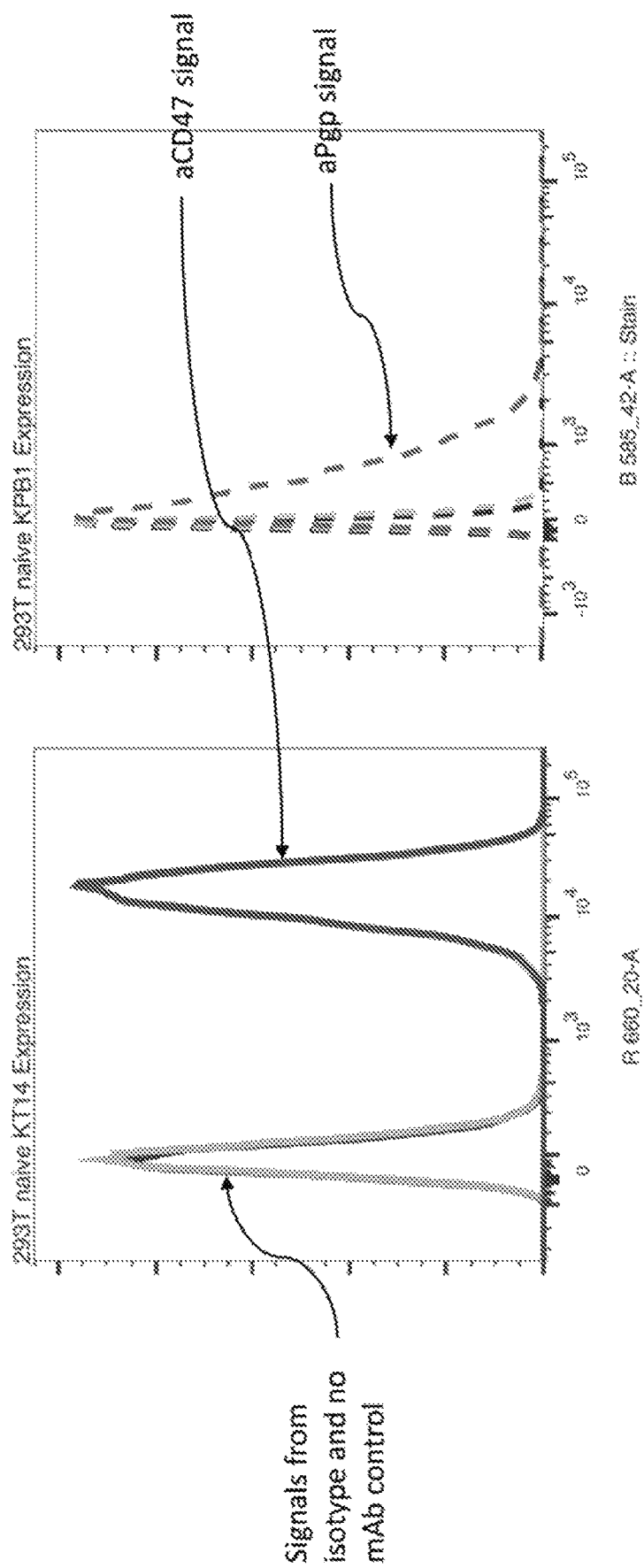

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, including antibodies comprising only heavy chains (e.g. VHH camelid antibodies), bispecific antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. An antibody may be monovalent or bivalent. The antibodies used herein may be used to assay expression of a target antigens(s) on a cell surface, e.g., in a cell sample or a tissue sample from a patient.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8 (10): 1057-1062 (1995)); single-chain antibody molecules, including antibodies comprising only heavy chains (e.g. VHH camelid antibodies); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen and can form the antigen binding site, although at a lower affinity than the entire binding site comprising the three CDRs of each variable domain.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv", "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. A MDR1-specific antibody binds specifically to an epitope within a MDR1 polypeptide. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

| | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |

TABLE 1-continued

| | CDR Definitions | | |
|---|---|---|---|
| | Kabat[1] | Chothia[2] | MacCallum[3] |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs. A VH chain can comprise three CDRs and four FRs arranged from N-terminus to C-terminus in the following order: FR1, CDR1, FR2, CDR2, FR3, CDR3, FR4. Similarly, a VL chain can comprise three CDRs and four FRs arranged from N-terminus to C-terminus in the following order: FR1, CDR1, FR2, CDR2, FR3, CDR3, FR4.

As used herein the term antibody encompasses a tetramer of two heavy and two light chains, wherein the heavy and light chains are interconnected by, for example, disulphide bonds. The heavy chain constant region is comprised of three domains, CH1, CH2 and CH3. The light chain constant region is comprised of one domain, CL. The variable regions of the heavy and light chains comprise binding regions that interact with antigen. The constant regions of the antibodies typically mediate the binding of the antibody to host tissues and factors, including various cells of the immune system and the first component of the complement system. The term "antibody" includes immunoglobulins of types IgA, IgG, IgE, IgD, IgM and subtypes thereof. In some embodiments, a subject antibody is an IgG isotype, e.g., IgG1.

As used herein the term "immunoglobulin" refers to a protein including one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes; and numerous immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g. gamma (encoding about 330 amino acids). In some embodiments, a subject antibody comprises a whole immunoglobulin comprising full-length immunoglobulin heavy chain and a full-length immunoglobulin light chain.

The term "antigen-binding fragment" refers to one or more fragments of a full-length antibody that are capable of specifically binding to an antigen. Examples of binding fragments include (i) a Fab fragment (a monovalent fragment including, e.g., consisting of, the VL, VH, CL and CH1 domains; (ii) a F(ab')$_2$ fragment (a bivalent fragment comprising two Fab fragments linked by a disulfide bridge at the hinge region; (iii) a Fd fragment (including, e.g., consisting of, the VH and CH1 domains); (iv) a Fv fragment (including, e.g., consisting of, the VH and VL domains of a single arm of an antibody); (v) a dAb fragment (including, e.g., consisting of, the VH domain); (vi) an isolated CDR; (vii) a single chain Fv (scFv) (including, e.g., consisting of, the VH and VL domains of a single arm of an antibody joined by a synthetic linker using recombinant means such that the VH and VL domains pair to form a monovalent molecule); (viii) diabodies (including, e.g., consisting of, two scFvs in which the VH and VL domains are joined such that they do not pair to form a monovalent molecule; the VH of each one of the scFv pairs with the VL domain of the other scFv to form a bivalent molecule).

The term "chimeric" antibody refers to an antibody in which a portion of the heavy and/or light chain is derived from a particular source or species, while the remainder of the heavy and/or light chain is derived from a different source or species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework (FR) which represents the most commonly occurring amino acid residues in a selection of human immunoglobulin variable light chain (VL) or variable heavy chain (VH) framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human CDRs and amino acid residues from human frameworks (FRs). At least a portion of a humanized antibody constant region derived from a human antibody. In preferred embodiments of the antibody molecules disclosed herein, the constant region is from a human IgG antibody, such as, human IgG1. In preferred embodiments, the antibody molecules disclosed herein include a heavy chain comprising a variable heavy chain region as provided herein and a human IgG1 constant region having the amino acid sequence set forth in UniProt: P01857-1, version 1. In preferred embodiments, the antibody molecules disclosed herein include a light chain comprising a variable light chain region as provided herein and a human light chain constant region. In preferred embodiments, the human light chain constant region is a human kappa light chain constant region. In certain aspects, the human IgG1 heavy chain constant region present in the subject antibodies may include mutations, e.g., substitutions to modulate Fc function. For example, the LALAPG effector function mutations (L234A, L235A, and P329G) or the N297A mutation may be introduced to reduce antibody dependent cellular cytotoxicity (ADCC). The numbering of the substitutions is based on the EU numbering system. The "EU numbering system" or "EU index" is generally used when referring to a residue in an immunoglobulin heavy chain constant region (e.g., the EU index reported in Kabat et al., Sequences of Proteins of Immunological Interest, 5th Ed. Public Health Service, National Institutes of Health, Bethesda, MD. (1991)). The "EU index as in Kabat" refers to the residue numbering of the human IgG 1 EU antibody.

A "humanized form" of an antibody, e.g., a non-human antibody, refers to an antibody that has undergone humanization.

The term "epitope" refers to a region of an antigen that is recognized by the immune system, for example by antibodies, B cells, or T cells. For example, the epitope is the specific region of the antigen to which an antibody binds.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

The term "cytotoxic agent" as used herein refers to a substance that inhibits or prevents a cellular function and/or causes cell death or destruction. A "chemotherapeutic agent," also referred to an "antineoplastic agent," can be a cytotoxic agent which is used for treating a cancer or other disease or disorder.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, including in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of a target-specific antibody that, when administered to a mammal or other subject for treating a disease, is sufficient to affect such treatment for the disease. The "therapeutically effective amount" will vary depending on the antibody, the disease and its severity and the age, weight, etc., of the subject to be treated.

The term "refractory", used herein, refers to a disease or condition that does not respond to treatment. With regard to cancer, "refractory cancer", as used herein, refers to cancer that does not respond to treatment. A refractory cancer may be resistant at the beginning of treatment or it may become resistant during treatment. Refractory cancer may also be called resistant cancer.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

Percent identity between a pair of sequences may be calculated by multiplying the number of matches in the pair by 100 and dividing by the length of the aligned region, including gaps. Identity scoring only counts perfect matches and does not consider the degree of similarity of amino acids to one another. Only internal gaps are included in the length, not gaps at the sequence ends. Percent Identity=(Matches× 100)/Length of aligned region (with gaps)

The phrase "conservative amino acid substitution" refers to substitution of amino acid residues within the following groups: 1) L, I, M, V, F; 2) R, K; 3) F, Y, H, W, R; 4) G, A, T, S; 5) Q, N; and 6) D, E. Conservative amino acid substitutions may preserve the activity of the protein by replacing an amino acid(s) in the protein with an amino acid with a side chain of similar acidity, basicity, charge, polarity, or size of the side chain.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

The term "stimulatory molecule," refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing cytoplasmic signaling sequence that is of particular use in the invention includes, but is not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to an MHC class I molecule, BTLA and a Toll ligand receptor, as well as OX40, CD27, CD28, CDS, ICAM-1, LFA-1 (CD11a/CD18), ICOS (CD278), and 4-1BB (CD137).

The term "autologous" refers to any material derived from the same individual to whom it is later to be re-introduced into the individual.

An "intracellular signaling domain," as the term is used herein, refers to an intracellular portion of a molecule. The intracellular signaling domain generates a signal that promotes an immune effector function of the CAR containing cell, e.g., a CAR-T cell. Examples of immune effector function, e.g., in a CAR-T cell, include cytolytic activity and helper activity, including the secretion of cytokines.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes.

Guidance for substitutions, insertions, or deletions may be based on alignments of amino acid sequences of proteins from different species or from a consensus sequence based on a plurality of proteins having the same or similar function.

DETAILED DESCRIPTION

Provided are anti-MDR1 antibodies that may be used as multi-specific antibodies that target both MDR1 and a tumor-associated antigen (TAA) as well as pharmaceutical compositions, nucleic acids, recombinant expression vectors, cells, and kits that include or encode such multi-specific antibodies. The multi-specific antibodies include a common variable light (VL) chain that includes an antigen-binding site for MDR1, a first variable heavy (VH) chain that includes an antigen-binding site for MDR1, and a second VH chain that includes an antigen-binding site for the TAA. Methods of treating a subject for a cancer that include administering to the subject a multi-specific antibody that targets both MDR1 and a TAA are also provided. The treating may involve administering the multi-specific antibody alone or administering the multi-specific antibody and a chemotherapeutic agent. Provided as well are methods of generating the described multi-specific antibodies and reagents related thereto, including genetically modified cell lines useful in the subject methods and methods of making such genetically modified cell lines.

The bispecific antibodies provided herein bind to cancer cells expressing both MDR1 and the TAA while showing reduced binding to non-cancer cells expressing MDR1 and/or the TAA. In other words, the bispecific antibodies provided herein bind with low affinity to (1) cells expressing TAA where MDR1 expression is low or absent and (2) cells expressing MDR1 where TAA expression is low or absent, and with high affinity to cancer cells that express at least one or both MDR1 and CD47 at relatively high levels, i.e., levels higher than normal cells.

Also disclosed herein are anti-MDR1 antibodies that have reduced affinity for MDR1 as compared to the anti-MDR1 antibody 15D3 and anti-CD47 antibodies that have reduced affinity for CD47 as compared to the anti-CD47 antibody 5F9. These antibodies find use in treatment of cancer in a subject when co-administered and to increase chemosensitivity of cancer cells to chemotherapy.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the methods and compositions have or will be described for the sake of grammatical fluidity with functional explanations, it is to be expressly understood that the claims, unless expressly formulated under 35 U.S.C. § 112 (f), are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 (f) are to be accorded full statutory equivalents under 35 U.S.C. § 112 (f).

Antibodies
Bispecific Antibodies

The present disclosure provides a bispecific antibody molecule that binds multidrug resistance protein 1 (MDR1) and a tumor associated antigen (TAA), the antibody molecule comprising two identical variable light (VL) chains, a first variable heavy (VH) chain, and a second VH chain, where the VL chains each comprise an antigen-binding site for MDR1, the first VH chain comprises an antigen-binding site for MDR1, and the second VH chain comprises an antigen-binding site for the TAA, and wherein the second VH chain binds the TAA when paired with one of the light chains. The bispecific antibody molecule binds to cancer cells expressing both MDR1 and the TAA while showing reduced binding to non-cancer cells expressing MDR1 and/or the TAA. In other words, the bispecific antibodies provided herein bind with low affinity to (1) cells expressing TAA where MDR1 expression is low or absent and (2) cells expressing MDR1 where TAA expression is low or absent, and with high affinity to cancer cells that express at least one or both MDR1 and CD47 at relatively high levels, i.e., levels higher than normal cells.

Relatively high levels refer to expression that is at least 1.5 times (e.g., at least 2×, at least 3×, at least 4×, at least 5× or more) the expression level in a normal cell of the same type as the cancer cell. Reduced affinity refers to binding affinity that is reduced by at least 10% (e.g. at least 20%, at least 30%, at least 40%, at least 50% or more) as compared to binding of the antibody molecule to a normal cell of the same type as the cancer cell. Reduced affinity also encompasses lack of detectable binding.

The term "antibody molecule" encompasses antibodies as defined herein and includes antigen-binding fragments thereof. In certain aspects, the antibody molecule includes two variable light (VL) and two variable heavy (VH) chain. In certain aspects, the antibody molecule includes heavy chain and light chain constant regions as well. The heavy and light chain constant regions may be from a human antibody, e.g., human IgG1 antibody. The human IgG1 heavy chain (HC) constant region may be modified to include mutations that reduce antibody dependent cellular cytotoxicity (ADCC). In addition, or alternatively, the two VH chains may each be conjugated to a different human IgG1 HC constant region where the individual human IgG1 HC constant region has substitutions that favour formation of dimers between the different human IgG1 HC constant regions. Such HC regions are described in further detail herein. In certain aspects, where the antibody molecule is a bispecific antibody molecule, one of the human IgG1 HC constant regions may include substitutions to introduce one or more amino acids having a positively-charged side chain and the other human IgG1 HC constant region may include substitutions to introduce one or more amino acids having a negatively-charged side chain to favour formation of dimers between the two different HCs.

In certain aspects, the antigen binding sites of the two VL chains comprise the light chain CDRs (LCDRs) of a VL chain having the sequence:
DVLMTQTPVSLSVSLGDQASISCRSSQSIVHSTGX[1]TYLEWYLQKPGQSPKLLIYKIS NRFSGVPDRFSGSG SGTDFTLKISRVEAEDLGVYYCFQASHFPRTFGGGT KLEIK (SEQ ID NO: 1), where $X^1$ is N, Q or S.

In certain aspects, the two VL chains comprise LCDRs 1-3 of the VL chain having the sequence:

```
(i)
DVLMTQTPVSLSVSLGDQASISCRSSQSIVHSTGNTYLEWYLQKPGQSPK

LLIYKISNRFSGVPDRFSGSGSGTDFTLKISRVEAEDLGVYYCFQASHFP

RTFGGGTKLEIK;

(ii)
DIVMTQTPLSSPVTLGQPASISCRSSQSIVHSTGQTYLEWYQQRPGQPPR

LLIYKISNRFSGVPDRFSGSGAGTDFTLKISRVEAEDVGVYYCFQASHFP

RTFGQGTKLEIK;
or (iii)
DIVMTQTPLSSPVTLGQPASISCRSSQSIVHSTGSTYLEWYQQRPGQPPR

LLIYKISNRFSGVPDRFSGSGAGTDFTLKISRVEAEDVGVYYCFQASHFP

RTFGQGTKLEIK.
```

In some aspects, the antibody described herein does not comprise (i) two VL chains comprising LCDRs of the VL chain having the sequence:

```
                                    (SEQ ID NO: 3)
DIVMTQTPLSSPVTLGQPASISCRSSQSIVHSTGQTYLEWYQQRPGQPP

RLLIYKISNRFSGVPDRFSGSGAGTDFTLKISRVEAEDVGVYYCFQASH

FPRTFGQGTKLEIK;
``` and a first VH chain comprising HCDRs of the VH chain having the sequence:

```
EVQLVESGGVVVQPGGSLRLSCAASGFTFSRYTMSWVRQAPGKGLEWVAT

ISSGGGSTYYPDSVKGRFTVSRDNSKNSLYLQMNSLRTEDTALYYCARYG

AGDAWFAYWGQGTLVTVSS.
```

In certain aspects, the CDRs of VL and VH light chains may be defined based on the Kabat nomenclature.

In certain aspects, i) the LCDR1 comprises the sequence: RSSQSIVHSTGX[1]TYLE (SEQ ID NO:5); (ii) the LCDR2 comprises the sequence: KISNRFS (SEQ ID NO:6); and (iii) the LCDR3 comprises the sequence: FQASHFPRT (SEQ ID NO:7); where $X^1$ is N, Q or S. These LCDRs are based on the Kabat nomenclature.

In certain aspects, the two VL chains are humanized. In certain aspects, the two VL chains are humanized to include framework regions from a human antibody.

In certain aspects, the two VL chains comprise a sequence that is at least 80%, at least 85%, at least 90%, at least 95%, or a 100% identical to the sequence:

```
DIVMTQTPLSSPVTLGQPASISCRSSQSIVHSTGNTYLEWYQQRPGQPPR
LLIYKISNRFSGVPDRFSGSGAGTDFTLKISRVEAEDVGVYYCFQASHFP
RTFGGGTKLEIK;
DIVMTQTPLSSPVTLGQPASISCRSSQSIVHSTGQTYLEWYQQRPGQPPR
LLIYKISNRFSGVPDRFSGSGAGTDFTLKISRVEAEDVGVYYCFQASHFP
RTFGQGTKLEIK;
or
DIVMTQTPLSSPVTLGQPASISCRSSQSIVHSTGSTYLEWYQQRPGQPPR
LLIYKISNRFSGVPDRFSGSGAGTDFTLKISRVEAEDVGVYYCFQASHFP
RTFGQGTKLEIK.
```

In particular aspects, the bispecific antibody molecule comprises two VL chains each comprising the sequence:

```
DIVMTQTPLSSPVTLGQPASISCRSSQSIVHSTGNTYLEWYQQRPGQPPR
LLIYKISNRFSGVPDRFSGSGAGTDFTLKISRVEAEDVGVYYCFQASHFP
RTFGGGTKLEIK.
```

In certain aspects, the bispecific antibody includes a light chain comprising the VL chain as described herein and a light chain constant region. The light chain constant region may be the human immunoglobulin kappa chain constant region having the amino acid sequence set forth in UniProtKB/Swiss-Prot: P01834.2.

In certain aspects, the bispecific antibody molecule includes the first VH chain where the VH chain comprises heavy chain CDRs 1-3 (HCDRs 1-3) of a VH chain having the sequence:
EVKVVESGGVLVRPGGSLKLSCAASGFTFSRYTMSWVRQTPEKRLEWVATISSGGGX$^2$TY YPDSVKGR FTVSRDNAMSSLYLQMSSLRSEDTALYYCARYGAGDAWFAYWGQGTLVTVS S (SEQ ID NO:9), wherein X$^2$ is N, Q or S.

In certain aspects, the first VH chain comprises the HCDRs 1-3 of the VH chain having the sequence:

```
(i)
EVKVVESGGVLVRPGGSLKLSCAASGFTFSRYTMSWVRQTPEKRLEWVAT
ISSGGGNTYYPDSVKGRFTVSRDNAMSSLYLQMSSLRSEDTALYYCARYG
AGDAWFAYWGQGTLVTVSS,
or
(ii)
EVQLVESGGVVVQPGGSLRLSCAASGFTFSRYTMSWVRQAPGKGLEWVAT
ISSGGGQTYYPDSVKGRFTVSRDNSKNSLYLQMNSLRTEDTALYYCARYG
AGDAWFAYWGQGTLVTVSS,
or
(iii)
EVQLVESGGVVVQPGGSLRLSCAASGFTFSRYTMSWVRQAPGKGLEWVAT
ISSGGGSTYYPDSVKGRFTVSRDNSKNSLYLQMNSLRTEDTALYYCARYG
AGDAWFAYWGQGTLVTVSS.
```

In certain aspects, the HCDRs 1-3 of the VH chain are defined based on the Kabat nomenclature.

In certain aspects, the first VH chain comprises: (i) the HCDR1 comprising the sequence: RYTMS (SEQ ID NO:13); (ii) the HCDR2 comprising the sequence: TISSGGGX$^2$TYYPDSVKG (SEQ ID NO:14); and (iii) the HCDR3 comprising the sequence:
YGAGDAWFAY (SEQ ID NO:15); where X$^2$ is N, Q or S. These HCDRs are based on the Kabat nomenclature.

In certain aspects, the first and/or second VH chain is humanized. In certain aspects, the VH chains are humanized to include framework regions from a human antibody.

In certain aspects, the first VH chain comprises the sequence:

```
EVQLVESGGVVVQPGGSLRLSCAASGFTFSRYTMSWVRQAPGKGLEWVAT
ISSGGGNTYYPDSVKGRFTVSRDNSKNSLYLQMNSLRTEDTALYYCARYG
AGDAWFAYWGQGTLVTVSS;
EVQLVESGGVVVQPGGSLRLSCAASGFTFSRYTMSWVRQAPGKGLEWVAT
ISSGGGQTYYPDSVKGRFTVSRDNSKNSLYLQMNSLRTEDTALYYCARYG
AGDAWFAYWGQGTLVTVSS;
or
EVQLVESGGVVVQPGGSLRLSCAASGFTFSRYTMSWVRQAPGKGLEWVAT
ISSGGGSTYYPDSVKGRFTVSRDNSKNSLYLQMNSLRTEDTALYYCARYG
AGDAWFAYWGQGTLVTVSS.
```

In certain aspects, the first VH chain comprises a sequence that is at least 80%, at least 85%, at least 90%, or at least 95% identical to the sequence:

```
EVQLVESGGVVVQPGGSLRLSCAASGFTFSRYTMSWVRQAPGKGLEWVAT
ISSGGGNTYYPDSVKGRFTVSRDNSKNSLYLQMNSLRTEDTALYYCARYG
AGDAWFAYWGQGTLVTVSS;
EVQLVESGGVVVQPGGSLRLSCAASGFTFSRYTMSWVRQAPGKGLEWVAT
ISSGGGQTYYPDSVKGRFTVSRDNSKNSLYLQMNSLRTEDTALYYCARYG
AGDAWFAYWGQGTLVTVSS;
or
EVQLVESGGVVVQPGGSLRLSCAASGFTFSRYTMSWVRQAPGKGLEWVAT
ISSGGGSTYYPDSVKGRFTVSRDNSKNSLYLQMNSLRTEDTALYYCARYG
AGDAWFAYWGQGTLVTVSS.
```

In certain aspects, the bispecific antibody includes a first heavy chain comprising the first VH chain as described herein and a human IgG1 heavy chain constant region.

In certain aspects, the second VH chain of the bispecific antibody is derived from a monospecific antibody molecule which binds the TAA, and wherein the affinity of the bispecific antibody molecule for the TAA is at least 2-fold lower (e.g. at least 3-fold lower, at least 4-fold lower, at least 5-fold lower) than the affinity of the monospecific antibody molecule for the TAA from which the VH chain is derived. The affinity of the bispecific antibody and the monospecific antibody is measured using the same assay. Any suitable method for measuring antibody affinity may be utilized. In certain aspects, affinity may be measured by calculating the equilibrium constant for the reversible binding of the antibody to an antigen and is expressed as a dissociation constant (Kd). In certain aspects, Kd may be measured by ELISA.

In certain aspects, the second VH chain of the bispecific antibody is derived from a monospecific antibody molecule which binds the TAA, and wherein the half-maximal effective concentration (EC50) of the bispecific antibody molecule for the TAA is at least 2-fold higher (e.g. at least 3-fold higher, at least 4-fold higher, at least 5-fold higher) than the EC50 of the monospecific antibody molecule for the TAA from which the VH chain is derived. The EC50 of the bispecific antibody and the monospecific antibody is measured using the same assay. Any suitable method for measuring EC50 of an antibody may be utilized. The concentration that provides half maximal response (e.g., half of the maximum fluorescence intensity) is measured as the EC50.

The EC50 of a test antibody many be determined by flow cytometry or ELISA. For example, flow cytometry may involve contacting a cell expressing an antigen (e.g. human wild type MDR1 or a mutant MDR1) with the antibody in a flow cytometry buffer, where the antibody is serially diluted, and incubating at room temperature or 4° C. for a period of time sufficient for the antibody to bind to the cells (e.g. 10 min-1 hr). After incubating, the cells may optionally be washed to remove and non-specifically bound antibody and/or the cells may be contacted with a fluorescently labeled secondary antibody that specifically binds to the test antibody. After incubation, the fluorescently labeled secondary antibody may be removed and the cells washed. The washed cells may be sorted by flow cytometry and the number of cells bound to the fluorescently labeled secondary antibody counted. The concentration that provides half maximal response (e.g., half of the maximum fluorescence intensity) is measured as the EC50. In variations of the flow cytometry assay, the cell may be a 293T cell overexpressing MDR1.

The TAA may be any antigen that is known to be overexpressed in cancer cells. For example, the TAA may be an antigen that is not expressed at detectable levels in a normal cell and is expressed in cancer cells, where the normal and cancer cells are the same cell type, e.g., epithelial cells. For example, TAAs may be neoantigens that are a class of tumor antigens that arise from a tumor-specific mutation(s) which alters the amino acid sequence of encoded proteins as compared to the amino acid sequence of the unmutated protein. In other aspects, a TAA is an antigen that is expressed in normal cells but is expressed at higher levels in cancer cells. In certain aspects, the TAA may be CD47.

Anti-MDR1 and Anti-CD47 Bispecific Antibody

In certain aspects, the bispecific antibody molecule binds to CD47 and the second VH chain comprises the HCDRs of a VH chain comprising the amino acid sequence:

QVQLVQSGAEVKKPGASVKVSCKASGYTFTNYNMHWVRQAPGQRLEWMGT

IYPGNDDTSYNQKFKDRVTITADTSASTAYMELSSLRSEDTAVYYCARGG

YRAMDYWGQGTLVTVSS.

In certain aspects, the second VH chain comprises the HCDR1 comprising the sequence: NYNMH (SEQ ID NO:18), the HCDR2 comprising the sequence: TIYPGNDDTSYNQKFKD (SEQ ID NO:19), and the HCDR3 comprising the sequence: GGYRAMDY (SEQ ID NO:20). The HCDRs1-3 are defined based on the Kabat nomenclature.

In certain aspects, the second VH chain comprises a sequence that is at least 80% identical (e.g., at least 85% identical, at least 90% identical, or at least 95% identical) to the amino acid sequence:

QVQLVQSGAEVKKPGASVKVSCKASGYTFTNYNMHWVRQAPGQRLEWMGT

IYPGNDDTSYNQKFKDRVTITADTSASTAYMELSSLRSEDTAVYYCARGG

YRAMDYWGQGTLVTVSS.

In certain aspects, the second VH chain comprises the amino acid sequence:

QVQLVQSGAEVKKPGASVKVSCKASGYTFTNYNMHWVRQAPGQRLEWMGT

IYPGNDDTSYNQKFKDRVTITADTSASTAYMELSSLRSEDTAVYYCARGG

YRAMDYWGQGTLVTVSS.

In certain aspects, the bispecific antibody that binds to MDR1 and CD47 may include a humanized VH chain that includes an antigen binding site for CD47 having the sequence:

EVQLVESGGGLVQPGGSLRLSCAASGYTFTNYNMHWVRQAPGKGLEWMGT

IYPGNDDTSYNQKFKDRVTISRDNSKNTLYLQMNSLRAEDTAVYYCARGG

YRAMDYWGQGTLVTVSS;

EVQLVQSGAEVKKPGESLKISCKGSGYTFTNYNMHWVRQMPGKGLEWMGT

IYPGNDDTSYNQKFKDQVTISADKSISTAYLQWSSLKASDTAMYYCARGG

YRAMDYWGQGTTVTVSS;
or

QVQLVQSGSELKKPGASVKVSCKASGYTFTNYNMHWVRQAPGQGLEWMGT

IYPGNDDTSYNQKFKDRFVFSLDTSVSTAYLQISSLKAEDTAVYYCARGG

YRAMDYWGQGTTVTVSS.

Additional aspects of the bispecific antibody are described elsewhere in the application and include variations humanized versions of the sequences disclosed herein and/or substitutions in the Fc region to promoter formation of heterodimers between the first and the second VH chains.

Anti-MDR1 and Anti-PD-L1 Bispecific Antibody

In certain aspects, the TAA may be Programmed death-ligand 1 (PD-L1). PD-L1 is also known as cluster of differentiation 274 (CD274) or B7 homolog 1 (B7-H1). In certain aspects, the bispecific antibody molecule that binds to MDR1 and PD-L1 includes the common light chain and the first VH chain as described in the preceding sections and the second VH chain comprises the HCDRs 1-3 of a VH chain comprising the amino acid sequence:

EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS

The HCDRs 1-3 defined as per Kabat nomenclature are:

HCDR1:      DSWIH
HCDR2:      WISPYGGSTYYADSVKG
HCDR3:      RHWPGGFDY

The second VH chain of the bispecific antibody that binds to MDR1 and PD-L1 may have an amino acid sequence at least 80%, at least 90%, at least 95%, or a 100% identical to the amino acid sequence:

EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS

The second VH chain of the bispecific antibody that binds to MDR1 and PD-L1 may be present in heavy chain having an amino acid sequence at least 80%, at least 90%, at least 95%, or a 100% identical to the amino acid sequence:

EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

As described elsewhere herein, at least one, two, or all of the VL chain, the first VH chain, and the second VH may be humanized. In addition, the Fc regions of the VH chains may include substitutions to increase heterodimerization between the first and second VH chain. In certain aspects, the first heavy chain may be humanized and include the charged pair substitutions K392D and K409D and the second heavy chain and include the charged pair substitutions E356K and D399K.

Anti-MDR1 and Anti-EGFR Bispecific Antibody

In certain aspects, the TAA may be epidermal growth factor receptor (EGFR). The HCDRs1-3 for the second VH chain that includes an antigen-binding site for EGFR may be derived from the VH chain of the anti-EGFR antibody necitumumab or cetuximab. The heavy chain of necitumumab has the following sequence:

QVQLQESGPGLVKPSQTLSLTCTVSGGSISSGDYYWSWIRQPPGKGLEWI

GYIYYSGSTDYNPSLKSRVIMSVDTSKNQFSLKVNSVTAADTAVYYCARV

SIFGVGTFDYWGQGTLVTVSSASTKGPSVLPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K

The heavy chain of cetuximab has the following sequence:

QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

In a first aspect, the anti-MDR1 anti-EGFR bispecific antibody includes the VL and first VH chain as described in the preceding sections and the second VH chain may include the HCDRs from VH region of necitumumab. The HCDRs defined as per Kabat nomenclature may have the following sequences:

HCDR1:      SGDYYWS
HCDR2:      YIYYSGSTDYNPSLKS
HCDR3:      VSIFGVGTFDY

In certain aspects, the second VH chain may have an amino acid sequence at least 80%, at least 90%, at least 95%, or a 100% identical to the amino acid sequence:

QVQLQESGPGLVKPSQTLSLTCTVSGGSISSGDYYWSWIRQPPGKGLEW

IGYIYYSGSTDYNPSLKSRVIMSVDTSKNQFSLKVNSVTAADTAVYYCA

RVSIFGVGTFDYWGQGTLVTVSS

The second VH chain of the bispecific antibody that binds to MDR1 and EGFR may be present in heavy chain having an amino acid sequence at least 80%, at least 90%, at least 95%, or a 100% identical to the amino acid sequence:

QVQLQESGPGLVKPSQTLSLTCTVSGGSISSGDYYWSWIRQPPGKGLEW

IGYIYYSGSTDYNPSLKSRVIMSVDTSKNQFSLKVNSVTAADTAVYYCA

RVSIFGVGTFDYWGQGTLVTVSSASTKGPSVLPLAPSSKSTSGGTAALG

CLVKDYFPEPVTVSWNSGALTSGVHTFPAVLQSSGLYSLSSVVTVPSSS

-continued

LGTQTYICNVNHKPSNTKVDKRVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYT

QKSLSLSPGK

In a second aspect, the anti-MDR1 anti-EGFR bispecific antibody includes the VL and first VH chain as described in the preceding sections and the second VH chain may include the HCDRs from VH region of cetuximab. The HCDRs defined as per Kabat nomenclature may have the following sequences:

HCDR1: NYGVH

HCDR2: VIWSGGNTDYNTPFTS

HCDR3: ALTYYDYEFAY

In certain aspects, the second VH chain may have an amino acid sequence at least 80%, at least 90%, at least 95%, or a 100% identical to the amino acid sequence:

QVQLKQSGPGLVQPSQSLSITCTVSGFSLTNYGVHWVRQSPGKGLEWLG

VIWSGGNTDYNTPFTSRLSINKDNSKSQVFFKMNSLQSNDTAIYYCARA

LTYYDYEFAYWGQGTLVTVSA

The second VH chain of the bispecific antibody that binds to MDR1 and EGFR may be present in heavy chain having an amino acid sequence at least 80%, at least 90%, at least 95%, or a 100% identical to the amino acid sequence:

QVQLKQSGPGLVQPSQSLSITCTVSGFSLTNYGVHWVRQSPGKGLEWLG

VIWSGGNTDYNTPFTSRLSINKDNSKSQVFFKMNSLQSNDTAIYYCARA

LTYYDYEFAYWGQGTLVTVSAASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK

The anti-MDR1 anti-EGFR bispecific antibodies described above include the same combination of VH and VL chains as the anti-MDR1 anti-CD47 bispecific antibodies and the anti-MDR1 anti-PD-L1 bispecific antibodies described above and may be referred to as 15D3 HC::MRK16 LC::necitumumab HC and 15D3 HC::MRK16 LC::cetuximab HC antibodies.

Also provided herein are bispecific antibody molecules that include a different combination of the common VL chain that includes an antigen-binding site for MDR1 and the first VH chain that includes an antigen-binding site for MDR1 but are not based on the MRK16 LC and/or the 15D3 HC as described above.

In certain aspects, an anti-MDR1 anti-EGFR bispecific antibody may have the following combination of heavy and light chains: (i) 15D3 HC::cetuximab HC: 15D3 LC; (ii) MRK16 HC::cetuximab HC::15D3 LC; or (iii) MRK16 HC::cetuximab HC::MRK16 LC.

The HCDRs and the LCDRs, the VL and VH regions, and the heavy chain and light chains may have the same sequence as provided herein.

The first HC may include the charged pair substitutions K392D and K409D and the second heavy chain may include the charged pair substitutions E356K and D399K or vice versa.

In certain aspects, the bispecific antibodies of the present disclosure do not encompass the bispecific antibody, UIC2 DD HC::cetuximab KK HC::MRK16 LC. This bispecific antibody includes a VH chain comprising HCDRs1-3 of the anti-MDR1 antibody, UIC2. However, this antibody does not retain binding to MDR1 as measured by FACS using 293T cells overexpressing MDR1. See FIG. 31. The VH chain of UIC2 HC is as provided elsewhere herein.

In certain aspects, the bispecific antibody includes a second heavy chain comprising the second VH chain as described herein and a heavy chain constant region. The heavy chain may comprise the human IgG1 heavy chain constant region sequence.

In certain aspects, the bispecific antibody molecule specifically binds a cell expressing both MDR1 and the TAA and has greater than twice the affinity for a cell expressing both MDR1 and the TAA as compared to a cell expressing either MDR1 or the TAA.

In certain aspects, the bispecific antibody molecule is capable of increasing sensitivity of a cancer cell to treatment with a chemotherapeutic agent, where the half maximal inhibitory concentration (IC50) of the chemotherapeutic agent when co-administered with the antibody is at least 2 times lower (e.g. at least 3 times lower, at least 4 times lower, at least 5 times lower, at least 10 times lower, at least 20 times lower, or at least 30 times lower) than the IC50 of the chemotherapeutic agent when co-administered with an anti-MDR1 antibody comprising a VH chain having the sequence: EVKVVESGGVLVRPGGSLKLSCAASGF-TFSRYTMSWVRQTPEKRLEWVATISSGGGNTYY PDSVKGRFTVSRDNAMSSLYLQMSSLRSEDTALYY-CARYGAGDAWFAYWGQGTLVTVSA (SEQ ID NO:24); and a VL chain having the sequence:

(SEQ ID NO: 25)
DVLMTQTPLSLPVSLGDQASISCRSSQSIVHSTGNTYLEWYLQKPGQSP

KLLIYKVSNRFSGVPDRFSGSGSGTDFTLKISRLEAEDLGVYYCFQGSH

FPRTFGGGTRLEIK.

In certain aspects, the anti-MDR1 antibody may be the 15D3 antibody described in U.S. Pat. No. 5,959,084.

In certain aspects, the bispecific antibody molecule binds to MDR1 with at least 2-fold lower affinity (e.g. at least 3 times lower, at least 4 times lower, at least 5 times lower, at least 10 times lower, at least 20 times lower, or at least 30 times lower affinity) than an anti-MDR1 antibody comprising a VH chain having the sequence: EVKVVESGGVLVRPGGSLKLSCAASGFTFSRYTMS-WVRQTPEKRLEWVATISSGGGNTYY PDSVKGRF-TVSRDNAMSSLYLQMSSLRSEDTALYYCARYGAG-DAWFAYWGQGTLVTVSA (SEQ ID NO:24); and a VL chain having the sequence:

(SEQ ID NO: 25)
DVLMTQTPLSLPVSLGDQASISCRSSQSIVHSTGNTYLEWYLQKPGQSP

KLLIYKVSNRFSGVPDRFSGSGSGTDFTLKISRLEAEDLGVYYCFQGSH

FPRTFGGGTRLEIK.

In certain aspects, the anti-MDR1 antibody may the 15D3 antibody described in U.S. Pat. No. 5,959,084.

In certain aspects, the bispecific antibody molecule when bound to a cell expressing a MDR1, inhibits efflux by the MDR1. Inhibition may be a decrease in efflux by at least 5%, at least 10%, at least 15%, at least 20%, at least 25%, at least 50%, or more, as compared to efflux by the MDR1 in absence of the bispecific antibody.

In certain aspects, the bispecific antibody molecule comprises a Fc domain that has been modified to reduce or abrogate binding of the antibody to one or more Fcγ receptors. In certain aspects, the IgG1 Fc domain may have one or more of the substitutions L234A, L235A, P329G and N297A/Q/G.

As summarized above, the present disclosure provides multi-specific antibodies having a domain that targets a cellular efflux pump and a domain that targets a cancer-associated antigen. Included are multi-specific antibodies that include a multidrug resistance protein 1 (MDR1)-binding domain and a leukocyte surface antigen CD47-binding domain. Multi-specific antibodies of the present disclosure specifically bind cells that express both MDR1 and CD47.

Accordingly, the multi-specific antibodies of the present disclosure target both MDR1 and CD47. MDR1, also known as P-glycoprotein 1 (Pgp), is an energy-dependent efflux pump responsible for decreased drug accumulation in multidrug-resistant cells that is expressed from the ATP binding cassette subfamily B member 1 (ABCB1). CD47, also known as integrin associated protein (IAP), is an immunoglobulin superfamily transmembrane protein that binds membrane integrins and also serves as a receptor for the ligands thrombospondin-1 (TSP-1) and signal-regulatory protein alpha (SIRPα) and is encoded by the CD47 gene. CD47 ligand binding can result in inhibition of phagocytosis and thus, as a target in immune therapy, masking of the CD47 extracellular domain prevents inhibition of immune-mediated killing of CD47-expressing cancer cells.

A schematic depiction of an embodiment of a multi-specific antibody of the present disclosure is provided in FIG. 1A. As depicted, the multi-specific antibody 100 includes a MDR1-binding domain 101 and a CD47-binding domain 102 and, optionally, all or a portion of an Fc domain 103. As illustrated in FIG. 1B, in the presence of a cell 104 that expresses MDR1 107, but where CD47 expression is low or absent, the multi-specific antibody 100 has low affinity for the cell. Correspondingly, in the presence of a cell 105 that expresses CD47 108, but where MDR1 expression is low or absent, the multi-specific antibody 100 has low affinity for the cell. However, in the presence of a cell 106 that expresses both MDR1 107 and CD47 108, the multi-specific antibody 100 has high affinity for the cell.

Thus, multi-specific antibodies of the present disclosure bind cells that express both MDR1 and CD47 with higher affinity than cells that express only MDR1 or CD47. Correspondingly, multi-specific antibodies of the present disclosure bind with much reduced affinity when low levels of the respective second target are present, e.g., as compared to when both first and second targets are present above low levels (e.g., at average, normal, and/or high levels). In some embodiments, the affinity with which the subject multi-specific antibodies bind cells that express both MDR1 and CD47 is greater than twice, including e.g., greater than 2.5 times, greater than 3 times, greater than 4 times, greater than 5 times, greater than 6 times, greater than 7 times, greater than 8 times, greater than 9 times, greater than 10 times, or more, as compared to the affinity with which the subject multi-specific antibodies bind cells that express either MDR1 or CD47 (or a low level of either MDR1 or CD47).

In some embodiments, the subject multi-specific antibodies may, when bound to a cell expressing MDR1, prevent the functioning of the cellular MDR1 protein. Accordingly, multi-specific antibodies of the present disclosure may inhibit efflux by the MDR1 protein, including e.g., where efflux is reduced by 5% or more, including e.g., 10% or more, 15% or more, 20% or more, 25% or more, 30% or more, 40% or more, 50% or more, 60% or more, 70% or more, 80% or more, or 90% or more, as compared to efflux by MDR1 in the absence of the subject multi-specific antibody.

In some embodiments, the subject multi-specific antibodies may, when bound to a cell expressing CD47, prevent the functioning of the cellular CD47 protein. Accordingly, multi-specific antibodies of the present disclosure may inhibit binding of a CD47-ligand or CD47 binding partner to CD47, including e.g., where ligand/binding partner binding is reduced by 5% or more, including e.g., 10% or more, 15% or more, 20% or more, 25% or more, 30% or more, 40% or more, 50% or more, 60% or more, 70% or more, 80% or more, or 90% or more, as compared to binding by CD47 in the absence of the subject multi-specific antibody.

Multi-specific antibodies of the present disclosure are at least bispecific for MDR1 and CD47, where the configuration of the antibody may vary. The term "antibody" refers to a protein comprising one or more (e.g., one or two) heavy chain variable regions (VH) and/or one or more (e.g., one or two) light chain variable regions (VL), or subfragments thereof capable of binding an epitope. With regard to the herein described multi-specific antibodies, such antibodies are capable of binding at least two different epitopes present on two different target proteins. The number of different target proteins, and thus different epitopes, bound by the subject multi-specific antibodies may vary and may be two (i.e., bispecific), three (tri-specific), four, or greater.

In some embodiments, multi-specific antibodies of the present disclosure may include a common light chain. As used herein, the term "common light chain" will generally refer to the use, and incorporation, of two copies of the same light chain into the multi-specific antibody. Put another way, a light chain, in the assembled multi-specific antibody, will associate with the MDR1-specific heavy chain and a second copy of the same light chain will associate with the CD47-specific heavy chain.

The VH and VL regions can be further subdivided into regions of hypervariability, termed "complementarity determining regions (CDR)", interspersed with regions that are more conserved, termed "framework regions (FR)". The extent of the FR and CDRs has been precisely defined (see, Kabat, et al. (1991) Sequences of Proteins of Immunological Interest, Fifth Edition, U.S. Department of Health and Human Services, NIH Publication No. 91-3242; Chothia et al. (1987) J. Mol. Biol. 196:901-917). A VH can comprise three CDRs and four FRs arranged from N-terminus to C-terminus in the following order: FR1, CDR1, FR2, CDR2, FR3, CDR3, FR4. Similarly, a VL can comprise three CDRs and four FRs arranged from N-terminus to C-terminus in the following order: FR1, CDR1, FR2, CDR2, FR3, CDR3, FR4.

The VH or VL chain of an antibody can further include all or part of a heavy or light chain constant region, to thereby form a heavy or light immunoglobulin chain, respectively. In one embodiment, the antibody is a tetramer of two heavy and two light chains, wherein the heavy and light chains are interconnected by, for example, disulphide bonds. The heavy chain constant region is comprised of three domains, CH1, CH2 and CH3. The light chain constant region is comprised of one domain, CL. The variable regions of the heavy and light chains comprise binding regions that interact with antigen. The constant regions of the antibodies typically mediate the binding of the antibody to host tissues and factors, including various cells of the immune system and the first component of the complement system. The term "antibody" includes immunoglobulins of types IgA, IgG, IgE, IgD, IgM and subtypes thereof. In some embodiments, a subject antibody is an IgG isotype.

As used herein the term "immunoglobulin" refers to a protein including one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes; and numerous immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g. gamma (encoding about 330 amino acids). In some embodiments, a subject antibody comprises full-length immunoglobulin heavy chain and a full-length immunoglobulin light chain.

In some embodiments, a subject antibody does not comprise a full-length immunoglobulin heavy chain and a full-length immunoglobulin light chain, and instead comprises antigen-binding fragments of one or more full-length immunoglobulin heavy chains and/or one or more antigen-binding fragments of a full-length immunoglobulin light chain. In some embodiments, the antigen-binding fragments are contained on separate polypeptide chains; in other embodiments, the antigen-binding fragments are contained within a single polypeptide chain.

The term "antigen-binding fragment" refers to one or more fragments of a full-length antibody that are capable of specifically binding to MDR1 or CD47 as described above. Examples of binding fragments include (i) a Fab fragment (a monovalent fragment including, e.g., consisting of, the VL, VH, CL and CH1 domains; (ii) a F(ab')₂ fragment (a bivalent fragment comprising two Fab fragments linked by a disulfide bridge at the hinge region; (iii) a Fd fragment (including, e.g., consisting of, the VH and CH1 domains); (iv) a Fv fragment (including, e.g., consisting of, the VH and VL domains of a single arm of an antibody); (v) a dAb fragment (including, e.g., consisting of, the VH domain); (vi) an isolated CDR; (vii) a single chain Fv (scFv) (including, e.g., consisting of, the VH and VL domains of a single arm of an antibody joined by a synthetic linker using recombinant means such that the VH and VL domains pair to form a monovalent molecule); (viii) diabodies (including, e.g., consisting of, two scFvs in which the VH and VL domains are joined such that they do not pair to form a monovalent molecule; the VH of each one of the scFv pairs with the VL domain of the other scFv to form a bivalent molecule).

In some embodiments, a subject antibody is a recombinant or modified antibody, e.g., a chimeric, humanized, deimmunized or an in vitro generated antibody. The term "recombinant" or "modified" antibody as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) antibodies prepared, expressed, created, or isolated by any other means that involves splicing of human immunoglobulin gene sequences to other DNA sequences. Such recombinant antibodies include humanized, CDR grafted, chimeric, deimmunized, and in vitro generated antibodies; and can optionally include constant regions derived from human germline immunoglobulin sequences.

Modified antibodies may include modified domains, including where any antibody domain may be modified from a naturally occurring form. In some embodiments, a modified antibody may include a modified heavy chain, including a modified Fc domain, including a modified CH2 and/or modified CH3 domain. In some instances, modified Fc domains may employ electrostatic steering effects, including but not limited to e.g., through the use of the procedures described in Gunasekeran et al, (2010) Journal of Biological Chemistry 285, 19637-19646; the disclosure of which is incorporated herein by reference in its entirety. In some instances, a bispecific antibody is assembled through charge pair substitutions at the CH3 domain, including but not limited to e.g., where one heavy chain is modified to contain K392D and K409D substitutions and the other heavy chain is modified to contained E356K and D399K substitutions. Charge pair substituted chains may preferentially form a heterodimer with one another. The numbering of the amino acid substitutions is per EU numbering system for HCs.

In some instances, an antibody of the present disclosure includes charge pair substitutions. In some instances, an antibody of the present disclosure does not include charge pair substitutions. In some instances, an alternative means of promoting preferential heterodimer formation of desired chains may be employed.

In some instances, a modified heavy chain may include a knob-into-hole modification. "Knobs-into-holes" amino acid modification is a rational design strategy in antibody engineering, used for heterodimerization of the heavy chains, in the production of multi-specific antibodies, including bispecific IgG antibodies. For example, in incorporating the knobs-into-holes strategy into a bispecific antibody made from two monoclonal antibodies of different specificities, amino acid changes are engineered in order to create a "knob" on the CH3 of the heavy chain of monoclonal antibody 1 (mAb1) and a "hole" on the CH3 of the heavy chain of monoclonal antibody 2 (mAb2). The knob may be represented by a large amino acid, such as e.g., a tyrosine (Y), whereas the hole may be represented by small amino acid, such as a threonine (T). For example, a knobs-into-holes pair modification may be created a T22Y substitution in a first CH3 domain and Y86T substitution in the partner CH3 domain. Examples of knobs-into-holes modifications are described in Carter, J. Immunol. Methods, 248 (1-2): 7-15 (2001); Ridgway, J. B. et al. Protein Eng. 9 (7): 617-2 (1996); and Merchant, A. M. et al. Nat. Biotechnol. 16 (7): 677-81 (1998); the disclosures of which are incorporated herein in their entirety. In antibodies generated from paired knob-into-hole modified domains the bispecific heterodimer will generally represent the major fraction.

As summarized above, multi-specific antibodies of the present disclosure will include a MDR1-binding domain and CD47-binding domain. Such domains may vary, including the epitopes bound by the domains, the variable region arrangement and sequences, etc.

A subject MDR1-binding domain specifically binds one or more epitopes of MDR1. Thus, the epitope is a MDR1 epitope. The size of a MDR1 epitope bound by a MDR1-binding domain may vary, including where the MDR1 epitope is formed by a polypeptide having a contiguous stretch of a MDR1 sequence that may range from 4 aa or less to 12 aa or more, including but not limited to e.g., 4 aa, 5 aa, 6 aa, 7 aa, 8 aa, 9 aa, 10 aa, 11 aa, 12 aa, 4 aa to 10 aa, 5 aa to 10 aa, 6 aa to 10 aa, 4 aa to 8 aa, 5 aa to 8 aa, 6 aa to 8 aa, etc.

In some embodiments, the MDR1 epitope can be formed by a polypeptide having at least about 75%, at least about 80%, at least about 85%, at least about 90%, at least about 95%, at least about 98%, at least about 99%, or 100%, amino acid sequence identity to a contiguous stretch of a MDR1 sequence, including but not limited to e.g., the human MDR1 sequence:

MDLEGDRNGGAKKKNFFKLNNKSEKDKKEKKPTVSVFSMFRYSNWLDKLYMVVGTLAAIIH GAGLPLMMLVFGEMTDIFANAGNLEDLMSNITNRSDINDTG-FFMNLEEDMTRYAYYYSGIG AGVLVAAYIQVSFWC-LAAGRQIHKIRKQFFHAIMRQEIGWFDVHDVGELN-TRLTDDVSKINE GIGDKIGMFFQSMATFFTGFIVGF-TRGWKLTLVILAISPVLGLSAAVWAKILSSFTDKEL-LAYA KAGAVAEEVLAAIRTVIAFGGQKKELERYNKN-LEEAKRIGIKKAITANISIGAAFLLIYASYALAF WYGT-TLVLSGEYSIGQVLTVFFSVLIGAFSVGQASPSIEAF-ANARGAAYEIFKIIDNKPSIDSY SKSGHKPDNIKGN-LEFRNVHFSYPSRKEVKILKGLNLKVQSGQTVALV-GNSGCGKSTTVQL MQRLYDPTEGMVSVDGQDIRT-INVRFLREIIGVVSQEPVLFATTIAENIRYGRENVTM-DEIEK AVKEANAYDFIMKLPHKFDTLVGERGAQL-SGGQKQRIAIARALVRNPKILLLDEATSALDTES EAVVQVALDKARKGRTTIVIAHRLSTVRNADVI-AGFDDGVIVEKGNHDELMKEKGIYFKLV™ QTAG-NEVELENAADESKSEIDALEMSSNDSRSSLIRKR-STRRSVRGSQAQDRKLSTKEALD ESIPPVSFW-RIMKLNLTEWPYFVVGVFCAIINGGLQPAFAIIFSK-IIGVFTRIDDPETKRQNSNL FSLLFLALGIISFITF-FLQGFTFGKAGEILTKRLRYMVFRSMLRQDVSWFD-DPKNTTGALTTRL ANDAAQVKGAIGSRLAVITQ-NIANLGTGIIISFIYGWQLTLLLLAIVPIIAIAGVVE-MKMLSGQAL KDKKELEGSGKIATEAIENFRTVVSL-TQEQKFEHMYAQSLQVPYRNSLRKAHIFGITFSFTQA MMYFSYAGCFRFGAYLVAHKLMSFEDVLLVFSA-VVFGAMAVGQVSSFAPDYAKAKISAAHII MIIEKTP-LIDSYSTEGLMPNTLEGNVTFGEVVFNYPTRPDIP-VLQGLSLEVKKGQTLALVGSS GCGKSTVVQLLER-FYDPLAGKVLLDGKEIKRLNVQWLRAHLGIVSQEP-ILFDCSIAENIAYGD NSRVVSQEEIVRAAKEANI-HAFIESLPNKYSTKVGDKGTQLSGGQKQRIAIAR-ALVRQPHILL LDEATSALDTESEKVVQEALDKARE-GRTCIVIAHRLSTIQNADLIVVFQNGRVKEHGTHQQLL AQKGIYFSMVSVQAGTKRQ (SEQ ID NO:61); or a rodent MDR1 sequence, such as e.g., the mouse MDR1 sequence:

MEFEENLKGRADKNFSKMGKKSKKEKKEKKPAV-GVFGMFRYADWLDKLCMILGTLAAIIHG TLLPLL-MLVFGNMTDSFTKAEASILPSITNQSGPNSTLIISNS-SLEEEMAIYAYYYTGIGAGVLI VAYIQVSLWC-LAAGRQIHKIRQKFFHAIMNQEIGWFDVHDVGELN-TRLTDDVSKINDGIGDKI GMFFQSITTFLAGFIIGFIS-GWKLTLVILAVSPLIGLSSALWAKVLTSFTNKELQAY-AKAGAVA EEVLAAIRTVIAFGGQQKELERYNKNLEE-AKNVGIKKAITASISIGIAYLLVYASYALAFWYGTS LVLSNEYSIGEVLTVFFSILLGTFSIGHLAPNIEAFA-NARGAAFEIFKIIDNEPSIDSFSTKGYKP DSIMGN-LEFKNVHFNYPSRSEVQILKGLNLKVKSGQTVALV-GNSGCGKSTTVQLMQRLYDP LEGVVSIDGQDIRT-INVRYLREIIGVVSQEPVLFATTIAENIRYGREDVTM-DEIEKAVKEANAY DFIMKLPHQFDTLVGER-GAQLSGGQKQRIAIARALVRNPKILLLDEATSALDT-ESEAVVQAAL DKAREGRTTIVIAHRLSTVRNADVI-AGFDGGVIVEQGNHDELMREKGIYFKLVMTQTRG-NEI EPGNNAYGSQSDTDASELTSEESKSPLIRR-SIYRSVHRKQDQERRLSMKEAVDEDVPLVSF WRILNLNLSEWPYLLVGVLCAVINGCIQPVFAIV-FSRIVGVFSRDDDHETKRQNCNLFSLFFL VMGLIS-FVTYFFQGFTFGKAGEILTKRVRYMVFKSMLRQDIS-WFDDHKNSTGSLTTRLASDA SSVKGAMGAR-LAVVTQNVANLGTGVILSLVYGWQLTLLLVVIIPLIV-LGGIIEMKLLSGQALKD KKQLEISGKIATEAIEN-FRTIVSLTREQKFETMYAQSLQVPYRNAMKKAH-VFGITFSFTQAMM YFSYAACFRFGAYLVAQQLMT-FENVMLVFSAVVFGAMAAGNTSSFAPDYAKAKV-SASHIIRI IEKTPEIDSYSTEGLKPTLLEGNVKFN-GVQFNYPTRPNIPVLQGLSLEVKKGQTLALVGSSG CGKSTVVQLLERFYDPMAGSVFLDGKEIKQLNVQW-LRAHLGIVSQEPILFDCSIAENIAYGD NSRAVSHEE-IVRAAKEANIHQFIDSLPDKYNTRVGDKGTQL-SGGQKQRIAIARALVRQPHILL LDEATSALD-TESEKVVQEALDKAREGRTCIVIAHRLSTIQNADLIV-VIENGKVKEHGTHQQLL AQKGIYFSMVQAGAKRS (SEQ ID NO:62), or a non-human primate sequence, such as e.g., the Pan troglodytes (Chimpanzee) sequence:

MDLEGDRNGGAKKKNFFKLNNKSEKDKKEKKPT-VSVFSMFRYSNWLDKLYMVVGTLAAIIH GAGLPLM-MLVFGEMTDIFANAGNLEDLMSNITNRSDINDTGFF-MNLEEDMTRYAYYYSGIG AGVLVAAYIQVSFWC-LAAGRQIHKIRKQFFHAIMRQEIGWFDVHDVGELN-TRLTDDVSKINE GIGDKIGMFFQSMATFFTG-FIVGFTRGWKLTLVILAISPVLGSAAVWAKILSSFT-DKELLAYA KAGAVAEEVLAAIRTVIAFGGQKKEL-ERYNKNLEEAKRIGIKKAITANISIGAAFLLIYASY-ALAF WYGTTLVLSGEYSIGQVLTVFFSVLIGAFS-VGQASPSIEAFANARGAAYEIFKIIDNKPSIDSY SKS-GHKPDNIKGNLEFRNVHFSYPSRKQVKILKGL-NLKVQSGQTVALVGNSGCGKSTTVQL MQRLYDP-TEGMVSVDGQDIRTINVRFLREIIGVVSQEPVLFATTI-AENIRYGRENVTMDEIEK AVKEANAYDFIMKL-PHKFDTLVGERGAQLSGGQKQRIAIARALVRNP-KILLLDEATSALDTES EAVVQVALDKARKGRTTIVI-AHRLSTVRNADVIAGFDDGVIVEKGNHDELMKEK-GIYFKLV™ QTAGNEVELENAADESKSEIDALE-MSSNDSRSSLIRKRSTRRSVRGSQAQDRKLSTKEALD ESIPPVSFWRIMKLNLTEWPYFVVGVFCAIING-GLQPAFAIIFSKIIGVFTRIDDPETKRQNSNL FSLL-FLVLGIISFITFFLQGFTFGKAGEILTKRLRYMVFRS-MLRQDVSWFDDPKNTTGALTTRL ANDAAQVK-GAIGSRLAVITQNIANLGTGIIISFIYGWQLTLLLLAIV-PIIAIAGVVEMKMLSGQAL KDKKELEGAGKIASE-AIENFRTVVSLTQEQKFEHMYAQSLQVPYRNSLRKA-HIFGITFSFTQA MMYFSYAGCFRFGAYLVAHKLMSFEDVLLVFS-AVVFGAMAVGQVSSFAPDYAKAKISAAHII MIIEKTPLIDSYSTEGLTPNTLEGNVTFGEVVFNYP-

TRPDIPVLQGLSLEVKKGQTLALVGSS GCGKSTVVQLLERFYDPLAGKVLLDGKEIKRLNVQWLRAHLGIVSQEPILFDCSIAENIAYGD NSRVVSQEEIVRAAKEANIHAFIESLPNKYSTRVGDKGTQLSGGQKQRIAIARALVRQPHILL LDEATSALDTESEKVVQEALDKAREGRTCIVIAHRLSTIQNADLIVVFQNGRVKEHGTHQQLL AQKGIYFSMVSVQAGTKRQ (SEQ ID NO:63), or the *Macaca fascicularis* (Crab-eating macaque) sequence:
MDLEGDRNGGAEKKNFFKLNNKSKKDKKERKPTVSVFSMFRYSNWLDKLYMVVGTLAAIIH GAGLPLMMLVFGDMTDTFANAGNLGDLGALLFNNTNSSNITDTVPVMNLEEDMTRYAYYY SGIGAGVLVAAYIQVSFWCLAAGRQIHKIRKQFFHAIMRQEIGWFDVHDVGELNTRLTDDVS KINEGIGDKIGMFFQSMATFFTGFIVGFTRGWKLTLVILAISPVLGLSAAVWAKILSSFTDKEL LAYAKAGAVAEEVLAAIRTVIAFGGQKKELERYNKNLEEAKRIGIKKAITANISIGAAFLLIYASYALAFWYGTTLVLSKEYSIGQVLTVFFSVLIGAFSVGQASPSIEAFANARGAAFEIFKIIDNKPSI DSYSKSGHKPDNIKGNLEFRNVHFSYPSRKEVKILKGLNLKVQSGQTVALVGNSGCGKSTT VQLMQRLYDPTEGMVSVDGQDIRTINVRFLREIIGVVSQEPVLFATTIAENIRYGREDVTMDE IEKAVKEANAYDFIMKLPQKFDTLVGERGAQLSGGQKQRIAIARALVRNPKILLLDEATSALD TESEAVVQVALDKARKGRTTIVIAHRLSTVRNADVIAGFDDGVIVEKGNHDELMKEKGIYFKL VTMQTAGNEIELENAADESKSEIDTLEMSSHDSGSSLIRKRSTRRSVRGSQGQDRKLSTKE ALDESIPPVSFWRIMKLNLTEWPYFVVGVFCAIINGGLQPAFAVIFSKIIGIFTRNDDAETKRQ NSNLFSLLFLVLGIVSFITFFLQGFTFGKAGEILTKRLRYMVFRSMLRQDVSWFDDPKNTTGA LTTRLANDAAQVKGAIGSRLAIITQNIANLGTGIIISLIYGWQLTLLLLAIVPIIAIAGVVEMKMLS GQALKDKKELEGAGKIATEAIENFRTVVSLTQEQKFEHMYDQSLQVPYRNSLRKAHIFGITF SFTQAMMYFSYAGCFRFGAYLVAHSLMSFEDVLLVFSAVVFGAMAVGQVSSFAPDYAKAK VSAAHIIMIIEKTPLIDSYSTEGLKPNTLEGNVTFNEVVFNYPTRLDIPVLQGLSLEVKKGQTLA LVGSSGCGKSTVVQLLERFYDPLAGKVLLDGKEIKQLNVQWLRAHLGIVSQEPILFDCSISE NIAYGDNSRVVSQEEIVRAAKEANIHAFIESLPNKYSTRVGDKGTQLSGGQKQRIAIARALVR QPHILLLDEATSALDTESEKVVQEALDKAREGRTCIVIAHRLSTIQNADLIVVFQNGRVKEHG THQQLLAQKGIYFSMVSVQAGAKRQ (SEQ ID NO:64), or the like.

A subject MDR1-binding domain exhibits high affinity binding to MDR1. For example, a subject MDR1-binding domain binds to MDR1 with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than 10-12 M. A subject MDR1-binding domain binds to an epitope present on MDR1 with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M, or greater than $10^{-12}$ M.

A subject MDR1-binding domain exhibits substantially no binding to any epitopes formed by amino acids within other related, but sequence dissimilar, proteins such as related but sequence dissimilar EPs. Any binding of a subject MDR1-binding domain to an epitope formed by amino acids within a related, but sequence dissimilar, protein is generally non-specific binding of a substantially lower affinity than the specific binding of the MDR1-binding domain to the epitope on MDR1. A substantially lower affinity is generally at least a two fold, three fold, five fold, 10 fold, 50 fold, 100 fold, 500 fold, or 1000 fold lower affinity.

A subject MDR1-binding domain can reduce transport of molecules through a MDR1 transporter. For example, a subject MDR1-binding domain can reduce transport by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the degree of transport in the absence of the MDR1-binding domain.

In some embodiments, a subject antibody comprises: a variable domain comprising: a) a heavy chain variable domain comprising: i. a CDR1 region that is identical in amino acid sequence to or includes the heavy chain CDR1 region of RYTMS (SEQ ID NO:13); ii. a CDR2 region that is identical in amino acid sequence to or includes the heavy chain CDR2 region of TISSGGGNTYYPDSVKG (SEQ ID NO:29); and iii. a CDR3 region that is identical in amino acid sequence to or includes the heavy chain CDR3 region of YGAGDAWFAY (SEQ ID NO:15). These CDR1-3 regions are those present in the VH chain of the 15D3 antibody, having the following sequence: EVKVVESGGVLVRPGGSLKLSCAASGFTFSRYTMSWVRQTPEKRLEWVATISSGGGNTYY PDSVKGRFTVSRDNAMSSLYLQMSSLRSEDTALYYCARYGAGDAWFAYWGQGTLVTVSA (SEQ ID NO:24) or a humanized version of this VH chain having the following sequence: EVOLVESGGVVVQPGGSLRLSCAASGFTFSRYTMSWVRQAPGKGLEWVATISSG GGX²TYYPDSVKGRFTVSRDNSKNSLYLQMNSLRTEDTALYYCARYGAGDAWFAYWGQG TLVTVSS (SEQ ID NO:65), where $X^2$ is N, Q or S. These CDRs are based on the Kabat nomenclature.

In some embodiments, a subject antibody comprises a heavy chain variable region comprising one, two, or three of the heavy chain CDRs having an amino acid sequence selected from one or more of CDR1 (RYTMS, (SEQ ID NO:13)), CDR2 (TISSGGGX²TYYPDSVKG (SEQ ID NO:14), where $X^2$ is N, Q or S), and CDR3 (YGAGDAWFAY, (SEQ ID NO:15)); and FR regions that are mammalian sequences, including e.g., rodent, non-human primate, and human sequences (e.g., encoded by the respective heavy chain FR-encoding sequences). For example, in some embodiments, a subject antibody comprises a heavy chain variable region that comprises, in order from N-terminus to C-terminus: a human heavy chain FR1; a CDR1 comprising the amino acid sequence RYTMS (SEQ ID NO:13); a human heavy chain FR2; a CDR2 comprising the amino acid sequence TISSGGGNTYYPDSVKG (SEQ ID NO:29); a human heavy chain FR3; a CDR3 comprising the amino acid sequence YGAGDAWFAY, (SEQ ID NO:15); and a human heavy chain FR4.

A subject antibody can comprise a heavy chain variable region comprising an amino acid sequence that is 85%, 86%, 87%, 88%, 89%, 90%, 91%, 92%, 93%, 94%, 95%, 96%, 97%, 98%, 99%, or more, including 100%, identical to the sequence: EVKVVESGGVLVRPGGSLKLSCAASGFTFSRYTMSWVRQTPEKRLEWVATISSGGGNTYY PDSVKGRFTVSRDNAMSSLYLQMSSLRSEDTALYYCARYGAGDAWFAYWGQGTLVTVSS (SEQ ID NO:10). A subject antibody can comprise a heavy chain variable region comprising one, two, or three of the heavy chain complementarity determining regions (CDRs) having an amino acid sequence selected from one or more of CDR1 (RYTMS, (SEQ ID NO:13)), CDR2 (TISSGGGN-TYYPDSVKG, (SEQ ID NO:29)), and CDR3 (YGAGDAWFAY, (SEQ ID NO: 15)). In certain aspects, the VH chain is humanized to include human framework regions and the humanized VH chain may include an amino acid sequence that is 85%, 86%, 87%, 88%, 89%, 90%, 91%, 92%, 93%, 94%, 95%, 96%, 97%, 98%, 99%, or more, including 100%, identical to the sequence: EVOLVES-GGVVVQPGGSLRLSCAASGFTFSRYTMSWVRQAP-GKGLEWVATISSGGGX$^2$TY YPDSVKGRFTVSRDNS-KNSLYLQMNSLRTEDTALYYCARYGAGDAWFAYW-GQGTLVTVS S (SEQ ID NO:65), where X$^2$ is N, Q or S.

A subject CD47-binding domain specifically binds one or more epitopes of CD47. Thus, the epitope is a CD47 epitope. The size of a CD47 epitope bound by a CD47-binding domain may vary, including where the CD47 epitope is formed by a polypeptide having a contiguous stretch of a CD47 sequence that may range from 4 aa or less to 12 aa or more, including but not limited to e.g., 4 aa, 5 aa, 6 aa, 7 aa, 8 aa, 9 aa, 10 aa, 11 aa, 12 aa, 4 aa to 10 aa, 5 aa to 10 aa, 6 aa to 10 aa, 4 aa to 8 aa, 5 aa to 8 aa, 6 aa to 8 aa, etc.

In some embodiments, the CD47 epitope can be formed by a polypeptide having at least about 75%, at least about 80%, at least about 85%, at least about 90%, at least about 95%, at least about 98%, at least about 99%, or 100%, amino acid sequence identity to a contiguous stretch of a CD47 sequence, including but not limited to e.g., the human CD47 sequence: MWPLVAALLLGSACCGSAQLLFNKTKS-VEFTFCNDTVVIPCFVTNMEAQNTTEVYVKWKFK GRDIYTFDGALNKSTVPTDFSSAKIEVSQLLKG-DASLKMDKSDAVSHTGNYTCEVTELTREG ETII-ELKYRVVSWFSPNENILIVIFPIFAILLFWGQFGIK-TLKYRSGGMDEKTIALLVAGLVITVIVI VGAIL-FVPGEYSLKNATGLGLIVTSTGILILLHYYVFSTAIG-LTSFVIAILVIQVIAYILAVVGLSLCI AACIPMHGPL-LISGLSILALAQLLGLVYMKFVASNQKTIQPPRKA-VEEPLNAFKESKGMMND E (SEQ ID NO:66); or a rodent CD47 sequence, such as e.g., the mouse CD47 sequence: MWPLAAALLLGSCCCGSAQLLFSNVN-SIEFTSCNETVVIPCIVRNVEAQSTEEMFVKWKLNK SYIFIYDGNKNSTTTDQNFTSAKISVSDLIN-GIASLKMDKRDAMVGNYTCEVTELSREGKTVI ELKNRTVSWFSPNEKILIVIFPILAILLFWGKFGILTL-KYKSSHTNKRIILLLVAGLVLTVIVVVGAI LLIPGEKP-VKNASGLGLIVISTGILILLQYNVFMTAFGMTSF-TIAILITQVLGYVLALVGLCLCIMA CEPVHGPLLIS-GLGIIALAELLGLVYMKFVASNQRTIQPPRNR (SEQ ID NO:67), or a non-human primate sequence, such as e.g., the Pongo abelii (Sumatran orangutan) sequence: MWPLVAALLLGSACCGSAQLLFNKTKSVEFTFC-NDTVVIPCFVTNMEAQNTTEVYVKWKFK GRDI-YTFDGALNKSTVPTDFSSAKIEVSQLLKGDASLK-MDKSDAVSHTGNYTCEVTELTREG ETIIELKYRV-VSWFSPNENILIVIFPIFAILLFWGQFGIKTLKYRSG-GMDEKTIALLVAGLIITVIVI VGAILFVPGEYS-LKNATGLGLIVTSTGILILLHYYVFSTAIGLNSFVIAIL-VIQVIAYILAVVGLSLC IAACIPMHGPLLISGLSILA-LAQLLGLVYMKFVASNQKTIQPPRKAVEEPLNAFKE-SKGMMND E (SEQ ID NO:68), or the *Macaca* mulatta (Rhesus macaque) sequence: MWPLVAALLLG-SACCGSAQLLFNKTKSVEFTFCNDTVVIPCFVTNM-EAQNTTEVYVKWKFK GRDIYTFDGALNKSTAPA-NFSSAKIEVSQLLKGDASLKMDKSDAVSHTGNYTCE-VTELTRE GETIIELKYRVVSWFSPNENILIVIFPIFAILL-FWGQFGIKTLKYRSGGMDEKTIALLVAGLMITVI VIVGAILFVPGEYSLKNATGLGLIVTSTGILILLHYY-VFSTAIGLTSFVIAILVIQVIAYILAVVGLSL CIAACIP-MHGPLLISGLSILALAQLLGLVYMKFVASNOKTIQP-PRKAVEEPLNAFKESKGMMN DE (SEQ ID NO:69), or the like.

A subject CD47-binding domain exhibits high affinity binding to CD47. For example, a subject CD47-binding domain binds to CD47 with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than $10^{-12}$ M. A subject CD47-binding domain binds to an epitope present on CD47 with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M, or greater than $10^{-12}$ M.

A subject CD47-binding domain exhibits substantially no binding to any epitopes formed by amino acids within other related, but sequence dissimilar, proteins such as related but sequence dissimilar immune checkpoint markers. Any binding of a subject CD47-binding domain to an epitope formed by amino acids within a related, but sequence dissimilar, protein is generally non-specific binding of a substantially lower affinity than the specific binding of the CD47-binding domain to the epitope on CD47. A substantially lower affinity is generally at least a two fold, three fold, five fold, 10 fold, 50 fold, 100 fold, 500 fold, or 1000 fold lower affinity.

A subject CD47-binding domain can reduce the binding of CD47-binding-partners to CD47, including e.g., thrombospondin-1 (TSP-1), signal-regulatory protein alpha (SIRPα) and integrins (e.g., integrin avb3). For example, a subject CD47-binding domain can reduce CD47-binding-partner binding by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the degree of binding in the absence of the CD47-binding domain.

In some embodiments, a subject antibody comprises: a variable domain comprising: a) a heavy chain variable domain comprising: i. a CDR1 region that is identical in amino acid sequence to or includes the heavy chain CDR1 region of NYNMH (SEQ ID NO:18); ii. a CDR2 region that is identical in amino acid sequence to or includes the heavy chain CDR2 region of TIYPGNDDTSYNQKFKD (SEQ ID NO:19); and iii. a CDR3 region that is identical in amino acid sequence to or includes the heavy chain CDR3 region of GGYRAMDY (SEQ ID NO: 20). These CDR1-3 regions are those present in the VH chain of the 5F9 antibody, having the following sequence: QVQLVQSGAEVKKP-GASVKVSCKASGYTFTNYNMHWVRQAPGQR-LEWMGTIYPGNDDT SYNQKFKDRVTITADTSAS-TAYMELSSLRSEDTAVYYCARGGYRAMDYWGQGT-LVTVSS (SEQ ID NO:17). These CDRs are based on the Kabat nomenclature.

A subject antibody can comprise a heavy chain variable region comprising an amino acid sequence that is 85%, 86%, 87%, 88%, 89%, 90%, 91%, 92%, 93%, 94%, 95%, 96%, 97%, 98%, 99%, or more, including 100%, identical t to the sequence: QVQLVQSGAEVKKPGASVKVSCKASGY-TFTNYNMHWVRQAPGQRLEWMGTIYPGNDDT SYN-QKFKDRVTITADTSASTAYMELSSLRSEDTAVYY-CARGGYRAMDYWGQGTLVTVSS (SEQ ID NO:17). A subject antibody can comprise a heavy chain variable region comprising one, two, or three of the heavy chain complementarity determining regions (CDRs) having an amino acid sequence selected from one or more of CDR1 (NYNMH, (SEQ ID NO:18)), CDR2 (TIYPGNDDTSYNQKFKD, (SEQ ID NO:19)), and CDR3 (GGYRAMDY, (SEQ ID NO:20)).

In some embodiments, a subject antibody comprises a heavy chain variable region comprising one, two, or three of the heavy chain CDRs having an amino acid sequence selected from one or more of CDR1 (NYNMH, (SEQ ID NO:18)), CDR2 (TIYPGNDDTSYNQKFKD, (SEQ ID NO:19)), and CDR3 (GGYRAMDY, (SEQ ID NO:20)); and FR regions that are mammalian, e.g., rodent, non-human primate, or human, sequences (e.g., encoded by the respective heavy chain FR-encoding sequences). For example, in some embodiments, a subject antibody comprises a heavy chain variable region that comprises, in order from N-terminus to C-terminus: a human heavy chain FR1; a CDR1 comprising the amino acid sequence NYNMH (SEQ ID NO:18); a human heavy chain FR2; a CDR2 comprising the amino acid sequence TIYPGNDDTSYNQKFKD, (SEQ ID NO:19); a human heavy chain FR3; a CDR3 comprising the amino acid sequence GGYRAMDY (SEQ ID NO: 20); and a human heavy chain FR4.

A subject antibody can comprise a light chain variable region comprising an amino acid sequence that is 85%, 86%, 87%, 88%, 89%, 90%, 91%, 92%, 93%, 94%, 95%, 96%, 97%, 98%, 99%, or more, including 100%, identical to the sequence:

```
DVLMTQTPVSLSVSLGDQASISCRSSQSIVHSTGX¹TYLEWYLQKPGQSP

KLLIYKISNRFSGVPDRFSGSGSGTDFTLKISRVEAEDLGVYYCFQASHF

PRTFGGGTKLEIK,
``` or a humanized version of this sequence, having the sequence:

```
                                              (SEQ ID NO: 70)
DIVMTQTPLSSPVTLGQPASISCRSSQSIVHSTGX¹TYLEWYQQRPGQP

PRLLIYKISNRFSGVPDRFSGSGAGTDFTLKISRVEAEDVGVYYCFQAS

HFPRTFGGGTKLEIK,
``` where $X^1$ is N, Q or S.

A subject antibody can comprise a light chain variable region comprising light chain CDRs having the amino acid sequence set forth in CDR1 (RSSQSIVHSTG X¹TYLEW, (SEQ ID NO: 71)), where $X^1$ is N, Q or S, CDR2 (KISNRFSG, (SEQ ID NO:72), and CDR3 (FQASHFPRTF, (SEQ ID NO:73)) or CDR1 (RSSQSLLHSDGFDYLNW, (SEQ ID NO:74)), CDR2 (ALSNRASG, (SEQ ID NO:75)) and CDR3 (MZALQAPITF, (SEQ ID NO:76)). In some instances, such light chain variable region may be employed in a common light chain of the subject multi-specific antibody.

In some embodiments, a subject antibody comprises a light chain variable region comprising light chain CDRs having the amino acid sequence set forth in CDR1 (RSSQSIVHSTG X¹TYLEW, (SEQ ID NO:71)), where $X^1$ is N, Q or S, CDR2 (KISNRFSG, (SEQ ID NO:72)), and CDR3 (FQASHFPRTF, (SEQ ID NO:73)) or CDR1 (RSSQSLLHSDGFDYLNW, (SEQ ID NO:74)), CDR2 (ALSNRASG, (SEQ ID NO:75)) and CDR3 (MZALQAPITF, (SEQ ID NO:76)); and FR regions that are mammalian, including e.g., rodent, non-human primate, or human, sequences (e.g., encoded by the respective light chain FR-encoding sequences). For example, in some embodiments, a subject antibody comprises a light chain variable region that comprises, in order from N-terminus to C-terminus: a human light chain FR1; a CDR1 comprising the amino acid sequence RSSQSIVHSTG X¹TYLEW (SEQ ID NO:71), where $X^1$ is N, Q or S; a human light chain FR2; a CDR2 comprising the amino acid sequence KISNRFSG (SEQ ID NO:72); a human light chain FR3; a CDR3 comprising the amino acid sequence set forth in FQASHFPRTF (SEQ ID NO:73); and a human light chain FR4.

In some embodiments, a subject antibody comprises: optionally a heavy chain FR1 region; a CDR1 comprising the amino acid sequence RYTMS (SEQ ID NO:13); a heavy chain FR2 region; a CDR2 comprising the amino acid sequence TISSGGG (N/S/Q) TYYPDSVKG (SEQ ID NO:14); a heavy chain FR3 region; a CDR3 comprising the amino acid sequence YGAGDAWFAY (SEQ ID NO:15); and a heavy chain FR4 region; and optionally a heavy chain FR1 region; a CDR1 comprising the amino acid sequence NYNMH (SEQ ID NO:18); a heavy chain FR2 region; a CDR2 comprising the amino acid sequence TIYPGNDDTSYNQKFKD (SEQ ID NO:19); a heavy chain FR3 region; a CDR3 comprising the amino acid sequence GGYRAMDY (SEQ ID NO:20); and a heavy chain FR4 region. In some of these embodiments, each of the FR regions is mammalian FR region, including e.g., a human FR region.

In some embodiments, a subject antibody comprises: the heavy chain sequences as described in the preceding paragraph and further: a light chain FR1 region; a CDR1 comprising the amino acid sequence RSSQSIVHSTGNTYLEW (SEQ ID NO:77) or RSSQSLLHSDGFDYLNW (SEQ ID NO:74); a light chain FR2 region; a CDR2 comprising the amino acid sequence KISNRFSG (SEQ ID NO:72) or ALSNRASG (SEQ ID NO:75); a light chain FR3 region; a CDR3 comprising the amino acid sequence FQASHFPRTF (SEQ ID NO: 73) or MZALQAPITF (SEQ ID NO:76); optionally a light chain FR4 region.

In some embodiments, a subject antibody comprises an anti-MDR1 heavy chain sequence that includes a charge-to-charge swap (KK) modification having the sequence: EVKVVESGGVLVRPGGSLKLSCAASGFTFSRYTMSWVRQTPEKRLEWVATISSGGGNTYY PDSVKGRFTVSRDNAMSSLYLQMSSLRSEDTALYYCARYGAGDAWFAYWGQGTLVTVSS ASTKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRKELTKN QVSLTCLVKGFYPSDIAVEWESNGQPENNYKTTPPVLKSDGSFFLYSKLTVDKSRWQQGN VFSCSVMHEALHNHYTQKSLSLSPG (SEQ ID NO:78), an anti-CD47 heavy chain sequence that includes a charge-to-charge swap (DD) modification having the sequence: QVQLVQSGAEVKKPGASVKVSCKASGYTFTNYNMHWVRQAPGQRLEWMGTIYPGNDDT SYNQKFKDRVTITADTSASTAYMELSSLRSEDTAVYYCARGGYRAMDYWGQGTLVTVSSA STKGPSVFPLAPSSKSTSGGTAALGCLVKDYFPEPVTVSWNSGALTSGVHTFPAVLQSSGL YSLSSVVTVPSSSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPPSRKELTKNQ VSLTCLVKGFYPSDIAVEWESNGQPENNYKTTPPVLKSDGSFFLYSKLTVDKSRW- QQGNV FSCSVMHEALHNHYTQKSLSLSPG (SEQ ID NO:79), and an anti-MDR1 light chain sequence having the sequence: DVLMTQTPVSLSVSLGDQASISCRSSQ-SIVHSTGNTYLEWYLQKPGQSPKLLIYKISNRFSG VPDRFSGSGSGTDFTLKISRVEAEDLGVYYCFQASH-FPRTFGGGTKLEIKRTVAAPSVFIFP PSDEQLKSG-TASVVCLLNNFYPREAKVQWKVDNALQSGNSQ-ESVTEQDSKDSTYSLSSTL TLSKADYEKHKVYACE-VTHQGLSSPVTKSFNRGEC (SEQ ID NO:80). In some instances, the subject antibody may include an alternative heterodimeric Fc pairing strategy.

The charge to charge swap modification refers to substitutions where one heavy chain is modified to contain K392D and K409D substitutions and the other heavy chain is modified to contained E356K and D399K substitutions. Charge pair substituted chains favor formation of heterodimer with one another. The numbering of the amino acid substitutions is per EU numbering system for Ig HCs.

Monospecific Bivalent Antibodies and Bispecific Antibodies

Also provided herein are antibodies that may be monospecific bivalent antibodies or bispecific antibodies derived therefrom.

In certain aspects, an antibody of the present disclosure comprises a variable light (VL) chain comprising light chain CDRs (LCDRs) of a VL chain having the sequence:

```
                                       (SEQ ID NO: 1)
DVLMTQTPVSLSVSLGDQASISCRSSQSIVHSTGX¹TYLEWYLQKPGQS

PKLLIYKISNRFSGVPDRFSGSGSGTDFTLKISRVEAEDLGVYYCFQAS

HFPRTFGGGTKLEIK,
``` where $X^1$ is N, Q or S; and a variable heavy (VH) chain comprising heavy chain CDRs (HCDRs) of a VH chain having the sequence: EVKVVESGGVLVRPGG- SLKLS-CAASGFTFSRYTMSWVRQTPEKRLEWVATIS-SGGGX²TY YPDSVKGRFTVSRDNAMSSLYLQMSSL-RSEDTALYYCARYGAGDAWFAYWGQGTLVTVSS (SEQ ID NO:9), where $X^2$ is N, Q or S.

In certain aspects, the VL chain comprises LCDRs of the VL chain having the sequence:

```
                                       (SEQ ID NO: 2)
DVLMTQTPVSLSVSLGDQASISCRSSQSIVHSTGNTYLEWYLQKPGQSP

KLLIYKISNRFSGVPDRFSGSGSGTDFTLKISRVEAEDLGVYYCFQASH

FPRTFGGGTKLEIK;
``` and the VH chain comprises HCDRs of the VH chain having the sequence: EVKVVESGGVLVRPGGSLKLS-CAASGFTFSRYTMSWVRQTPEKRLEWVATISSGGGN-TYY PDSVKGRFTVSRDNAMSSLYLQMSSLRSED-TALYYCARYGAGDAWFAYWGQGTLVTVSS (SEQ ID NO:10), or the VL chain comprises LCDRs of the VL chain having the sequence:

```
                                       (SEQ ID NO: 3)
DIVMTQTPLSSPVTLGQPASISCRSSQSIVHSTGQTYLEWYQQRPGQPP

RLLIYKISNRFSGVPDRFSGSGAGTDFTLKISRVEAEDVGVYYCFQASH

FPRTFGQGTKLEIK;
``` and the VH chain comprises HCDRs of the VH chain having the sequence: EVQLVESGGVVVQPGGSLRLS-CAASGFTFSRYTMSWVRQAPGKGLEWVATISSGGG-QTY YPDSVKGRFTVSRDNSKNSLYLQMNSLRTED-TALYYCARYGAGDAWFAYWGQGTLVTVS S (SEQ ID NO:11), or the VL chain comprises LCDRs of the VL chain having the sequence:

```
                                       (SEQ ID NO: 4)
DIVMTQTPLSSPVTLGQPASISCRSSQSIVHSTGSTYLEWYQQRPGQPP

RLLIYKISNRFSGVPDRFSGSGAGTDFTLKISRVEAEDVGVYYCFQASH

FPRTFGQGTKLEIK;
``` and the VH chain comprises LCDRs of the VH chain having the sequence:

```
EVQLVESGGVVVQPGGSLRLSCAASGFTFSRYTMS

WVRQAPGKGLEWVATISSGGGSTYYPDSVKGRFTV

SRDNSKNSLYLQMNSLRTEDTALYYCARYGAGDAW

FAYWGQGTLVTVSS.
```

In certain aspects, the LCDR1 comprises the sequence: RSSQSIVHSTGNTYLE (SEQ ID NO: 44), RSSQSIVH-STGQTYLE (SEQ ID NO:27), or RSSQSIVHSTGSTYLE (SEQ ID NO: 28), the LCDR2 comprises the sequence: KISNRFS (SEQ ID NO:6), and the LCDR3 comprises the sequence: FQASHFPRT (SEQ ID NO:7).

In certain aspects, the HCDR1 comprises the sequence: RYTMS (SEQ ID NO:13), the HCDR2 comprises the sequence: TISSGGGNTYYPDSVKG (SEQ ID NO:29), TISSGGGQTYYPDSVKG (SEQ ID NO:30), or TISSGGG-STYYPDSVKG (SEQ ID NO:31), and the HCDR3 comprises the sequence: YGAGDAWFAY (SEQ ID NO:15).

In certain aspects, the LCDR1 comprises the sequence: RSSQSIVHSTGNTYLE (SEQ ID NO: 44), the LCDR2 comprises the sequence: KISNRFS (SEQ ID NO:6), and the LCDR3 comprises the sequence: FQASHFPRT (SEQ ID NO:7); and the HCDR1 comprises the sequence: RYTMS (SEQ ID NO:13), the HCDR2 comprises the sequence: TISSGGGNTYYPDSVKG (SEQ ID NO:29), and the HCDR3 comprises the sequence: YGAGDAWFAY (SEQ ID NO:15).

In certain aspects, the LCDR1 comprises the sequence: RSSQSIVHSTGQTYLE (SEQ ID NO: 27), the LCDR2 comprises the sequence: KISNRFS (SEQ ID NO:6), and the LCDR3 comprises the sequence: FQASHFPRT (SEQ ID NO:7); and the HCDR1 comprises the sequence: RYTMS (SEQ ID NO:13), the HCDR2 comprises the sequence: TISSGGGQTYYPDSVKG (SEQ ID NO:30), and the HCDR3 comprises the sequence: YGAGDAWFAY (SEQ ID NO:15).

In certain aspects, the LCDR1 comprises the sequence: RSSQSIVHSTGSTYLE (SEQ ID NO: 28), the LCDR2 comprises the sequence: KISNRFS (SEQ ID NO:6), and the LCDR3 comprises the sequence: FQASHFPRT (SEQ ID NO:7); and the HCDR1 comprises the sequence: RYTMS (SEQ ID NO:13), the HCDR2 comprises the sequence: TISSGGGSTYYPDSVKG (SEQ ID NO:31), and the HCDR3 comprises the sequence: YGAGDAWFAY (SEQ ID NO:15).

In certain aspects, the LCDR1 comprises the sequence: RSSQSIVHSTGNTYLE (SEQ ID NO: 44), the LCDR2 comprises the sequence: KISNRFS (SEQ ID NO:6), and the LCDR3 comprises the sequence: FQASHFPRT (SEQ ID NO:7); and the HCDR1 comprises the sequence: RYTMS (SEQ ID NO:13), the HCDR2 comprises the sequence:

TISSGGGQTYYPDSVKG (SEQ ID NO:30), and the HCDR3 comprises the sequence: YGAGDAWFAY (SEQ ID NO:15), or the LCDR1 comprises the sequence: RSSQSIVHSTGNTYLE (SEQ ID NO:44), the LCDR2 comprises the sequence: KISNRFS (SEQ ID NO:6), and the LCDR3 comprises the sequence: FQASHFPRT (SEQ ID NO:7); and the HCDR1 comprises the sequence: RYTMS (SEQ ID NO:13), the HCDR2 comprises the sequence: TISSGGGSTYYPDSVKG (SEQ ID NO:31), and the HCDR3 comprises the sequence: YGAGDAWFAY (SEQ ID NO:15).

In certain aspects, the LCDR1 comprises the sequence: RSSQSIVHSTGQTYLE (SEQ ID NO: 27), the LCDR2 comprises the sequence: KISNRFS (SEQ ID NO:6), and the LCDR3 comprises the sequence: FQASHFPRT (SEQ ID NO:7); and the HCDR1 comprises the sequence: RYTMS (SEQ ID NO:13), the HCDR2 comprises the sequence: TISSGGGNTYYPDSVKG (SEQ ID NO:29), and the HCDR3 comprises the sequence: YGAGDAWFAY (SEQ ID NO:15).

In certain aspects, the LCDR1 comprises the sequence: RSSQSIVHSTGSTYLE (SEQ ID NO: 28), the LCDR2 comprises the sequence: KISNRFS (SEQ ID NO:6), and the LCDR3 comprises the sequence: FQASHFPRT (SEQ ID NO:7); and the HCDR1 comprises the sequence: RYTMS (SEQ ID NO:13), the HCDR2 comprises the sequence: TISSGGGNTYYPDSVKG (SEQ ID NO:29), and the HCDR3 comprises the sequence: YGAGDAWFAY (SEQ ID NO:15).

In certain aspects, the LCDR1 comprises the sequence: RSSQSIVHSTGSTYLE (SEQ ID NO: 28), the LCDR2 comprises the sequence: KISNRFS (SEQ ID NO:6), and the LCDR3 comprises the sequence: FQASHFPRT (SEQ ID NO:7); and the HCDR1 comprises the sequence: RYTMS (SEQ ID NO:13), the HCDR2 comprises the sequence: TISSGGGQTYYPDSVKG (SEQ ID NO:30), and the HCDR3 comprises the sequence: YGAGDAWFAY (SEQ ID NO:15).

In certain aspects, the LCDR1 comprises the sequence: RSSQSIVHSTGNTYLE (SEQ ID NO: 44), the LCDR2 comprises the sequence: KISNRFS (SEQ ID NO:6), and the LCDR3 comprises the sequence: FQASHFPRT (SEQ ID NO:7); and the HCDR1 comprises the sequence: RYTMS (SEQ ID NO:13), the HCDR2 comprises the sequence: TISSGGGQTYYPDSVKG (SEQ ID NO:30), and the HCDR3 comprises the sequence: YGAGDAWFAY (SEQ ID NO:15).

In certain aspects, the antibody is a monospecific bivalent antibody that specifically binds to MDR-1. In certain aspects, the monospecific bivalent antibody that specifically binds to MDR-1 comprises a humanized VL chain having an amino acid sequence at least 80% identical (e.g., at least 85% identical, at least 90% identical, at least 95% identical, or a 100% identical) to the VL chain having the amino acid sequence:

```
DIVMTQTPLSSPVTLGQPASISCRSSQSIVHSTGN

TYLEWYQQRPGQPPRLLIYKISNRFSGVPDRFSGS

GAGTDFTLKISRVEAEDVGVYYCFQASHFPRTFGG

GTKLEIK;
```

```
DIVMTQTPLSSPVTLGQPASISCRSSQSIVHSTGQ

TYLEWYQQRPGQPPRLLIYKISNRFSGVPDRFSGS

GAGTDFTLKISRVEAEDVGVYYCFQASHFPRTFGQ

GTKLEIK;
or

DIVMTQTPLSSPVTLGQPASISCRSSQSIVHSTGS

TYLEWYQQRPGQPPRLLIYKISNRFSGVPDRFSGS

GAGTDFTLKISRVEAEDVGVYYCFQASHFPRTFGQ

GTKLEIK.
```

In certain aspects, the amino acid residues that differ from the VL chain sequence or the VH chain sequence are located in the framework regions.

In certain aspects, the monospecific bivalent antibody that specifically binds to MDR-1 comprises a humanized VH chain having an amino acid sequence at least 80% identical (e.g., at least 85% identical, at least 90% identical, at least 95% identical, or a 100% identical) to the VH chain having the amino acid sequence:

```
EVQLVESGGVVVQPGGSLRLSCAASGFTFSRYTMS

WVRQAPGKGLEWVATISSGGGNTYYPDSVKGRFTV

SRDNSKNSLYLQMNSLRTEDTALYYCARYGAGDAW

FAYWGQGTLVTVSS;

EVQLVESGGVVVQPGGSLRLSCAASGFTFSRYTMS

WVRQAPGKGLEWVATISSGGGQTYYPDSVKGRFTV

SRDNSKNSLYLQMNSLRTEDTALYYCARYGAGDAW

FAYWGQGTLVTVSS;
or

EVQLVESGGVVVQPGGSLRLSCAASGFTFSRYTMS

WVRQAPGKGLEWVATISSGGGSTYYPDSVKGRFTV

SRDNSKNSLYLQMNSLRTEDTALYYCARYGAGDAW

FAYWGQGTLVTVSS.
```

In certain aspects, the antibody is a bi-specific antibody comprising the VL chain as a common light chain.

In certain aspects, the bispecific antibody comprises an MDR-1 binding domain and a tumor associated antigen (TAA) binding domain wherein each of the MDR-1 binding domain and the TAA binding domain comprises the LCDR1-3 of the VL chain.

In certain aspects, the TAA is CD47 and wherein the TAA binding domain comprises HCDRs of the VH chain having the sequence:

```
QVQLVQSGAEVKKPGASVKVSCKASGYTFTNYNMH

WVRQAPGQRLEWMGTIYPGNDDTSYNQKFKDRVTI

TADTSASTAYMELSSLRSEDTAVYYCARGGYRAMD

YWGQGTLVTVSS.
```

In certain aspects, the VH chain of the CD47 binding domain comprises the HCDR1 comprising the sequence:

NYNMH (SEQ ID NO:18), the HCDR2 comprising the sequence: TIYPGNDDTSYNQKFKD (SEQ ID NO:19), and the HCDR3 comprising the sequence: GGYRAMDY (SEQ ID NO:20).

In certain aspects, an antibody of the present disclosure comprises a variable light (VL) chain comprising light chain CDRs (LCDRs) of a VL chain having the sequence:

DVLMTQTPVSLSVSLGDQASISCRSSQSIVHSTGX$^1$TYLEWYLQKPGQSPKLLIYKIS NRFSGVPDRFSGSGSGTDFTLKISRVEAEDLGVYYCFQASHFPRTFGGGTKLEIK (SEQ ID NO: 1), wherein X$^1$ is N, Q or S; and a variable heavy (VH) chain comprising heavy chain CDRs (HCDRs) of a VH chain having the sequence:

```
QVQLVQSGAEVKKPGASVKVSCKASGYTFTNYNMH

WVRQAPGQRLEWMGTIYPGNDDTSYNQKFKDRVTI

TADTSASTAYMELSSLRSEDTAVYYCARGGYRAMD

YWGQGTLVTVSS.
```

In certain aspects, the VH chain comprises the HCDR1 comprising the sequence: NYNMH (SEQ ID NO:18), the HCDR2 comprising the sequence: TIYPGNDDTSYNQKFKD (SEQ ID NO:19), and the HCDR3 comprising the sequence: GGYRAMDY (SEQ ID NO:20).

In certain aspects, the antibody is a monospecific bivalent antibody that specifically binds to CD47. In other aspects, the antibody is a bispecific antibody that binds to CD47 and MRD-1.

In certain aspects, a monospecific bivalent antibody that specifically binds to MDR-1 and a monospecific bivalent antibody that specifically binds to CD47 as described herein may be used in a method for treating cancer in a subject, the method may involve co-administering the two antibodies to the subject in an amount effective for treating the cancer. In certain aspects, the method may further involve administering a chemotherapeutic agent to the subject.

Regions and/or chains of the subject antibodies may or may not be joined by one or more linker regions. Where present, the linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

Linkers suitable for use in a subject antibody include "flexible linkers". If present, the linker molecules are generally of sufficient length to permit some flexible movement between linked regions. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers (G)$_n$, glycine-serine polymers (including, for example, (GS)$_n$, GSGGS$_n$ (SEQ ID NO:50) and GGGS$_n$ (SEQ ID NO:51), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992). Exemplary flexible linkers include, but are not limited to GGSG (SEQ ID NO:52), GGSGG (SEQ ID NO:53), GSGSG (SEQ ID NO:54), GSGGG (SEQ ID NO:55), GGGSG (SEQ ID NO:56), GSSSG (SEQ ID NO:57), and the like. The ordinarily skilled artisan will recognize that design of a peptide conjugated to any elements described above can include linkers that are all or partially flexible, such that the linker can include a flexible linker as well as one or more portions that confer less flexible structure.

In some embodiments, a subject antibody is "humanized." The term "humanized antibody" refers to an antibody comprising at least one chain comprising variable region framework residues substantially from a human antibody chain (referred to as the acceptor immunoglobulin or antibody) and at least one CDR substantially from a non-human antibody (such as e.g., a rodent (e.g., mouse antibody), non-human primate, etc.), (referred to as the donor immunoglobulin or antibody). See, Queen et al., Proc. Natl. Acad. Sci. USA 86:10029 10033 (1989), U.S. Pat. Nos. 5,530,101, 5,585,089, 5,693,761, WO 90/07861, and U.S. Pat. No. 5,225,539. The constant region(s), if present, can also be substantially or entirely from a human immunoglobulin. In some embodiments, a subject antibody comprises one or more MDR1 CDRs and one or more CD47 CDRs and one or more FR regions from a human antibody. Methods of making humanized antibodies are known in the art. See, e.g., U.S. Pat. No. 7,256,273.

The substitution of mouse CDRs into a human variable domain framework can result in retention of their correct spatial orientation where, e.g., the human variable domain framework adopts the same or similar conformation to the mouse variable framework from which the CDRs originated. This can be achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., Protein Engineering 4:773 (1991); Kolbinger et al., Protein Engineering 6:971 (1993).

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIA-CORE) and/or solid-phase ELISA analysis. In many embodiments, a subject humanized antibody does not substantially elicit a HAMA response in a human subject.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

CDR and framework regions are as defined by Kabat, Sequences of Proteins of Immunological Interest (National Institutes of Health, Bethesda, Md., 1987 and 1991). An alternative structural definition has been proposed by Chothia et al., J. Mol. Biol. 196:901 (1987); Nature 342:878 (1989); and J. Mol. Biol. 186:651 (1989) (collectively referred to as "Chothia"). When framework residues, as defined by Kabat, supra, constitute structural loop residues as defined by Chothia, supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk J M B 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986)) and selecting these amino acids from the donor may be desirable to keep all the antigen contacts that provide affinity in the original antibody.

In some embodiments, a subject antibody comprises scFv multimers. For example, in some embodiments, a subject antibody is an scFv dimer (e.g., comprises two tandem scFv (scFv2)), an scFv trimer (e.g., comprises three tandem scFv (scFv3)), an scFv tetramer (e.g., comprises four tandem scFv (scFV4)), or is a multimer of more than four scFv (e.g., in tandem). The scFv monomers can be linked in tandem via linkers of from about 2 amino acids to about 10 amino acids in length, e.g., 2 aa, 3 aa, 4 aa, 5 aa, 6 aa, 7 aa, 8 aa, 9 aa, or 10 aa in length. Suitable linkers include, e.g., $(Gly)_x$, where x is an integer from 2 to 10. Other suitable linkers are those discussed above. In some embodiments, each of the scFv monomers in a subject scFV multimer is humanized, as described above.

In some embodiments, a subject antibody comprises a constant region of an immunoglobulin (e.g., an Fc region). The Fc region, if present, can be a human Fc region. If constant regions are present, the antibody can contain both light chain and heavy chain constant regions. Suitable heavy chain constant region include CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

In some embodiments, a subject antibody comprises a free thiol (—SH) group at the carboxyl terminus, where the free thiol group can be used to attach the antibody to a second polypeptide (e.g., another antibody, including a subject antibody), a scaffold, a carrier, etc.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one-step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidhexane (BMH), 1,5-difluoro-2,4-dinitrobenzene (DFDNB), and 1,4-di-(3',2'-pyridyldithio) propinoamido butane (DPDPB).

Compositions and Formulations

The present disclosure provides a composition comprising a subject antibody. A subject antibody composition can comprise, in addition to a subject antibody, one or more of: a salt, e.g., NaCl, $MgCl_2$, KCl, $MgSO_4$, etc.; a buffering agent, e.g., a Tris buffer, N-(2-Hydroxyethyl) piperazine-N'-(2-ethanesulfonic acid) (HEPES), 2-(N-Morpholino) ethanesulfonic acid (MES), 2-(N-Morpholino) ethanesulfonic acid sodium salt (MES), 3-(N-Morpholino) propanesulfonic acid (MOPS), N-tris [Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Compositions of the present disclosure also include pharmaceutical compositions that include a multi-specific antibody described herein. In general, a formulation comprises an effective amount of the subject antibody. An "effective amount" means a dosage sufficient to produce a desired result, e.g., reduction in a cancer of a subject, reduction in the growth rate of a cancer in a subject, amelioration of a symptom of cancer, and the like. Generally, the desired result is at least a reduction in a symptom of a cancer, reduction in the growth of a cancer, reduction in the size of a cancer, etc., as compared to a control. A subject antibody can be delivered, or be formulated, in such a manner as to avoid the blood-brain barrier. In some instances, an antibody may include a delivery enhancer, including where such enhancers may facilitate crossing of the blood-brain barrier, increased permeability, e.g., allowing for efficient transdermal delivery, and the like. Useful delivery enhancers include but are not limited to e.g., cereport, regadenoson, borneol, puerarin, propylene glycols, oleic acid, azone, N-methyl pyrrolidone, Tween 80, limonene, lipid-based nanoparticles (NPs), liposomes, niosomes, transfersomes, ethosomes, dendrimers, micellar NPs, polymeric nanostructures, metallic nanostructures, magnetic nanostructures, recombinant human hyaluronidase, and the like.

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject antibody can be administered in conjunction with a pharmaceutically acceptable excipient, or they may also be used alone or in appropriate association, as well as in combination, with other pharmaceutically active compounds. The following methods and excipients are merely exemplary and are in no way limiting.

For oral preparations, a subject antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. In some instances, oral delivery of antibodies may be enhanced through complexation of the antibody with an appropriate hydrogel.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject antibody are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

Exemplary antibody concentrations in a subject pharmaceutical composition may range from about 1 mg/mL to about 200 mg/ml or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlorm-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/ml of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/ml of a subject antibody; 0.04% Tween 20 w/v; 20 mM L-histidine; and 250 mM Sucrose; and has a pH of 5.5.

As another example, a subject parenteral formulation comprises a lyophilized formulation comprising: 1) 15 mg/mL of a subject antibody; 0.04% Tween 20 w/v; 20 mM L-histidine; and 250 mM sucrose; and has a pH of 5.5; or 2) 75 mg/ml of a subject antibody; 0.04% Tween 20 w/v; 20 mM L-histidine; and 250 mM sucrose; and has a pH of 5.5; or 3) 75 mg/ml of a subject antibody; 0.02% Tween 20 w/v; 20 mM L-histidine; and 250 mM Sucrose; and has a pH of 5.5; or 4) 75 mg/mL of a subject antibody; 0.04% Tween 20 w/v; 20 mM L-histidine; and 250 mM trehalose; and has a pH of 5.5; or 6) 75 mg/ml of a subject antibody; 0.02% Tween 20 w/v; 20 mM L-histidine; and 250 mM trehalose; and has a pH of 5.5.

As another example, a subject parenteral formulation is a liquid formulation comprising: 1) 7.5 mg/ml of a subject antibody; 0.022% Tween 20 w/v; 120 mM L-histidine; and 250 125 mM sucrose; and has a pH of 5.5; or 2) 37.5 mg/mL of a subject antibody; 0.02% Tween 20 w/v; 10 mM L-histidine; and 125 mM sucrose; and has a pH of 5.5; or 3) 37.5 mg/ml of a subject antibody; 0.01% Tween 20 w/v; 10 mM L-histidine; and 125 mM sucrose; and has a pH of 5.5; or 4) 37.5 mg/mL of a subject antibody; 0.02% Tween 20 w/v; 10 mM L-histidine; 125 mM trehalose; and has a pH of 5.5; or 5) 37.5 mg/mL of a subject antibody; 0.01% Tween 20 w/v; 10 mM L-histidine; and 125 mM trehalose; and has a pH of 5.5; or 6) 5 mg/ml of a subject antibody; 0.02% Tween 20 w/v; 20 mM L-histidine; and 250 mM trehalose; and has a pH of 5.5; or 7) 75 mg/ml of a subject antibody; 0.02% Tween 20 w/v; 20 mM L-histidine; and 250 mM mannitol; and has a pH of 5.5; or 8) 75 mg/ml of a subject antibody; 0.02% Tween 20 w/v; 20 mM L histidine; and 140 mM sodium chloride; and has a pH of 5.5; or 9) 150 mg/mL of a subject antibody; 0.02% Tween 20 w/v; 20 mM L-histidine; and 250 mM trehalose; and has a pH of 5.5; or 10) 150 mg/ml of a subject antibody; 0.02% Tween 20 w/v; 20 mM L-histidine; and 250 mM mannitol; and has a pH of 5.5; or 11) 150 mg/mL of a subject antibody; 0.02% Tween 20 w/v; 20 mM L-histidine; and 140 mM sodium chloride; and has a pH of 5.5; or 12) 10 mg/ml of a subject antibody; 0.01% Tween 20 w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like.

Furthermore, a subject antibody can be made into suppositories by mixing with a variety of bases such as emulsifying bases or water-soluble bases. A subject antibody can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for a subject antibody may depend on the particular antibody employed and the effect to be achieved, and the pharmacodynamics associated with each antibody in the host.

Other modes of administration will also find use with the subject invention. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

A subject antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the antibody encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pennsylvania, 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(-)-3-hydroxybutyric acid. Possible loss of biological activity and possible changes in immunogenicity of antibodies comprised in sustained-release preparations may be prevented by using appropriate additives, by controlling moisture content and by developing specific polymer matrix compositions.

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, Extended-Release Dosage Forms, 1987 (CRC Press, Inc.).

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 µg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, intraarterial, rectal, nasal, oral, and other enteral and parenteral routes of administration. Routes of administration may be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as cancer and/or the growth of a cancer and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject," "individual," and "patient") are treatable according to the subject methods. Generally, such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the hosts will be humans.

Kits with unit doses of a subject antibody, e.g. in oral or injectable doses, are provided. In some embodiments, in addition to the containers containing the unit doses will be an informational package insert describing the use and attendant benefits of the antibody in treating pathological condition of interest.

Nucleic Acids

The present disclosure provides nucleic acids comprising nucleotide sequences encoding a subject antibody. A nucleotide sequence encoding a subject antibody can be operably linked to one or more regulatory elements, such as a promoter and enhancer, that allow expression of the nucleotide sequence in the intended target cells (e.g., a cell that is genetically modified to synthesize and/or secrete the encoded antibody).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

A nucleotide sequence encoding a subject antibody can be present in an expression vector and/or a cloning vector. Where a subject antibody comprises two or more separate polypeptides, nucleotide sequences encoding the two polypeptides can be cloned in the same or separate vectors. Separate polypeptides may be expressed from a single nucleic acid or single vector using various strategies, such as separate promoters, one or more internal ribosomal entry sites (IRES), one or more self-cleaving sequences (e.g., 2A cleavage sequences, e.g., P2A, T2A, E2A, and F2A), combinations thereof, and the like. An expression vector can include a selectable marker, an origin of replication, and other features that provide for replication and/or maintenance of the vector.

Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, a subject nucleic acid comprises a nucleotide sequence encoding a subject multi-specific antibody. A subject nucleic acid can comprise a nucleotide sequence encoding heavy- and light-chain CDRs, including MDR1 CDRs and CD47 CDRs. In some embodiments, a subject nucleic acid comprises a nucleotide sequence encoding heavy- and/or light-chain MDR1 CDRs, where the CDR-encoding sequences are interspersed with FR-encoding nucleotide sequences. In some embodiments, a subject nucleic acid comprises a nucleotide sequence encoding heavy- and/or light-chain CD47 CDRs, where the CDR-encoding sequences are interspersed with FR-encoding nucleotide sequences. In some embodiments, the FR-encoding nucleotide sequences are human FR-encoding nucleotide sequences.

In some embodiments, a subject nucleic acid comprises a nucleotide sequence encoding an amino acid sequence, wherein the amino acid sequence has at least about 75%, at least about 80%, at least about 85%, at least about 90%, at least about 95%, at least about 98%, at least about 99%, or 100% sequence identity, to the following amino acid sequence:

EVKVVESGGVLVRPGGSLKLSCAASGFTFSRYTMS

WVRQTPEKRLEWVATISSGGGNTYYPDSVKGRFTV

SRDNAMSSLYLQMSSLRSEDTALYYCARYGAGDAW

FAYWGQGTLVTVSS.

In some embodiments, a subject nucleic acid comprises a nucleotide sequence encoding an amino acid sequence, wherein the amino acid sequence has at least about 75%, at least about 80%, at least about 85%, at least about 90%, at least about 95%, at least about 98%, at least about 99%, or 100% sequence identity, to the following amino acid sequence:

QVQLVQSGAEVKKPGASVKVSCKASGYTFTNYNMH

WVRQAPGQRLEWMGTIYPGNDDTSYNQKFKDRVTI

TADTSASTAYMELSSLRSEDTAVYYCARGGYRAMD

YWGQGTLVTVSS.

In some embodiments, a subject nucleic acid comprises a nucleotide sequence encoding an amino acid sequence, wherein the amino acid sequence has at least about 75%, at least about 80%, at least about 85%, at least about 90%, at least about 95%, at least about 98%, at least about 99%, or 100% sequence identity, to the following amino acid sequence:

```
DVLMTQTPVSLSVSLGDQASISCRSSQSIVHSTGN

TYLEWYLQKPGQSPKLLIYKISNRFSGVPDRFSGS

GSGTDFTLKISRVEAEDLGVYYCFQASHFPRTFGG

GTKLEIK.
```

Nucleic acids, e.g., as described herein, may, in some instances, be introduced into a cell, e.g., by contacting the cell with the nucleic acid. Cells with introduced nucleic acids will generally be referred to herein as genetically modified cells. Various methods of nucleic acid delivery may be employed including but not limited to e.g., naked nucleic acid delivery, viral delivery, chemical transfection, biolistics, and the like.

Cells

The present disclosure provides isolated genetically modified cells (e.g., in vitro cells, ex vivo cells, cultured cells, etc.) that are genetically modified with a subject nucleic acid. In some embodiments, a subject isolated genetically modified cell can produce a subject antibody. In some instances, a genetically modified cell can deliver an antibody, e.g., to a subject in need thereof. In some instances, a genetically modified cell may be used in the production, screening, and/or discovery of multi-specific antibodies. Genetically modified cells may also, in some instances, include cells where endogenous gene expression has been reduced, e.g., inhibited, knocked-down, etc., or abolished, e.g., knocked-out. Genetically modified cells may also, in some instances, include cells where expression of a gene has been enhanced, e.g., the expression of an endogenous gene is increased or the expression of a heterologous gene is increased.

Suitable cells include eukaryotic cells, such as a mammalian cell, an insect cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, Hela cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some instances, useful mammalian cells may include cells derived from a mammalian tissue or organ. In some instances, cells employed are kidney cells, including e.g., kidney cells of an established kidney cell line, such as HEK 293T cells.

Suitable yeast cells or fungi or algae cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) J. Immunol. 148:1176-1181; U.S. Pat. No. 6,447,784; and Sizemore et al. (1995) Science 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella* disenteriae. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli*.

In some instances, cells of the present disclosure may be immune cells. As used herein, the term "immune cells" generally includes white blood cells (leukocytes) which are derived from hematopoietic stem cells (HSC) produced in the bone marrow. "Immune cells" includes, e.g., lymphocytes (T cells, B cells, natural killer (NK) cells) and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), T-regulatory cells (Treg) and gamma-delta T cells. A "cytotoxic cell" includes CD8+ T cells, natural-killer (NK) cells, and neutrophils, which cells are capable of mediating cytotoxicity responses.

In some instances, useful cells expressing a multi-specific antibody of the present disclosure may include producer T cells. Nonlimiting examples of producer T cells include those described in Tsai & Davila Oncoimmunology. (2016) 5 (5): e1122158; the disclosure of which is incorporated herein by reference in its entirety. Producer T cells engineered to include nucleic acid sequence encoding a multi-specific antibody of the present disclosure may, in some instances, be employed to deliver the antibody to a subject in need thereof.

Cells of the present disclosure also include cells genetically modified to change and/or amend expression of one or more of MDR1 and CD47 in the cell. Such modified cells are useful for various purposes including assaying the binding of multi-specific antibodies, including but not limited to those produced according to the description and methods provided herein. In some instances, MDR1 may be knocked out or knocked down in a subject cell line. In some instances, CD47 may be knocked out or knocked down in a subject cell line. In some instances, MDR1 may be constitutively or inducibly overexpressed in a subject cell line. In some instances, CD47 may be constitutively or inducibly overexpressed in a subject cell line. In some instances, both MDR1 and CD47 may knocked down, knocked out, or constitutively or inducibly overexpressed in a subject cell line. Any convenient and appropriate method for knockdown, knockout and/or overexpression may be employed. Introduced nucleic acid may be stably integrated or present transiently.

In some embodiments, cells of the present disclosure include a genetically modified human cell line that expresses CD47 and includes an exogenous nucleic acid comprising a sequence encoding MDR1 for overexpression of MDR1. In such cells CD47 expression may by endogenous or exogenously derived (i.e., introduced) and MDR1 expression may be stable or transient. In some instances, cells lines of the present disclosure, that express CD47, may be configured to produce a genetically modified human cell expressing CD47 and stably overexpressing MDR1.

Cells and cell lines of the present disclosure may be cultured, including e.g., through use of culture methods described herein. In some instances, a cell, into which nucleic acid have been introduced to genetically modify the cell, may be cultured to produce a cell line. Useful cells lines may include but are not limited to e.g., genetically modified cell lines, including human cell lines, expressing CD47 and stably over expressing MDR1.

Cells of the present disclosure, and cell lines thereof, may be employed in various methods of the disclosure, e.g., as test samples, controls, and the like. For example, in some instances cells in which MDR1 and/or CD47 have been knocked out and/or knocked down may be employed as reference cells, e.g., to which the binding of a multi-specific antibody of the present disclosure may be compared. Other useful reference cells include but are not limited to e.g., non-cancerous cells, as well as normal cells and cells expressing normal levels of various proteins, including normal level of MDR1 and/or CD47.

Methods

As summarized above, methods of the present disclosure include methods of contacting a cell with an antibody of the present disclosure, methods of treating a subject according to a method that involves administering to the subject an antibody of the present disclosure, methods of making elements described in the instant application, including e.g., multi-specific antibodies, compositions and formulations, nucleic acids, expression vectors, cells, and the like.

As summarized above, methods of the present disclosure include contacting a cancer cell with the multi-specific antibody of the present disclosure, e.g., to facilitate and/or enhance killing of the cancer cell. In some instances, killing of the cancer cell is mediated by an immune response or immune cell acting upon the cancer cell as a result of opsonization of the cancer cell by bispecific targeting when the two targets are co-expressed on the cancer cell. In some instances, killing of the cancer cell is mediated by an immune response or immune cell acting upon the cancer cell, e.g., as a result of masking or antagonizing of a CD47 epitope present on the surface of the cancer cell by the multi-specific antibody. In some instances, killing of the cancer cell is mediated by inhibition of cellular efflux of the cancer cell, e.g., as a result of MDR1 antagonism on the cancer cell by the multi-specific antibody. In some instances, the cell contacted with the multi-specific antibody may be a multidrug resistant cancer cell. Methods that involve contacting a cancer cell with a multi-specific antibody of the present disclosure may or may not include contacting the cancer cell with an additional therapy or active agent, including e.g., a chemotherapeutic, an immunotherapy, radiation therapy, or the like.

Contacting a cancer cell with a multi-specific antibody of the present disclosure will generally enhance the killing of the cancer cell, e.g., as compared to the level of killing of the cancer cell in the absence of the multi-specific antibody. In some instances, where an additional active agent is employed, enhanced killing of the cancer cell may be seen as compared to the level of killing observed using the additional active agent alone. The amount of enhancement of cancer cell killing attributable to the multi-specific antibody will vary and may range from at least a 5% increase in cancer cell killing to at least 90% or more, including but not limited to e.g., at least 10%, at least 20%, at least 30%, at least 40%, at least 50%, at least 60%, at least 70%, at least 80%, etc. Such increases may be compared to contacting with one or more additional active agents alone.

Enhanced killing of a cancer cell may be assessed by a variety of means including but not limited to e.g., observational studies, in vitro cell-based cytotoxicity assays, flow cytometry, cell viability labeling (e.g., using one or more cell viability stains), and the like.

Treatment Methods

The present disclosure provides methods of treating a cancer, the methods generally involving administering to an individual in need thereof (e.g., an individual having a cancer) an effective amount of a subject multi-specific antibody, alone (e.g., in monotherapy) or in combination (e.g., in combination therapy) with one or more additional therapeutic agents. Administration of a multi-specific antibody of the present disclosure may be performed by any convenient and appropriate route of delivery.

Aspects of the present disclosure include the bispecific antibody molecule according to the preceding section of the specification for use in a method of treating cancer in a subject, the method comprising administering the antibody to the subject. The method comprises administering the antibody in combination with at least one additional active agent, wherein the at least one additional active agent comprises a chemotherapeutic agent, an inhibitor of a multidrug resistance transporter, an immunotherapy agent, or a combination thereof. In certain aspects, the at least one additional active agent is a chemotherapeutic agent, optionally wherein the chemotherapeutic agent is a taxol, a *vinca* alkaloid, or an anthracycline. Some chemotherapeutic agents that are substrates for MDR1 pump include paclitaxel, Colchicine, Verapamil, Vinblastine, Topotecan, Doxorubicin, Daunorubicin, Etoposide, and Nilotinib.

Also disclosed herein is a chemotherapy agent for use in a method of treating cancer in a subject, the method comprising administering the chemotherapy agent in combination with the antibody described herein to the subject, optionally wherein the chemotherapy agent is a taxol, a *vinca* alkaloid, or an anthracycline.

Accordingly, administration includes but is not limited to e.g., delivery of the antibody by injection, delivery of the antibody by infusion, delivery of a nucleic acid or expression vector encoding the multi-specific antibody, delivery of the antibody by administering to the subject a cell that expresses and secretes the multi-specific antibody, and the like. Administration of an agent, a nucleic acid encoding an agent, a cell expressing an agent, etc. may include contacting with the agent, contacting with the nucleic acid, contacting with the cell, etc.

In some embodiments, an effective amount of a subject multi-specific antibody is an amount that, when administered alone (e.g., in monotherapy) or in combination (e.g., in combination therapy) with one or more additional therapeutic agents, in one or more doses, is effective to reduce an adverse symptom of cancer by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the severity of the adverse symptom in the absence of treatment with the antibody.

In some embodiments, an effective amount of a subject multi-specific antibody is an amount that, when administered alone (e.g., in monotherapy) or in combination (e.g., in combination therapy) with one or more additional therapeutic agents, in one or more doses, is effective to improve the cancer (i.e., slow the growth of the cancer, stop the growth of the cancer, reverse the growth of the cancer, kill cancer cells (including tumor cells, or the like) in the individual being treated. For example, an effective amount of a subject antibody can reduce a cancer growth rate or reduce a cancer size in an individual by at least about 5%, at least about 10%, at least about 15%, at least about 20%, at least about 25%, at least about 30%, at least about 40%, at least about 50%, or more, compared to in the absence of treatment with the multi-specific antibody.

In some instances, a subject may be treated systemically, including with the subject multi-specific antibody, with or without one or more additional reagents. By "systemic treatment", as used herein, is meant a treatment that is not directed solely to target a specific tumor (such as e.g., a primary tumor or a defined secondary tumor) or a specific cancer containing tissue (such as e.g., the liver in the case of liver cancer, the blood in the case of a blood cancer, etc.). Systemic treatments will generally be directed to the subject's body as a whole and may include but are not limited to e.g., systemic radiation therapy, systemic chemotherapy, systemic immunotherapy, combinations thereof and the like.

In some instances, a subject may be treated locally, including with the subject multi-specific antibody, with or without one or more additional reagents. By "local treatment", as used herein, is meant a treatment that is specifically directed to the location of a tumor (such as e.g., a primary tumor or a defined secondary tumor) or specifically directed to a cancer containing tissue (such as e.g., the liver in the case of liver cancer, the blood in the case of a blood cancer, etc.). In some instances, local treatment may also be administered in such a way as to affect the environment surrounding a tumor, such as tissue surrounding the tumor, such as tissue immediately adjacent to the tumor. Local treatment will generally not affect or not be targeted to tissues distant from the site of cancer including the site of a tumor, such as a primary tumor. Useful local treatments that may be administered in addition to or in combination with a subject multi-specific antibody, e.g., include but are not limited to surgery, local radiation therapy, local cryotherapy, local laser therapy, local topical therapy, combinations thereof, and the like.

In some embodiments, a subject treatment method involves administering a subject multi-specific antibody and one or more additional therapeutic agents. Suitable additional therapeutic agents include, but are not limited to, chemotherapeutic agents, radiation therapy reagents, immunotherapy reagents, other antibody or multi-specific antibody agents, and the like. Additional therapies that may be administered to a subject before, during or after a subject administering a multi-specific antibody of the present disclosure will vary depending on numerous factors including e.g., the type of cancer, the subject's medical history, general state of health and/or any co-morbidities, and the like. Useful cancer therapies include but are not limited to e.g., radiation therapy, chemotherapy, immunotherapy, and the like.

Radiation therapy includes, but is not limited to, x-rays or gamma rays that are delivered from either an externally applied source such as a beam, or by implantation of small radioactive sources.

Suitable antibodies for use in cancer treatment include, but are not limited to, naked antibodies, e.g., trastuzumab (Herceptin), bevacizumab (Avastin™), cetuximab (Erbitux™), panitumumab (Vectibix™), Ipilimumab (Yervoy™), rituximab (Rituxan), alemtuzumab (Lemtrada™), Ofatumumab (Arzerra™), Oregovomab (OvaRex™), Lambrolizumab (MK-3475), pertuzumab (Perjeta™), ranibizumab (Lucentis™) etc., and conjugated antibodies, e.g., gemtuzumab ozogamicin (Mylortarg™), Brentuximab vedotin (Adcetris™), 90Y-labelled ibritumomab tiuxetan (Zevalin™), 131I-labelled tositumoma (Bexxar™), etc. Suitable antibodies for use in cancer treatment also include, but are not limited to, antibodies raised against tumor-associated antigens. Such antigens include, but are not limited to, CD20, CD30, CD33, CD52, EpCAM, CEA, gpA33, Mucins, TAG-72, CAIX, PSMA, Folate-binding protein, Gangliosides (e.g., GD2, GD3, GM2, etc.), Le y, VEGF, VEGFR, Integrin alpha-V-beta-3, Integrin alpha-5-beta-1, EGFR, ERBB2, ERBB3, MET, IGF1R, EPHA3, TRAILR1, TRAILR2, RANKL, FAP, Tenascin, etc.

Conventional cancer therapies also include targeted therapies for cancer including but not limited to e.g., Ado-trastuzumab emtansine (Kadcyla) targeting HER2 (ERBB2/neu) (approved for use in Breast cancer); Afatinib (Gilotrif) targeting EGFR (HER1/ERBB1), HER2 (ERBB2/neu) (approved for use in Non-small cell lung cancer); Aldesleukin (Proleukin) targeting (approved for use in Renal cell carcinoma, Melanoma); Alectinib (Alecensa) targeting ALK (approved for use in Non-small cell lung cancer); Alemtuzumab (Campath) targeting CD52 (approved for use in B-cell chronic lymphocytic leukemia); Atezolizumab (Tecentriq) targeting PD-L1 (approved for use in Urothelial carcinoma, Non-small cell lung cancer); Avelumab (Bavencio) targeting PD-L1 (approved for use in Merkel cell carcinoma); Axitinib (Inlyta) targeting KIT, PDGFRB, VEGFR1/2/3 (approved for use in Renal cell carcinoma); Belimumab (Benlysta) targeting BAFF (approved for use in Lupus erythematosus); Belinostat (Beleodaq) targeting HDAC (approved for use in Peripheral T-cell lymphoma); Bevacizumab (Avastin) targeting VEGF ligand (approved for use in Cervical cancer, Colorectal cancer, Fallopian tube cancer, Glioblastoma, Non-small cell lung cancer, Ovarian cancer, Peritoneal cancer, Renal cell carcinoma); Blinatumomab (Blincyto) targeting CD19/CD3 (approved for use in Acute lymphoblastic leukemia (precursor B-cell)); Bortezomib (Velcade) targeting Proteasome (approved for use in Multiple myeloma, Mantle cell lymphoma); Bosutinib (Bosulif) targeting ABL (approved for use in Chronic myelogenous leukemia); Brentuximab vedotin (Adcetris) targeting CD30 (approved for use in Hodgkin lymphoma, Anaplastic large cell lymphoma); Brigatinib (Alunbrig) targeting ALK (approved for use in Non-small cell lung cancer (ALK+)); Cabozantinib (Cabometyx, Cometriq) targeting FLT3, KIT, MET, RET, VEGFR2 (approved for use in Medullary thyroid cancer, Renal cell carcinoma); Carfilzomib (Kyprolis) targeting Proteasome (approved for use in Multiple myeloma); Ceritinib (Zykadia) targeting ALK (approved for use in Non-small cell lung cancer); Cetuximab (Erbitux) targeting EGFR (HER1/ERBB1) (approved for use in Colorectal cancer, Squamous cell cancer of the head and neck); Cobimetinib (Cotellic) targeting MEK (approved for use in Melanoma); Crizotinib (Xalkori) targeting ALK, MET, ROS1 (approved for use in Non-small cell lung cancer);

Dabrafenib (Tafinlar) targeting BRAF (approved for use in Melanoma, Non-small cell lung cancer); Daratumumab (Darzalex) targeting CD38 (approved for use in Multiple myeloma); Dasatinib (Sprycel) targeting ABL (approved for use in Chronic myelogenous leukemia, Acute lymphoblastic leukemia); Denosumab (Xgeva) targeting RANKL (approved for use in Giant cell tumor of the bone); Dinutuximab (Unituxin) targeting B4GALNT1 (GD2) (approved for use in Pediatric neuroblastoma); Durvalumab (Imfinzi) targeting PD-L1 (approved for use in Urothelial carcinoma); Elotuzumab (Empliciti) targeting SLAMF7 (CS1/CD319/CRACC) (approved for use in Multiple myeloma); Enasidenib (Idhifa) targeting IDH2 (approved for use in Acute myeloid leukemia); Erlotinib (Tarceva) targeting EGFR (HER1/ERBB1) (approved for use in Non-small cell lung cancer, Pancreatic cancer); Everolimus (Afinitor) targeting mTOR (approved for use in Pancreatic, gastrointestinal, or lung origin neuroendocrine tumor, Renal cell carcinoma, Nonresectable subependymal giant cell astrocytoma, Breast cancer); Gefitinib (Iressa) targeting EGFR (HER1/ERBB1) (approved for use in Non-small cell lung cancer); Ibritumomab tiuxetan (Zevalin) targeting CD20 (approved for use in Non-Hodgkin's lymphoma); Ibrutinib (Imbruvica) targeting BTK (approved for use in Mantle cell lymphoma, Chronic lymphocytic leukemia, Waldenstrom's macroglobulinemia); Idelalisib (Zydelig) targeting PI3Kδ (approved for use in Chronic lymphocytic leukemia, Follicular B-cell non-Hodgkin lymphoma, Small lymphocytic lymphoma); Imatinib (Gleevec) targeting KIT, PDGFR, ABL (approved for use in GI stromal tumor (KIT+), Dermatofibrosarcoma protuberans, Multiple hematologic malignancies); Ipilimumab (Yervoy) targeting CTLA-4 (approved for use in Melanoma); Ixazomib (Ninlaro) targeting Proteasome (approved for use in Multiple Myeloma); Lapatinib (Tykerb) targeting HER2 (ERBB2/neu), EGFR (HER1/ERBB1) (approved for use in Breast cancer (HER2+)); Lenvatinib (Lenvima) targeting VEGFR2 (approved for use in Renal cell carcinoma, Thyroid cancer); Midostaurin (Rydapt) targeting FLT3 (approved for use in acute myeloid leukemia (FLT3+)); Necitumumab (Portrazza) targeting EGFR (HER1/ERBB1) (approved for use in Squamous non-small cell lung cancer); Neratinib (Nerlynx) targeting HER2 (ERBB2/neu) (approved for use in Breast cancer); Nilotinib (Tasigna) targeting ABL (approved for use in Chronic myelogenous leukemia); Niraparib (Zejula) targeting PARP (approved for use in Ovarian cancer, Fallopian tube cancer, Peritoneal cancer); Nivolumab (Opdivo) targeting PD-1 (approved for use in Colorectal cancer, Head and neck squamous cell carcinoma, Hodgkin lymphoma, Melanoma, Non-small cell lung cancer, Renal cell carcinoma, Urothelial carcinoma); Obinutuzumab (Gazyva) targeting CD20 (approved for use in Chronic lymphocytic leukemia, Follicular lymphoma); Ofatumumab (Arzerra, HuMax-CD20) targeting CD20 (approved for use in Chronic lymphocytic leukemia); Olaparib (Lynparza) targeting PARP (approved for use in Ovarian cancer); Olaratumab (Lartruvo) targeting PDGFRa (approved for use in Soft tissue sarcoma); Osimertinib (Tagrisso) targeting EGFR (approved for use in Non-small cell lung cancer); Palbociclib (Ibrance) targeting CDK4, CDK6 (approved for use in Breast cancer); Panitumumab (Vectibix) targeting EGFR (HER1/ERBB1) (approved for use in Colorectal cancer); Panobinostat (Farydak) targeting HDAC (approved for use in Multiple myeloma); Pazopanib (Votrient) targeting VEGFR, PDGFR, KIT (approved for use in Renal cell carcinoma); Pembrolizumab (Keytruda) targeting PD-1 (approved for use in Classical Hodgkin lymphoma, Melanoma, Non-small cell lung cancer (PD-L1+), Head and neck squamous cell carcinoma, Solid tumors (MSI-H)); Pertuzumab (Perjeta) targeting HER2 (ERBB2/neu) (approved for use in Breast cancer (HER2+)); Ponatinib (Iclusig) targeting ABL, FGFR1-3, FLT3, VEGFR2 (approved for use in Chronic myelogenous leukemia, Acute lymphoblastic leukemia); Ramucirumab (Cyramza) targeting VEGFR2 (approved for use in Colorectal cancer, Gastric cancer or Gastroesophageal junction (GEJ) adenocarcinoma, Non-small cell lung cancer); Regorafenib (Stivarga) targeting KIT, PDGFRB, RAF, RET, VEGFR1/2/3 (approved for use in Colorectal cancer, Gastrointestinal stromal tumors, Hepatocellular carcinoma); Ribociclib (Kisqali) targeting CDK4, CDK6 (approved for use in Breast cancer (HR+, HER2−)); Rituximab (Rituxan, Mabthera) targeting CD20 (approved for use in Non-Hodgkin's lymphoma, Chronic lymphocytic leukemia, Rheumatoid arthritis, Granulomatosis with polyangiitis); Rituximab/hyaluronidase human (Rituxan Hycela) targeting CD20 (approved for use in Chronic lymphocytic leukemia, Diffuse large B-cell lymphoma, Follicular lymphoma); Romidepsin (Istodax) targeting HDAC (approved for use in Cutaneous T-cell lymphoma, Peripheral T-cell lymphoma); Rucaparib (Rubraca) targeting PARP (approved for use in Ovarian cancer); Ruxolitinib (Jakafi) targeting JAK1/2 (approved for use in Myelofibrosis); Siltuximab (Sylvant) targeting IL-6 (approved for use in Multicentric Castleman's disease); Sipuleucel-T (Provenge) targeting (approved for use in Prostate cancer); Sonidegib (Odomzo) targeting Smoothened (approved for use in Basal cell carcinoma); Sorafenib (Nexavar) targeting VEGFR, PDGFR, KIT, RAF (approved for use in Hepatocellular carcinoma, Renal cell carcinoma, Thyroid carcinoma); Temsirolimus (Torisel) targeting mTOR (approved for use in Renal cell carcinoma); Tositumomab (Bexxar) targeting CD20 (approved for use in Non-Hodgkin's lymphoma); Trametinib (Mekinist) targeting MEK (approved for use in Melanoma, Non-small cell lung cancer); Trastuzumab (Herceptin) targeting HER2 (ERBB2/neu) (approved for use in Breast cancer (HER2+), Gastric cancer (HER2+)); Vandetanib (Caprelsa) targeting EGFR (HER1/ERBB1), RET, VEGFR2 (approved for use in Medullary thyroid cancer); Vemurafenib (Zelboraf) targeting BRAF (approved for use in Melanoma); Venetoclax (Venclexta) targeting BCL2 (approved for use in Chronic lymphocytic leukemia); Vismodegib (Erivedge) targeting PTCH, Smoothened (approved for use in Basal cell carcinoma); Vorinostat (Zolinza) targeting HDAC (approved for use in Cutaneous T-cell lymphoma); Ziv-aflibercept (Zaltrap) targeting PIGF, VEGFA/B (approved for use in Colorectal cancer); and the like.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α; (7) interferon-γ; (8) colony-stimulating factors; (9) inhibitors of angiogenesis; and (10) antagonists of tumor necrosis factor.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl) propoxy) quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERET (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, paclitaxel-xylose, or paclitaxel-albumin).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Useful immunotherapies include: anti-PD-1/PD-L1 immunotherapies, and/or other immunotherapy targets, such as e.g., immune check point markers, such as CTLA-4, LAG-3 and TIM-3, that may be targeted in treatment methods. Anti-PD-1/PD-L1 immunotherapies which include but are not limited to e.g., those therapies that include administering to a subject an effective amount of one or more anti-PD-1/PD-L1 therapeutic antagonists where such antagonists include but are not limited to e.g., OPDIVO® (nivolumab), KEYTRUDA® (pembrolizumab), Tecentriq™ (atezolizumab), durvalumab (MEDI4736), avelumab (MSB0010718C), BMS-936559 (MDX-1105), CA-170, BMS-202, BMS-8, BMS-37, BMS-242 and the like.

CTLA-4, also known as CD152, binds to CD80 and CD86. Antibodies against CTLA-4 have been approved for treating some cancer types. The co-inhibitory effect of CTLA-4 with other immunotherapies make CTLA-4 a good candidate for use in combination with other immunotherapies to treat certain cancers. TIM-3 may also be targeted for immunotherapy for several cancer types.

LAG-3 is in clinical trials for treating cancers. Anti-LAG-3 immunotherapies include those that employ antagonist LAG-3 antibodies that can both activate T effector cells (by downregulating the LAG-3 inhibiting signal into preactivated LAG-3+ cells) and inhibit induced (i.e. antigen-specific) Treg suppressive activity. Useful LAG-3 antagonistic antibodies include relatlimab (BMS-986016; developed by Bristol-Myers Squibb), IMP701 (developed by Immutep), TSR-033 (anti-LAG-3 mAb; developed by TESARO, Inc.), and the like.

Immunotherapies also include T cell-based immunotherapies such as e.g., adoptive cell therapy (ACT) and chimeric antigen receptor (CAR) T cell therapies. For example, a subject may be administered a population of CAR T cells engineered to target an antigen expressed by the subject's cancer. A T cell-based therapy may involve, in some instances, obtaining a cellular sample from a subject, such as a blood sample or a tumor biopsy, and culturing immune cells from the sample ex vivo, with or without genetic modification of the cultured immune cells. As an example, immune cells may be obtained from a subject, cultured ex vivo and modified with a CAR specific for an antigen expressed by the cancer to produce a population of CAR T cells. Then, the CAR T cells may be reintroduced into the subject to target the cancer. T cell-based immunotherapies may be configured in various ways, e.g., by targeting various antigens, by collecting/culturing various cell types, etc., depending on a particular cancer to be treated. In addition, T cell-based immunotherapies may be administered systemically, e.g., by intravenous injection, or locally, e.g., by infusion (e.g., intraperitoneal infusion, pleural catheter infusion, etc.), direct injection, and the like.

In some instances, a method of treatment described herein may include administering to a subject one or more inhibitors of a multidrug resistance transporter, including but not limited to e.g., a multidrug resistance transporter other than MDR1. Useful inhibitors of multidrug resistance transporters include e.g., tyrosine kinase inhibitors, natural products, microRNAs, and small molecule inhibitors. Inhibitors of multidrug resistance transporters include ABC transporter inhibitors. A summary of such MDR modulators or reverters is provided in Choi (2005), Cancer Cell Int, 5:30; the disclosure of which is incorporated by reference herein in its entirety.

Individuals suitable for treatment using a method of the present disclosure include an individual having a cancer; an individual diagnosed as having a cancer; an individual being treated for a cancer with chemotherapy, radiation therapy, antibody therapy, surgery, etc.); an individual who has been treated for a cancer (e.g., with one or more of chemotherapy, radiation therapy, antibody therapy, surgery, etc.), and who has failed to respond to the treatment; an individual who has been treated for a cancer (e.g., with one or more of chemotherapy, radiation therapy, antibody therapy, surgery, etc.), and who initially responded to the treatment but who subsequently relapsed, i.e., the cancer recurred.

The methods of the present disclosure may be employed to target and treat a variety of cancers, including e.g., primary cancer, secondary cancers, re-growing cancers, recurrent cancers, refractory cancers and the like. For example, in some instances, the methods of the present disclosure may be employed as an initial treatment of a primary cancer identified in a subject. In some instances, the methods of the present disclosure may be employed as a non-primary (e.g., secondary or later) treatment, e.g., in a subject with a cancer that is refractory to a prior treatment, in a subject with a cancer that is re-growing following a prior treatment, in a subject with a mixed response to a prior treatment (e.g., a positive response to at least one tumor in the subject and a negative or neutral response to at least a second tumor in the subject), and the like.

In some instances, the methods of the present disclosure may be employed to treat a subject with a drug resistant cancer, such as a multi-drug resistant cancer. Multidrug resistance (MDR) is the mechanism by which many cancers develop resistance to chemotherapy drugs, resulting in minimal cell death and the expansion of drug-resistant tumors. MDR cancers may involve one or more resistance mechanisms including but not limited to e.g., increased expression of efflux pumps, decreased absorption of drug, inhibition of cell death or apoptosis, modulating drug metabolism, and the like. In some instances, the methods of the present disclosure may prevent, reverse or circumvent MDR.

In some instances, methods of the present disclosure may include treating a subject having a cancer that is resistant to a first agent with an effective amount of a subject multi-specific antibody described herein in combination with a second agent that is different from the first agent. For example, in some instances, cancer of a subject may be resistant to a first chemotherapeutic and the subject may be treated by administering an effective amount of a subject multi-specific antibody as described herein in combination with a second chemotherapeutic that is different from the first. Various combinations of first and second chemotherapeutics may be employed depending on e.g., the type of cancer to be treated, the likelihood of developing resistance, etc.

Numerous cancers are known to develop drug resistance. For this and other reasons the methods of the present disclosure may find use in treating various cancers including but not limited to, e.g., Acute Lymphoblastic Leukemia (ALL), Acute Myeloid Leukemia (AML), Adrenocortical Carcinoma, AIDS-Related Cancers (e.g., Kaposi Sarcoma, Lymphoma, etc.), Anal Cancer, Appendix Cancer, Astrocytomas, Atypical Teratoid/Rhabdoid Tumor, Basal Cell Carcinoma, Bile Duct Cancer (Extrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Burkitt Lymphoma, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Duct (e.g., Bile Duct, Extrahepatic, etc.), Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma, Retinoblastoma, etc.), Fibrous Histiocytoma of Bone (e.g., Malignant, Osteosarcoma, etc.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Hairy Cell Leukemia, Head and Neck Cancer, Heart Cancer, Hepatocellular (Liver) Cancer, Histiocytosis (e.g., Langerhans Cell, etc.), Hodgkin Lymphoma, Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic (ALL), Acute Myeloid (AML), Chronic Lymphocytic (CLL), Chronic Myelogenous (CML), Hairy Cell, etc.), Lip and Oral Cavity Cancer, Liver Cancer (Primary), Lobular Carcinoma In Situ (LCIS), Lung Cancer (e.g., Non-Small Cell, Small Cell, etc.), Lymphoma (e.g., AIDS-Related, Burkitt, Cutaneous T-Cell, Hodgkin, Non-Hodgkin, Primary Central Nervous System (CNS), etc.), Macroglobulinemia (e.g., Waldenström, etc.), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia (e.g., Chronic (CML), etc.), Myeloid Leukemia (e.g., Acute (AML), etc.), Myeloproliferative Neoplasms (e.g., Chronic, etc.), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer (e.g., Lip, etc.), Oropharyngeal Cancer, Osteosarcoma and Malignant Fibrous Histiocytoma of Bone, Ovarian Cancer (e.g., Epithelial, Germ Cell Tumor, Low Malignant Potential Tumor, etc.), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Pleuropulmonary Blastoma, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (e.g., Ewing, Kaposi, Osteosarcoma, Rhabdomyosarcoma, Soft Tissue, Uterine, etc.), Sezary Syndrome, Skin Cancer (e.g., Childhood, Melanoma, Merkel Cell Carcinoma, Nonmelanoma, etc.), Small Cell Lung Cancer, Small Intestine Cancer, Soft Tissue Sarcoma, Squamous Cell Carcinoma, Squamous Neck Cancer (e.g., with Occult Primary, Metastatic, etc.), Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.), Uterine Sarcoma, Vaginal Cancer, Vulvar Cancer, Waldenstrom Macroglobulinemia, Wilms Tumor, and the like.

The methods of treating described herein may, in some instances, be performed in a subject that has previously undergone one or more conventional treatments. For example, in the case of oncology, the methods described herein may, in some instances, be performed following a conventional cancer therapy including but not limited to e.g., conventional chemotherapy, conventional radiation therapy, conventional immunotherapy, surgery, etc. In some instances, the methods described herein may be used when a subject has not responded to or is refractory to a conventional therapy. In some instances, the methods described herein may be used when a subject has responded to a conventional therapy.

In some instances, the method of the present disclosure may be employed to target, treat or clear a subject for minimal residual disease (MRD) remaining after a prior cancer therapy. Targeting, treating and/or clearance of MRD may be pursued using the instant methods whether the MRD is or has been determined to be refractory to the prior treatment or not. In some instances, a method of the present disclosure may be employed to target, treat and/or clear a subject of MRD following a determination that the MRD is refractory to a prior treatment or one or more available treatment options other than those employing the herein described multi-specific antibodies.

In some instances, the instant methods may be employed prophylactically for surveillance. For example, a subject in need thereof may be administered a treatment involving one or more of the herein described multi-specific antibodies when the subject does not have detectable disease but is at risk of developing a recurrent cancer, including e.g., a drug resistant cancer. In some instances, a prophylactic approach may be employed when a subject is at particularly high risk of developing a primary cancer that would be predicted to be drug resistant or expected to become drug resistant. In some instances, a prophylactic approach may be employed when a subject has been previously treated for a cancer and is at risk of reoccurrence or development of drug resistance.

In some instances, methods of the present disclosure may involve analyzing a cancer for expression of one or more markers or therapeutic targets. For example, in some instances, methods may involve analyzing a sample of a cancer from a subject to determine whether the cancer expresses MDR1 above a predetermined threshold, a TAA (e.g., CD47, PD-L1, or EGFR) above a predetermined threshold, or both.

In some instances, whether a subject is treated with a multi-specific antibody of the present disclosure may depend on the results of the TAA and/or MDR1 testing. For example, in some instances, if a cancer expresses the TAA at or above a predetermined threshold then the subject may be treated with a multi-specific antibody of the present disclosure, and if the cancer expresses the TAA below the predetermined threshold then the subject may not be treated with the multi-specific antibody, e.g., the subject may be treated with a conventional therapy for the relevant cancer without the subject multi-specific antibody. In some instances, if a cancer expresses MDR1 at or above a predetermined threshold then the subject may be treated with a multi-specific antibody of the present disclosure, and if the cancer expresses MDR1 below the predetermined threshold then the subject may not be treated with the multi-specific antibody, e.g., the subject may be treated with a conventional therapy for the relevant cancer without the subject multi-specific antibody. In some instances, if a cancer expresses both the TAA and MDR1 at or above predetermined thresholds then the subject may be treated with a multi-specific antibody of the present disclosure, and if the cancer expresses the TAA and MDR1 below the predetermined thresholds then the subject may not be treated with the multi-specific antibody, e.g., the subject may be treated with a conventional therapy for the relevant cancer without the subject multi-specific antibody.

Any convenient assay may be employed for analyzing MDR1 and/or TAA levels, including but not limited to e.g., flow cytometry, nucleic acid-based assays (e.g., amplification, sequencing, etc.), cell cytometry, immunohistochemistry, and the like. Any convenient biological sample may be employed, including but not limited to e.g., cancer biopsy samples. Useful predetermined thresholds for assessing expression of one or more markers and/or targets may be determined by any convenient and appropriate method, including comparison of the measured level of expression to a corresponding control. For example, in some instances, a useful predetermined threshold for the level of MDR1 and/or TAA assayed in a sample may correspond to a level of MDR1 and/or TAA as measured in a reference cell, such as a healthy/normal cell. The TAA may be CD47, PD-L1, or EGFR.

Methods of Making

As summarized above, methods of the present disclosure also include methods or making and/or identifying multispecific antibodies as described herein. A subject antibody can be produced by any known method, e.g., conventional synthetic methods for protein synthesis; recombinant DNA methods; etc.

Where a subject antibody is a single chain polypeptide, it can synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A, Merrifield, et al. J. Am. Chem. Soc., 85:2149-2156 (1963); Stewart et al., Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce the polypeptides of the present invention (e.g., polynucleotides encoding immunoglobulins or fragments thereof). See Winnacker, From Genes to Clones, VCH Publishers, N.Y., N.Y. (1987). Suitable mammalian host cells include CHO cell lines, various Cos cell lines, Hela cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148: 1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

In some embodiments, method of generating a multi-specific antibody of the present disclosure may include producing candidate antibodies and screening for activity. Such methods may generate a multi-specific antibody that specifically binds a cell expressing both MDR1 and CD47 through the use of a series of steps. Steps of such methods may include: producing a multi-specific antibody or a plurality of antibodies that each include or are expected to include a MDR1-binding domain and a CD47-binding domain; contacting a first test cell expressing MDR1 and CD47 with the multi-specific antibody or plurality of antibodies; contacting a second cell expressing either MDR1 or CD47 with the multi-specific antibody or plurality of antibodies; comparing the binding of the multi-specific antibody, or the antibodies of the plurality, to the first cell with the binding of the multi-specific antibody to the second cell to determine a binding-specificity ratio; and identifying the multi-specific antibody, or one or more of the antibodies of the plurality, as specific for the cell expressing both MDR1 and CD47 when the ratio is above a predetermined threshold. Where such a threshold for comparative binding is employed, the threshold may vary and may range from 1.5:1 or more, including but not limited to e.g., 2:1, 3:1, 4:1, 5:1, 6:1, 7:1, 8:1, 9:1, 10:1, 20:1, 50:1, 100:1, etc.

Various cells may be used in such methods, including but not limited to e.g., the cells described herein. In some instances, the binding of the antibody to both MDR1-only expressing cells and CD47-only expressing cells may be performed. For example, in some instances, the method may include, relative to the steps describe above, where the second cell expresses MDR1 and not CD47 and the method further comprises contacting a third cell expressing CD47 but not MDR1 with the multi-specific antibody.

In some instances, such methods may employ one or more controls, including but not limited to e.g., control cells, control reagents, and the like. Useful control cells include those that have a known expression or known lack of expression of one or more relevant genes or proteins. Useful control reagents may include but are not limited to e.g., control antibodies such as but not limited to e.g., monospecific antibodies to known targets. For example, in some instances, such methods of the present disclosure may further include contacting the first cell, the second cell, and/or the third cell with a control antibody selected from: a monospecific anti-MDR1 antibody and a monospecific anti-CD47 antibody. Depending on the particular method used, various other or additional controls, as appropriate, may be employed.

Kits

Aspects of the present disclosure also include kits. The kits may include, e.g., any combination of the multi-specific antibodies, reagents, compositions, formulations, cells, nucleic acids, expression vectors, or the like, described herein. A subject kit can include one or more of: a subject multi-specific antibody, a nucleic acid encoding the same, or a cell comprising a subject multi-specific nucleic acid. Kits may be configured for various purposes, including e.g., treatment kits (e.g., where a kit may include a multi-specific antibody and e.g., one or more additional active agents, such as a chemotherapeutic), kits for producing antibodies, kits for screening antibodies, and the like.

Optional components of the kit will vary and may, e.g., include: a buffer; a protease inhibitor; etc. Where a subject kit comprises a subject nucleic acid, the nucleic acid may also have restrictions sites, multiple cloning sites, primer sites, etc. The various components of the kit may be present in separate containers or certain compatible components may be pre-combined into a single container, as desired.

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below. It will be apparent to one of ordinary skill in the art that various changes and modifications can be made without departing from the spirit or scope of the invention.

1. A bispecific antibody molecule that binds multidrug resistance protein 1 (MDR1) and a tumor associated antigen (TAA), the antibody molecule comprising two identical variable light (VL) chains, a first variable heavy (VH) chain, and a second VH chain,
   wherein the VL chains each comprise an antigen-binding site for MDR1, the first VH chain comprises an antigen-binding site for MDR1, and the second VH chain comprises an antigen-binding site for the TAA, and wherein the second VH chain binds the TAA when paired with one of the VL chains,
   wherein the bispecific antibody binds to cancer cells expressing both MDR1 and the TAA while showing reduced binding to non-cancer cells expressing MDR1 and/or the TAA.

2. The bispecific antibody molecule according to aspect 1, wherein the antigen-binding site of the two VL chains comprises light chain CDRs 1-3 (LCDRs 1-3) of a VL chain having the sequence:
   DVLMTQTPVSLSVSLGDQASISCRSSQSIVHSTGX$^1$ TYLEWYLQKPGQSPKLLIYKIS NRFSGVPD-RFSGSGSGTDFTLKISRVEAEDLGVYYCFQ-ASHFPRTFGGGTKLEIK (SEQ ID NO: 1), wherein X$^1$ is N, Q or S.

3. The bispecific antibody molecule according to aspect 2, wherein the two VL chains comprise LCDRs 1-3 of the VL chain having the sequence:

(i)
(SEQ ID NO: 2)
DVLMTQTPVSLSVSLGDQASISCRSSQSIVHSTGNTYLEWYLQKPGQSPK

LLIYKISNRFSGVPDRFSGSGSGTDFTLKISRVEAEDLGVYYCFQASHFP

RTFGGGTKLEIK;

(ii)
(SEQ ID NO: 3)
DIVMTQTPLSSPVTLGQPASISCRSSQSIVHSTGQTYLEWYQQRPGQPPR

LLIYKISNRFSGVPDRFSGSGAGTDFTLKISRVEAEDVGVYYCFQASHFP

RTFGQGTKLEIK;
or (iii)
(SEQ ID NO: 4)
DIVMTQTPLSSPVTLGQPASISCRSSQSIVHSTGSTYLEWYQQRPGQPPR

LLIYKISNRFSGVPDRFSGSGAGTDFTLKISRVEAEDVGVYYCFQASHFP

RTFGQGTKLEIK.

4. The bispecific antibody molecule according to aspect 2 or 3, wherein:
  (i) the LCDR1 comprises the sequence: RSSQSIVHSTGX$^1$TYLE (SEQ ID NO:5);
  (ii) the LCDR2 comprises the sequence: KISNRFS (SEQ ID NO:6); and
  (iii) the LCDR3 comprises the sequence: FQASHFPRT (SEQ ID NO:7);
  wherein X$^1$ is N, Q or S.

5. The bispecific antibody molecules of any one of the preceding aspects, wherein the two VL chains are humanized.

6. The bispecific antibody molecule according to any one of aspects 2 to 5, wherein the two VL chains comprise the sequence or an amino acid at least 90% identical to the sequence:

(SEQ ID NO: 8)
DIVMTQTPLSSPVTLGQPASISCRSSQSIVHSTGN

TYLEWYQQRPGQPPRLLIYKISNRFSGVPDRFSGS

GAGTDFTLKISRVEAEDVGVYYCFQASHFPRTFGG

GTKLEIK;

(SEQ ID NO: 3)
DIVMTQTPLSSPVTLGQPASISCRSSQSIVHSTGQ

TYLEWYQQRPGQPPRLLIYKISNRFSGVPDRFSGS

GAGTDFTLKISRVEAEDVGVYYCFQASHFPRTFGQ

GTKLEIK
or (SEQ ID NO: 4)
DIVMTQTPLSSPVTLGQPASISCRSSQSIVHSTGS

TYLEWYQQRPGQPPRLLIYKISNRFSGVPDRFSGS

GAGTDFTLKISRVEAEDVGVYYCFQASHFPRTFGQ

GTKLEIK.

7. The bispecific antibody molecule according to aspect 6, wherein the two VL chains comprise the sequence or a sequence at least 90% identical to the sequence:

(SEQ ID NO: 8)
DIVMTQTPLSSPVTLGQPASISCRSSQSIVHSTGN

TYLEWYQQRPGQPPRLLIYKISNRFSGVPDRFSGS

GAGTDFTLKISRVEAEDVGVYYCFQASHFPRTFGQ

GTKLEIK.

8. The bispecific antibody molecule according to any one of the preceding aspects, wherein the antigen binding site of first VH chain comprises heavy chain CDRs 1-3 (HCDRs 1-3) of a VH chain having the sequence:
EVKVVESGGVLVRPGGSLKLSCAASGFTFSRYT-MSWVRQTPEKRLEWVATISSGG GX$^2$TYYPDSV-KGRFTVSRDNAMSSLYLQMSSLRSEDTALYY-CARYGAGDAWFAYWGQGT LVTVSS (SEQ ID NO:9), wherein X$^2$ is N, Q or S.

9. The bispecific antibody molecule according to any one of the preceding aspects, wherein the antigen binding site of the first VH chain comprises HCDRs 1-3 of the VH chain having the sequence:

(i)
(SEQ ID NO: 10)
EVKVVESGGVLVRPGGSLKLSCAASGFTFSRYTMS

WVRQTPEKRLEWVATISSGGGNTYYPDSVKGRFTV

SRDNAMSSLYLQMSSLRSEDTALYYCARYGAGDAW

FAYWGQGTLVTVSS, or
(ii)
(SEQ ID NO: 11)
EVQLVESGGVVVQPGGSLRLSCAASGFTFSRYTMS

WVRQAPGKGLEWVATISSGGGQTYYPDSVKGRFTV

SRDNSKNSLYLQMNSLRTEDTALYYCARYGAGDAW

FAYWGQGTLVTVSS,
or (iii)
(SEQ ID NO: 12)
EVQLVESGGVVVQPGGSLRLSCAASGFTFSRYTMS

WVRQAPGKGLEWVATISSGGGSTYYPDSVKGRFTV

SRDNSKNSLYLQMNSLRTEDTALYYCARYGAGDAW

FAYWGQGTLVTVSS.

10. The bispecific antibody molecule according to aspect 8 or 9, wherein:
  (i) the HCDR1 comprises the sequence: RYTMS (SEQ ID NO:13);
  (ii) the HCDR2 comprises the sequence: TISSGGGX$^2$TYYPDSVKG (SEQ ID NO:14); and
  (iii) the HCDR3 comprises the sequence: YGAGDAW-FAY (SEQ ID NO:15);
  wherein X$^2$ is N, Q or S.

11. The bispecific antibody molecule according to any one of the preceding aspects, wherein the first and/or second VH chain is humanized.

12. The bispecific antibody molecule according to any one of aspects 8 to 11, wherein the first VH chain comprises the amino acid sequence or an amino acid at least 90% identical to the amino acid sequence:

```
                                                  (SEQ ID NO: 16)
EVQLVESGGVVVQPGGSLRLSCAASGFTFSRYTMSWVRQAPGKGLEWVAT

ISSGGGNTYYPDSVKGRFTVSRDNSKNSLYLQMNSLRTEDTALYYCARYG

AGDAWFAYWGQGTLVTSS;

(SEQ ID NO: 11)
EVQLVESGGVVVQPGGSLRLSCAASGFTFSRYTMSWVRQAPGKGLEWVAT

ISSGGGQTYYPDSVKGRFTVSRDNSKNSLYLQMNSLRTEDTALYYCARYG

AGDAWFAYWGQGTLVTSS;
or
                                                  (SEQ ID NO: 12)
EVQLVESGGVVVQPGGSLRLSCAASGFTFSRYTMSWVRQAPGKGLEWVAT

ISSGGGSTYYPDSVKGRFTVSRDNSKNSLYLQMNSLRTEDTALYYCARYG

AGDAWFAYWGQGTLVTSS.
```

13. The bispecific antibody molecule according to any one of aspects 2-12, wherein:
(i) the LCDR1 comprises the sequence: RSSQSIVHSTGNTYLE (SEQ ID NO:26),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGGNTYYPDSVKG (SEQ ID NO:29), and
the HCDR3 comprises the sequence: YGAGDAWFAY (SEQ ID NO:15), or
(ii) the LCDR1 comprises the sequence: RSSQSIVHSTGQTYLE (SEQ ID NO:27),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGGQTYYPDSVKG (SEQ ID NO:30), and
the HCDR3 comprises the sequence: YGAGDAWFAY (SEQ ID NO:15), or
(iii) the LCDR1 comprises the sequence: RSSQSIVHSTGSTYLE (SEQ ID NO:28),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGGSTYYPDSVKG (SEQ ID NO:31), and
the HCDR3 comprises the sequence: YGAGDAWFAY (SEQ ID NO:15), or
(iv) the LCDR1 comprises the sequence: RSSQSIVHSTGNTYLE (SEQ ID NO:26),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGGQTYYPDSVKG (SEQ ID NO:30), and
the HCDR3 comprises the sequence: YGAGDAWFAY (SEQ ID NO:15), or
(v) the LCDR1 comprises the sequence: RSSQSIVHSTGNTYLE (SEQ ID NO:26),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGGSTYYPDSVKG (SEQ ID NO:31), and
the HCDR3 comprises the sequence: YGAGDAWFAY (SEQ ID NO:15), or
(vi) the LCDR1 comprises the sequence: RSSQSIVHSTGQTYLE (SEQ ID NO:27),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGGNTYYPDSVKG (SEQ ID NO:29), and
the HCDR3 comprises the sequence: YGAGDAWFAY (SEQ ID NO:15), or
(vii) the LCDR1 comprises the sequence: RSSQSIVHSTGSTYLE (SEQ ID NO:28),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGGNTYYPDSVKG (SEQ ID NO:29), and
the HCDR3 comprises the sequence: YGAGDAWFAY (SEQ ID NO:15), or
(viii) the LCDR1 comprises the sequence: RSSQSIVHSTGSTYLE (SEQ ID NO:28),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGGQTYYPDSVKG (SEQ ID NO:30), and
the HCDR3 comprises the sequence: YGAGDAWFAY (SEQ ID NO:15), or
(ix) the LCDR1 comprises the sequence: RSSQSIVHSTGNTYLE (SEQ ID NO:26),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGGQTYYPDSVKG (SEQ ID NO:30), and
the HCDR3 comprises the sequence: YGAGDAWFAY (SEQ ID NO:15).

14. The bispecific antibody molecule according to any one of the preceding aspects, wherein the second VH chain is derived from a monospecific antibody molecule which binds the TAA, and wherein the affinity of the bispecific antibody molecule for the TAA when paired with one of the light chains is at least 2-fold lower than the affinity of the monospecific antibody molecule for the TAA from which the VH chain is derived.

15. The bispecific antibody molecule according to any one of the preceding aspects, wherein the TAA is CD47.

16. The bispecific antibody molecule according to aspect 15, wherein the antigen-binding site of the second VH chain comprises the HCDRs 1-3 of a VH chain comprising the amino acid sequence:

```
                                          (SEQ ID NO: 17)
QVQLVQSGAEVKKPGASVKVSCKASGYTFTNYNMHWVRQAPGQRLEWMGT

IYPGNDDTSYNQKFKDRVTITADTSASTAYMELSSLRSEDTAVYYCARGG

YRAMDYWGQGTLVTVSS.
```

17. The bispecific antibody molecule according to aspect 15 or 16, wherein the second VH chain comprises the HCDR1 comprising the sequence: NYNMH (SEQ ID NO:18), the HCDR2 comprising the sequence: TIYPGNDDTSYNQKFKD (SEQ ID NO:19), and the HCDR3 comprising the sequence: GGYRAMDY (SEQ ID NO:20).

18. The bispecific antibody molecule according to any one of aspects 15 to 16, wherein the second VH chain comprises the amino acid sequence or an amino acid sequence at least 90% identical to the amino acid sequence:

```
                                          (SEQ ID NO: 17)
QVQLVQSGAEVKKPGASVKVSCKASGYTFTNYNMHWVRQAPGQRLEWMGT

IYPGNDDTSYNQKFKDRVTITADTSASTAYMELSSLRSEDTAVYYCARGG

YRAMDYWGQGTLVTVSS, (SEQ ID NO: 21)
EVQLVESGGGLVQPGGSLRLSCAASGYTFTNYNMHWVRQAPGKGLEWMGT

IYPGNDDTSYNQKFKDRVTISRDNSKNTLYLQMNSLRAEDTAVYYCARGG

YRAMDYWGQGTLVTVSS, (SEQ ID NO: 22)
EVQLVQSGAEVKKPGESLKISCKGSGYTFTNYNMHWVRQMPGKGLEWMGT

IYPGNDDTSYNQKFKDQVTISADKSISTAYLQWSSLKASDTAMYYCARGG

YRAMDYWGQGTTVTVSS,
or
                                          (SEQ ID NO: 23)
QVQLVQSGSELKKPGASVKVSCKASGYTFTNYNMHWVRQAPGQGLEWMGT

IYPGNDDTSYNQKFKDRFVFSLDTSVSTAYLQISSLKAEDTAVYYCARGG

YRAMDYWGQGTTVTVSS.
```

19. The bispecific antibody molecule according to any one of aspects 1-14, wherein the TAA is PD-L1.

20. The bispecific antibody molecule according to aspect 19, wherein the antigen-binding site of the second VH chain comprises the HCDRs 1-3 of a VH chain comprising the amino acid sequence:

```
                                          (SEQ ID NO: 32)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS.
```

21. The bispecific antibody molecule according to aspect 19 or 20, wherein the antigen-binding site of the second VH chain comprises the HCDR1 comprising the sequence: DSWIH (SEQ ID NO:33), the HCDR2 comprising the sequence: WISPYGGSTYYADSVKG (SEQ ID NO:34), and the HCDR3 comprising the sequence: RHWPGGFDY (SEQ ID NO:35).

22. The bispecific antibody molecule according to any one of aspects 19 to 21, wherein the second VH chain comprises the amino acid sequence or an amino acid sequence at least 90% identical to the amino acid sequence:

```
                                          (SEQ ID NO: 32)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS.
```

23. The bispecific antibody molecule according to any one of aspects 1-14, wherein the TAA is EGFR.

24. The bispecific antibody molecule according to aspect 23, wherein the antigen-binding site of the second VH chain comprises the HCDRs 1-3 of a VH chain comprising the amino acid sequence:

```
                                          (SEQ ID NO: 36)
QVQLQESGPGLVKPSQTLSLTCTVSGGSISSGDYYWSWIRQPPGKGLEWI

GYIYYSGSTDYNPSLKSRVTMSVDTSKNQFSLKVNSVTAADTAVYYCARV

SIFGVGTFDYWGQGTLVTVSS.
```

25. The bispecific antibody molecule according to aspect 23 or 24, wherein the antigen-binding site of the second VH chain comprises the HCDR1 comprising the sequence: SGDYYWS (SEQ ID NO:37), the HCDR2 comprising the sequence: YIYYSGSTDYNPSLKS (SEQ ID NO:38), and the HCDR3 comprising the sequence: VSIFGVGTFDY (SEQ ID NO:39).

26. The bispecific antibody molecule according to any one of aspects 24 to 25, wherein the second VH chain comprises the amino acid sequence or an amino acid sequence at least 90% identical to the amino acid sequence:

```
                                          (SEQ ID NO: 36)
QVQLQESGPGLVKPSQTLSLTCTVSGGSISSGDYYWSWIRQPPGKGLEWI

GYIYYSGSTDYNPSLKSRVIMSVDTSKNQFSLKVNSVTAADTAVYYCARV

SIFGVGTFDYWGQGTLVTVSS.
```

27. The bispecific antibody molecule according to aspect 23, wherein the antigen-binding site of the second VH chain comprises the HCDRs 1-3 of a VH chain comprising the amino acid sequence:

```
                                          (SEQ ID NO: 40)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSA.
```

28. The bispecific antibody molecule according to aspect 26 or 27, wherein the second VH chain comprises the HCDR1 comprising the sequence: NYGVH (SEQ ID NO:41), the HCDR2 comprising the sequence: VIWSGG- NTDYNTPFTS (SEQ ID NO:42), and the HCDR3 comprising the sequence: ALTYYDYEFAY (SEQ ID NO:43).

29. The bispecific antibody molecule according to any one of aspects 26 to 28, wherein the second VH chain comprises the amino acid sequence or an amino acid sequence at least 90% identical to the amino acid sequence:

(SEQ ID NO: 40)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSA.

30. The bispecific antibody molecule according to aspect 1, wherein the antigen-binding site of the two VL chains comprises light chain CDRs 1-3 (LCDRs 1-3) of a VL chain having the sequence:

(SEQ ID NO: 25)
DVLMTQTPLSLPVSLGDQASISCRSSQSIVHSTGNTYLEWYLQKPGQSPK

LLIYKVSNRFSGVPDRFSGSGSGTDFTLKISRLEAEDLGVYYCFQGSHFP

RTFGGGTRLEIK.

31. The bispecific antibody molecule according to aspect 30, wherein:
 (i) the LCDR1 comprises the sequence: RSSQSIVHSTGNTYLE (SEQ ID NO:44);
 (ii) the LCDR2 comprises the sequence: KISRLEA (SEQ ID NO:45); and
 (iii) the LCDR3 comprises the sequence: FQGSHFPRT (SEQ ID NO:46).

32. The bispecific antibody molecule according to aspect 30 or 31, wherein the VL chain comprises the amino acid sequence or an amino acid sequence at least 90% identical to the amino acid sequence:

(SEQ ID NO: 25)
DVLMTQTPLSLPVSLGDQASISCRSSQSIVHSTGNTYLEWYLQKPGQSPK

LLIYKVSNRFSGVPDRFSGSGSGTDFTLKISRLEAEDLGVYYCFQGSHFP

RTFGGGTRLEIK.

33. The bispecific antibody molecule according to any one of aspects 30-32, wherein the antigen binding site of first VH chain comprises heavy chain CDRs 1-3 (HCDRs 1-3) of a VH chain having the sequence:

EVILVESGGGLVKPGGSLKLSCAASGFTFSSYTMSWVRQTPEKRLEWVAT

ISSGGGNTYYPDSVKGRFTISRDNAKNNLYLQMSSLRSEDTALYYCARYY

RYEAWFASWGQGTLVTVSA.

34. The bispecific antibody molecule according to aspect 33, wherein:
 (i) the HCDR1 comprises the sequence: SYTMS (SEQ ID NO:48);
 (ii) the HCDR2 comprises the sequence: TISSGGGNTYYPDSVKG (SEQ ID NO:29); and
 (iii) the HCDR3 comprises the sequence: YYRYEAWFAS (SEQ ID NO:49).

35. The bispecific antibody molecule according to any one of aspects 30-34, wherein the first VH chain comprises the amino acid sequence or an amino acid at least 90% identical to the amino acid sequence:

EVILVESGGGLVKPGGSLKLSCAASGFTFSSYTMSWVRQTPEKRLEWVAT

ISSGGGNTYYPDSVKGRFTISRDNAKNNLYLQMSSLRSEDTALYYCARYY

RYEAWFASWGQGTLVTVSA.

36. The bispecific antibody molecule according to any one of aspects 30-32, wherein the antigen binding site of first VH chain comprises heavy chain CDRs 1-3 (HCDRs 1-3) of a VH chain having the sequence:
 EVKVVESGGVLVRPGGSLKLSCAASGFTFSRYT-
 MSWVRQTPEKRLEWVATISSGGGX$^2$TY
 YPDSVKGRFTVSRDNAMSSLYLQMSSLRSED-
 TALYYCARYGAGDAWFAYWGQGTLVTVS S
 (SEQ ID NO:9), wherein X$^2$ is N, Q or S.

37. The bispecific antibody molecule according to aspect 36, wherein:
 (i) the HCDR1 comprises the sequence: RYTMS (SEQ ID NO:13);
 (ii) the HCDR2 comprises the sequence: TISSGGGX$^2$TYYPDSVKG (SEQ ID NO:14); and
 (iii) the HCDR3 comprises the sequence: YGAGDAWFAY (SEQ ID NO:15);
 wherein X$^2$ is N, Q or S.

38. The bispecific antibody molecule according to any one of aspects 36-37, wherein the first VH chain comprises the amino acid sequence or an amino acid at least 90% identical to the amino acid sequence:

(SEQ ID NO: 16)
EVQLVESGGVVVQPGGSLRLSCAASGFTFSRYTMSWVRQAPGKGLEWVAT

ISSGGGNTYYPDSVKGRFTVSRDNSKNSLYLQMNSLRTEDTALYYCARYG

AGDAWFAYWGQGTLVTVSS;

(SEQ ID NO: 11)
EVQLVESGGVVVQPGGSLRLSCAASGFTFSRYTMSWVRQAPGKGLEWVAT

ISSGGGQTYYPDSVKGRFTVSRDNSKNSLYLQMNSLRTEDTALYYCARYG

AGDAWFAYWGQGTLVTVSS;
or (SEQ ID NO: 12)
EVQLVESGGVVVQPGGSLRLSCAASGFTFSRYTMSWVRQAPGKGLEWVAT

ISSGGGSTYYPDSVKGRFTVSRDNSKNSLYLQMNSLRTEDTALYYCARYG

AGDAWFAYWGQGTLVTVSS.

39. The bispecific antibody molecule according to any one of aspects 1-7, wherein the antigen binding site of first VH chain comprises heavy chain CDRs 1-3 (HCDRs 1-3) of a VH chain having the sequence:

EVILVESGGGLVKPGGSLKLSCAASGFTFSSYTMSWVRQTPEKRLEWVAT

ISSGGGNTYYPDSVKGRFTISRDNAKNNLYLQMSSLRSEDTALYYCARYY

RYEAWFASWGQGTLVTVSA.

40. The bispecific antibody molecule according to aspect 39, wherein:
 (i) the HCDR1 comprises the sequence: SYTMS (SEQ ID NO:48);
 (ii) the HCDR2 comprises the sequence: TISSGGGNTYYPDSVKG (SEQ ID NO:29); and
 (iii) the HCDR3 comprises the sequence: YYRYEAWFAS (SEQ ID NO:49).

41. The bispecific antibody molecule according to any one of aspects 39-40, wherein the first VH chain comprises the sequence or an amino acid at least 90% identical to the sequence:

```
EVILVESGGGLVKPGGSLKLSCAASGFTFSSYTMSWVRQTPEKRLEWVAT
ISSGGGNTYYPDSVKGRFTISRDNAKNNLYLQMSSLRSEDTALYYCARYY
RYEAWFASWGQGTLVTVSA.
```

42. The bispecific antibody molecule according to any one of aspects 30-41, wherein the second VH chain is derived from a monospecific antibody molecule which binds the TAA, and wherein the affinity of the bispecific antibody molecule for the TAA when paired with one of the light chains is at least 2-fold lower than the affinity of the monospecific antibody molecule for the TAA from which the VH chain is derived.

43. The bispecific antibody molecule according to any one of aspects 30-42, wherein the TAA is CD47.

44. The bispecific antibody molecule according to aspect 43, wherein the second VH chain comprises the HCDRs 1-3 of a VH chain comprising the amino acid sequence:

```
                                      (SEQ ID NO: 17)
QVQLVQSGAEVKKPGASVKVSCKASGYTFTNYNMHWVRQAPGQRLEWMGT
IYPGNDDTSYNQKFKDRVTITADTSASTAYMELSSLRSEDTAVYYCARGG
YRAMDYWGQGTLVTVSS.
```

45. The bispecific antibody molecule according to aspect 44, wherein the second VH chain comprises the HCDR1 comprising the sequence: NYNMH (SEQ ID NO:18), the HCDR2 comprising the sequence: TIYPGNDDTSYN-QKFKD (SEQ ID NO:19), and the HCDR3 comprising the sequence: GGYRAMDY (SEQ ID NO:20).

46. The bispecific antibody molecule according to aspect 44 or 45, wherein the second VH chain comprises the amino acid sequence or an amino acid sequence at least 90% identical to the sequence:

```
                                      (SEQ ID NO: 17)
QVQLVQSGAEVKKPGASVKVSCKASGYTFTNYNMHWVRQAPGQRLEWMGT
IYPGNDDTSYNQKFKDRVTITADTSASTAYMELSSLRSEDTAVYYCARGG
YRAMDYWGQGTLVTVSS,
                                      (SEQ ID NO: 21)
EVQLVESGGGLVQPGGSLRLSCAASGYTFTNYNMHWVRQAPGKGLEWMGT
IYPGNDDTSYNQKFKDRVTISRDNSKNTLYLQMNSLRAEDTAVYYCARGG
YRAMDYWGQGTLVTVSS,
                                      (SEQ ID NO: 22)
EVQLVQSGAEVKKPGESLKISCKGSGYTFTNYNMHWVRQMPGKGLEWMGT
IYPGNDDTSYNQKFKDQVTISADKSISTAYLQWSSLKASDTAMYYCARGG
YRAMDYWGQGTTVTVSS,
or
                                      (SEQ ID NO: 23)
QVQLVQSGSELKKPGASVKVSCKASGYTFTNYNMHWVRQAPGQGLEWMGT
IYPGNDDTSYNQKFKDRFVFSLDTSVSTAYLQISSLKAEDTAVYYCARGG
YRAMDYWGQGTTVTVSS.
```

47. The bispecific antibody molecule according to any one of aspects 30-42, wherein the TAA is PD-L1.

48. The bispecific antibody molecule according to aspect 47, wherein the second VH chain comprises the HCDRs 1-3 of a VH chain comprising the amino acid sequence:

```
                                      (SEQ ID NO: 32)
EVQLVESGGGLVQPGGSLRLSCAASGFTFSDSWIHWVRQAPGKGLEWVAW
ISPYGGSTYYADSVKGRFTISADTSKNTAYLQMNSLRAEDTAVYYCARRH
WPGGFDYWGQGTLVTVSS.
```

49. The bispecific antibody molecule according to aspect 47 or 48, wherein the second VH chain comprises the HCDR1 comprising the sequence: DSWIH (SEQ ID NO:33), the HCDR2 comprising the sequence: WISPYGG-STYYADSVKG (SEQ ID NO:34), and the HCDR3 comprising the sequence: RHWPGGFDY (SEQ ID NO:35).

50. The bispecific antibody molecule according to any one of aspects 48 to 49, wherein the second VH chain comprises the amino acid sequence or an amino acid sequence at least 90% identical to the amino acid sequence:

```
                                      (SEQ ID NO: 32)
EVQLVESGGGLVQPGGSLRLSCAASGFTFSDSWIHWVRQAPGKGLEWVAW
ISPYGGSTYYADSVKGRFTISADTSKNTAYLQMNSLRAEDTAVYYCARRH
WPGGFDYWGQGTLVTVSS.
```

51. The bispecific antibody molecule according to any one of aspects 30-42, wherein the TAA is EGFR.

52. The bispecific antibody molecule according to aspect 51, wherein the antigen binding site of the second VH chain comprises the HCDRs 1-3 of a VH chain comprising the amino acid sequence:

```
                                      (SEQ ID NO: 36)
QVQLQESGPGLVKPSQTLSLTCTVSGGSISSGDYYWSWIRQPPGKGLEWI
GYIYYSGSTDYNPSLKSRVTMSVDTSKNQFSLKVNSVTAADTAVYYCARV
SIFGVGTFDYWGQGTLVTVSS.
```

53. The bispecific antibody molecule according to aspect 52, wherein the second VH chain comprises the HCDR1 comprising the sequence: SGDYYWS (SEQ ID NO:37), the HCDR2 comprising the sequence: YIYYSGSTDYNPSLKS (SEQ ID NO:38), and the HCDR3 comprising the sequence: VSIFGVGTFDY (SEQ ID NO:39).

54. The bispecific antibody molecule according to any one of aspects 52 to 53, wherein the second VH chain comprises the amino acid sequence or an amino acid sequence at least 90% identical to the amino acid sequence:

```
                                      (SEQ ID NO: 36)
QVQLQESGPGLVKPSQTLSLTCTVSGGSISSGDYYWSWIRQPPGKGLEWI
GYIYYSGSTDYNPSLKSRVTMSVDTSKNQFSLKVNSVTAADTAVYYCARV
SIFGVGTFDYWGQGTLVTVSS.
```

55. The bispecific antibody molecule according to aspect 51, wherein the antigen binding site of the second VH chain comprises the HCDRs 1-3 of a VH chain comprising the amino acid sequence:

(SEQ ID NO: 40)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSA.

56. The bispecific antibody molecule according to aspect 52, wherein the antigen binding site of the second VH chain comprises the HCDR1 comprising the sequence: NYGVH (SEQ ID NO:41), the HCDR2 comprising the sequence: VIWSGGNTDYNTPFTS (SEQ ID NO: 42), and the HCDR3 comprising the sequence: ALTYYDYEFAY (SEQ ID NO:43).

57. The bispecific antibody molecule according to any one of aspects 52 to 53, wherein the second VH chain comprises the amino acid sequence or an amino acid sequence at least 90% identical to the amino acid sequence:

(SEQ ID NO: 40)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSA.

58. The bispecific antibody molecule according to any one of the preceding aspects, wherein the antibody has greater than twice the affinity for a cell expressing both MDR1 and the TAA as compared to a cell expressing either MDR1 or the TAA.

59. The bispecific antibody molecule according to any one of the preceding aspects, wherein the antibody is capable of increasing sensitivity of a cancer cell to treatment with a chemotherapeutic agent, wherein the half maximal inhibitory concentration (IC50) of the chemotherapeutic agent when co-administered with the antibody is at least 2 times lower than the IC50 of the chemotherapeutic agent when co-administered with the anti-MDR1 antibody 15D3 comprising a VH chain having the sequence:
EVKVVESGGVLVRPGGSLKLSCAASGFTFSRYTMSWVRQTPEKRLEWVATISSGG GNTYYPDSVKGRFTVSRDNAMSSLYLQMSSLRSEDTALYYCARYGAGDAWFAYWGQGTL VTVSA (SEQ ID NO:24); and
a VL chain having the sequence:
DVLMTQTPLSLPVSLGDQASISCRSSQSIVHSTGNTYLEWYLQKPGQSPKLLIYKVS NRFSGVPDRFSGSGSGTDFTLKISRLEAEDLGVYYCFQGSHFPRTFGGGTRLEIK (SEQ ID NO: 25), wherein optionally the IC50 is measured in vitro.

60. The bispecific antibody molecule according to aspect 59, wherein the cancer cell is a NALM6 ADR cell and optionally wherein the chemotherapeutic agent comprises paclitaxel, Colchicine, Verapamil, Vinblastine, Topotecan, Doxorubicin, Daunorubicin, Etoposide, or Nilotinib.

61. The bispecific antibody molecule according to any one of the preceding aspects, wherein the antibody, when bound to a cell expressing a MDR1, inhibits efflux by the MDR1.

62. The bispecific antibody molecule according to any one of the preceding aspects, wherein the antibody binds to MDR1 with at least 2-fold lower affinity than the anti-MDR1 antibody 15D3 comprising a VH chain having the sequence:
EVKVVESGGVLVRPGGSLKLSCAASGFTFSRYTMSWVRQTPEKRLEWVATISSGG GNTYYPDSVKGRFTVSRDNAMSSLYLQMSSLRSEDTALYYCARYGAGDAWFAYWGQGTL VTVSA (SEQ ID NO:24); and
a VL chain having the sequence:

(SEQ ID NO: 25)
DVLMTQTPLSLPVSLGDQASISCRSSQSIVHSTGNTYLEWYLQKPGQSPK

LLIYKVSNRFSGVPDRFSGSGSGTDFTLKISRLEAEDLGVYYCFQGSHFP

RTFGGGTRLEIK.

63. The bispecific antibody molecule according to any one of the preceding aspects, wherein the antibody comprises a Fc domain that has been modified to reduce or abrogate binding of the antibody to one or more Fcγ receptors.

64. The bispecific antibody molecule according to any one of the preceding aspects for use in a method of treating cancer in a subject, the method comprising administering the antibody to the subject.

65. The bispecific antibody molecule for use according to aspect 64, wherein the method comprises administering the antibody in combination with at least one additional active agent, wherein the at least one additional active agent comprises a chemotherapeutic agent, an inhibitor of a multidrug resistance transporter, an immunotherapy agent, or a combination thereof.

66. The bispecific antibody molecule for use according to aspect 65, wherein the at least one additional active agent is a chemotherapeutic agent, optionally wherein the chemotherapeutic agent is a taxol, a *vinca* alkaloid, or an anthracycline.

67. A chemotherapy agent for use in a method of treating cancer in a subject, the method comprising administering the chemotherapy agent in combination with the antibody according to any one of aspects 1 to 63 to the subject, optionally wherein the chemotherapy agent is a taxol, a *vinca* alkaloid, or an anthracycline.

68. The bispecific antibody molecule for use according to aspects 67, wherein the subject being treated has a cancer that has been determined to be resistant to the chemotherapeutic agent.

69. A method of treating a subject for a cancer, the method comprising administering to the subject a therapeutically effective amount of the bispecific antibody molecule according to any of aspects 1 to 63.

70. The method according to aspect 69, wherein the method comprises administering the bispecific antibody molecule in combination with at least one additional active agent, wherein the at least one additional active agent comprises a chemotherapeutic agent, an inhibitor of a multidrug resistance transporter, an immunotherapy agent, or a combination thereof.

71. The method according to aspect 70, wherein the at least one additional active agent is a chemotherapeutic agent, optionally wherein the chemotherapeutic agent is a taxol, a *vinca* alkaloid, or an anthracycline.

72. The method according to aspect 71, wherein the subject being treated has a cancer that has been determined to be resistant to treatment with the chemotherapeutic agent, wherein optionally the chemotherapeutic agent comprises paclitaxel, Colchicine, Verapamil, Vinblastine, Topotecan, Doxorubicin, Daunorubicin, Etoposide, or Nilotinib.

73. An antibody comprising:
a variable light (VL) chain comprising light chain CDRs (LCDRs) of a VL chain having the sequence:

DVLMTQTPVSLSVSLGDQASISCRSSQSIVHSTGX$^1$TYLEWYLQKPGQS

PKLLIYKISNRFSGVPDRFSGSGSGTDFTLKISRVEAEDLGVYYCFQAS

HFPRTFGGGTKLEIK, wherein X$^1$ is N, Q or S; and
a variable heavy (VH) chain comprising heavy chain CDRs (HCDRs) of a VH chain having the sequence:

EVKVVESGGVLVRPGGSLKLSCAASGFTFSRYTMSWVRQTPEKRLEWVA

TISSGGGX$^2$TYYPDSVKGRFTVSRDNAMSSLYLQMSSLRSEDTALYYCA

RYGAGDAWFAYWGQGTLVTVSS, wherein X$^2$ is N, Q or S; or
an antibody comprising:
a variable light (VL) chain comprising light chain CDRs (LCDRs) of a VL chain having the sequence:
DVLMTQTPLSLPVSLGDQASISCRSSQSIVHSTGN-TYLEWYLQKPGQSPKLLIYKVS NRFSGVPDRFSGSGSGTDFTLKISRLEAE-DLGVYYCFQGSHFPRTFGGGTRLEIK (SEQ ID NO: 25); and
a variable heavy (VH) chain comprising heavy chain CDRs (HCDRs) of a VH chain having the sequence:

EVILVESGGGLVKPGGSLKLSCAASGFTFSSYTMSWVRQTPEKRLEWVAT

ISSGGGNTYYPDSVKGRFTISRDNAKNNLYLQMSSLRSEDTALYYCARYY

RYEAWFASWGQGTLVTVSA.

74. The antibody according to aspect 73, wherein:
the VL chain comprises LCDRs 1-3 of the VL chain having the sequence:
DVLMTQTPVSLSVSLGDQASISCRSSQSIVHSTGN-TYLEWYLQKPGQSPKLLIYKIS NRFSGVPDRFSGSGSGTDFTLKISRVEAE-DLGVYYCFQASHFPRTFGGGTKLEIK (SEQ ID NO: 2); and
the VH chain comprises HCDRs 1-3 of the VH chain having the sequence:
EVKVVESGGVLVRPGGSLKLSCAASGFTFSRYT-MSWVRQTPEKRLEWVATISSGG GNTYYP-DSVKGRFTVSRDNAMSSLYLQMSSLRSED-TALYYCARYGAGDAWFAYWGQGTL VTVSS (SEQ ID NO:10), or
the VL chain comprises LCDRs 1-3 of the VL chain having the sequence:
DIVMTQTPLSSPVTLGQPASISCRSSQSIVHSTGQ-TYLEWYQQRPGQPPRLLIYKIS NRFSGVPD-RFSGSGAGTDFTLKISRVEAEDVGVYYCFQ-ASHFPRTFGQGTKLEIK (SEQ ID NO: 3); and
the VH chain comprises HCDRs 1-3 of the VH chain having the sequence:
EVQLVESGGVVVQPGGSLRLS-CAASGFTFSRYTMSWVRQAPGKGLEWVATISSG GGQTYYPDSVKGRFTVSRDNSKNS-LYLQMNSLRTEDTALYYCARYGAGDAW-FAYWGQGT LVTVSS (SEQ ID NO:11), or
the VL chain comprises LCDRs 1-3 of the VL chain having the sequence:
DIVMTQTPLSSPVTLGQPASISCRSSQSIVHSTG-STYLEWYQQRPGQPPRLLIYKISN RFSGVP-DRFSGSGAGTDFTLKISRVEAEDVGVYYCFQ-ASHFPRTFGQGTKLEIK (SEQ ID NO: 4); and the VH chain comprises LCDRs 1-3 of the VH chain having the sequence:

EVQLVESGGVVVQPGGSLRLSCAASGFTFSRYTMSWVRQAPGKGLEWVAT

ISSGGGSTYYPDSVKGRFTVSRDNSKNSLYLQMNSLRTEDTALYYCARYG

AGDAWFAYWGQGTLVTVSS.

75. The antibody according to aspect 74, wherein:
the LCDR1 comprises the sequence: RSSQSIVHSTGN-TYLE (SEQ ID NO:44), RSSQSIVHSTGQTYLE (SEQ ID NO:27), or RSSQSIVHSTGSTYLE (SEQ ID NO:28),
the LCDR2 comprises the sequence: KISNRFS (SEQ ID NO:6), and
the LCDR3 comprises the sequence: FQASHFPRT (SEQ ID NO:7).

76. The antibody according to aspect 75, wherein:
(i) the HCDR1 comprises the sequence: RYTMS (SEQ ID NO:13);
(ii) the HCDR2 comprises the sequence: TISSGGGX$^2$TYYPDSVKG (SEQ ID NO:14); and
(iii) the HCDR3 comprises the sequence: YGAGDAW-FAY (SEQ ID NO:15);
wherein X$^2$ is N, Q or S.

77. The antibody according to any one of aspects 74-75, wherein:
(i) the LCDR1 comprises the sequence: RSSQSIVH-STGNTYLE (SEQ ID NO: 44),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGGN-TYYPDSVKG (SEQ ID NO:29), and
the HCDR3 comprises the sequence: YGAGDAWFAY (SEQ ID NO:15), or
(ii) the LCDR1 comprises the sequence: RSSQSIVH-STGQTYLE (SEQ ID NO: 27),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TIS-SGGGQTYYPDSVKG (SEQ ID NO:30), and
the HCDR3 comprises the sequence: YGAGDAWFAY (SEQ ID NO:15), or
(iii) the LCDR1 comprises the sequence: RSSQSIVH-STGSTYLE (SEQ ID NO: 28),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGG-STYYPDSVKG (SEQ ID NO:31), and
the HCDR3 comprises the sequence: YGAGDAWFAY (SEQ ID NO:15), or (iv) the LCDR1 comprises the sequence: RSSQSIVH-STGNTYLE (SEQ ID NO: 44),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TIS-SGGGQTYYPDSVKG (SEQ ID NO:30), and
the HCDR3 comprises the sequence: YGAGDAWFAY (SEQ ID NO:15), or (v) the LCDR1 comprises the sequence: RSSQSIVH-STGNTYLE (SEQ ID NO: 44),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGG-STYYPDSVKG (SEQ ID NO:31), and
the HCDR3 comprises the sequence: YGAGDAWFAY (SEQ ID NO:15), or (vi) the LCDR1 comprises the sequence: RSSQSIVH-STGQTYLE (SEQ ID NO: 27),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGGN-TYYPDSVKG (SEQ ID NO:29), and
the HCDR3 comprises the sequence: YGAGDAWFAY (SEQ ID NO:15), or (vii) the LCDR1 comprises the sequence: RSSQSIVH-STGSTYLE (SEQ ID NO: 28),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TISSGGGN-TYYPDSVKG (SEQ ID NO:29), and
the HCDR3 comprises the sequence: YGAGDAWFAY (SEQ ID NO:15), or (viii) the LCDR1 comprises the sequence: RSSQSIVH-STGSTYLE (SEQ ID NO: 28),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TIS-SGGGQTYYPDSVKG (SEQ ID NO:30), and
the HCDR3 comprises the sequence: YGAGDAWFAY (SEQ ID NO:15), or (ix) the LCDR1 comprises the sequence: RSSQSIVH-STGNTYLE (SEQ ID NO: 44),
the LCDR2 comprises the sequence: KISNRFS (SEQ ID NO:6), and
the LCDR3 comprises the sequence: FQASHFPRT (SEQ ID NO:7); and
the HCDR1 comprises the sequence: RYTMS (SEQ ID NO:13),
the HCDR2 comprises the sequence: TIS-SGGGQTYYPDSVKG (SEQ ID NO:30), and
the HCDR3 comprises the sequence: YGAGDAWFAY (SEQ ID NO:15).

78. The antibody according to any one of aspects 73-77, wherein the VL chain of the antibody comprises the amino acid sequence or comprises an amino acid sequence at least 90% identical to the amino acid sequence:
DVLMTQTPVSLSVSLGDQASISCRSSQSIVHSTGX$^1$TYLEWYLQKPGQSPKLLIYKIS NRFSGVPD-RFSGSGSGTDFTLKISRVEAEDLGVYYCFQ-ASHFPRTFGGGTKLEIK (SEQ ID NO: 1), and
wherein the VH chain of the antibody comprises the amino acid sequence or comprises an amino acid sequence at least 90% identical to the amino acid sequence:

(SEQ ID NO: 9)
EVKVVESGGVLVRPGGSLKLSCAASGFTFSRYTMSWVRQTPEKRLEWVA

TISSGGGX$^2$TYYPDSVKGRFTVSRDNAMSSLYLQMSSLRSEDTALYYCA

RYGAGDAWFAYWGQGTLVTVSS.

79. The antibody according to aspect 73, wherein the an antibody comprises: a variable light (VL) chain comprising light chain CDRs 1-3 (LCDRs) of a VL chain having the sequence:
DVLMTQTPLSLPVSLGDQASISCRSSQSIVHSTGN-TYLEWYLQKPGQSPKLLIYKVS NRFSGVPD-RFSGSGSGTDFTLKISRLEAEDLGVYYCF-QGSHFPRTFGGGTRLEIK (SEQ ID NO: 25); and
a variable heavy (VH) chain comprising heavy chain CDRs 1-3 (HCDRs) of a VH chain having the sequence:

EVILVESGGGLVKPGGSLKLSCAASGFTFSSYTMSWVRQTPEKRLEWVAT

ISSGGGNTYYPDSVKGRFTISRDNAKNNLYLQMSSLRSEDTALYYCARYY

RYEAWFASWGQGTLVTVSA.

80. The antibody according to aspect 79, wherein:
(i) the LCDR1 comprises the sequence: RSSQSIVH-STGNTYLE (SEQ ID NO:44);
(ii) the LCDR2 comprises the sequence: KISRLEA (SEQ ID NO:45); and
(iii) the LCDR3 comprises the sequence: FQGSHFPRT (SEQ ID NO:46); and
(i) the HCDR1 comprises the sequence: SYTMS (SEQ ID NO:48);
(ii) the HCDR2 comprises the sequence: TISSGGGN-TYYPDSVKG (SEQ ID NO:29); and
(iii) the HCDR3 comprises the sequence: YYRYEAW-FAS (SEQ ID NO:49).

81. The antibody according to aspect 79 or 80, wherein the VL chain of the antibody comprises the amino acid sequence or comprises an amino acid sequence at least 90% identical to the amino acid sequence:

(SEQ ID NO: 25)
DVLMTQTPLSLPVSLGDQASISCRSSQSIVHSTGNTYLEWYLQKPGQSPK

LLIYKVSNRFSGVPDRFSGSGSGTDFTLKISRLEAEDLGVYYCFQGSHFP

RTFGGGTRLEIK;

and wherein the VH chain of the antibody comprises the amino acid sequence or comprises an amino acid sequence at least 90% identical to the amino acid sequence:

EVILVESGGGLVKPGGSLKLSCAASGFTFSSYTMSWVRQTPEKRLEWVAT

ISSGGGNTYYPDSVKGRFTISRDNAKNNLYLQMSSLRSEDTALYYCARYY

RYEAWFASWGQGTLVTVSA.

82. The antibody according to any one of aspects 73-81, wherein the antibody is a monospecific bivalent antibody that specifically binds to MDR-1.

83. The antibody according to any one of aspects 73-81, wherein the antibody is a bi-specific antibody comprising the VL chain as a common light chain.

84. The antibody according to aspect 83, wherein the bispecific antibody comprises an MDR-1 binding domain and a tumor associated antigen (TAA) binding domain wherein each of the MDR-1 binding domain and the TAA binding domain comprises the LCDRs 1-3 of the VL chain.

85. The antibody according to aspect 84, wherein the TAA is CD47 and wherein the TAA binding domain comprises HCDRs 1-3 of the VH chain having the sequence:

QVQLVQSGAEVKKPGASVKVSCKASGYTFTNYNMHWVRQAPGQRLEWMGT

IYPGNDDTSYNQKFKDRVTITADTSASTAYMELSSLRSEDTAVYYCARGG

YRAMDYWGQGTLVTVSS.

86. The antibody according to aspect 85, wherein the VH chain of the CD47 binding domain comprises the HCDR1 comprising the sequence: NYNMH (SEQ ID NO:18), the HCDR2 comprising the sequence: TIYPGNDDTSYN-QKFKD (SEQ ID NO:19), and the HCDR3 comprising the sequence: GGYRAMDY (SEQ ID NO:20).

87. The antibody according to aspect 84, wherein the TAA is PD-L1 and wherein the PD-L1 binding domain comprises HCDRs 1-3 of the VH chain having the sequence:

(SEQ ID NO: 32)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS.

88. The antibody according to aspect 87, wherein the VH chain of the PD-L1 binding domain comprises the HCDR1 comprising the sequence: DSWIH (SEQ ID NO:33), the HCDR2 comprising the sequence: WISPYGGSTYY-ADSVKG (SEQ ID NO:34), and the HCDR3 comprising the sequence: RHWPGGFDY (SEQ ID NO:35).

89. The antibody according to aspect 84, wherein the TAA is EGFR and wherein the EGFR binding domain comprises HCDRs of the VH chain having the sequence:

(SEQ ID NO: 36)
QVQLQESGPGLVKPSQTLSLTCTVSGGSISSGDYYWSWIRQPPGKGLEWI

GYIYYSGSTDYNPSLKSRVTMSVDTSKNQFSLKVNSVTAADTAVYYCARV

SIFGVGTFDYWGQGTLVTVSS.

90. The antibody according to aspect 89, wherein the VH chain of the EGFR binding domain comprises the HCDR1 comprising the sequence: SGDYYWS (SEQ ID NO: 37), the HCDR2 comprising the sequence: YIYYSGST-DYNPSLKS (SEQ ID NO:38), and the HCDR3 comprising the sequence: VSIFGVGTFDY (SEQ ID NO:39).

91. The antibody according to aspect 84, wherein the TAA is EGFR and wherein the EGFR binding domain comprises HCDRs of the VH chain having the sequence:

(SEQ ID NO: 40)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSA.

92. The antibody according to aspect 91, wherein the VH chain of the EGFR binding domain comprises the HCDR1 comprising the sequence: NYGVH (SEQ ID NO:41), the HCDR2 comprising the sequence: VIWSGGNTDYN-TPFTS (SEQ ID NO:42), and the HCDR3 comprising the sequence: ALTYYDYEFAY (SEQ ID NO:43).

93. An antibody comprising:
a variable light (VL) chain comprising light chain CDRs (LCDRs) of a VL chain having the sequence:

(SEQ ID NO: 1)
DVLMTQTPVSLSVSLGDQASISCRSSQSIVHSTGX$^1$TYLEWYLQKPGQS

PKLLIYKISNRFSGVPDRFSGSGSGTDFTLKISRVEAEDLGVYYCFQAS

HFPRTFGGGTKLEIK, wherein X$^1$ is N, Q or S; or
DVLMTQTPLSLPVSLGDQASISCRSSQSIVHSTGN-TYLEWYLQKPGQSPKLLIYKVS NRFSGVPDRFSGSGSGTDFTLKISRLEAE-DLGVYYCFQGSHFPRTFGGGTRLEIK (SEQ ID NO: 25); and
a variable heavy (VH) chain comprising heavy chain CDRs (HCDRs) of a VH chain having the sequence:

QVQLVQSGAEVKKPGASVKVSCKASGYTFTNYNMHWVRQAPGQRLEWMGT

IYPGNDDTSYNQKFKDRVTITADTSASTAYMELSSLRSEDTAVYYCARGG

YRAMDYWGQGTLVTVSS;
or (SEQ ID NO: 32)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS;
or (SEQ ID NO: 36)
QVQLQESGPGLVKPSQTLSLTCTVSGGSISSGDYYWSWIRQPPGKGLEWI

GYIYYSGSTDYNPSLKSRVTMSVDTSKNQFSLKVNSVTAADTAVYYCARV

SIFGVGTFDYWGQGTLVTVSS;
or (SEQ ID NO: 40)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSA.

94. The antibody according to aspect 93, wherein the VL chain comprises the (i) the LCDR1 comprises the sequence: RSSQSIVHSTGX$^1$TYLE (SEQ ID NO:5); (ii) the LCDR2 comprises the sequence: KISNRFS (SEQ ID NO:6); and (iii)

the LCDR3 comprises the sequence: FQASHFPRT (SEQ ID NO:7), wherein $X^1$ is N, Q or S and wherein the VH chain comprises:
- (i) the HCDR1 comprising the sequence: NYNMH (SEQ ID NO:18), the HCDR2 comprising the sequence: TIYPGNDDTSYNQKFKD (SEQ ID NO:19), and the HCDR3 comprising the sequence: GGYRAMDY (SEQ ID NO:20); or
- (ii) the HCDR1 comprising the sequence: DSWIH (SEQ ID NO:33), the HCDR2 comprising the sequence: WISPYGGSTYYADSVKG (SEQ ID NO:34), and the HCDR3 comprising the sequence: RHWPGGFDY (SEQ ID NO:35); or
- (iii) the HCDR1 comprising the sequence: SGDYYWS (SEQ ID NO:37), the HCDR2 comprising the sequence: YIYYSGSTDYNPSLKS (SEQ ID NO:38), and the HCDR3 comprising the sequence: VSIFGVGTFDY (SEQ ID NO:39); or
- (iv) the HCDR1 comprising the sequence: NYGVH (SEQ ID NO:41), the HCDR2 comprising the sequence: VIWSGGNTDYNTPFTS (SEQ ID NO:42), and the HCDR3 comprising the sequence: ALTYYDYEFAY (SEQ ID NO:43).

95. The antibody according to aspect 93, wherein the VL chain comprises the (i) the LCDR1 comprising the sequence: RSSQSIVHSTGNTYLE (SEQ ID NO:44); (ii) the LCDR2 the sequence: KISRLEA (SEQ ID NO:45); and (iii) the LCDR3 the sequence: FQGSHFPRT (SEQ ID NO:46) and wherein the VH chain comprises:
- the HCDR1 comprising the sequence: NYNMH (SEQ ID NO:18), the HCDR2 comprising the sequence: TIYPGNDDTSYNQKFKD (SEQ ID NO:19), and the HCDR3 comprising the sequence: GGYRAMDY (SEQ ID NO:20); or
- the HCDR1 comprising the sequence: DSWIH (SEQ ID NO:33), the HCDR2 comprising the sequence: WISPYGGSTYYADSVKG (SEQ ID NO:34), and the HCDR3 comprising the sequence: RHWPGGFDY (SEQ ID NO:35); or
- the HCDR1 comprising the sequence: SGDYYWS (SEQ ID NO:37), the HCDR2 comprising the sequence: YIYYSGSTDYNPSLKS (SEQ ID NO:38), and the HCDR3 comprising the sequence: VSIFGVGTFDY (SEQ ID NO:39); or
- the HCDR1 comprising the sequence: NYGVH (SEQ ID NO:41), the HCDR2 comprising the sequence: VIWSGGNTDYNTPFTS (SEQ ID NO:42), and the HCDR3 comprising the sequence: ALTYYDYEFAY (SEQ ID NO:43).

96. The antibody according to any one of aspects 93-95, wherein the antibody is a bispecific antibody.

97. The antibody according to any one of aspects 1-96, wherein the antibody is a humanized antibody or a chimeric antibody comprising human Fc domain.

98. The antibody according to aspect 97, comprising immunoglobulin G1 (IgG1) Fc domain.

99. The antibody according to any one of aspects 1-98, wherein a first VH chain is fused to a first Fc domain and a second VH chain is fused to a second Fc domain.

100. The antibody according to aspect 99, wherein the Fc domains comprise modified CH3 domains that preferentially form heterodimers comprising the first and second VH chains.

101. The antibody according to aspect 100, wherein the first and second Fc domains are human immunoglobulin G1 (IgG1) Fc domains.

102. A pharmaceutical composition comprising:
the antibody of any of the preceding aspects; and
a pharmaceutically acceptable excipient.

103. The pharmaceutical composition according to aspect 102, further comprising at least one additional active agent.

104. The pharmaceutical composition according to aspect 103, wherein the at least one additional active agent comprises a chemotherapy agent.

105. The pharmaceutical composition according to aspect 104, wherein the chemotherapy agent is a taxol, a *vinca* alkaloid, or an anthracycline.

106. The pharmaceutical composition according to any of aspects 103 to 105, wherein the at least one additional active agent comprises an inhibitor of a multidrug resistance transporter.

107. The pharmaceutical composition according to aspect 103, wherein the at least one additional active agent comprises an immunotherapy agent.

108. One or more nucleic acids comprising one or more sequences encoding the antibody according to any of the preceding aspects.

109. The one or more nucleic acid according to aspect 108, wherein the one or more sequences are operably linked to a promoter.

110. One or more recombinant expression vectors comprising the one or more nucleic acids according to aspect 108 or 109.

111. A mammalian cell genetically modified with the one or more recombinant expression vectors according to aspect 110.

112. The cell according to aspect 111, wherein the cell is an immune cell.

113. A kit comprising:
the antibody or a nucleic acid encoding the antibody, according to any of aspects 1 to 63 and 73-101; and
at least one additional active agent.

114. The kit according to aspect 113, wherein the at least one additional active agent comprises a chemotherapy agent, an inhibitor of a multidrug resistance transporter, an immunotherapy agent, or a combination thereof.

115. A method of killing a cancer cell, the method comprising contacting the cancer cell with the antibody according to any of aspects 1 to 63 and 73-101.

116. The method according to aspect 115, comprising administering at least one additional active agent.

117. The method according to aspect 116, wherein the at least one additional active agent comprises a chemotherapy agent.

118. The method according to aspect 116 or 117, wherein the method increases the killing of the cancer cell by at least 5% as compared to contacting with the at least one additional active agent alone.

119. The method according to any of aspects 115 to 118, wherein the cancer cell is a drug resistant cancer cell.

120. A method of treating a subject for a cancer, the method comprising administering to the subject the antibody according to any of aspects 1 to 63 and 73-101 or the pharmaceutical composition according to any of aspects 102-107.

121. The method according to aspect 120, wherein the subject has been treated previously for the cancer.

122. The method according to aspect 120 or 121, wherein the cancer is drug resistant or multidrug resistant.

123. The method according to aspect 122, wherein the cancer is resistant to a chemotherapeutic agent.

124. The method according to aspect 122, wherein the cancer is resistant to an immunotherapy agent.

125. The method according to any of aspects 120 to 122, wherein the cancer is resistant to an inhibitor of a multidrug resistance transporter.

126. The method according to any of aspects 120 to 125, further comprising administering at least one additional active agent to the subject.

127. The method according to aspect 126, wherein the at least one additional active agent comprises a chemotherapy agent.

128. The method according to aspect 127, wherein the chemotherapy agent is a taxol, a *vinca* alkaloid, or an anthracycline.

129. The method according to any of aspects 126 to 128, wherein the at least one additional active agent comprises an inhibitor of a multidrug resistance transporter.

130. The method according to any of aspects 126 to 128, wherein the at least one additional active agent comprises an immunotherapy agent.

131. The method according to any of aspects 126 to 128, wherein the method increases the effectiveness of the at least one additional active agent as compared to treatment with the at least one additional active agent alone.

132. The method according to aspect 131, wherein the increased effectiveness comprises an at least 5% increase in cancer cell killing.

133. The method according to any of aspects 120 to 132, further comprising analyzing a sample of the cancer to determine whether the cancer expresses MDR1 above a predetermined threshold, a tumor associated antigen (TAA) above a predetermined threshold, or both, wherein optionally the TAA comprises CD47.

134. The method according to aspect 133, wherein the predetermined threshold corresponds to a level of MDR1 and/or TAA expressed by a reference cell.

135. The method according to aspect 134, wherein MDR1 and/or TAA has been knocked-out of or knocked-down in the reference cell.

136. The method according to aspect 134 or 135, wherein the reference cell is a non-cancerous cell.

137. The method according to aspect 134, wherein the non-cancerous cell expresses a normal level of MDR1 and/or TAA.

138. The method according to any of aspects 120 to 137, wherein if the cancer expresses MDR1 and TAA at or above the predetermined thresholds then the subject is administered the multi-specific antibody, and if the cancer expresses MDR1 or TAA below the predetermined thresholds then the subject is treated with a conventional therapy without administering the multi-specific antibody.

139. A method of generating a multi-specific antibody that specifically binds a cell expressing both multidrug resistance protein 1 (MDR1) and a tumor associated antigen (TAA), wherein optionally the TAA comprises CD47, PD-L1, or EGFR, the method comprising:
  producing a multi-specific antibody comprising a MDR1-binding domain and a TAA-binding domain;
  contacting a first cell expressing MDR1 and TAA with the multi-specific antibody;
  contacting a second cell expressing either MDR1 or TAA with the multi-specific antibody;
  comparing the binding of the multi-specific antibody to the first cell with the binding of the multi-specific antibody to the second cell to determine a binding-specificity ratio; and
  identifying the multi-specific antibody as specific for the cell expressing both MDR1 and TAA when the ratio is above a predetermined threshold.

140. The method according to aspect 139, wherein the predetermined threshold is greater than 2:1.

141. The method according to aspect 139 or 140, wherein the second cell expresses MDR1 and not the TAA and the method further comprises contacting a third cell expressing the TAA but not MDR1 with the multi-specific antibody.

142. The method according to any of aspects 139 or 140, wherein the method further comprises contacting the first cell, the second cell, and/or the third cell with a control antibody selected from: a monospecific anti-MDR1 antibody and a monospecific anti-TAA antibody.

143. A genetically modified human cell line, the cell line expressing a tumor associate antigen (TAA), wherein optionally the TAA comprises leukocyte surface antigen CD47 and comprising an exogenous nucleic acid comprising a sequence encoding a multidrug resistance protein 1 (MDR1) for overexpression of MDR1.

144. The cell line according to aspect 143, wherein the cell line is a kidney cell line. 145. The cell line according to aspect 144, wherein the cell line is a HEK 293T cell line.

146. A method of making the cell line according to any of aspects 143 to 145, the method comprising contacting a human cell that expresses the TAA with the exogenous nucleic acid under conditions sufficient to introduce the exogenous nucleic acid into the cell to produce a genetically modified human cell expressing the TAA and stably overexpressing MDR1; and
  culturing the genetically modified human cell under conditions sufficient to produce a genetically modified human cell line expressing the TAA and stably overexpressing MDR1.

The following example(s) is/are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

Example 1: Generation of Bispecific mAbs that Bind Specifically to, and Re-Sensitize, Cells Simultaneously Expressing Pgp (MDR1) and CD47, but not Cells Having Reduced or Absent Expression of Either Protein This example demonstrates the development of molecules based on antibody formats that can effectively blockade efflux by binding to extracellular domains of EPs in a selective manner while also specifically targeting antigens expressed by cancer cells. EP blockade results in the re-sensitization and killing of cells that are or have become resistant to chemotherapeutic agents. In this example bispecific antibody molecules have been constructed that bind the extracellular domain (ECD) of an EP, blockading efflux while also targeting a cancer immune checkpoint protein. Application of the bispecific antibody described below re-sensitizes cells to chemotherapeutic agents in a selective manner when the EP is co-expressed with the targeted immune checkpoint protein.

Materials and Methods
Cell Lines and Cell Viability Experiments

HEK 293T, MCF-7, N6ADR and SKNF7 cell lines expressing Pgp were obtained from the American Type Culture Collection. N6/ADR cells is also referred to as NALM6/ADR cells. All cell lines and lines derived from them were maintained in RPMI 1640 or DMEM supplemented with up to 10% fetal bovine serum (Sigma), nonessential amino acids, and 2 mmol/L L-glutamine at 37° C. and 5% CO2 in a humidified incubator (unless otherwise indicated). Cells were used as supplied or were modified to overexpress (Ox) Pgp or were subject to having Pgp expression knocked down (KD) with lentiviral-mediated short hairpin RNA or knock out (KO) of the functional CD47 gene by CRISPR/Cas-mediated knock out technology essentially as described (Cong, L. et al. (2013) Science 339, 819-823). For vincristine and paclitaxel IC50 determination, cells were plated in normal growth medium and allowed to adhere overnight. Paclitaxel or vincristine (Sigma) were added in a dilution series and any modulators were added within ranges of 0 to 500 μM/L. Cell viability was measured 72 h later using the Celltiter-Glo Luminescent Cell Viability Assay (Promega). The concentration of drug resulting in 50% inhibition of cell viability (IC50) was calculated from a multi-parameter curve analysis (GraphPad Prism software GraphPad Software, Inc.) and was determined from a minimum of 2 repeats. Cell lines that did not show 50% reduction in cell viability in response to drug and/or modulator treatment in the majority of experiments conducted were considered to not have reached an IC50 by definition and are listed as having an IC50 of >1000 nmol/L for paclitaxel or the drug/modulator combination under study.

Recombinant cell lines with stable expression of the described monoclonal antibodies (mAbs) were also produced.

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. Reagents were used according to the manufacturer's instructions. General information regarding the nucleotide sequences of human immunoglobulins light and heavy chains is given in: Kabat, E. A. et al., (1991) Sequences of Proteins of Immunological Interest, 5th ed., NIH Publication No. 91-3242 Amino acids of antibody chains were numbered and referred to according to Kabat, E. A., et al., Sequences of Proteins of Immunological Interest, 5th ed., Public Health Service, National Institutes of Health, Bethesda, Md., (1991).

DNA Sequence Determination

DNA sequences were determined by double strand sequencing.

DNA and Protein Sequence Analysis and Sequence Data Management

The Vector NTI (ThermoFisher) software package was used for sequence mapping, analysis, annotation and illustration.

Cell Culture Techniques and Antibody Production

Standard cell culture techniques are used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

293 & CHO cells were used for transient production of mAbs, Fab'2s, Fabs and bispecific mAbs. Different antibody constructs were expressed using polymer-based co-transfection of Expi293 cells (A14527, ThermoFisher). Cells were grown in suspension with the mammalian expression vectors following the manufacturer's recommendations.

For preparation of bispecific constructs, cells were transfected with the corresponding expression vectors in a 1:1:4 ratio (heavy chain KK:heavy chain DD:light chain). For standard antibody expression a 1:2 ratio (heavy chain:light chain) was used.

Six days after transfection the cells were harvested by centrifugation. In detail, 1 μg of total encoding DNA per 1 ml of transfected culture was diluted into of Opti-MEM® medium (Life Technologies), and incubated with Expifectamine reagent (Life Technologies) in the same medium for 20 min. The mixture was then added into the Expi293® cells growing in suspension in Expi293® Expression medium (Life Technologies) at 2.5 million cells/ml at 37° C. with and overlay of 8% of CO2 in air. After 6 days, the medium containing the antibody construct was harvested by centrifugation.

Reagent Cell Lines Used to Test: Binding, Efflux Blockade, Cell Sensitization to Chemotherapeutics Human embryonic kidney (HEK) cell line HEK 293 FT (Life Technologies) was maintained in Dulbecco's modified Eagle's Medium (DMEM) supplemented with 10% fetal bovine serum (HyClone), 2 mM GlutaMAX (Life Technologies), 100 U/mL penicillin, and 100 g/mL streptomycin at 37° C. with 5% $CO_2$ incubation.

293T cells were transiently transfected with the Human P Glycoprotein Tagged ORF Clone in pLenti-C-Myc-DDK-P2A-Puro plasmid using the optimized PEIPro™ transfection protocol (Polyplus). DNA and JetPEI® were respectively diluted in culture media before being gently mixed for approximately 10 min. This mixing led to the formation of a transfection complex, which was directly added to the cell culture. Efflux blockade was measure using the Multidrug Resistance Direct Dye Efflux Assay (Chemicon) following the manufacturer's protocol.

Sources of Target Sequences, Antibody Sequences and Specific Anti-Target Antibody Sequences P Glycoprotein (Pgp), also known as Multidrug resistance protein 1 (MDR1), (gene ABCB1) (NM_000927) Human Tagged ORF Clone in pLenti-C-Myc-DDK-P2A-Puro was obtained from Origene, anti CD47 antibody (CC2C6, Seiffert M, et al. (1999) Blood 94:3633) from Biolegend, anti-ABCB1 JSB-1 (MAB4120) from Millipore.

Generation of a Stable ABCB1 Overexpressing (Ox) Cell Lines

In order to characterize both binding and in vitro efficacy, a cell line that stably over-expressed ABCB1 was developed. Adherent 293T naïve cells obtained from American Type Culture Collection (ATCC) were utilized. As characterized by flow cytometry using a commercially available ABCB1 antibody (Biolegend, clone 4E3.16), this cell line expresses ABCB1 endogenously at a low to moderate degree on the cell surface. 293T naïve cells were transfected with ABCB1 using Polyplus PEIpro reagent. Three days after transfection, cells were put under selection using a Hygromycin B solution (Millipore Sigma). Fourteen days after continuous Hygromycin B selection 293T cells were evaluated for ABCB1 cell surface expression. To ensure non-transfected cells would not expand in future cultures, a bulk sort using fluorescent activated cell sorting (FACS) of ABCB1 positive 293T cells was performed using a FACSArial (BD Biosciences). The bulk sorted 293T ABCB1 over-expressing cells were expanded and ABCB1 over-expression was subsequently re-confirmed. Similar methods were used to generate ABCB1 over-expressing cells from 293T-CD47 Knock-Out cells generated as described herein.

Generation of a Stable ABCB1 KD 293T Cell Line

In order to characterize both binding and in vitro efficacy a cell line that had a stable knockdown of ABCB1 expression was developed. Lentivirus was produced in 293T naïve cells by transfection with a R8.74 helper plasmid, a VSVG envelope plasmid, and a GE Dharmacon GIPZ lentiviral vector containing a shRNA for ABCB1. Harvested lentivirus was then used to transduce adherent 293T naïve cells. Three days post transduction, the 293T transduced cells were evaluated for ABCB1 cell surface expression by flow cytometry (Biolegend, clone 4E3.16). As compared to 293T naïve cells, which express ABCB1 endogenously at a low level, the transduced 293T cells had no ABCB1 expression. In addition to this, the GIPZ lentiviral vector contains GFP. All transduced 293T cells were GFP+, indicating, in conjunction with the decrement in expression, that the transduction was successful. A lack of ABCB1 expression was re-confirmed by flow cytometry in subsequent passages.

Generation of KO Cell Lines

To construct ABCB1, and CD47 gene knockout HEK293 cell line, HEK293 host cells were first cultured in DMEM (Dulbecco's Modified Eagle's Medium, Gibco, Grand Island, N.Y., USA) supplemented with 10% (v/v) FBS, and glutamine via adhesion culture. Cells were cultivated at 37° C. with 5% CO2 at saturated humidity.

The design of the gRNAs was performed using the online CHOPCHOP web tool for selecting target sites for CRISPR/Cas9, CRISPR/Cpf1 or TALEN-directed mutagenesis. (see Kornel Labun et al., (2016). Nucleic Acids Research; and Tessa G. Montague et al., (2014) Nucleic Acids Res. 42: W401-W407). All designed gRNAs were chemically synthesized (ThermoFisher).

Transfection of 293T cells was performed by lipid-based transfection using CRISPRMax reagent (ThermoFisher) according to the manufacturer's protocol. Briefly, one day prior to transfection, adherent cells were plated onto 96-well plates at 0.2×10⁵ cells per well. On the day of transfection, a solution of GeneArt Platinum Cas9 protein, gRNA and transfecting reagent was added to cells. 72 h post-transfection, cell culture was continued for 2 weeks in a 96 well plate format after the selection of single cells by a limiting dilution method. Subsequently, the picked clones were passaged to 24-well plates and tested by genotype confirmation using Guide-it kit (Takara) according to the manufacturer's protocol. The genomic region surrounding a CRISPR target site for each gene was PCR amplified to determine whether gene editing resulted in indels on one allele (monoallelic) or both alleles (biallelic) in singly isolated clones. The expression of the protein of interest on the clones with mutations in both alleles where tested by FACS.

Construction of the Human-Mouse Sequences of the Molecules as Tested (Human Fc. Mouse Fvs)

Expression Vectors: For the generation of the antibody expression vectors, the variable regions of heavy and light chain DNA sequences were subcloned in frame with either the human IgG1 constant heavy chain or the human IgG1 kappa constant light chain pre-inserted into the respective generic recipient expression vector optimized for expression in mammalian cell lines. The genes to be expressed were cloned into the pCI-neo Mammalian Expression Vector (Promega) that uses the full-length human cytomegalovirus (CMV) immediate-early promoter for high level gene expression. The two antibody chains were cloned into two different vectors.

The N-terminal signal sequences from mouse IgG heavy chain and kappa light chain were used for the secreted expression of the heavy and light chain, respectively. The signal peptide was cleaved during expression, leaving intact N-terminus. In the Fab constructs, the C-terminus of the CH1 IgG1 constant region was fused with a 6× His tag to facilitate purification.

For the generation of bispecific antibody vectors, the IgG1 derived bispecific molecules include at least of two antigen binding moieties capable of binding specifically to two distinct targets: Pgp (ABCB1) and CD47. The antigen binding moieties are Fab fragments composed of a heavy and a light chain, each including a variable and a constant region. A common light chain was identified that was able to pair and effect acceptable binding both as Fab anti-Pgp (aPgp) and Fab anti-CD47 (aCD47); its use enabled the avoidance of LC mispairing (see e.g., U.S. Pat. No. 8,765, 412, the disclosure of which is incorporated herein by reference in its entirety). Bispecific constructs were made based on electrostatic steering effects, (see e.g., Gunasekeran et al, (2010) Journal of Biological Chemistry 285, 19637-19646; the disclosure of which is incorporated herein by reference in its entirety). Briefly, the polypeptide chains or half antibodies against the targets are assembled as a bispecific antibody through charge pair substitutions at the CH3 domain: one heavy chain contained K392D and K409D substitutions and the other contained E356K and D399K substitutions.

FIG. 2 provides a diagram of a bispecific mAb that includes sections containing sequences from: A, 15D3; B, 5F9, both on a human IgG1Fc together with C, a common light chain kappa sequence derived from MRK16.

Monoclonal antibody 15D3 (see e.g., U.S. Pat. No. 5,959, 084; the disclosure of which is incorporated herein by reference in its entirety) and MRK16 (Iwahashi et al., Cancer Research 53, 1993; the disclosure of which is incorporated herein by reference in its entirety) monoclonal antibodies raised previously against Pgp were cloned as recombinant engineered antibodies into a Human IgG1/Kappa expression vector.

Variable heavy and light chain fragments from mouse hybridoma sequences are available and were cloned into the same background of leader sequence and constant region.

Anti CD47 (5F9; see e.g., U.S. Pat. No. 9,017,675; the disclosure of which is incorporated herein by reference in its entirety) antibody variable heavy and light fragments were cloned into the same background of leader sequence and constant region in two separate vectors.

Numerous combinations of these and other heavy and light chain fragments were generated and tested. The majority of the tested constructs did not generate acceptable binding or activity. Examples of antibodies constructed and tested, as well as their binding and cell killing properties, are provided in FIG. 8.

FIG. 8 provides comparisons of binding and enhanced cell killing by different bispecific antibodies (with various humanized or chimerized heavy or light chain combinations). Specifically, column 1 ("Ab") of FIG. 8 provides the various bispecific formats tested, e.g., in row 1: 15D3 IgG1 DD/5F9 IgG1 KK/MRK16 indicates: i) 15D3 heavy chain sequence (chimerized in a human IgG1 framework) with the DD CH3 mutations described herein, ii) 5F9 heavy chain sequence with the KK CH3 mutations as described herein, and iii) MRK16 light chain (chimerized in a human IgG Kappa framework). All the light chains shown were in the human Kappa format. Binding (FIG. 8, col. 2-3; "Kd (nM)" and "Bmax") and killing (FIG. 8, col. 3; "Killing") were determined as follows: "Kd (nM)", binding by ELISA (solid phase with Fc-tagged CD47 as capture layer on the plate); "Bmax", Bmax binding to the plates in described for "Kd (nM)"; "Killing", enhanced 293 naïve cell-killing (sensitization) in the presence of paclitaxel titration (20 μM-$10^{-8}$ UM range); "−"=zero, "±"=0 to 0.5 Log shift (at 50% cell kill curve), "+"=1 to 2 Log shift, "++"≥2 Log shift. Columns 5-8 ("Binding (293)", "Binding (293 KO CD47)", Binding (293 KO CD47, OX ABCB1)", and "Binding (293 OX ABCB1)") provide FACS mean fluorescence intensities of antibodies binding to the indicated cell lines compared with non-binding control antibodies: "−"=~zero, "±"=0 to ~0.5 Log shift, "+"=~1 Log shift, "++"=1→2 Log shift (see FIG. 3A for examples of non-binding controls and binding antibodies).

Of note are those antibodies constructed and tested that showed unacceptable binding characteristics or inefficient killing of target cells that express both MDR1 and CD47, particularly as compared to the lead candidate.

For example, as shown in FIG. 8, the antibody containing 15D3 and 5F9 heavy chain charge-to-charge swapped Fc regions and a common MRK16 derived light chain ("15D3 IgG1 DD/5F9 IgG1 KK/MRK16") was tested showed desirable binding characteristics and produced enhanced killing (++) of target cells expressing both MDR1 and CD47. This antibody was thus selected as the lead candidate. In comparison, when the common light chain of the lead candidate (i.e., "MRK16") was substituted with alternative common light chains, such as "UIC2" (see e.g., "15D3 IgG1 DD/5F9 IgG1 KK/UIC2") or "9F11" (see e.g., "15D3 IgG1 KK/5F9 IgG1 DD/9F11") light chains, essentially no specific killing of cells that express both CD47 and MDR1 was observed. In addition, substituting alternative anti-MDR1 heavy chains, such as "MM4.17 2" or "UIC2" heavy chains, for the "15D3" heavy chain also resulted in significantly reduced specific killing of cells expressing both CD47 and MDR1 (see e.g., FIG. 8, e.g., "MM4.17 2 IgG1 DD/5F9 IgG1 KK/MRK16" and "UIC2 IgG1 KK/5F9 IgG1 DD/MRK16").

The effect of swapping the employed light chain (i.e., "LC shuffle") on antibody binding cells expressing the antigens was evaluated by ELISA and FACS binding assays. In testing LC shuffling with a CD47-specific heavy chain, the modified anti-CD47 heavy chain (5F9) was combined with a M89, 15D3, MRK16 or UIC2 light chain and binding was assessed. Results showing the effect of LC shuffle on the bispecific antibody binding of various anti-MDR1 molecules to CD47-Fc coated plates by ELISA are provided in Table 2:

TABLE 2

|  | 5F9/5F9 | 5F9/M89 | 5F9/15D3 | 5F9/MRK16 | 5F9/UIC2 |
|---|---|---|---|---|---|
| Bmax | 2.782 | 4.22 | 2.957 | 2.939 | 3.076 |
| Kd (nM) | 0.001968 | 1510 | 0.2571 | 0.1695 | 6.297 |

Of note in the above table is the 100-fold decrease in affinity seen in the combination of 5F9/MRK16 as compared to the un-swapped 5F9 control. Antibodies having a Kd for CD47 similar to the 5F9/MRK16 combination are preferred as they provide the requisite degree of specificity when used in a bispecific format such that the bispecific antibody has lower binding to normal cells and increased specificity for cancer cells that express CD47 at a higher level than a normal cell.

The results of LC shuffle testing, showing the effects of combining the 15D3 heavy chain with UIC2, MRK16 or 5F9 light chains on binding to CD47 as measured by ELISA, are provided in Table 3:

TABLE 3

|  | 15D3/15D3 | 15D3/UIC2 | 15D3/MRK16 | 15D3/5F9 |
|---|---|---|---|---|
| Bmax | 3.202 | 3.449 | 3.935 | 3.095 |
| Kd (nM) | 10.9 | 168.6 | 229.1 | 251.9 |

Of note in the above table is the surprising affinity of 15D3 to CD47 which was decreased ~20-fold after the combination of 15D3 HC with the MRK16 LC compared to the un-swapped 15D3 control.

The candidate construct having a combination of 15D3 and 5F9 heavy chains with a common MRK16 light chain has acceptable binding and target antagonizing characteristics. In comparison, other tested heavy and light chain combinations showed unacceptable binding and/or target cell killing results when tested. See FIG. 8.

Purification of mAbs

To purify antibody formats containing the Fc, 10 μl of MabSelect™ SuRe™ (GE Healthcare) per 1 ml of supernatant were added to the harvested medium and kept stirring at 4° C. overnight. The next day, the protein A resin was applied in a 24 well filter plate using a vacuum manifold unit (Pall Lifesciences, USA). The resin was washed with PBS and the antibody eluted in 50 mM phosphate pH 3 and neutralized with 10×PBS pH 13.

Histidine-tagged Fabs were purified following the same procedure using Ni Sepharose 6 Fast Flow histidine-tagged protein purification resin (GE Healthcare). The beads were washed with PBS followed by washes with 25 mM phosphate buffer pH 7.4, 150 mM NaCl supplemented with 20 mM of imidazole. The complex was eluted with 2 volumes of 25 mM phosphate buffer pH 7.4, 150 mM NaCl supplemented with 500 mM of imidazole. Finally, purified Fab was buffer-exchanged into PBS.

Sequences

Pgp/MDR1 has the following amino acid sequence:

MDLEGDRNGGAKKKNFFKLNNKSEKDKKEKKPTVSVFSMFRYSNWLDKLY

MVVGTLAAIIHGAGLPLMMLVFGEMTDIFANAGNLEDLMSNITNRSDIND

```
TGFFMNLEEDMTRYAYYYSGIGAGVLVAAYIQVSFWCLAAGRQIHKIRKQ

FFHAIMRQEIGWFDVHDVGELNTRLTDDVSKINEGIGDKIGMFFQSMATF

FTGFIVGFTRGWKLTLVILAISPVLGLSAAVWAKILSSFTDKELLAYAKA

GAVAEEVLAAIRTVIAFGGQKKELERYNKNLEEAKRIGIKKAITANISIG

AAFLLIYASYALAFWYGTTLVLSGEYSIGQVLTVFFSVLIGAFSVGQASP

SIEAFANARGAAYEIFKIIDNKPSIDSYSKSGHKPDNIKGNLEFRNVHFS

YPSRKEVKILKGLNLKVQSGQTVALVGNSGCGKSTTVQLMQRLYDPTEGM

VSVDGQDIRTINVRFLREIIGVVSQEPVLFATTIAENIRYGRENVTMDEI

EKAVKEANAYDFIMKLPHKFDTLVGERGAQLSGGQKQRIAIARALVRNPK

ILLLDEATSALDTESEAVVQVALDKARKGRTTIVIAHRLSTVRNADVIAG

FDDGVIVEKGNHDELMKEKGIYFKLVTMQTAGNEVELENAADESKSEIDA

LEMSSNDSRSSLIRKRSTRRSVRGSQAQDRKLSTKEALDESIPPVSFWRI

MRLNLTEWPYFVVGVFCAIINGGLQPAFAIIFSKIIGVFTRIDDPETKRQ

NSNLFSLLFLALGIISFITFFLQGFTFGKAGEILTKRLRYMVFRSMLRQD

VSWFDDPKNTTGALTTRLANDAAQVKGAIGSRLAVITQNIANLGTGIIIS

FIYGWQLTLLLLAIVPIIAIAGVVEMKMLSGQALKDKKELEGSGKIATEA

IENFRTVVSLTQEQKFEHMYAQSLQVPYRNSLRKAHIFGITFSFTQAMMY

FSYAGCFRFGAYLVAHKLMSFEDVLLVFSAVVFGAMAVGQVSSFAPDYAK

AKISAAHIIMIIEKTPLIDSYSTEGLMPNTLEGNVTFGEVVFNYPTRPDI

PVLQGLSLEVKKGQTLALVGSSGCGKSTVVQLLERFYDPLAGKVLLDGKE

IKRLNVQWLRAHLGIVSQEPILFDCSIAENIAYGDNSRVVSQEEIVRAAT

EANIHAFIESLPNKYSTKVGDKGTQLSGGQKQRIAIARALVRQPHILLLD

EATSALDTESEKVVQEALDKAREGRTCIVIAHRLSTIQNADLIVVFQNGR

VKEHGTHQQLLAQKGIYFSMVSVQAGTKRQ.
```

Nucleic acid sequences encoding Pgp/MDR1 are available: P Glycoprotein (ABCB1) (NM_000927) Human genomic DNA *Homo sapiens* ATP binding cassette subfamily B member 1 (ABCB1), Ref Seq Gene on chromosome 7 (NG_011513 gen)

Nucleic acid sequences encoding CD47 are available: *Homo sapiens* CD47 molecule (CD47), transcript variant 1, mRNA NCBI Reference Sequence: NM_001777.3

Anti CD47 5F9 antibody variable heavy chain sequence is as follows:

```
QVQLVQSGAEVKKPGASVKVSCKASGYTFTNYNMHWVRQAPGQRLEWMGT

IYPGNDDTSYNQKFKDRVTITADTSASTAYMELSSLRSEDTAVYYCARGG

YRAMDYWGQGTLVTVSS.
```

Anti-CD47 5F9 antibody variable light chain sequence is as follows:

```
DIVMTQSPLSLPVTPGEPASISCRSSQSIVYSNGNTYLGWYLQKPGQSPQ

LLIYKVSNRFSGVPDRFSGSGSGTDFTLKISRVEADVGVYYCFQGSHVPY

TFGQGTKLEIK.
```

Anti-MDR1 MRK16 antibody variable heavy chain sequence is as follows:

```
EVILVESGGGLVKPGGSLKLSCAASGFTFSSYTMSWVRQTPEKRLEWVAT

ISSGGGNTYYPDSVKGRFTISRDNAKNNLYLQMSSLRSEDTALYYCARYY

RYEAWFASWGQGTLVTVSA.
```

The sequence of the MRK16 antibody variable light chain is as follows:

```
DVLMTQTPVSLSVSLGDQASISCRSSQSIVHSTGNTYLEWYLQKPGQSPK

LLIYKISNRFSGVPDRFSGSGSGTDFTLKISRVEAEDLGVYYCFQASHFP

RTFGGGTKLEIK.
```

Antibody 15D3 sequences are available from U.S. Pat. No. 5,849,877, wherein the antibody 15D3 Heavy chain sequence is as follows: EVKVVESGGVLVRPGGSLKLS-CAASGFTFSRYTMSWVRQTPEKRLEWVATISSGGGN-TYY PDSVKGRFTVSRDNAMSSLYLQMSSLRSED-TALYYCARYGAGDAWFAYWGQGTLVTVSA (SEQ ID NO:24), and the antibody 15D3 Light chain sequence is as follows:

```
DVLMTQTPLSLPVSLGDQASISCRSSQSIVHSTGNTYLEWYLQKPGQSPK

LLIYKVSNRFSGVPDRFSGSGSGTDFTLKISRLEAEDLGVYYCFQGSHFP

RTFGGGTRLEIK.
```

The sequence of the anti-MDR1 UIC2 antibody light chain employed as described herein is as follows:

```
DVVMTQTPRSLPVSLGDQASISCRSSQSLLHSNGNTYLHWYLQKPGQSPK

LLIYKVSNRFSGVPDRFSGSGSGTDFTLKISRVEAEDLGVYFCSQSTHIP

PWTFGGGTKLDIK.
```

The sequence of the anti-MDR1 UIC2 antibody heavy chain employed as described herein is as follows:

```
AVQLQQSGPELVKTGASVKISCKASGYSFSNYYIHWVKQSHGKSLEWIGF

ISCYNGATFYNQKFKGKATFTVDTSSSTAYMKFNSLTFEDSAVYYCARLP

IQFGNFYPMDYWGQGTSVTVSS.
```

The sequence of the anti-MDR1 9F11 antibody light chain employed as described herein is as follows:

```
DVLMTQTPLSLPVSLGDQASISCRSSQSIVHRTGNTYLEWYLQKPGQSPK

LLIYKVSNRFSGVPDRFSGSGSGTDFTLKISRVEAEDLGVYYCFQGSHVP

YTFGGGTKLEIK.
```

The sequence of the anti-MDR1 9F11 antibody heavy chain employed as described herein is as follows:

```
EVKLVESGGGLVKFGGSLKLSCAASGFTLSSYYMSWVRQSPEKRLELVAV

INSNGGSTYYPDTVKGRFTISRDNAKNTLYLQMSSLKSEDTALYYCARPF

YYSNSPFAYWGQGTLVTVSS.
```

The sequence of the anti-MDR1 MM4.17 antibody heavy chain employed as described herein is as follows:

QVQLQESGGDLVKPGGSLKLSCAASGFTFSRYGMSWVRQTPDKRLEWVAT

ISSGGSYTYFPDSVKGRFTISRDNAKNTLYLQVSSLKSEDTAMYYCARPA

EFRGYSWFAYWGQGTTVTVSS.

The sequence of the anti-MDR1 M89 antibody light chain employed as described herein is as follows:

EIVLTQSPATLSLSPGERATLSCRASQSVGGSYLAWYQQKPGQAPRLLIY

GASRRATGIPARFSGSGSGTDFTLTISSLQPEDFASYFCQQTNTFPLTFG

GGTKVEIK.

The sequence of the anti-MDR1 M89 antibody heavy chain employed as described herein is as follows:

QVQLVQSGGGVVQPGRSLRLSCAASGFTFSSYGMHWVRQDPGKGLMWVSS

ISTDGSATKYADSVKGRFTISRDNAKNTVSLQMNSLRAEDTAVYYCVGGF

LGWWGQGTLVTVSS.

Results
Biophysical Analytical Test for Purified mAbs (GXII Instrument, Reduced and Non-Reduced Protein)

Purity and monomer content of the final protein preparation was determined by high-throughput analysis on a Caliper LabChip GXII using Protein Express LabChip Kit (Perkin-Elmer) as described by the manufacturer. The chip was automatically primed on the instrument with polymer solution containing 0.2% SDS and fluorescent staining dye. The de-stain channels were filled with polymer solution free of SDS and dye. Briefly, proteins in reducing and not reducing conditions were prepared by mixing a small volume (2-5 μL) of sample with the caliper sample buffer with or without DDT. The samples were denatured at 75° C. for 5 minutes, centrifuged at 2000 g for 3 minutes, and then run. Electropherograms were generated by LabChip GXII Touch software (Perkin Elmer).

Detection of CD47 and ABCB1 Specific Binding

Binding specificity of the mAbs, Fab and Bispecific IgG1 targeting CD47 was tested by ELISA using human CD47-Fc fusion protein (R&D systems). Briefly, microtiter plates were coated with 50 μl purified human CD47-Fc fusion protein at 0.5 μg/ml in PBS, and then blocked with 100 μl of 0.4% BSA in PBS. Dilutions of the different antibody formats were added in ⅓ sequential dilutions to each well and incubated for 1 hour at room temperature. The 5F9 known anti-CD47 antibody was used as a positive control, and human IgG1 was used as an isotype control. Plates were subsequently washed three times with PBS/Tween and then incubated with HRP-conjugated donkey anti-human constant specific secondary reagent for 1 hour at room temperature. After washing, plates were developed with HRP substrate. The reaction was stopped with 2M $H_2SO_4$, and OD was measured at 520 nM.

Binding specificity of the mAbs, Fab and Bispecific IgG1 was tested by FACS using 293T cell lines naturally expressing CD47, 293T naïve cells overexpressing human ABCB1 target, 293T naïve cells having ABCB1 knocked down using Lentiviral RNA vectors, CD47 knock out 293T cells and CD47 knock out 293T cells overexpressing human ABCB1. Briefly, the different cell lines were incubated with various amounts of mAbs or bispecific mAbs, or a human IgG1 isotype control antibody on ice for 1 hr. The cells were washed three times with FACS buffer (PBS containing 0.5% BSA). Alexa647 labeled goat anti-human antibody was added as a secondary antibody, and the samples were incubated on ice for another 1 hour. Samples were washed and analyzed using a BD FACS Canto (BD Biosciences).

This example demonstrates that construction of a bispecific hetero-bivalent antibody molecule, one arm of which binds to the efflux pump MDR1/Pgp and the other arm of which binds to the cancer checkpoint protein CD47. When both targets are simultaneously present on the surface of a cell, the bispecific antibody binds to the cell with relatively high affinity/avidity. In comparison, if either MDR1/Pgp or CD47 are absent, or substantially reduced, the binding of the bispecific antibody is significantly reduced or undetectable. (FIG. 4).

The bispecific antibody built, illustrated in FIG. 2, contains one arm (arm A) that binds to and antagonizes a transporter protein, (the efflux pump Pgp), and renders the cells more sensitive to chemotherapeutic agents. At the same time the other arm (arm B) binds to an "immuno-don't eat me" signal, (CD47), on the cell surface which, together with the IgG1 Fc, permits a more robust immune response against the cell.

Figure 3B:
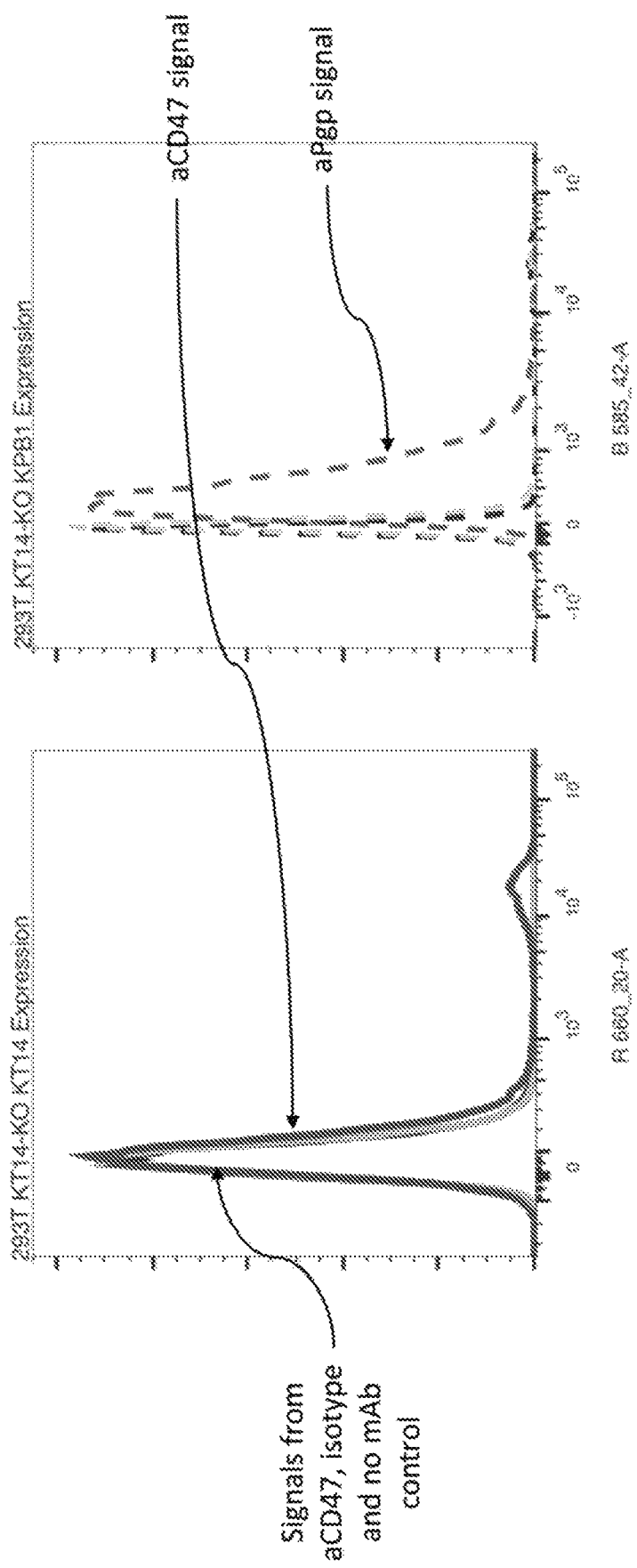
Figure 3C:
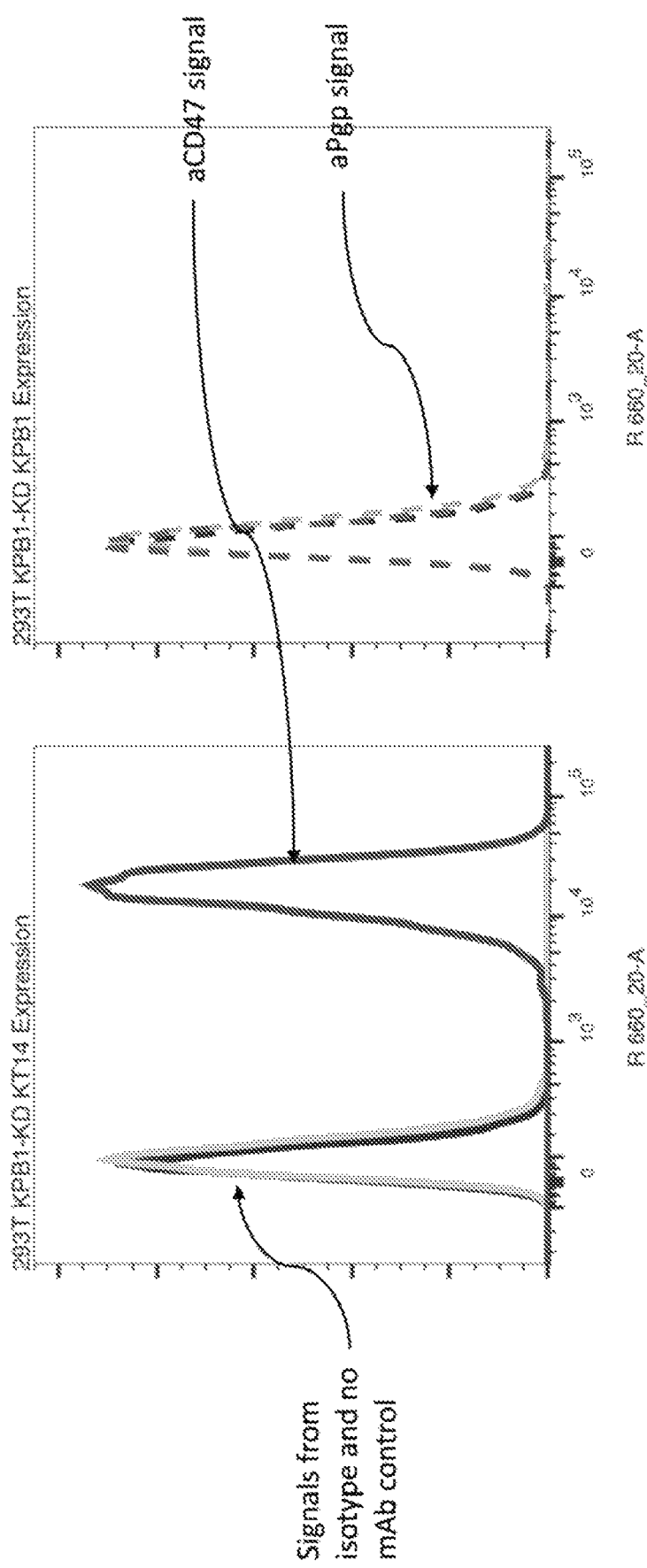
Figure 3D:
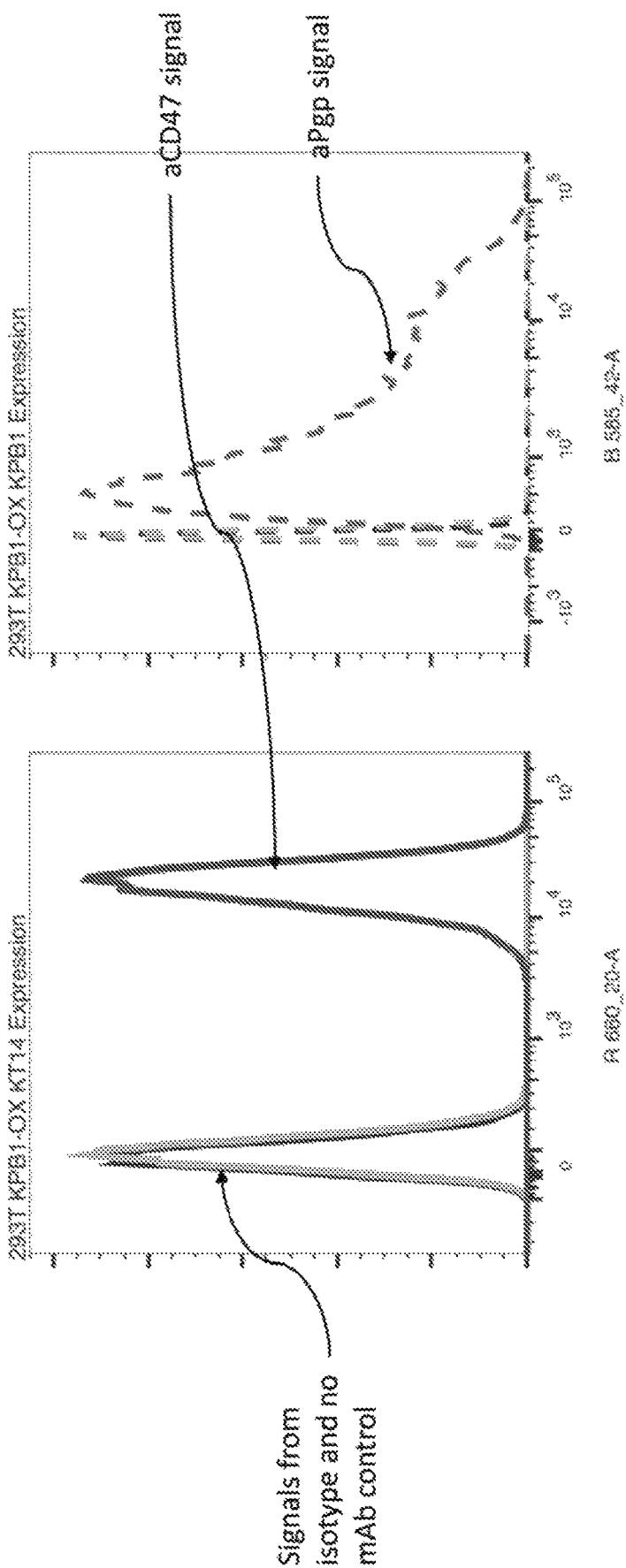
Figure 3F:
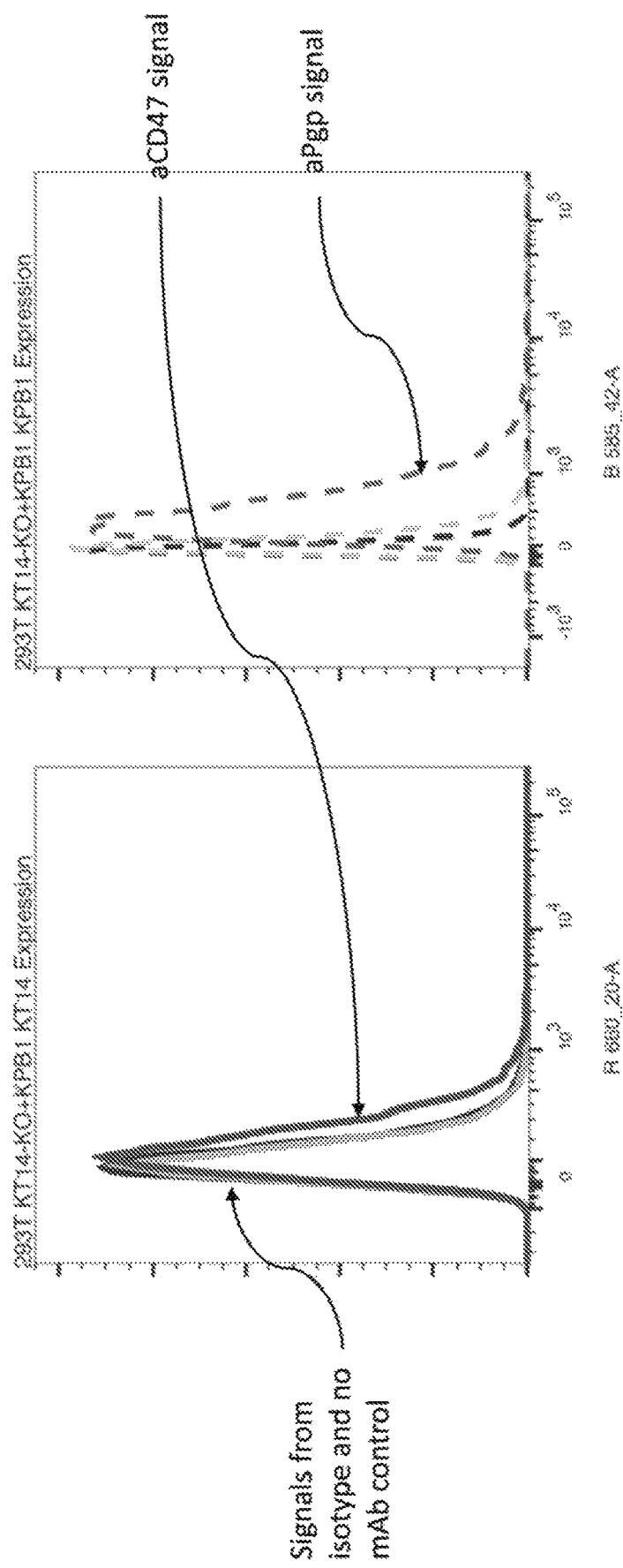

FIG. 3A-3F provide illustrations of FACS binding of the various reagent cell lines used to test candidate molecules. Some of these reagent cell lines were engineered, as described in the Methods and Materials section, with knock-down, knock-out or overexpression of target proteins to enable a precise and clear understanding of the targets involved; their presence or absence and the susceptibility of the cells to various antineoplastic agents. Specifically, FIG. 3A shows binding to naïve 293T cells, FIG. 3B shows binding to 293T CD47-KO (Knock-out) cells, FIG. 3C shows binding to 293T Pgp-KD (Knock-down) cells, FIG. 3D shows binding to 293T Pgp-ox ('over-expressors'), FIG. 3E shows binding to N6ADR (NALM6 Adriamycin resistant) cells, and FIG. 3F shows binding to 293T CD47-KO+ Pgp-ox cells.

Figure 4A:
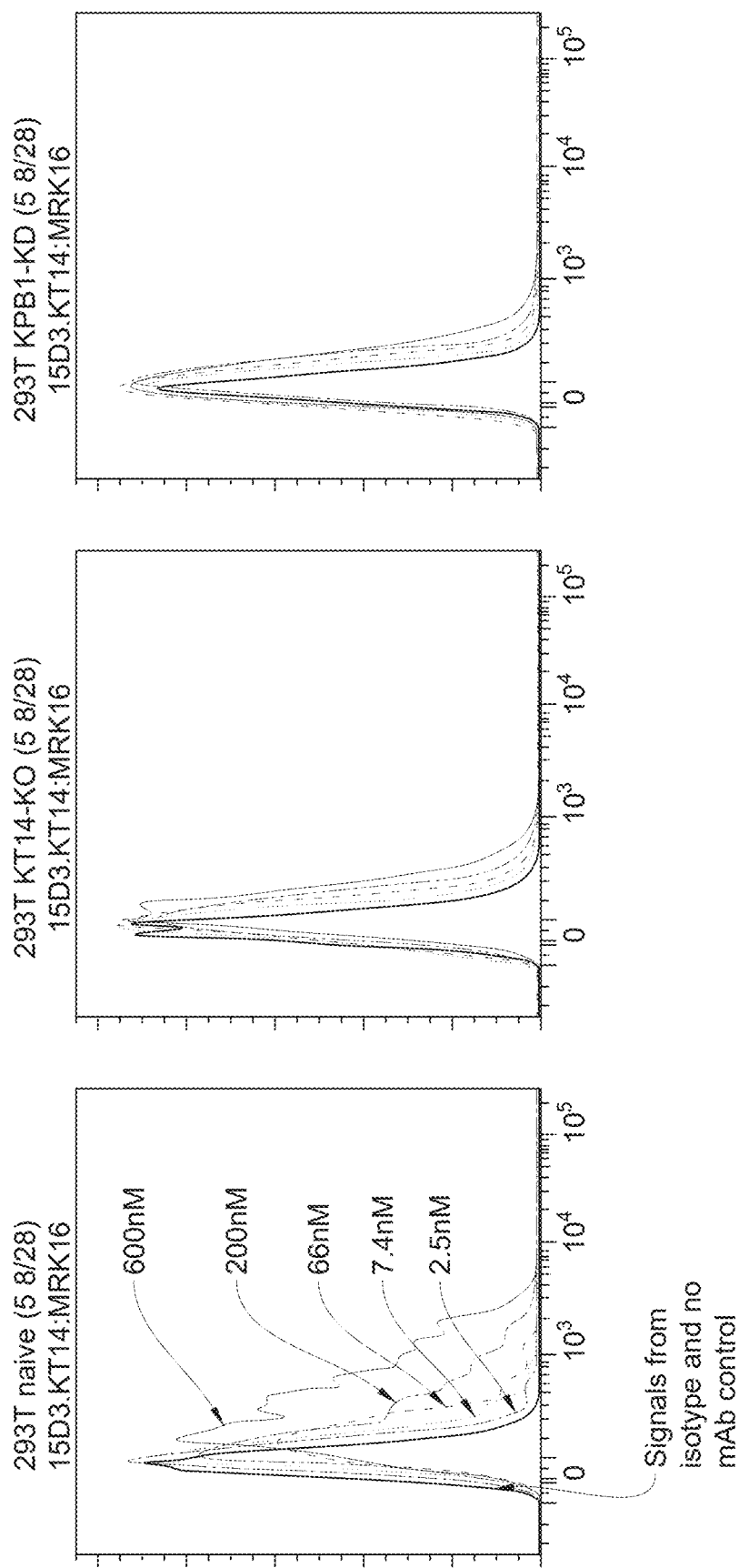
FIG. 4A-4B provide FACS analysis of binding of bispecific antibody (HC-15D3:HC-5F9:LC-MRK16) binding to a variety of reagent cell lines indicating specific binding when both targets are co-expressed (e.g., 293T naïve cells) and significantly reduced binding when only one of the targets is present (e.g., 293 KT14-KO and KPB1-KD (Pgp is also referred to in some instances herein as "KPB1")).
Figure 4B:
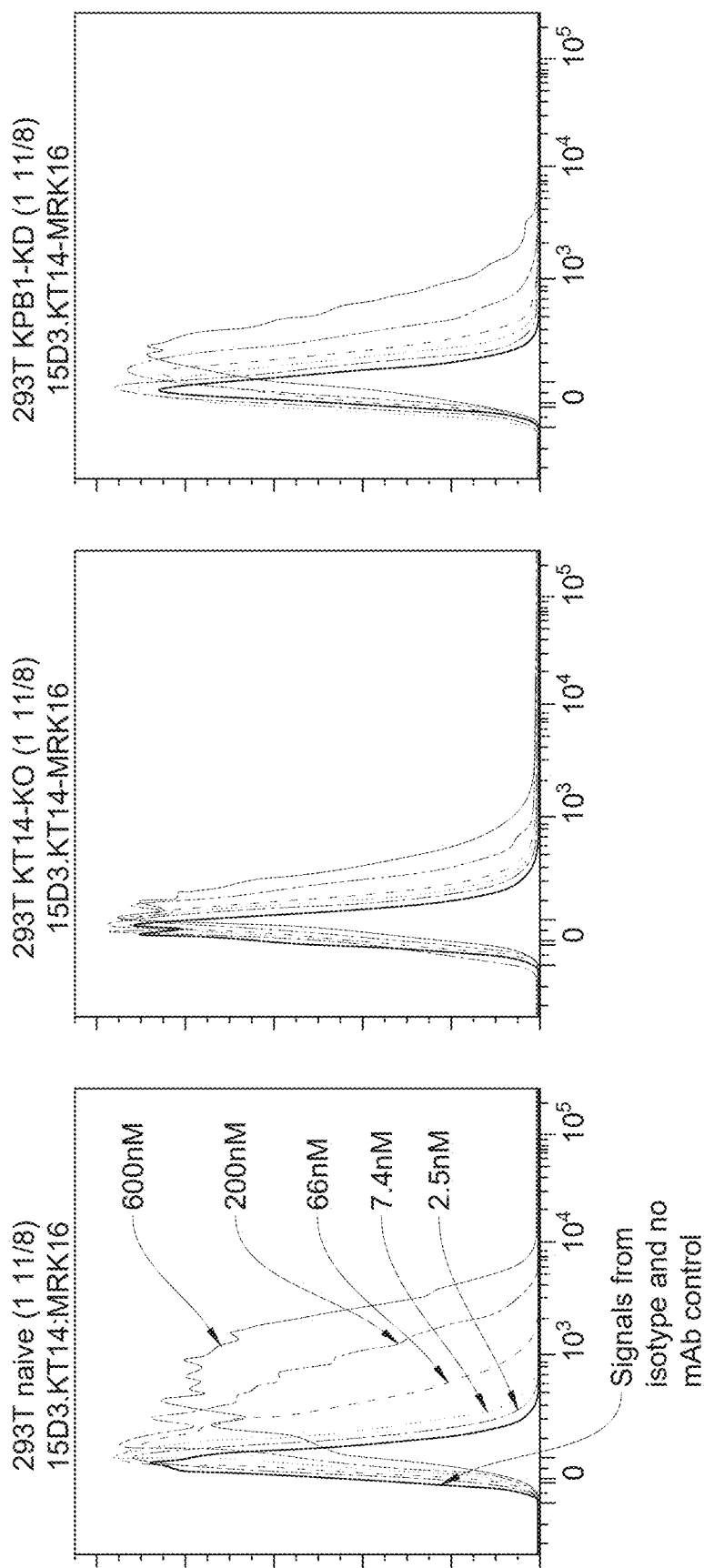

In FIG. 4A-4B, the binding of the bispecific antibody is shown by FACS analysis against a variety of cell lines. The first scan (left panel in FIG. 4A and FIG. 4B) illustrates binding of the antibody to cells co-expressing both targets, (Pgp and CD47). The next two scans (middle and right panels in FIG. 4A and FIG. 4B) illustrate the absence or significantly diminished binding when either Pgp (referred to as "KBP1", right panel) or CD47 (referred to as "KT14", middle panel) is knocked down (KD) or knocked out (KO) of the cell line. FIG. 4A-4B further show binding with titrated antibody concentrations of 600 nM, 200 nM, 66 nM, 7.4 nM and 2 nM, with the signal measured from isotype and no antibody control also provided. The respective antibody concentrations are indicated in the left panel of FIG. 4A and FIG. 4B, and the measured signal from these different concentrations are generally overlapping in the middle and right panels of FIGS. 4A and 4B. FIG. 4A and FIG. 4B represent results obtained from two different batches of antibody.

Figure 5:
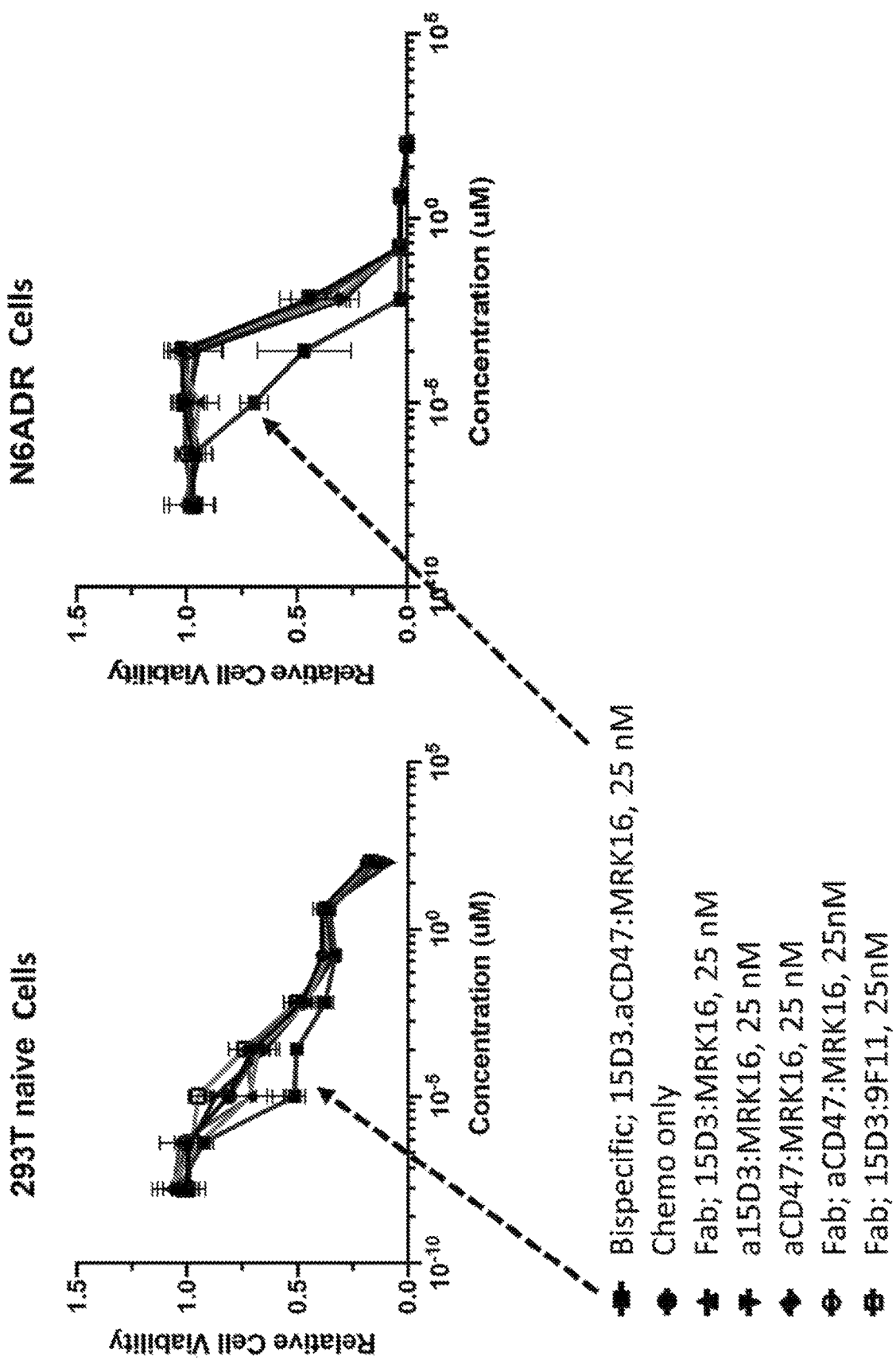
FIG. 5 provides chemosensitivity analysis showing naïve 293T and N6ADR cell line susceptibility to paclitaxel in the presence of various monovalent, Fab and bispecific antibody molecules described herein. The cells (naïve 293T cells (left panel) and N6ADR cells (right panel)) showed enhanced sensitivity in the presence of the 15D3.aCD47:MRK16 bispecific, e.g., as compared to treatment with chemotherapy only ("Chemo only") or chemotherapy in combination with the other antibodies (15D3:MRK16 Fab; a15D3:MRK16 antibody; aCD47:MRK16 antibody; aCD47:MRK16 Fab; and 15D3:9F11 Fab).

FIG. 5 and FIG. 6A-6C illustrate the enhanced killing of cells, by the antineoplastic agent paclitaxel, when cells are bound by the 15D3.aCD47:MRK16 bispecific antibody (highlighted with arrows). The data provided in FIG. 5 shows that the sensitivity of naïve 293T cells and N6ADR cells to the chemotherapeutic was enhanced by the 15D3.aCD47:MRK16 bispecific antibody, e.g., as compared to treatment with chemotherapy only ("Chemo only") or chemotherapy in combination with the other antibodies (15D3:MRK16 Fab; a15D3:MRK16 antibody; aCD47: MRK16 antibody; aCD47:MRK16 Fab; and 15D3:9F11 Fab).

Figure 6A:
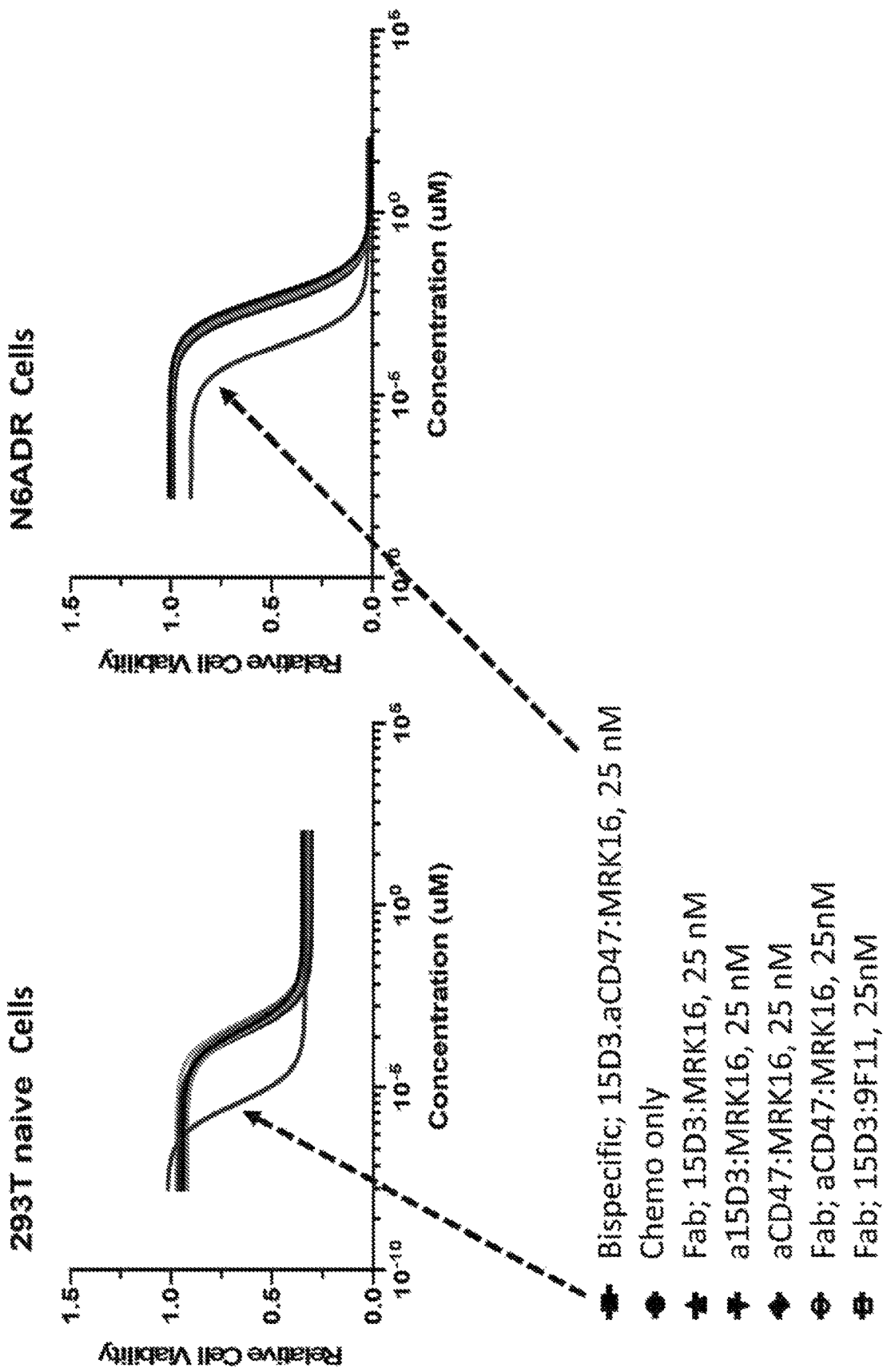
Figure 6B:
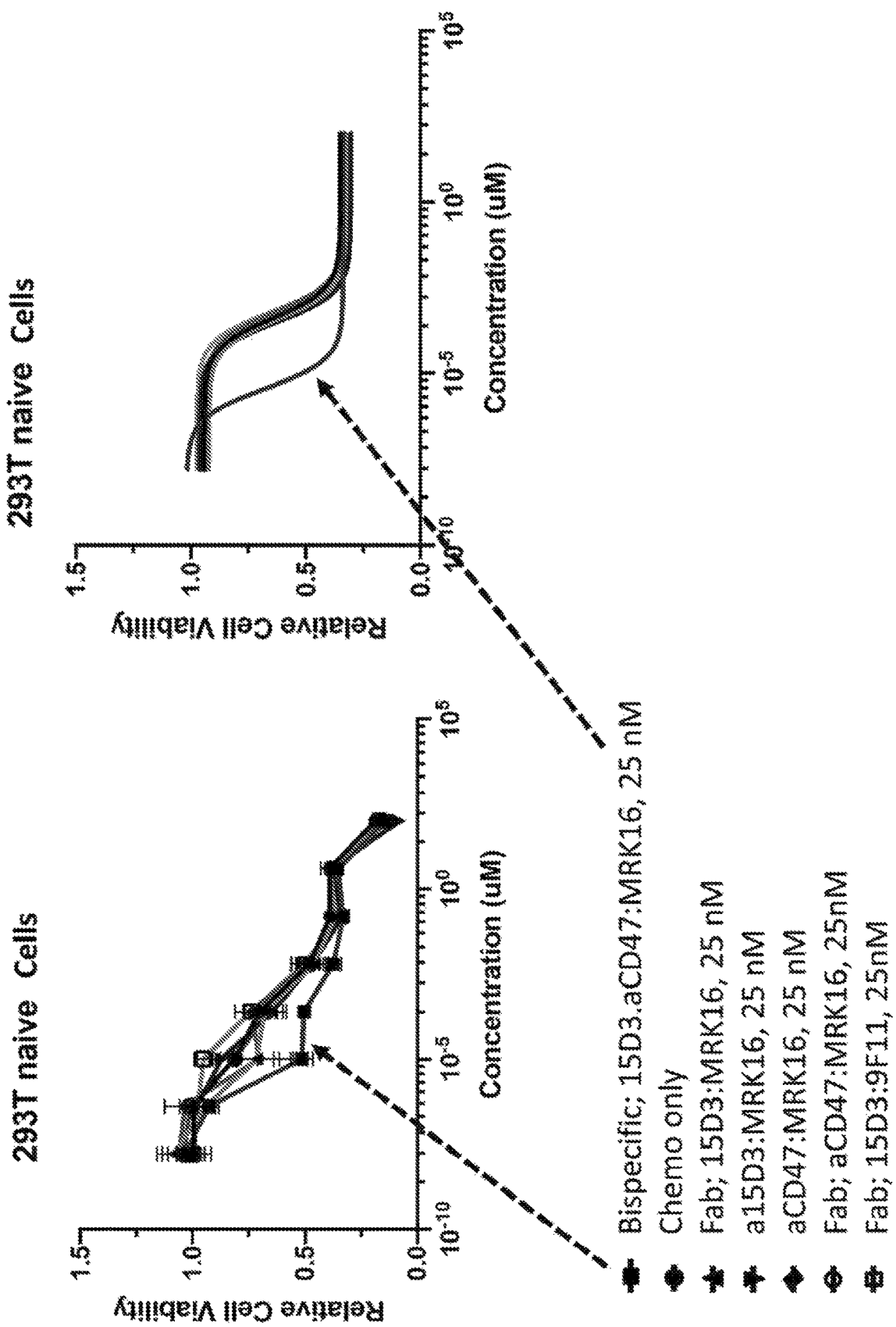

FIG. 6A provides form-fitted plots of the data provided in FIG. 5, produced using GraphPad Prism software, GraphPad Software, Inc. FIG. 6B provides a re-representation of the data shown in FIG. 5 and FIG. 6A, showing a side-by-side comparison of the raw data (left) with the fitted data (right) for the naïve 293T cells. FIG. 6C provides a re-representation of the data shown in FIG. 5 and FIG. 6A, showing a side-by-side comparison of the raw data (left) with the fitted data (right) for the N6ADR cells. Collectively these data illustrate enhanced susceptibility and/or a drug sensitizing effect of two different drug resistant cell lines (293T and N6ADR) that co-express the targets Pgp and CD47 to a chemotherapeutic when in the presence of the 15D3.aCD47: MRK16 bispecific antibody. In comparison, a variety of other tested antibodies directed to the same targets have no significant sensitization effects.

Figure 7:
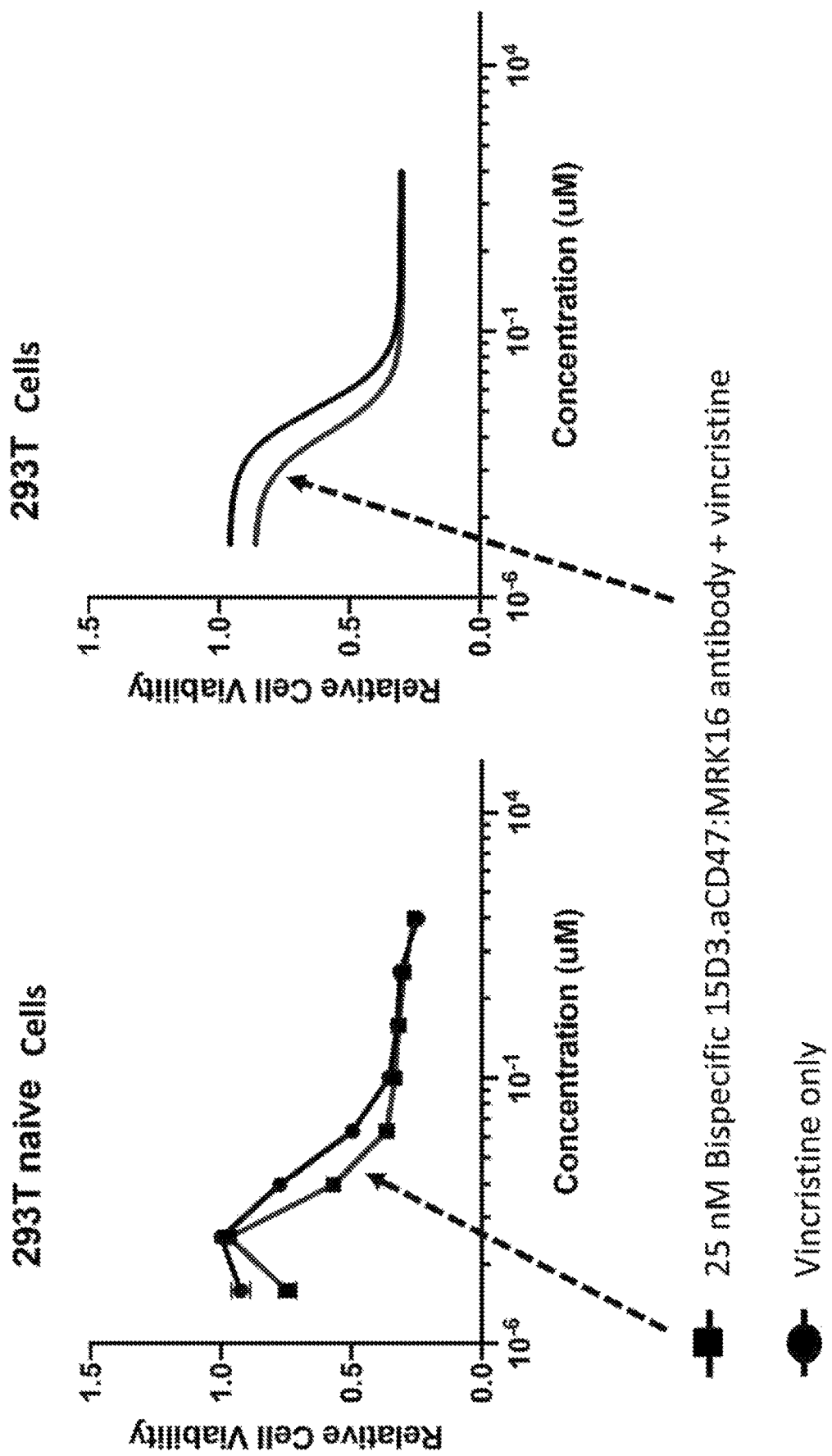
FIG. 7 demonstrates a drug sensitizing effect of the 15D3.aCD47:MRK16 antibody when the antibody was used in combination with vincristine.

FIG. 7 shows enhanced in vitro killing of naïve 293T in the presence of 15D3.aCD47:MRK16 bispecific antibody (25 nM) and the chemotherapeutic vincristine, e.g., as compared to cells treated with vincristine alone. These data demonstrate that the drug sensitizing effect is not limited to treatment with paclitaxel and that the 15D3.aCD47:MRK16 bispecific antibody broadly enhances drug sensitivity when used in combination with multiple different agents.

This combination of specific and concomitant targeting revealed in these results demonstrates enhanced therapeutic effects with antineoplastic agents against cancer cells, including those that may be chemo-resistant, while sparing normal tissue from these antagonistic effects. At the same time, the binding to and potentially antagonizing or masking the second protein, e.g. the "don't eat me" signal in this example, is confined to cancer cells co-overexpressing this target together with the transporter protein (efflux pump) thereby enabling simultaneous, specific and beneficial targeting of this second protein.

Thus, specificity is achieved by preferential binding when the combination of targets is displayed on the cell surface. This binding by itself may focus an immune response against the cells (e.g., by incorporation of an IgG1 Fc into the bispecific molecule) but there are also added benefits where the bispecific molecule counteracts activity of one or both of the pair of target proteins involved in the specific binding—as is the case demonstrated in this example. Put another way, in addition to the desirable degree of tissue (tumor) specificity that the bispecific antibody provides, the antibodies of this disclosure also provide the benefits of concurrently targeting two different cellular mechanisms whereby the result may be additive, synergistic or otherwise advantageous. The effects of this "orthogonal targeting" by the antibody molecule may be further enhanced by tuning or adapting the Fc region of the antibody to enhance or reduce a concomitant immune response towards the bound molecules or cells.

Accordingly, this approach has many potential applications in the realms of cancer therapy where drug resistance, multi-drug resistance, immuno-masking or other combinations of targetable cell surface proteins are involved, (including e.g., TK activators, signaling proteins, aberrantly over-expressed proteins, etc.), particularly if one of the involved proteins is a transporter protein. Furthermore, where more than two different targets may be simultaneously co-over-expressed on cancer cells, this approach is applicable with the use of appropriate tri-valent, or other multi-valent, molecules that enable specific and active targeting of such cells.

In many cases, relative to normal cells, co-overexpression of certain proteins occurs on cancer cells, particularly cancer cells that are multi-drug resistant. The bispecific molecule described herein binds a cell strongly when two different target proteins (i.e., the transporter protein and the second protein) are present but less strongly when the concentration of one or the other of this pair of proteins is absent or reduced, e.g. as seen on normal cells. When bound, the bispecific antibody modulates viability, activity or susceptibility of the bound cell by antagonizing, activating or masking (or a combination of these effects) the surface proteins targeted.

In an advantageous format the two distinct Heavy Chains, each binding to separate targets, are brought together using standard methods (to form a hetero-bivalent pair). These distinct Heavy Chains may be employed in some embodiments in combination with an appropriate single Light Chain that permits binding of either HC to its cognate target separately but also permits each arm to bind their respective targets when they are combined into the resulting bispecific antibody format. If both targets are present simultaneously on a cell surface (rather than only one or the other) the binding of the bispecific antibody is significantly enhanced thus resulting in tissue specificity.

In this instance, the bispecific antibody may bind strongly and specifically to a cancer cell displaying the described combination of targets while antagonizing one or both of these targets, and/or inhibiting their normal functions, to render the cell more susceptible or sensitized, e.g., to further chemotherapeutic agents and/or the subject's immune system.

Example 2: Reduced Affinity Monospecific Bivalent Anti-MDR1 Antibody and Anti-CD47 Antibody Anti-Cancer Activity and Comparison to the Bispecific Antibody This example demonstrates that reduced affinity anti-MDR1 antibody and anti-CD47 antibody while ineffective in treating cancer when administered alone, do reduce tumor volume when co-administered. The bispecific antibody (15D3 HC::MRK16 LC::5F9 HC::MRK16 LC) was more efficacious than the co-administration of the anti-MDR1 antibody and anti-CD47 antibody in the absence of a chemotherapeutic agent. 15D3 HC::MRK16 LC::5F9 HC::MRK16 LC is also referred to herein as 15D3 HC::MRK16 LC::5F9 HC.

The anti-MDR1 antibody included two heavy chains of the 15D3 antibody and two light chains of the MRK16 antibody. This antibody is referred to as 15D3/MRK16 monoclonal in FIG. 9. The anti-CD47 antibody included two heavy chains of the 5F9 antibody and two light chains of the MRK16 antibody. This antibody is referred to as KT14/MRK16 monoclonal in FIG. 9. The bispecific antibody included 15D3 HC::MRK16 LC::5F9 HC::MRK16 LC and is referred to as KbisP1.1 in FIG. 9.

Figure 9:
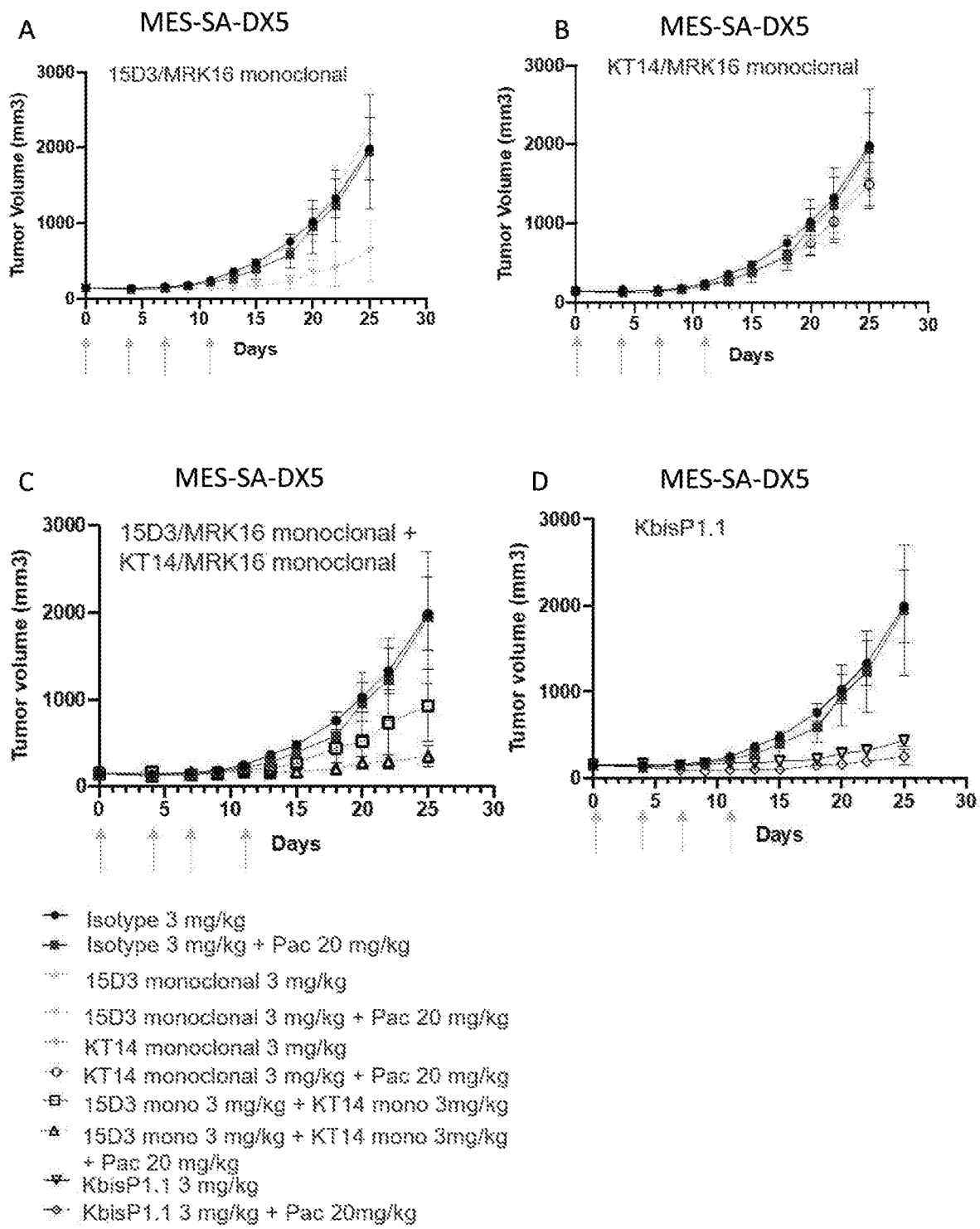
FIG. 9 shows effect of the indicated antibodies, without chemotherapy, on MES-SA-DX5 (Uterine sarcoma) tumor volume.

FIG. 9 shows the effect of administration of the indicated antibodies on the volume of tumors containing multidrug resistant N6ADR cells. N6ADR cells were injected into a cohort of 6 mice per test group prior to administration of the indicated antibodies. The antibodies were administered once palpable tumors reached a size of about 100-150 mm³ (about 7 days after injection of tumor cells). Antibodies were administered on day 0, day 4, day 7, and day 11. Tumor volumes were measured and are plotted. Panel A: 15D3/MRK16 monoclonal anti-MDR1 antibody. Panel B: KT14/MRK16 monoclonal anti-CD47 antibody. Panel C: Co-administration of 15D3/MRK16 monoclonal anti-MDR1 antibody and KT14/MRK16 monoclonal anti-CD47 antibody. Panel D: KbisP1.1 antibody.

The indicated antibodies were administered with or without the chemotherapeutic agent paclitaxel. Antibody was dosed about 1-4 hrs prior to Paclitaxel.

The 15D3/MRK16 monoclonal anti-MDR1 antibody and the KT14/MRK16 monoclonal anti-CD47 antibody alone showed no significant effect on tumor volume. The 15D3/MRK16 monoclonal anti-MDR1 antibody rendered the chemoresistant N6ADR cells sensitive to paclitaxel. The chemosensitization effect was specific to 15D3/MRK16 monoclonal anti-MDR1 antibody and was not observed for the KT14/MRK16 monoclonal anti-CD47 antibody. See Panels A and B.

The co-administration of the 15D3/MRK16 monoclonal anti-MDR1 antibody and the KT14/MRK16 monoclonal anti-CD47 antibody reduced tumor volume to an extent similar to seen when 15D3/MRK16 monoclonal anti-MDR1 antibody and paclitaxel were co-administered. The efficacy of co-administration of the 15D3/MRK16 monoclonal anti-MDR1 antibody and the KT14/MRK16 monoclonal anti-CD47 antibody against the tumor was further increased when paclitaxel was also administered. These data show that the co-administration of the 15D3/MRK16 monoclonal anti-MDR1 antibody and the KT14/MRK16 monoclonal anti-CD47 antibody can be used in the presence or absence of a chemotherapeutic agent to treat cancer. See Panel C.

Panel D shows that the bispecific antibody is more efficacious than co-administration of the 15D3/MRK16 monoclonal anti-MDR1 antibody and the KT14/MRK16 monoclonal anti-CD47 antibody.

The materials and methods for this example are similar to those described for Example 1.

Example 3: The Bispecific Antibody is Efficacious Against N6ADR Cell-Based Xenografts Materials:
Cells: NALM6 (ATCC) and NALM6 ADR (ATCC), B cell precursor lymphoblastic leukemia cell lines used in this study. NALM6 ADR is a multidrug resistant cell line derived from NALM6 cells.

Mice: Sixty-five 5-6-weeks-old female SCID-Beige mice (Charles River) were used in this study.

Reagents: BisP1.1 (15D3 heavy chain/KT14 heavy chain/MRK16 light chain), Human Isotype IgG1 (Bioxcell), Paclitaxel (Sigma), Valspodar (Sigma).

Methods:
Cell culture: Both NALM6 and NALM6 ADR cells were maintained in RPMI medium supplemented with 10% FBS and 1% penicillin and 1% streptomycin at 37° C., 5% $CO_2$. Cell lines used were authentic and confirmed to be *mycoplasma* negative.

Inoculation-$2\times10^6$ cells diluted in PBS:Matrigel (1:1) were subcutaneously injected using a 27G insulin syringe into fifty anesthetized 5-6-week-old female SCID-Beige mice under sterile conditions.

Dosing—
NALM6 subcutaneous tumors: Mice were randomized into three groups of five mice each—(i) Control vehicle, (ii) 5 mg/kg and (iii) 20 mg/kg of paclitaxel.

NALM6 ADR subcutaneous tumors: Mice were randomized into nine groups of five mice each—(i) Control isotype IgG1 15 mg/kg, (ii) Control isotype IgG1 15 mg/kg and 5 mg/kg of paclitaxel, (iii) Control isotype IgG1 15 mg/kg and 20 mg/kg of paclitaxel, (iv) BisP1.1 15 mg/kg, (v) BisP1.1 15 mg/kg and 5 mg/kg of paclitaxel, (vi) BisP1.1 15 mg/kg and 20 mg/kg of paclitaxel (vii) Valspodar 20 mg/kg (viii) Valspodar 20 mg/kg and 5 mg/kg of paclitaxel and (ix) Valspodar 20 mg/kg and 5 mg/kg of paclitaxel. Antibody, Valspodar and paclitaxel were dosed intraperitoneally twice a week for four consecutive weeks. Antibody/valspodar were injected at least 4 hours prior to paclitaxel injection.

Paclitaxel preparation: Since paclitaxel is poorly soluble, a master stock of 50 mg/ml was prepared in absolute ethanol:Kolliphor (1:1). Prior to injection the stock was diluted to recommended doses of 5 mg/kg or 20 mg/kg with PBS maintaining a ratio of (1:16).

Measurements: Tumor measurements were done thrice a week using a calibrated Vernier Caliper and tumor volume calculated as per the formula $\frac{1}{2}*L*S*S$ where L is the long axis and s is the short axis of the tumor. Body weights were recorded before treatment started and were continuously monitored throughout the study. Animal survival was evaluated from the first day of treatment until death. To avoid suffering, mice were euthanized when turning moribund according to the above-mentioned predefined criteria: rapid weight loss, loss of ability to ambulate, labored respiration, or inability to drink or feed.

Statistics: Tumor volume and body weights were compared between different experimental groups using exact one-way analysis of variance (ANOVA). Kaplan-Meier survival curves were compared between different treatment groups using the log-rank (Mantel-Cox) test. Statistical analyses were performed using Graph Pad Prism (GraphPad, San Diego, CA, USA) software. The level of significance was set at $p<0.05$ for all analyses.

Figure 10:
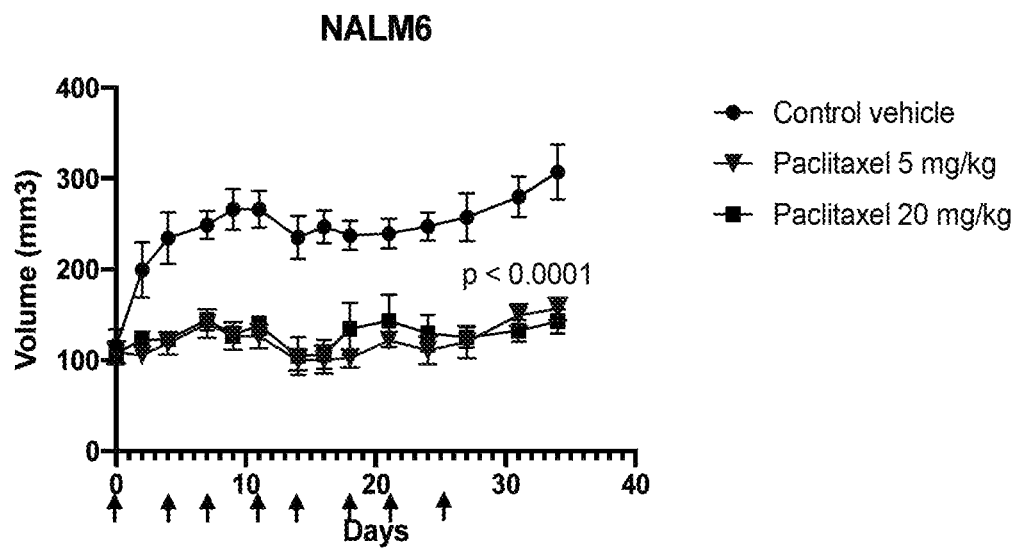
FIG. 10 shows effect of paclitaxel on tumor growth inhibition of NALM6 cells.
Figure 11:
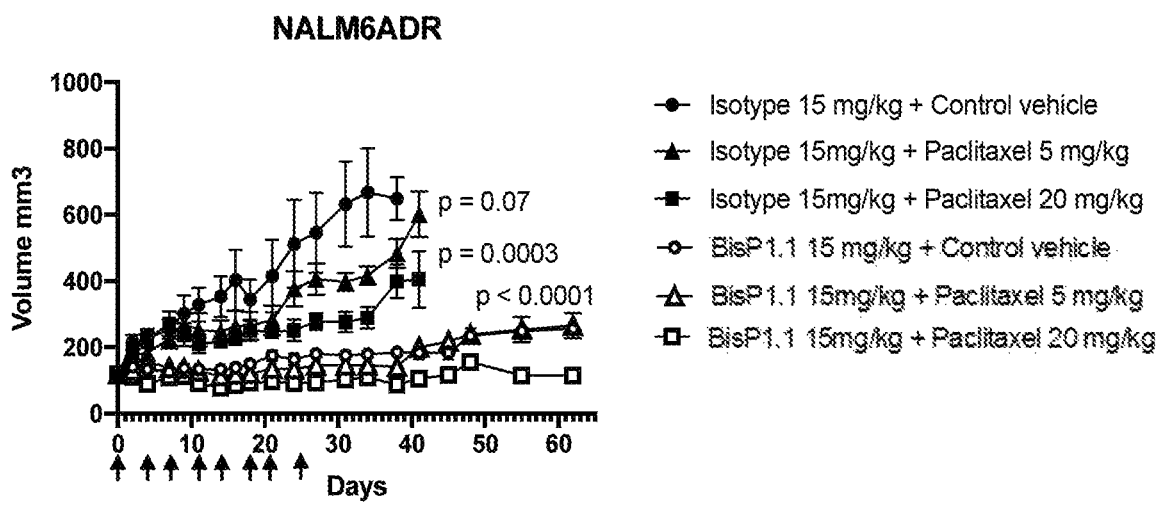
FIG. 11 shows effect of BisP1.1 on tumor growth inhibition of paclitaxel resistant NALM6ADR cells.

Results
NALM6 cells demonstrated increased sensitivity to paclitaxel compared to the multidrug resistant NALM6ADR cells. NALM6 cells demonstrated significant ($p<0.0001$) tumor growth inhibition to paclitaxel at doses of 5 mg/kg and 20 mg/kg. In contrast NALM6ADR cells showed significantly less tumor growth inhibition at 5 mg/kg with modest inhibition at 20 mg/kg (FIG. 11). This confirmed paclitaxel resistance in NALM6ADR cells in vivo (FIG. 10 and FIG. 11).

Figure 12:
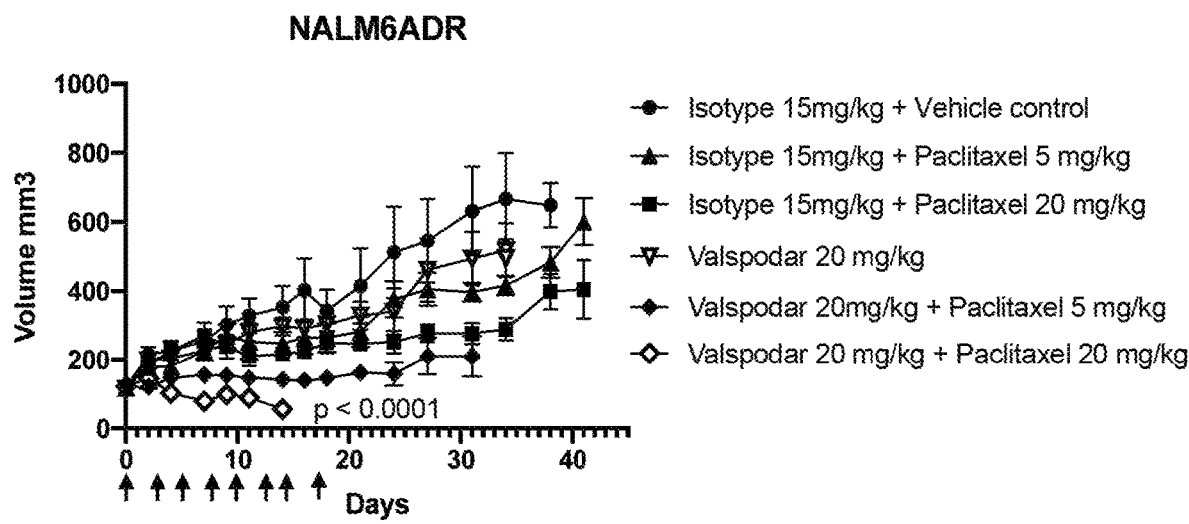
FIG. 12 shows effect of valspodar on tumor growth inhibition of paclitaxel resistant NALM6ADR cells.
Figure 13:
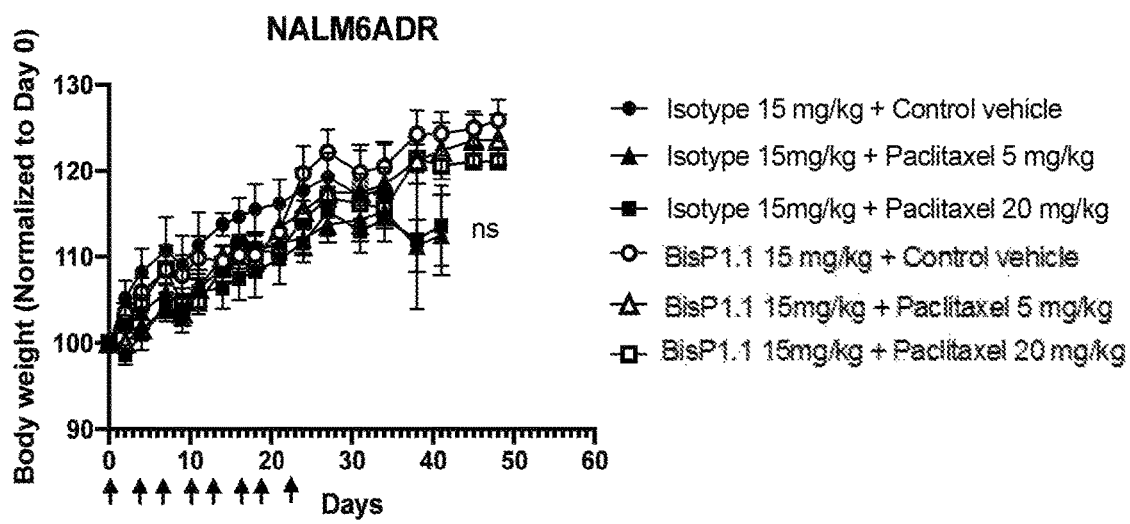
FIG. 13 shows effect of BisP1.1 on body weight of mice implanted with paclitaxel resistant NALM6ADR cells.
Figure 14:
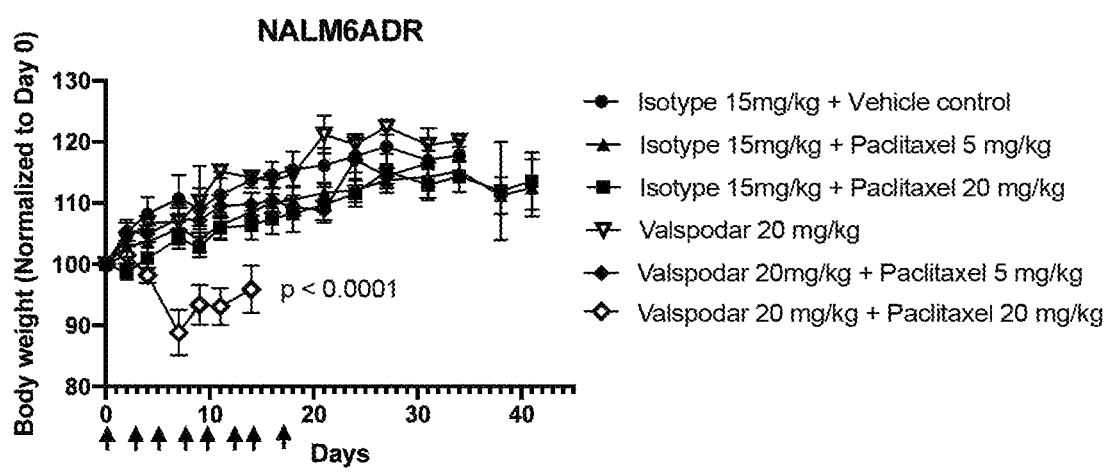
FIG. 14 shows effect of valspodar on body weight of mice implanted with paclitaxel resistant NALM6ADR cells.

Further in NALM6ADR models injection of BisP1.1 at 15 mg/kg dose had a strong inhibition of tumor growth (FIG. 11). Similarly, BisP1.1 at 15 mg/kg in combination with 5 mg/kg and 20 mg/kg of paclitaxel significantly reduced tumor growth (FIG. 11). Consistently valspodar, a small molecule inhibitor of ABCB1, chemosensitized NALM6ADR tumors (FIG. 12). However, in contrast to the BisP1.1 plus paclitaxel combination group, mice treated with a combination of valspodar and paclitaxel 20 mg/kg showed significant reduction in body weight (FIG. 13 and FIG. 14).

Figure 15:
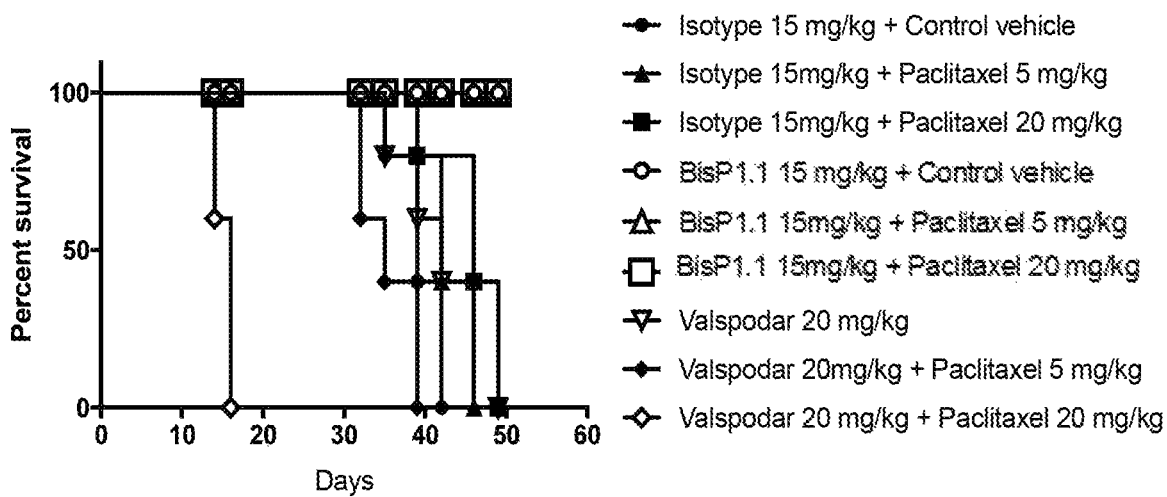
FIG. 15 shows effect of KBisP1.1 on survival of mice implanted with paclitaxel resistant NALM6ADR cells.

Mice treated with valspodar and paclitaxel 20 mg/kg had the lowest survival compared to control. Mice treated with BisP1.1 or BisP1.1 plus paclitaxel had prolonged survival compared to control or paclitaxel treated mice (FIG. 15).

Conclusion: BisP1.1 significantly inhibited tumor growth of NALM6ADR cells both alone and in combination with paclitaxel. BisP1.1 did not induce any loss in mouse body weight. Mice treated with BisP1.1 and Bis1.1 plus paclitaxel combination demonstrated prolonged survival in mice compared to control and paclitaxel treated cohorts.

Figure 16:
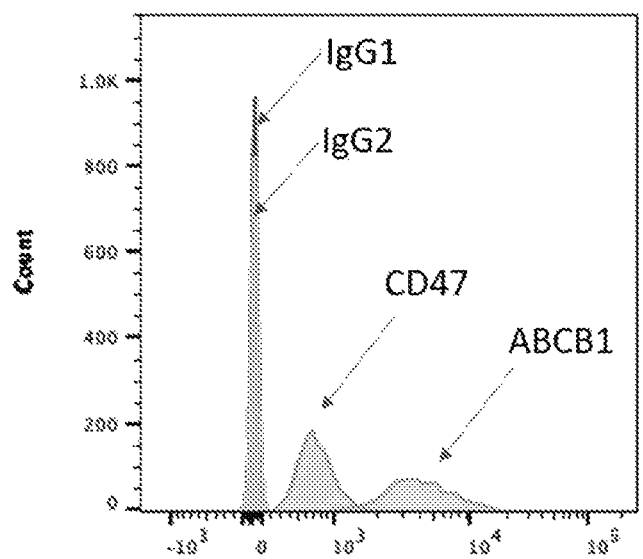
FIG. 16 shows expression of CD47 and ABCB1 on surface of A2780ADR cells.
Figure 17:
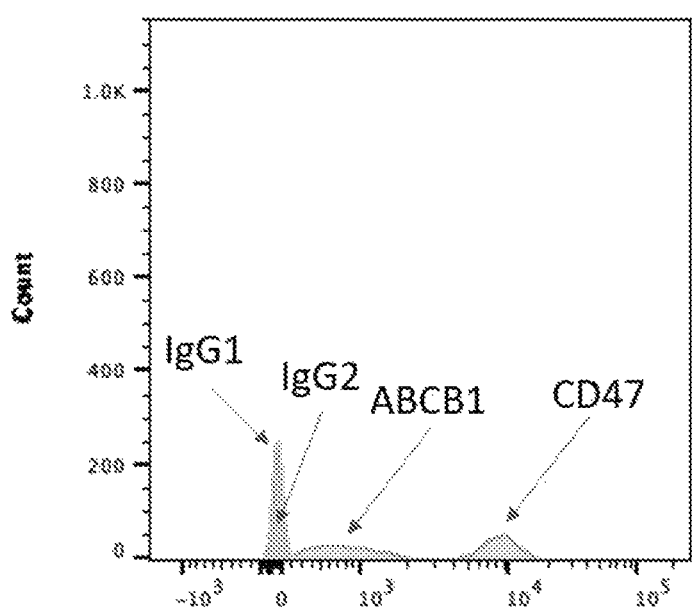
FIG. 17 shows expression of CD47 and ABCB1 on surface of HeyT30 cells.

Example 4: The Bispecific Antibody is Efficacious Against Multiple Different Cancer Models The BisP1.1 bispecific antibody was efficacious against two additional multidrug resistant (MDR) cancer cell lines in xenograft studies. The A2780ADR MDR cancer cell line expresses both CD47 and ABCB1. The HeyT30 MDR cancer cell line also expresses both CD47 and ABCB1 but at a lower level compared to A2780ADR cells (FIGS. 16 and 17). Both the A2780ADR and the HeyT30 cell lines are of ovarian origin. PE-conjugated, commercially available anti-MDR1 and anti-CD47 reagent antibodies were used; for MDR1, Biolegend Cat. No. 348606 and, CD47, Biolegend Cat. No. 323108.

Figure 18:
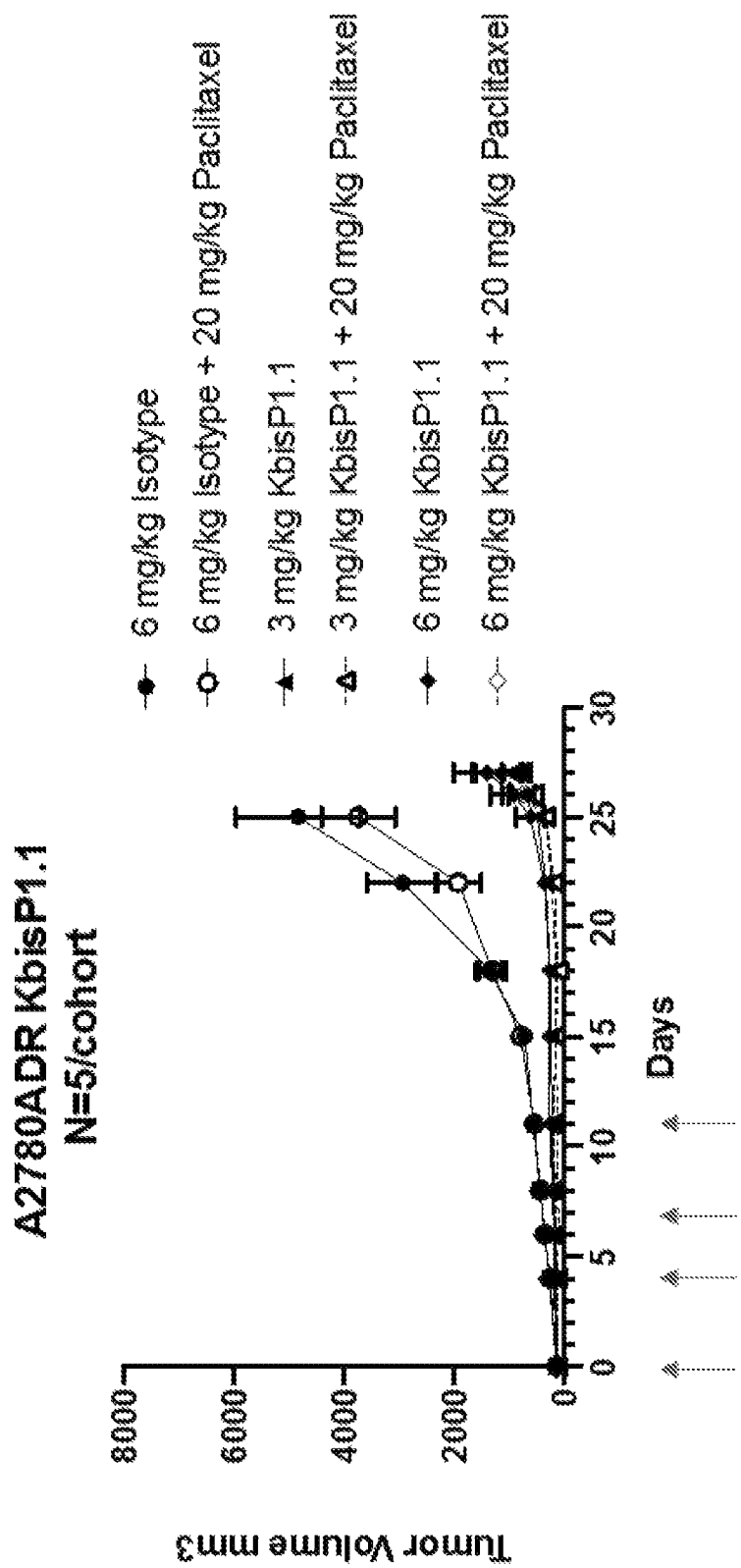
FIG. 18 shows reduction in A2780ADR tumor volume in vivo following administration of KBisP1.1 with or without Paclitaxel.
Figure 19:
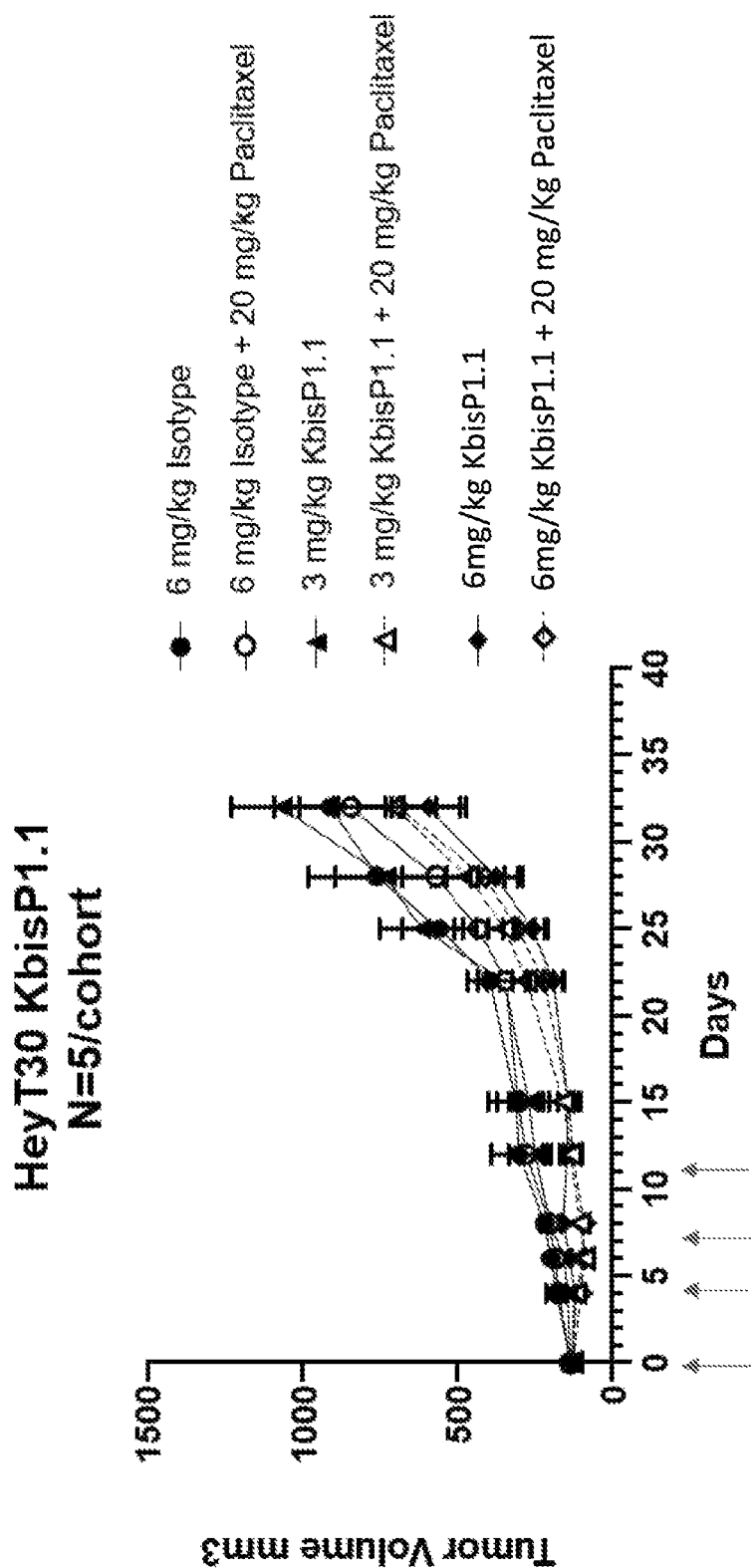
FIG. 19 shows reduction in HeyT30 tumor volume in vivo following administration of KBisP1.1 with or without Paclitaxel.

A2780ADR MDR cancer cell line and HeyT30 MDR cancer cell line were injected into mice according to protocols described in Example 3. Mice were treated with BisP1.1 bispecific antibody with or without paclitaxel. As seen in FIG. 18, BisP1.1 bispecific antibody is efficacious in reducing A2780ADR MDR cancer cell tumor volume with or without paclitaxel. BisP1.1 bispecific antibody is also efficacious in reducing HeyT30 MDR cancer cell tumor volume with paclitaxel when a lower concentration of the antibody is used. At a higher concentration the BisP1.1 bispecific antibody was efficacious with and without paclitaxel (FIG. 19).

Example 5: KbisP1.1 Bispecific Antibody is More Efficacious than Anti-MDR1 15D3 Antibody Against MDR Cells and Chemo-Sensitizes MDR Cancer Cells in a Dose Dependent Manner Tumors formed by injecting multidrug resistant N6ADR cells in mice were treated by administering the anti-MDR1 antibody 15D3, with or without paclitaxel or administering KbisP1.1 with or without paclitaxel.

Figure 20:
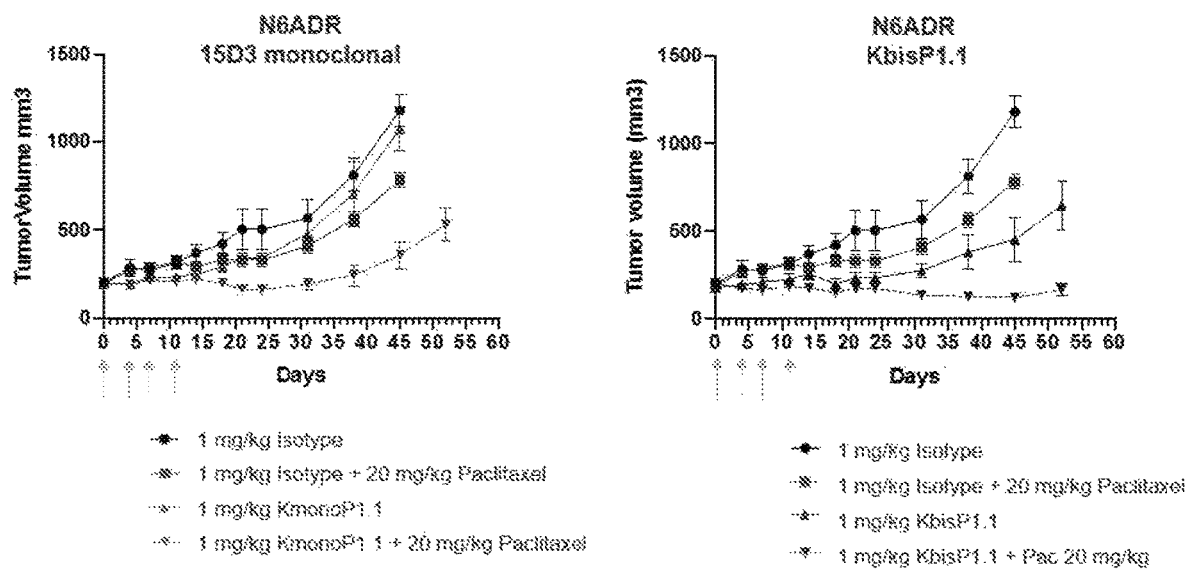
FIG. 20 shows that KbisP1.1 is more efficacious than the 15D3 antibody against N6ADR cell tumors in vivo.

As seen in FIG. 20, KbisP1.1 is more efficacious than the 15D3 antibody against in vivo N6ADR cell tumors.

Figure 21:
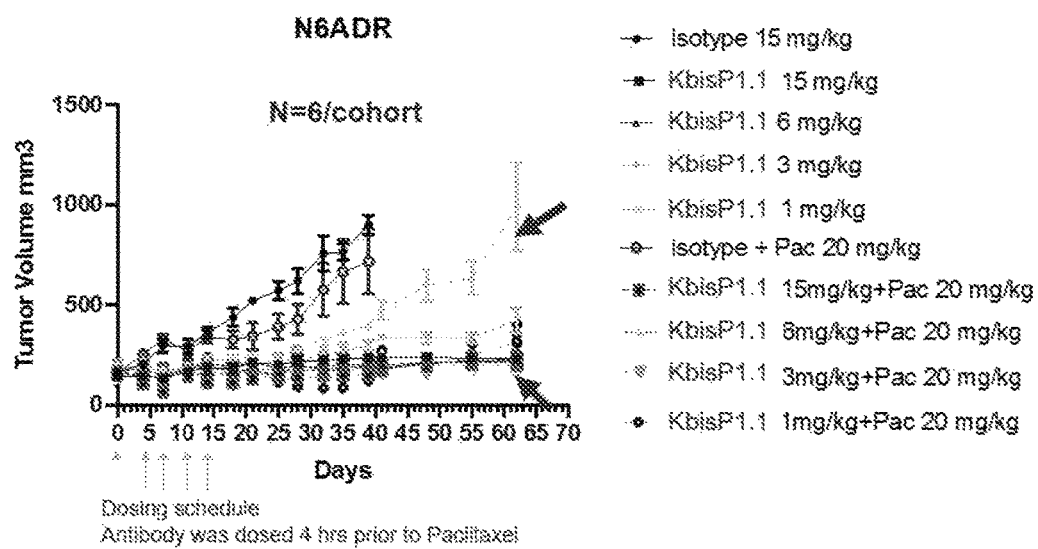
FIG. 21 shows KbisP1.1 chemo-sensitization of multidrug resistant N6ADR tumor to Paclitaxel is dose-dependent, in-vivo.

FIG. 21 shows KbisP1.1 chemo-sensitization of multidrug resistant N6ADR tumor to Paclitaxel is dose-dependent, in-vivo.

Figure 22A:
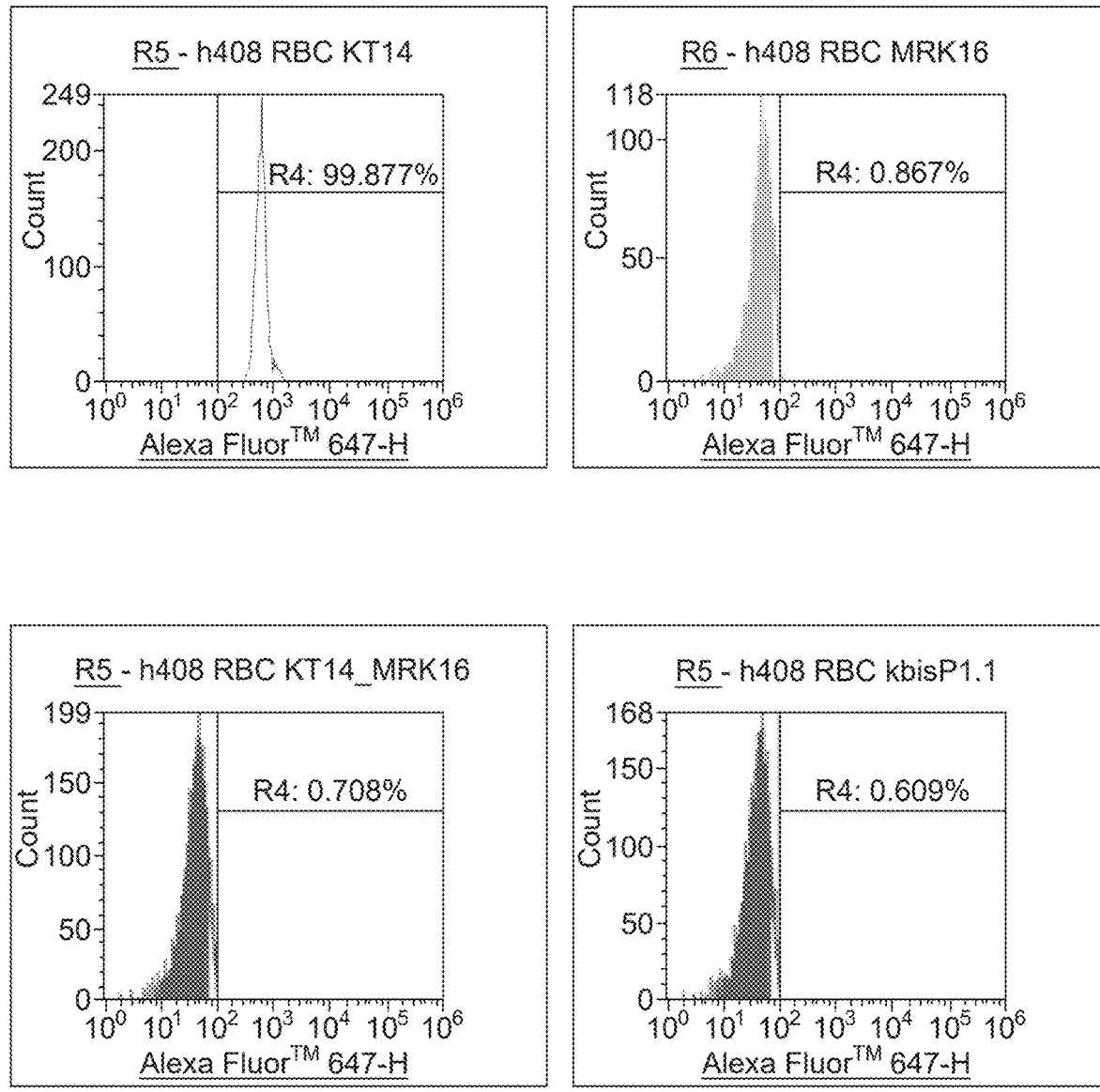
FIGS. 22A-22B show that KBisP1.1 antibody exhibits no significant binding to human red blood cells (RBCs) (FIG. 22A) and cynomolgus RBCs (FIG. 22B) in contrast to the anti-CD47 5F9 antibody and that an anti-CD47 antibody comprising 5F9 HCs and MRK16 LCs ("KT14_MRK16") does not significantly bind to RBCs in contrast to the anti-CD47 5F9 antibody ("KT14").
Figure 22B:
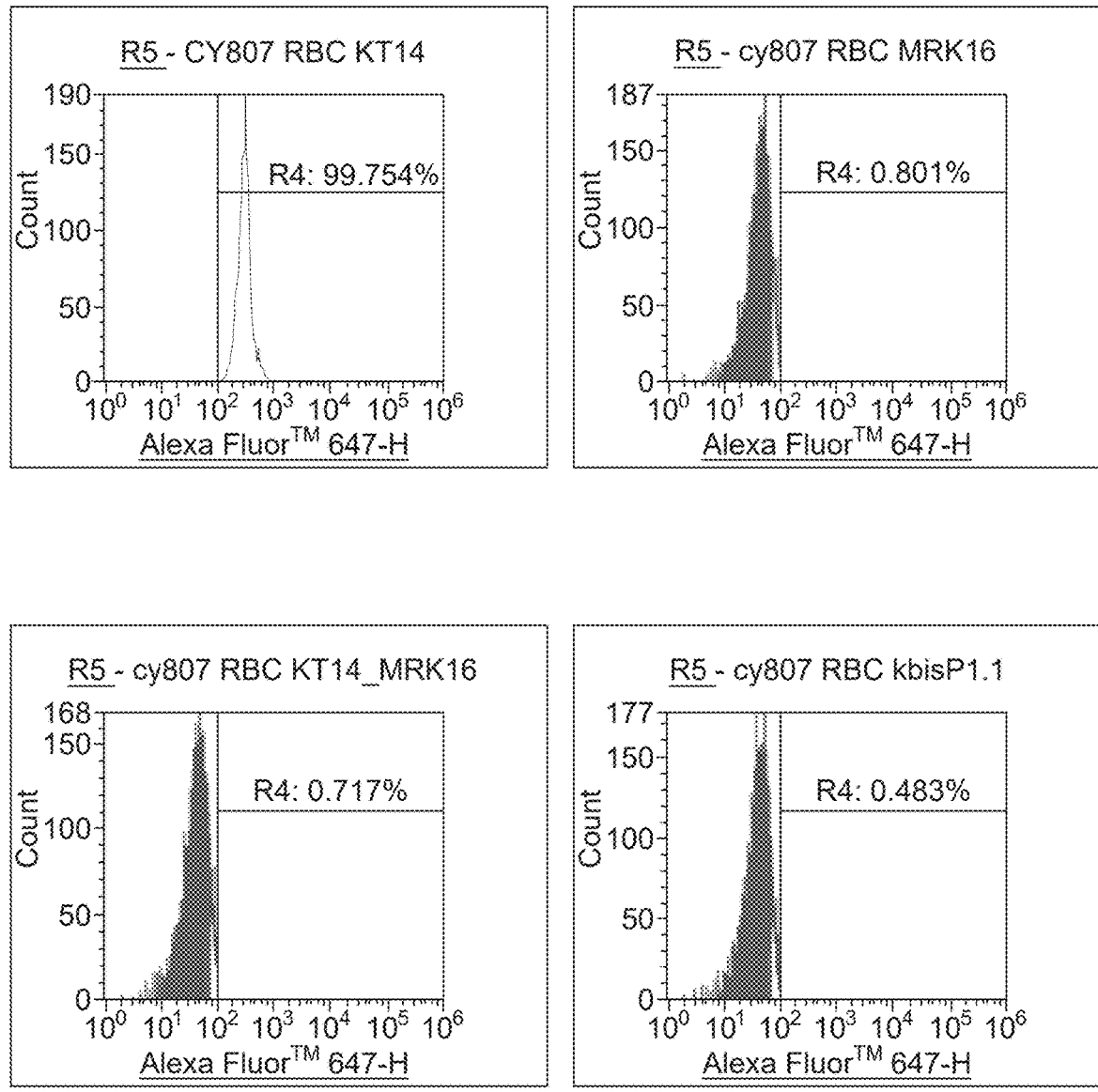

Example 6: Significantly Reduced Binding of KbisP1.1 Bispecific Antibody to Human and Cynomolgus Erythrocytes KBisP1.1 antibody exhibits no significant binding to human and cynomolgus erythrocytes in contrast to the anti-CD47 5F9 antibody and is thus not expected to cause general cytotoxicity or be subject to an erythrocyte 'antigen sink'. Human and cynomolgus RBC binding data are shown in FIGS. 22A and 22B, respectively. FIGS. 22A and 22B also show that an anti-CD47 antibody comprising 5F9 HCs and MRK16 LCs ("KT14_MRK16") does not significantly bind to human and cynomolgus red blood cells (RBCs) in contrast to the anti-CD47 5F9 antibody ("KT14").

Subsequent testing of the KBisP1.1 antibody in cynomolgus monkeys showed that the antibody does not result in significant reduction in body weight, hemolytic anemia, and no increase in morbidity was associated with this antibody. Furthermore, the clearance of the KBisp1.1 appeared normal without an apparent 'antigen sink' effect being observed.

The cynomolgus monkeys were administered the KBisP1.1 antibody at a dose of 10 mg/kg. The half-life of the antibody was from 114-148 hrs.

Example 7: KbisP1.1 Bispecific Antibody Cynomolgus Monkey Toxicity Study

Fifteen cynomolgus monkeys (*Macaca fascicularis*) were enrolled in a single dose study to evaluate KbisP1.1 toxicity. Monkeys were divided into 5 cohorts (n=3 animals/cohort):

| Cohort | KBisP1.1 dose | paclitaxel dose |
|---|---|---|
| 1 | 10 mg/kg | none |
| 2 | 10 mg/kg | 2 mg/kg |
| 3 | 50 mg/kg | none |
| 4 | 50 mg/kg | 2 mg/kg |
| 5 | none | 2 mg/kg |

All animals received their full dose of antibody and/or paclitaxel. No animals exhibited any signs of infusion reaction. Post infusion of Paclitaxel there was the expected amount of minimal erythema at the infusion site. There was no erythema at the site of the infusion of the antibody alone.

KBisP1.1 was well tolerated in all cohorts with no changes in activity or appetite. Weight remained stable and detailed clinical examinations were normal.

A slight decrease in hematocrit in 11 of 15 animals was observed at 7 days post dosing which did not correlate with KbisP1.1 dose or having received paclitaxel. All other clinical chemistry and hematology finding were normal.

Example 8: KbisP1.1 Bispecific Antibody Modified to Reduce Immunogenicity or Modify ADCC Materials and Methods Cells: MES-SA/Dx5 cell line (Sigma, catalogue no 95051031) is a uterine sarcoma, derived from parent MES-SA cell line (Sigma, catalogue no 95051030), was used in this study. MES-SA/Dx5 cell line demonstrates ~100-fold more resistance to doxorubicin compared to its parent cells.

Mice: 5-6-week-old female nude mice (Charles River) were used in this study.

Human Isotype IgG1 (Bioxcell) served as control.

Cell culture—MES-SA/Dx5 cells were maintained in RPMI medium supplemented with 10% FBS and 1% penicillin and 1% streptomycin at 37° C., 5% $CO_2$. Treatment with 10E-7 M Adriamycin at least once a week. Cell lines used were authentic and confirmed to be *mycoplasma* negative.

Inoculation-0.5×$10^6$ cells diluted in PBS:Matrigel (1:1) were subcutaneously injected using a 27G insulin syringe into thirty anesthetized 5-6-week-old female nude mice under sterile conditions. All animal maintenance, handling, surveillance, and animal procedures were performed in accordance with and approval from the APLAC protocol.

Dosing—

MES-SA/Dx5 subcutaneous tumors: Once tumors reached 100-150 $mm^3$, mice were randomized into six groups of five mice each—(i) Control isotype IgG1 3 mg/kg, (ii) Control isotype IgG1 3 mg/kg and 20 mg/kg of paclitaxel, (iii) KNJYBisP1.1 3 mg/kg, (iv) KNJYBisP1.1 3 mg/kg and 20 mg/kg of paclitaxel, (v) KNJYBisP1.1 LALAPG 3 mg/kg and (vi) KNJYBisP1.1 LALAPG 3 mg/kg and 20 mg/kg of paclitaxel. Antibody and paclitaxel were dosed intraperitoneally twice a week for two consecutive weeks. Antibodies were injected at least 4 hours prior to paclitaxel injection.

Paclitaxel preparation: Since paclitaxel is poorly soluble, a master stock of 50 mg/ml was prepared in absolute ethanol:Kolliphor (1:1). Prior to injection the stock was diluted to recommended doses of 20 mg/kg with PBS maintaining a ratio of (1:16).

Measurements—Tumor measurements were done thrice a week using a calibrated Vernier Caliper and tumor volume calculated as per the formula ½*L*S*S where L is the long axis and s is the short axis of the tumor. Body weights were recorded before treatment started and were continuously monitored throughout the study. Animal survival was evaluated from the first day of treatment until death. Animals were euthanized when turning moribund according to the above-mentioned predefined criteria rapid weight loss, loss of ability to ambulate, labored respiration, or inability to drink or feed to avoid animal suffering.

KbisP1.1 antibody is also referred to herein as KNJYBisP1.1. The same protocols were followed for KNJYBisP1.1 N297A antibody.

KbisP1.1 Humanized Antibody

KbisP1.1 antibody (also referred to herein as KNJYBisP1.1) was modified to reduce immunogenicity by making chimeric and humanized versions of the KbisP1.1 antibody. KbisP1.1 chimeric antibody included the 15D3 variable heavy chain region fused to human IgG1 Fc region with the charged pair substitutions K392D and K409D and 5F9 variable heavy chain region fused to human IgG1 Fc region with the charged pair substitutions E356K and D399K.

In order to select human antibody framework regions (FR) to be used as templates for CDR-grafting, the mouse 15D3 VH and MRK16 VL regions were compared with those of human germline sequences. The FRs of the mouse 15D3 VH regions were found to have the highest homology with human IGHV3 subgroup. The FRs of the mouse MRK16 VL region exhibited the highest homology with human IGKV2 subgroup. To reduce potential posttranslational modification and improve the stability of the antibodies, N56Q/N56S was introduced in the 15D3 CDR H2, and N30Q/N30S was introduced in the MRK16 CDR L1. Three versions of each humanized VH (15D3 Hz0, 15D3 Hz1, and 15D3 Hz2) and VL (MRK16 Hz0, MRK16 Hz1, and MRK16 Hz2) were designed. The variable region sequences are as follows:

```
15D3 Hz0:
EVQLVESGGVVVQPGGSLRLSCAASGFTFSRYTMSWVRQAPGKGLEWVAT

ISSGGGNTYYPDSVKGRFTVSRDNSKNSLYLQMNSLRTEDTALYYCARYG

AGDAWFAYWGQGTLVTSS

15D3 Hz1:
EVQLVESGGVVVQPGGSLRLSCAASGFTFSRYTMSWVRQAPGKGLEWVAT

ISSGGGQTYYPDSVKGRFTVSRDNSKNSLYLQMNSLRTEDTALYYCARYG

AGDAWFAYWGQGTLVTSS

15D3 Hz2:
EVQLVESGGVVVQPGGSLRLSCAASGFTFSRYTMSWVRQAPGKGLEWVAT

ISSGGGSTYYPDSVKGRFTVSRDNSKNSLYLQMNSLRTEDTALYYCARYG

AGDAWFAYWGQGTLVTSS

MRK16 Hz0:
DIVMTQTPLSSPVTLGQPASISCRSSQSIVHSTGNTYLEWYQQRPGQPPR

LLIYKISNRFSGVPDRFSGSGAGTDFTLKISRVEAEDVGVYYCFQASHFP

RTFGGGTKLEIK

MRK16 Hz1:
DIVMTQTPLSSPVTLGQPASISCRSSQSIVHSTGQTYLEWYQQRPGQPPR

LLIYKISNRFSGVPDRFSGSGAGTDFTLKISRVEAEDVGVYYCFQASHFP

RTFGQGTKLEIK

MRK16 Hz2:
DIVMTQTPLSSPVTLGQPASISCRSSQSIVHSTGSTYLEWYQQRPGQPPR

LLIYKISNRFSGVPDRFSGSGAGTDFTLKISRVEAEDVGVYYCFQASHFP

RTFGQGTKLEIK
```

Sequence alignments of each version are provided in FIGS. 23-24.

Figure 25:
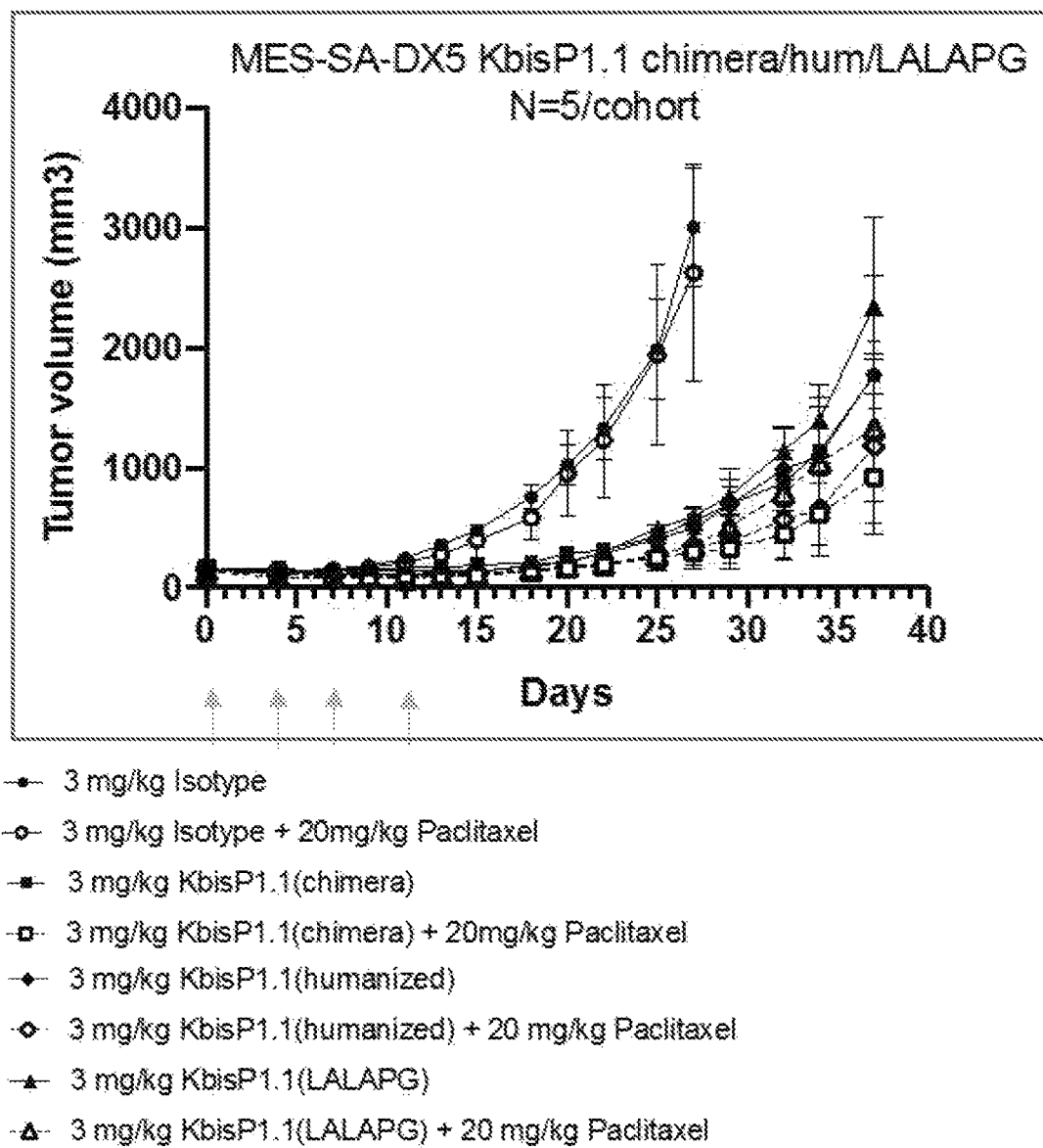
FIG. 25 shows humanized, muted Fc bispecific antibody chemosensitizes multidrug resistant MES-SA-DX5 tumor.
Figure 26:
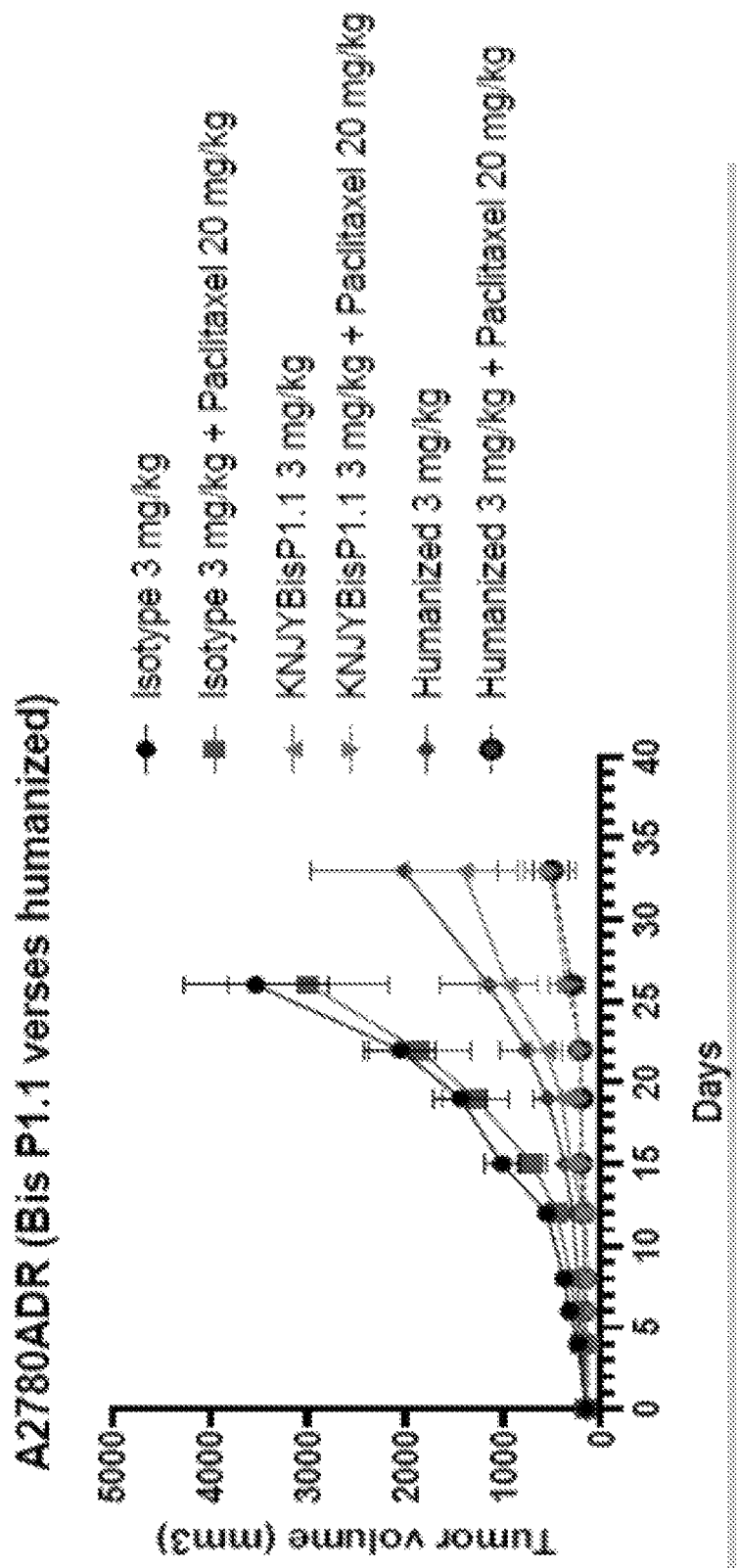
FIG. 26 shows that humanized KBisP1.1 antibody chemosensitizes multidrug resistant A2780ADR cell-generated tumors in mice.

As shown in FIG. 25, humanized antibody chemosensitized multidrug resistant MES-SA-DX5 cell-generated tumors in mice. As shown in FIG. 26, humanized antibody chemosensitized multidrug resistant A2780ADR cell-generated tumors in mice. In FIG. 26, the KBisP1.1 antibody is referred to as "KNJYBisP1.1" and the humanized KBisP1.1 antibody is referred to as "Humanized."

Humanized KBisP1.1 antibodies were characterized by binding titration and chemotoxicity assay.

Cell Binding Assays. Antibody binding to cells was evaluated by flow cytometry. 293T cells stably transfected to express human ABCB1 (293T_ABCB1_OX) were washed once in flow cytometry buffer (PBS+2% FBS+0.02% sodium azide), resuspended at 2×10^6 cells/mL in flow cytometry buffer, and dispensed into 96-well microtiter plates at 0.1 mL/well. Recombinant antibodies were added to cells at 5 µg/mL for initial binding confirmation, or serially diluted from 100 µg/mL in flow cytometry buffer. After incubating cells on ice for 30 min, cells were washed twice with flow cytometry buffer. Bound antibody was detected with PE-labeled F(ab')$_2$ fragment goat anti-human IgG (Jackson ImmunoResearch) and evaluated on an Attune N×T flow cytometer. EC50 is calculated to be the concentration of antibody that gives half maximal response.

Cytotoxicity Assays. The effect of antibodies on vincristine cytotoxicity was evaluated on N6/ADR, a doxorubicin-selected, B1-positive variant of the human acute lymphoblastic leukemia (ALL) cell line, NALM6. Cells were plated in 0.05 mL of Assay Media (RPMI-1640+10% FBS) at 5000 cells/well in white flat bottom 96-well tissue culture plates. Vincristine was prepared at 2× final assay concentration by serial dilution from 200 uM in assay media containing test antibodies or control antibodies at 100 µg/mL (2× final concentration), or valspodar, a small molecule B1 inhibitor at 7 uM (2× final concentration). An equivalent volume (0.05 mL) of the vincristine/antibody mixture was added to the N6/ADR cells in 96-well plates. The plates were then incubated at 37° C., in 5% CO2. After 72 hr plates were equilibrated to room temperature and cell viability assessed using Promega® CellTiter-Glo® Luminescent Cell Viability Assay according to the manufacturer's recommended protocol. Luminescence was measured on a Molecular Devices® FlexStation® 3 Multi-Mode Microplate Reader and data analyzed using GraphPad Prism 8.0 software. IC50 is the concentration of drug (vincristine or other chemotherapy cytotoxic agent) where the response (cell growth) is reduced by 50%.

Cell Binding of bispecific antibodies to 293T_ABCB1_OX cell is summarized in Table 4:

| EC50 (nM) | Ab | HC1 | HC2 | LC |
|---|---|---|---|---|
| 75.5 | Ab1 | 15D3 IgG1 DD | KT14 IgG1 KK | MRK16 VL-Hz1 |
| 212.4 | Ab2 | 15D3 IgG1 DD | KT14 IgG1 KK | MRK16 VL-Hz2 |
| 79.1 | Ab3 | 15D3 IgG1 DD | KT14 IgG1 KK | MRK16 VL Hz0 |
| 101.1 | Ab4 | 15D3 HC-Hz1 DD hIgG1 | KT14 IgG1 KK | MRK16 VL Hz0 |
| 137.1 | Ab5 | 15D3 HC-Hz1 DD hIgG1 | KT14 IgG1 KK | MRK16 VL-Hz1 |
| 230.4 | Ab6 | 15D3 HC-Hz1 DD hIgG1 | KT14 IgG1 KK | MRK16 VL-Hz2 |
| 63.5 | Ab7 | 15D3 HC-Hz2 DD hIgG1 | KT14 IgG1 KK | MRK16 VL-Hz0 |
| 216.6 | Ab8 | 15D3 HC-Hz2 DD hIgG1 | KT14 IgG1 KK | MRK16 VL-Hz1 |
| 218.8 | Ab9 | 15D3 HC-Hz2 DD hIgG1 | KT14 IgG1 KK | MRK16 VL-Hz2 |
| 34.7 | Ab10 | 15D3 IgG1 DD Hz0 | KT14 IgG1 KK | MRK16 VL-Hz1 |
| 52.4 | Ab11 | 15D3 IgG1 DD Hz0 | KT14 IgG1 KK | MRK16 VL-Hz2 |
| 33.5 | Ab12 | 15D3 IgG1 DD Hz0 | KT14 IgG1 KK | MRK16 VL Hz0 |
| 14.6 | 15D3 | | | |
| 0.3 | KT14 | | | |
| 40.3 | KBisP1.1 | | | |

The effect of antibodies on vincristine cytotoxicity is summarized in Table 5:

| Vincristine IC50 (nM) | Ab | HC1 | HC2 | LC |
|---|---|---|---|---|
| 0.0020 | Ab1 | 15D3 IgG1 DD | KT14 gG1 KK | MRk16 VL-Hz1 |
| 0.0030 | Ab2 | 15D3 IgG1 DD | KT14 IgG1 KK | MRK16 VL-Hz2 |
| 0.0003 | Ab3 | 15D3 IgG1 DD | KT14 IgG1 KK | MRK16 VL Hz0 |
| 0.0024 | Ab4 | 15D3 HC-Hz1 DD hIgG1 | KT14 IgG1 KK | MRK16 VL Hz0 |
| 0.0589 | Ab5 | 15D3 HC-Hz1 DD hIgG1 | KT14 IgG1 KK | MRK16 VL-Hz1 |
| 0.0479 | Ab6 | 15D3 HC-Hz1 DD hIgG1 | KT14 IgG1 KK | MRK16 VL-Hz2 |
| 0.0076 | Ab7 | 15D3 HC-Hz2 DD hIgG1 | KT14 IgG1 KK | MRK16 VL-Hz0 |
| 0.5084 | Ab8 | 15D3 HC-Hz2 DD hIgG1 | KT14 IgG1 KK | MRK16 VL-Hz1 |
| 0.2417 | Ab9 | 15D3 HC-Hz2 DD hIgG1 | KT14 IgG1 KK | MRK16 VL-Hz2 |
| 0.0572 | Ab10 | 15D3 IgG1 DD HzO | KT14 IgG1 KK | MRK16 VL-Hz1 |
| 0.1074 | Ab11 | 15D3 IgG1 DD HzO | KT14 IgG1 KK | MRK16 VL-Hz2 |
| 0.0001 | Ab12 | 15D3 IgG1 DD HzO | KT14 IgG1 KK | MRK16 VL Hz0 |
| 0.4663 | 15D3 | | | |
| 0.7335 | MRK16 | | | |
| 0.0461 | KBisP1.1 | | | |
| 0.5429 | Vincristine alone | | | |
| 0.7869 | Human IgG1 | | | |

KbisP1.1 LALAPG Fc-Muted Antibody

The IgG1 Fc region of the chimeric antibodies was modified to include the LALAPG effector function mutation (L234A, L235A, and P329G) or the N297A mutation to reduce antibody dependent cellular cytotoxicity (ADCC). Such antibodies are referred herein as muted antibodies. The position of the substitutions are with reference to the amino acid sequence of human Ig G1.

As shown in FIG. 25 muted Fc LALAPG bispecific antibody chemosensitized multidrug resistant MES-SA-DX5 cell-generated tumors in mice. The data for muted Fc LALAPG bispecific antibody suggests that Fc effector functions of KNJYBisP1.1 are dispensable for chemosensitization of multidrug resistant tumors to paclitaxel. Fc effector functions of KNJYBisP1.1 appear to be partially responsible for anti-tumor effects of antibody alone in the absence of chemotherapy.

KbisP1.1 N297A Fc-Muted Antibody

The IgG1 Fc region of the chimeric antibodies was modified to the include N297A mutation to reduce antibody dependent cellular cytotoxicity (ADCC). Such antibodies are referred herein as muted antibodies. The position of the substitution is with reference to the amino acid sequence of human Ig G1.

Figure 27A:
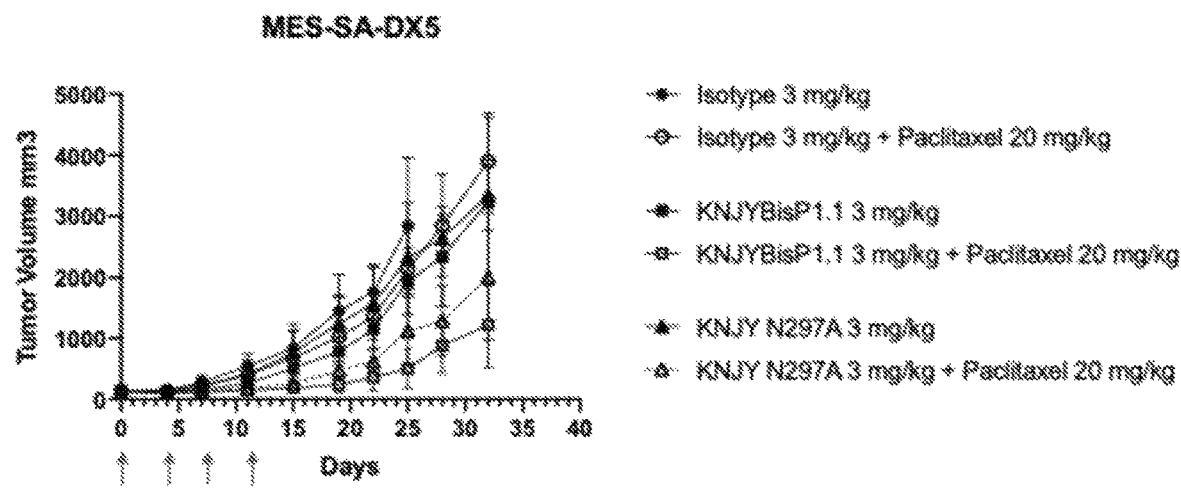
FIG. 27A shows that the KBisP1.1 bispecific antibody with N297A substitution chemosensitizes multidrug resistant MES-SA/Dx5 cell tumors to paclitaxel in mice.

FIG. 27A shows that the KBisP1.1 bispecific antibody with N297A substitution (labeled as KNJY N297A in the figure) chemosensitizes multidrug resistant MES-SA/Dx5 cell tumors to paclitaxel in vivo. The Fc effector functions of KBisP1.1 appear to be dispensable for chemosensitization of multidrug resistant tumors to paclitaxel. The Fc effector functions of KBisP1.1 appear to be partially responsible for anti-tumor effects of antibody alone in the absence of chemotherapy.

KbisP1.1 N297A Fc-muted antibody was also tested against a different cancer cell line, the A2780ADR cell line.

Materials and Methods

Cells: A2780ADR cell line (Sigma, catalogue no 93112520) is an epithelial ovarian carcinoma, derived from parent A2780 cell line (Sigma, catalogue no 93112519), was used in this study.

Mice: 5-6-weeks-old female nude mice (Charles River) were used in this study. We accounted for 10% extra mice that did not undergo treatment.

Human Isotype IgG1 (Bioxcell) served as control.

Cell culture—A2780ADR cells were maintained in RPMI medium supplemented with 10% FBS and 1% penicillin and 1% streptomycin at 37° C., 5% $CO_2$. Treatment with 10E-7 M Adriamycin at least once a week. Cell lines used were authentic and confirmed to be *mycoplasma* negative.

Inoculation—$0.5 \times 10^6$ cells diluted in PBS:Matrigel (1:1) were subcutaneously injected using a 27G insulin syringe into thirty anesthetized 5-6-week-old female nude mice under sterile conditions. All animal maintenance, handling, surveillance, and animal procedures were performed in accordance with and approval from the APLAC protocol.
Dosing—
A2780ADR subcutaneous tumors: Mice were randomized into six groups of five mice each—(i) Control isotype IgG1 3 mg/kg, (ii) Control isotype IgG1 3 mg/kg and 20 mg/kg of paclitaxel, (iii) KNJYBisP1.1 3 mg/kg, (iv) KNJYBisP1.1 3 mg/kg and 20 mg/kg of paclitaxel, (v) KNJYBisP1.1 N297A 3 mg/kg and (vi) KNJYBisP1.1 N297A 3 mg/kg and 20 mg/kg of paclitaxel. Antibody and paclitaxel were dosed intraperitoneally twice a week for two consecutive weeks. Antibodies were injected at least 4 hours prior to paclitaxel injection. Paclitaxel preparation: Since paclitaxel is poorly soluble, a master stock of 50 mg/ml was prepared in absolute ethanol:Kolliphor (1:1). Prior to injection the stock was diluted to recommended doses of 20 mg/kg with PBS maintaining a ratio of (1:16).

Measurements-Tumor measurements were done thrice a week using a calibrated Vernier Caliper and tumor volume calculated as per the formula ½*L*S*S where L is the long axis and s is the short axis of the tumor. Body weights were recorded before treatment started and were continuously monitored throughout the study. Animal survival was evaluated from the first day of treatment until death. Animals were euthanized when turning moribund according to the above-mentioned predefined criteria rapid weight loss, loss of ability to ambulate, labored respiration, or inability to drink or feed to avoid animal suffering.

Figure 27B:
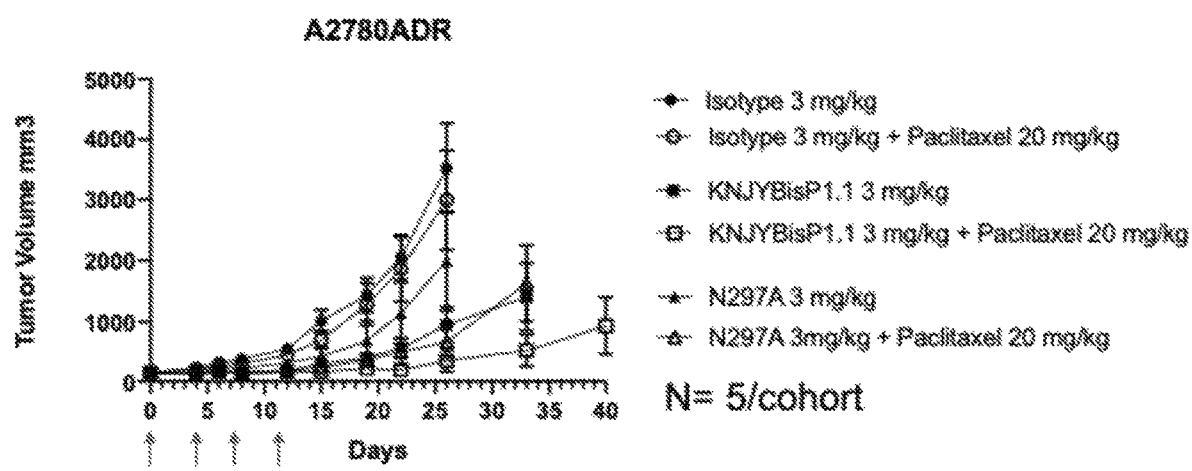
FIG. 27B shows that the KBisP1.1 N297A antibody (labeled as "N297A") chemosensitizes multidrug resistant A2780ADR cells to paclitaxel in vivo.

FIG. 27B shows that KBisP1.1 N297A antibody (labeled as N297A in the figure) chemosensitizes multidrug resistant A2780ADR cells to paclitaxel in vivo. In this model the Fc effector functions of KBisP1.1 are dispensable for chemosensitization of multidrug resistant tumors to paclitaxel. The Fc effector functions of KBisP1.1 are partially responsible for anti-tumor effects of antibody alone in the absence of chemotherapy.

Example 9: KbisP1.1 Bispecific Antibody Compared to Monospecific Antibodies Binding to the Same Targets The anti-tumor effects of KNJYBisP1.1 antibody in comparison to the anti-MDR1 monoclonal antibody, 15D3 and the anti-CD47 KT14 monoclonal antibody was assessed using an A2780ADR and a MES-SA/Dx5 in vivo multidrug resistance model.
Materials and Methods
Cell lines and tumor models are as described in Example 7.
Dosing—
A2780ADR subcutaneous tumors: Once tumors reached 100-150 mm$^3$, mice were randomized into ten groups of five mice each—(i) Control isotype IgG1 3 mg/kg, (ii) Control isotype IgG1 3 mg/kg and 20 mg/kg of paclitaxel, (iii) KNJYBisP1.1 3 mg/kg, (iv) KNJYBisP1.1 3 mg/kg and 20 mg/kg of paclitaxel, (v) 15D3 hybridoma monoclonal Ab 3 mg/kg, (vi) 15D3 hybridoma 3 mg/kg and 20 mg/kg of paclitaxel, (vii) KT14/KT14 monoclonal Ab 3 mg/kg, (viii) KT14/KT14 monoclonal Ab 3 mg/kg and 20 mg/kg of paclitaxel, (ix) 15D3 hybridoma+KT14/KT14, 1.5 mg each and (x) 15D3 hybridoma+KT14/KT14, 1.5 mg each and 20 mg/kg of paclitaxel. Antibodies and paclitaxel were dosed intraperitoneally twice a week for two consecutive weeks. Antibody were injected at least 4 hours prior to paclitaxel injection. Paclitaxel preparation: Since paclitaxel is poorly soluble, a master stock of 50 mg/ml was prepared in absolute ethanol:Kolliphor (1:1). Prior to injection the stock was diluted to recommended doses of 20 mg/kg with PBS maintaining a ratio of (1:16).

MES-SA/Dx5 subcutaneous tumors: Once tumors reached 100-150 mm$^3$, mice were randomized into ten groups of five mice each—(i) Control isotype IgG1 3 mg/kg, (ii) Control isotype IgG1 3 mg/kg and 20 mg/kg of paclitaxel, (iii) KNJYBisP1.1 3 mg/kg, (iv) KNJYBisP1.1 3 mg/kg and 20 mg/kg of paclitaxel, (v) 15D3 hybridoma monoclonal Ab 3 mg/kg, (vi) 15D3 hybridoma 3 mg/kg and 20 mg/kg of paclitaxel, (vii) KT14 monoclonal Ab 3 mg/kg, (viii) KT14 monoclonal Ab 3 mg/kg and 20 mg/kg of paclitaxel, (ix) 15D3 hybridoma+KT14, 1.5 mg each and (x) 15D3 hybridoma+KT14, 1.5 mg each and 20 mg/kg of paclitaxel. Antibody and paclitaxel were dosed intraperitoneally twice a week for two consecutive weeks. Antibodies were injected at least 4 hours prior to paclitaxel injection. Paclitaxel preparation: Since paclitaxel is poorly soluble, a master stock of 50 mg/ml was prepared in absolute ethanol:Kolliphor (1:1). Prior to injection the stock was diluted to recommended doses of 20 mg/kg with PBS maintaining a ratio of (1:16).

Figure 28:
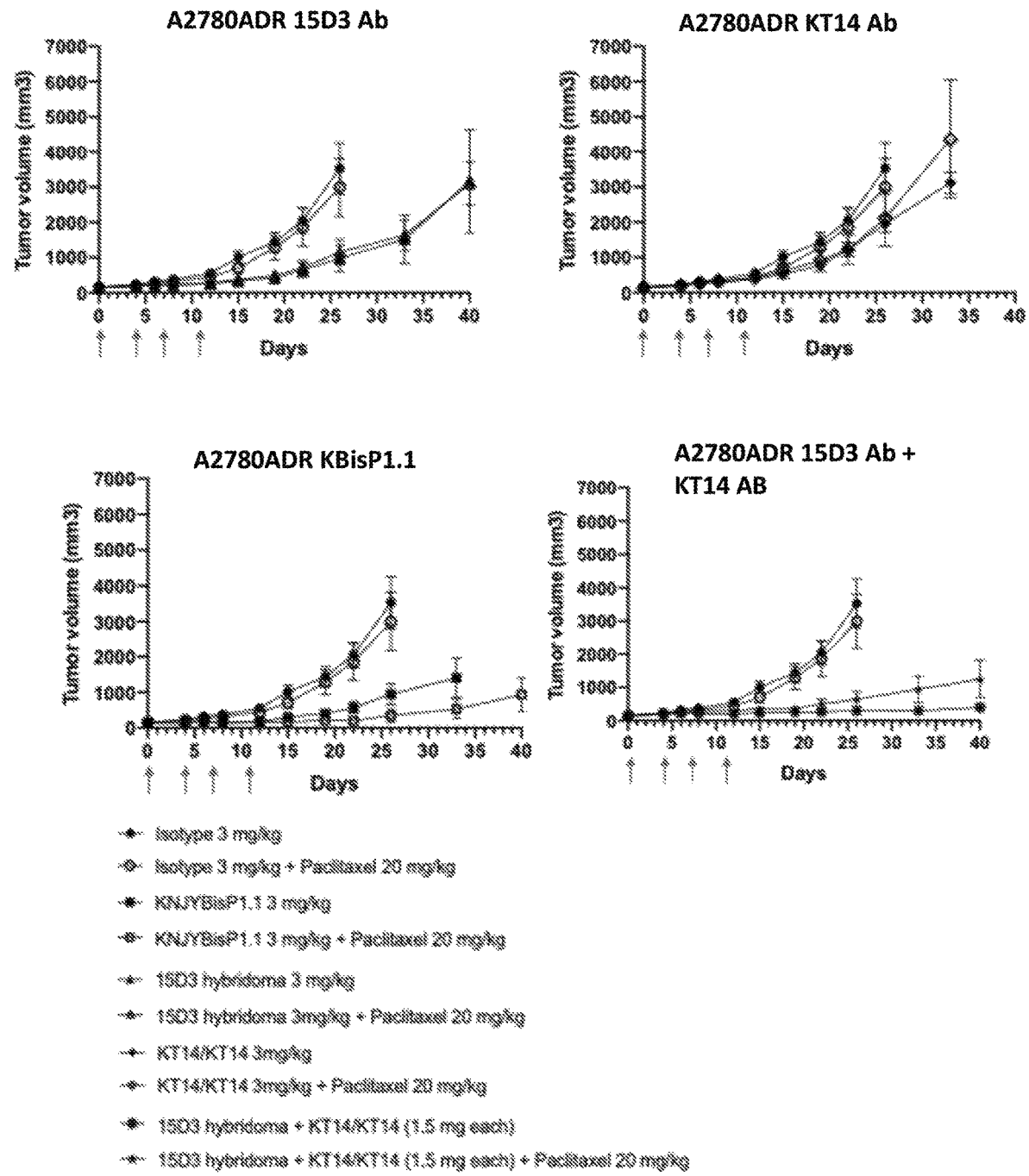
FIG. 28 shows that the KBisP1.1 antibody chemosensitizes multidrug resistant A2780ADR cells to paclitaxel in vivo.

FIG. 28 shows that the KBisP1.1 antibody chemosensitizes multidrug resistant A2780ADR cells to paclitaxel in vivo. The chemosensitizing effect of KBisP1.1 was stronger compared to either the anti-MDR1 15D3 hybridoma antibody or anti-CD47 KT14 monoclonal antibody. The chemosensitizing effect of KNJYBisP1.1 was comparable with co-injections of 15D3 hybridoma+KT14 monoclonal antibodies. Although both the 15D3 hybridoma and the KT14 monoclonal antibodies demonstrate strong binding to their respective targets ex vivo KNJYBisP1.1 is more efficacious than either the 15D3 or KT14 monoclonal antibodies.

Figure 29:
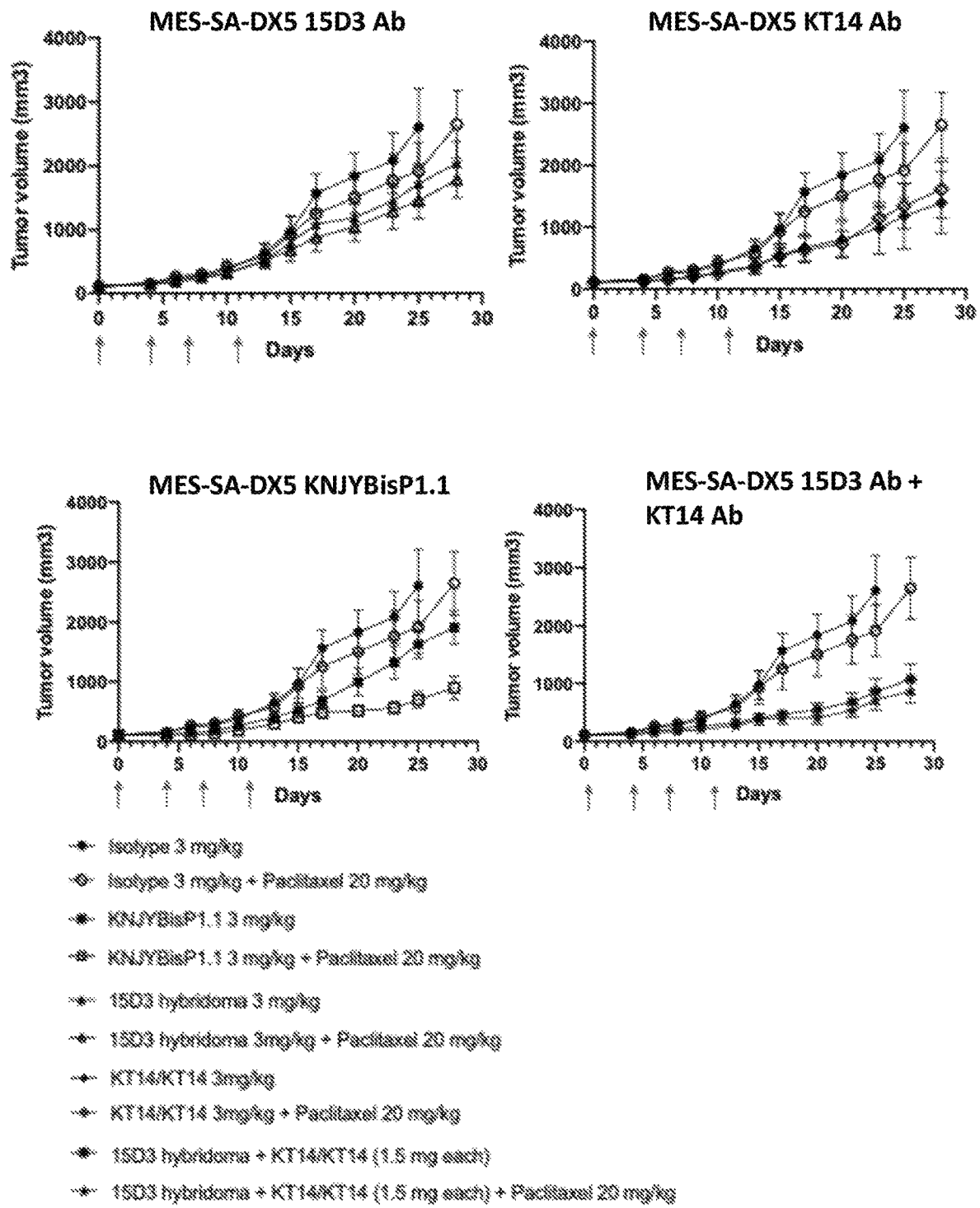
FIG. 29 shows that the KBisP1.1 antibody chemosensitizes multidrug resistant MES-SA/Dx5 cells to paclitaxel in vivo.

As shown in FIG. 29, the KBisP1.1 antibody chemosensitizes multidrug resistant MES-SA/Dx5 cells to paclitaxel in vivo. The chemosensitizing effect of KBisP1.1 was stronger than either the 15D3 hybridoma or KT14 monoclonal antibodies. Combined with paclitaxel the chemosensitizing effect of the single KBisP1.1 bispecific antibody was comparable to the co-injection combination of the 15D3 hybridoma+KT14 monoclonal antibodies.

In FIGS. 28-29, KBisP1.1 antibody=KNJYBisP1.1; 15D3 hybridoma=anti-MDR1 monoclonal antibody 15D3; KT14/KT14-anti-CD47 monoclonal antibody 5F9.

The effect of KBis P1.1 treatment as a single bispecific antibody plus paclitaxel is consistent with in vitro results shown in FIG. 6B indicating that an efficacious paclitaxel payload accumulates in otherwise resistant tumors that co-express high concentrations of the two targets. The KBis P1.1 antibody does not show significant binding to cells not expressing both target antigens (see FIGS. 4A) and will therefore provide more specificity in targeting cancer cells that express both target antigens as compared to the individual monoclonal antibodies.

Example 10: Anti-Tumor Effects of KBisP1.1 in Patient-Derived Breast Cancer Model CTG-2616 In Vivo Materials and Methods
Cells: CTG-2616 is a ER$^+$/Her2$^+$ primary breast cancer, derived from a patient presenting with recurrent ductal adenocarcinoma of the breast.
Mice: 5-6-weeks-old athymic Nude-Foxn1nu female nude mice (Envigo) were used in this study.
Inoculation—Snap-Frozen pieces of patient-derived tumors were thawed, cut into 5×5×5 mm and were subcutaneously injected into anesthetized 5-6-week-old female nude mice under sterile conditions. For tumor implantation procedure, a 1-1.5 cm incision was made on the implantation site and forceps were used to implant the tumor fragment. When sufficient stock animals reached 1000-1500 mm³, tumors were harvested for re-implantation into pre-study animals. Pre-study animals were implanted unilaterally on the left flank with tumor fragments harvested from stock animals. Each animal was implanted from a specific passage lot and documented. Pre-study tumor volumes were recorded for each experiment beginning seven to ten days after implantation. When tumors reached an average tumor volume of 150-300 mm³, animals were matched by tumor volume into treatment or control groups to be used for dosing and dosing initiated on Day 0. All surgical procedures were conducted under sterile conditions.

Dosing—

CTG-2616 subcutaneous tumors: Once tumors were in the range of 150-300 mm³, mice were randomized into three groups of three mice each—(i) Control isotype IgG1 (Bioxcell) 6 mg/kg+vehicle, (ii) Control isotype IgG1 6 mg/kg and 5 mg/kg of paclitaxel and (iii) KNJYBisP1.1 6 mg/kg and 5 mg/kg of paclitaxel. Antibody and paclitaxel were dosed intraperitoneally twice a week for four consecutive weeks. Antibodies were injected at least 4 hours prior to paclitaxel injection. Paclitaxel preparation: Prior to injection the stock was diluted to recommended doses of 5 mg/kg with PBS.

Measurement of tumor volume was carried out as described in the previous examples.

Figure 30:
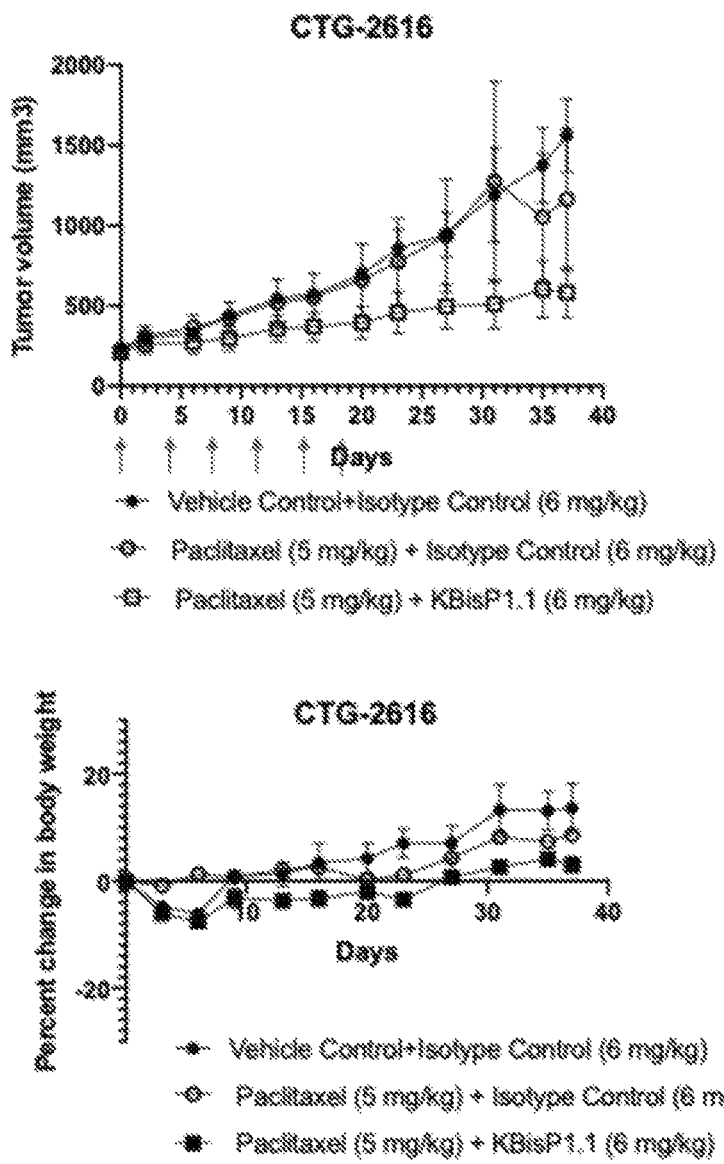
FIG. 30 shows that the KBisP1.1 bispecific antibody chemosensitizes paclitaxel resistant CTG-2616 patient-derived breast tumors and resulted in tumor growth inhibition in vivo.

FIG. 30 shows that KBisP1.1 bispecific antibody chemosensitizes paclitaxel resistant CTG-2616 patient-derived breast tumors and resulted in tumor growth inhibition in vivo. KNJYBisP1.1 did not induce any change in body weight in CTG-2616 bearing animals. Thus, the KNJYBisP1.1 bispecific antibody, in combination with paclitaxel, is efficacious in chemosensitizing paclitaxel-resistant Her2⁺ CTG-2616 patient-derived breast tumors in vivo.

Example 11: Generation of Bispecific mAbs that Bind PD-L1 and MDR-1

Strategy used for generation of the KBis1.1 antibody described in Examples 1-8 was utilized for generating a bispecific antibody that simultaneously binds MDR-1 and PD-L1. This antibody is referred to herein as KBis2.1. A common variable light (VL) chain from the MRK16 antibody with an antigen-binding site for MDR1, a first variable heavy (VH) chain from the 15D3 antibody with an antigen-binding site for MDR1 and a second VH chain with an antigen-binding site for PD-L1 was utilized to make the bispecific antibody. The MRK16 VL chain and the 15D3 VH chain are the same as that used for the KBis1.1 antibody. The VH chain of the anti-PD-L1 antibody atezolizumab served as the second VH chain with an antigen-binding site for PD-L1. This antibody is referred to as: 15D3 HC::PDL1 HC::MRK16 LC. A variant of this antibody where the humanized versions of the 15D3 HC and MRK16 LC was used was also constructed. This antibody may be referred to as: 15D3 HC Hz::PDL1 HC::MRK16 LC Hz. The 15D3 Hz0 VH chain and the MRK16 Hz0 VL chain was used. The atezolizumab VH chain when paired with MRK16 VL chain retains binding to PD-L1 as measured by ELISA (data not shown). ELISA was carried out in the manner described for CD47 in Example 1. In addition, as expected from the data from the KBisP1.1 antibody, the 15D3 HC::MRK16 LC arm of the KBisP2.1 antibody retained binding to MDR1 as measured by FACS using 293 T cells overexpressing MDR1 (data not shown). FACS measurement for MDR1 binding was performed as described in Example 1. This data is summarized in FIG. 31.

The use of the common light chain not only increases the yield of the correctly paired antibody but also decreases the affinity of each arm of the antibody for its target as compared to the originally paired VH-VL antibody, e.g., as in the 15D3 monoclonal antibody and the anti-PD-L1 antibody atezolizumab. This decreased affinity increases the specificity of the KBis2.1 antibody for cancer cells that express at least one of MDR1 and PD-L1 at a high level as compared to normal cells that express only one of the targets at relatively low levels or both targets at a low level.

The sequences for the 15D3 VH chain and the MRK16 VL chain in the KBis2.1 antibody is in the preceding examples. Both the chimeric and humanized versions of the 15D3 heavy chain and MRK16 light chain were used. The heavy chain of atezolizumab has the following sequence:

EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK.

The Fc region of the heavy chain was mutated to introduce charge pair substitutions "KK" to encourage pairing with the 15D3 heavy chain with "DD" substitutions. DD substitutions refer to K392D and K409D substitutions, KK substitutions refer to E356K and D399K substitutions. The numbering of the amino acid substitutions is per EU numbering system for HCs.

The HCDRs 1-3 of the anti-PDL1 antibody atezolizumab defined as per Kabat nomenclature are as follows:

| | |
|---|---|
| HCDR1: | DSWIH |
| HCDR2: | WISPYGGSTYYADSVKG |
| HCDR3: | RHWPGGFDY |

While the light chain of the anti-PDL1 antibody atezolizumab was not used in the bispecific antibody, the sequence is provided below for sake of completeness:

DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

The LCDRs1-3 defined as per Kabat nomenclature are as follows:

> LCDR1: RASQDVSTAVA
>
> LCDR2: SASFLYS
>
> LCDR3: QQYLYHPAT

The EC50 for the anti-PDL1 antibody atezolizumab as measured using 293T cells overexpressing PDL1 is 0.29 nM.

Example 12: Generation of Bispecific mAbs that Bind EGFR and MDR-1

Anti-MDR1 Anti-EGFR Bispecific Antibody Version 1

Strategy used for generation of the KBis1.1 antibody described in Examples set forth above was utilized for generating a bispecific antibody that simultaneously binds MDR-1 and EGFR.

A common variable light (VL) chain from the MRK16 antibody with an antigen-binding site for MDR1, a first variable heavy (VH) chain from the 15D3 antibody with an antigen-binding site for MDR1, and a second VH chain with an antigen-binding site for EGFR was utilized to make the bispecific antibodies. The MRK16 VL chain and the 15D3 VH chain are the same as that described in this application. The VH chain of the anti-EGFR antibody cetuximab or necitumumab served as the second VH chain with an antigen-binding site for EGFR.

The Kd for cetuximab measured by ELISA as described herein ranges from 0.05 nM-0.1 nM. The EC50 for necitumumab measured by FACS using 293T cells overexpressing EGFR is 0.044 nM.

The bispecific antibodies included the following combination of the heavy and light chains:
  i. 15D3 DD HC::cetuximab KK HC::MRK16 LC
  ii. 15D3 DD HC::necitumumab KK HC::MRK16 LC The abbreviations "DD" and "KK" refer to the charged pair substitutions.

The 15D3 DD HC::cetuximab KK HC::MRK16 LC antibody retained binding to MDR1 (as measured by FACS using 293T cell overexpressing MDR1) and to EGFR (as measured by ELISA).

The 15D3 DD HC::necitumumab KK HC::MRK16 LC antibody retained binding to MDR1 (as measured by FACS using 293T cell overexpressing MDR1) and to EGFR (as measured by FACS using 293T cell overexpressing EGFR). This antibody did not show significant binding in ELISA assay.

Additional combination of VH and VL chains were also tested. The VH chain of the anti-MDR1 antibody UIC2 was used instead of 15D3 to generate the bispecific antibody:

UIC2 DD HC::cetuximab KK HC::MRK16 LC. UIC2 VH sequence is provided in the detailed description of the application. However, this antibody did not show significant binding to MDR1.

These data are summarized in FIG. 31.

Anti-MDR1 Anti-EGFR Bispecific Antibody Version 2

The VH chain of the anti-MDR1 MRK16 antibody and the VL chain of the anti-MDR1 antibody 15D3 were tested in combination with the VH region of the anti-EGFR antibody cetuximab to generate the antibody-MRK16 DD HC::cetuximab KK HC::15D3 LC. This antibody also retained binding to MDR1 (as measured by FACS using 293T cell overexpressing MDR1) and to EGFR (as measured by ELISA).

Anti-MDR1 Anti-EGFR Bispecific Antibody Version 3

Bispecific antibodies that retained VH and VL regions from the same anti-MDR1 antibody and combined with the cetuximab VH region were generated:
  i. MRK16 DD HC::cetuximab KK HC::MRK16 LC
  ii. 15D3 DD HC::cetuximab KK HC::15D3 LC As summarized in FIG. 31, the 15D3 DD HC::cetuximab KK HC::15D3 LC antibody binds to both MDR-1 and EGFR. The MRK16 DD HC::cetuximab KK HC::MRK16 LC also binds to both MDR-1 and EGFR, although binding to EGFR with a lower affinity compared to the 15D3 DD HC::cetuximab KK HC::15D3 LC antibody.

UIC2 HC DD::EGFR HC KK::15D3 LC antibody was also constructed. Similar to the observation when MRK16 LC was combined with the UIC HC, this antibody also failed to bind to MDR1. See FIG. 31.

The sequences for the 15D3 VH/VL chain and the MRK16 VL/VH chain in the bispecific antibody is in the detailed description of the application. The amino acid sequences of the heavy and light chain regions of cetuximab and necitumumab are provided below.

```
Cetuximab Heavy chain
QVQLKQSGPGLVQPSQSLSITCTVSGFSLTNYGVHWVRQSPGKGLEWLGVIWSGGNT

DYNTPFTSRLSINKDNSKSQVFFKMNSLQSNDTAIYYCARALTYYDYEFAYWGQGTLVTVSAA

STKGPSVFPLAPSSKSTSGGTAALGCLVKDYFPEPVTVSWNSGALTSGVHTFPAVLQSSGLYS

LSSVVTVPSSSLGTQTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALHN

HYTQKSLSLSPGK

HCDR1: NYGVH

HCDR2: VIWSGGNTDYNTPFTS

HCDR3: ALTYYDYEFAY
```

-continued

```
Cetuximab Light chain
DILLTQSPVILSVSPGERVSFSCRASQSIGTNIHWYQQRTNGSPRLLIKYASESISGIPSR

FSGSGSGTDFTLSINSVESEDIADYYCQQNNNWPTTFGAGTKLELKRTVAAPSVFIFPPSDEQL

KSGTASVVCLLNNFYPREAKVQWKVDNALQSGNSQESVTEQDSKDSTYSLSSTLTLSKADYEK

HKVYACEVTHQGLSSPVTKSFNRGEC

LCDR1: RASQSIGTNIH

LCDR2: YASESIS

LCDR3: QQNNNWPTT

Necitumumab Heavy chain
QVQLQESGPGLVKPSQTLSLICTVSGGSISSGDYYWSWIRQPPGKGLEWIGYIYYSGS

TDYNPSLKSRVTMSVDTSKNQFSLKVNSVTAADTAVYYCARVSIFGVGTFDYWGQGTLVTVSS

ASTKGPSVLPLAPSSKSTSGGTAALGCLVKDYFPEPVTVSWNSGALTSGVHTFPAVLQSSGLY

SLSSVVTVPSSSLGTQTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQGNVFSCSVMHEAL

HNHYTQKSLSLSPGK

HCDR1: SGDYYWS

HCDR2: YIYYSGSTDYNPSLKS

HCDR3: VSIFGVGTFDY

Necitumumab Light chain
EIVMTQSPATLSLSPGERATLSCRASQSVSSYLAWYQQKPGQAPRLLIYDASNRATGIP

ARFSGSGSGTDFTLTISSLEPEDFAVYYCHQYGSTPLTFGGGTKAEIKRTVAAPSVFIFPPSDEQ

LKSGTASVVCLLNNFYPREAKVQWKVDNALQSGNSQESVTEQDSKDSTYSLSSTLTLSKADYE

KHKVYACEVTHQGLSSPVTKSFNRGEC

LCDR1: RASQSVSSYLA

LCDR2: DASNRAT

LCDR3: HQYGSTPLT
```

FIG. 31 summarized binding of the indicated antibodies to MDR1 (measured by FACs) or to a TAA (measured by ELISA or FACS). aCD47=anti-CD47; aEGFR=anti-EGFR; aPDL1=anti-PDL1.

"+" in FIG. 31 indicates that the EC50 ranged from 5 nM-700 nM. "±" in FIG. 31 indicates that the EC50 ranged from 701 nM-900 nM. "−" in FIG. 31 indicates that the EC50 was >1000 nM.

Figure 32A:
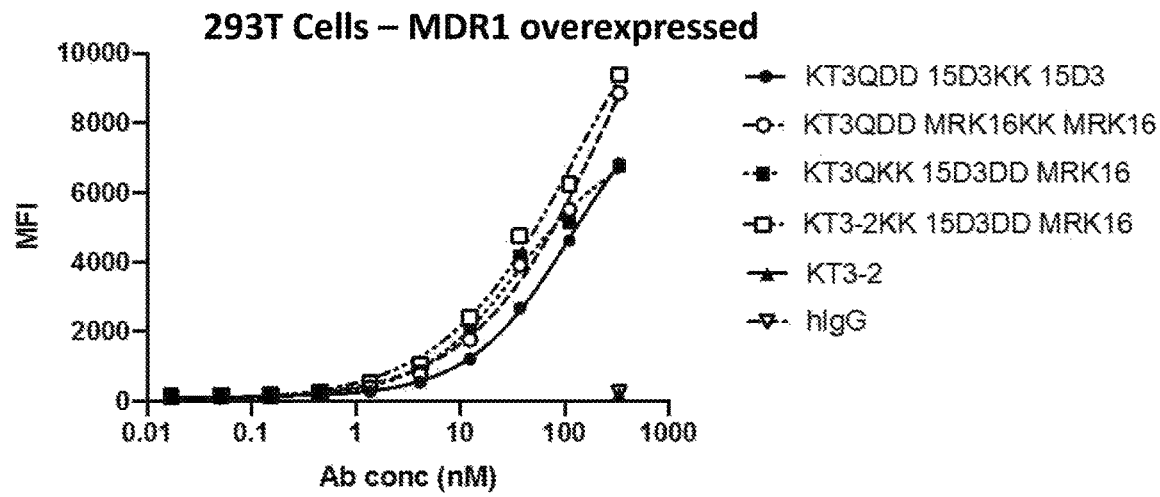
FIG. 32A shows MFI for the listed antibodies measured using 293T cells overexpressing MDR1.
Figure 32B:
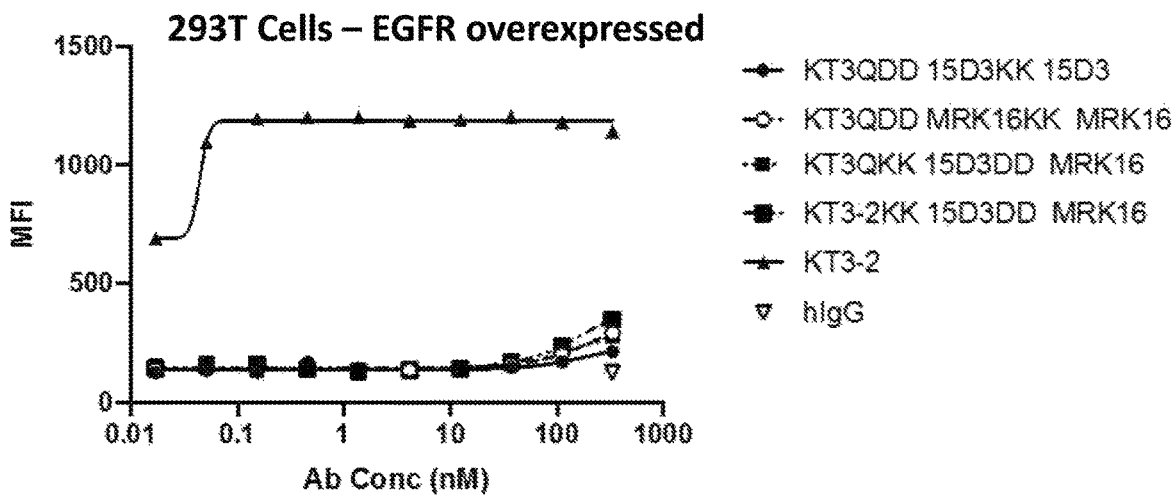
FIG. 32B shows MFI for the listed antibodies measured using 293T cells overexpressing EGFR.
Figure 32C:
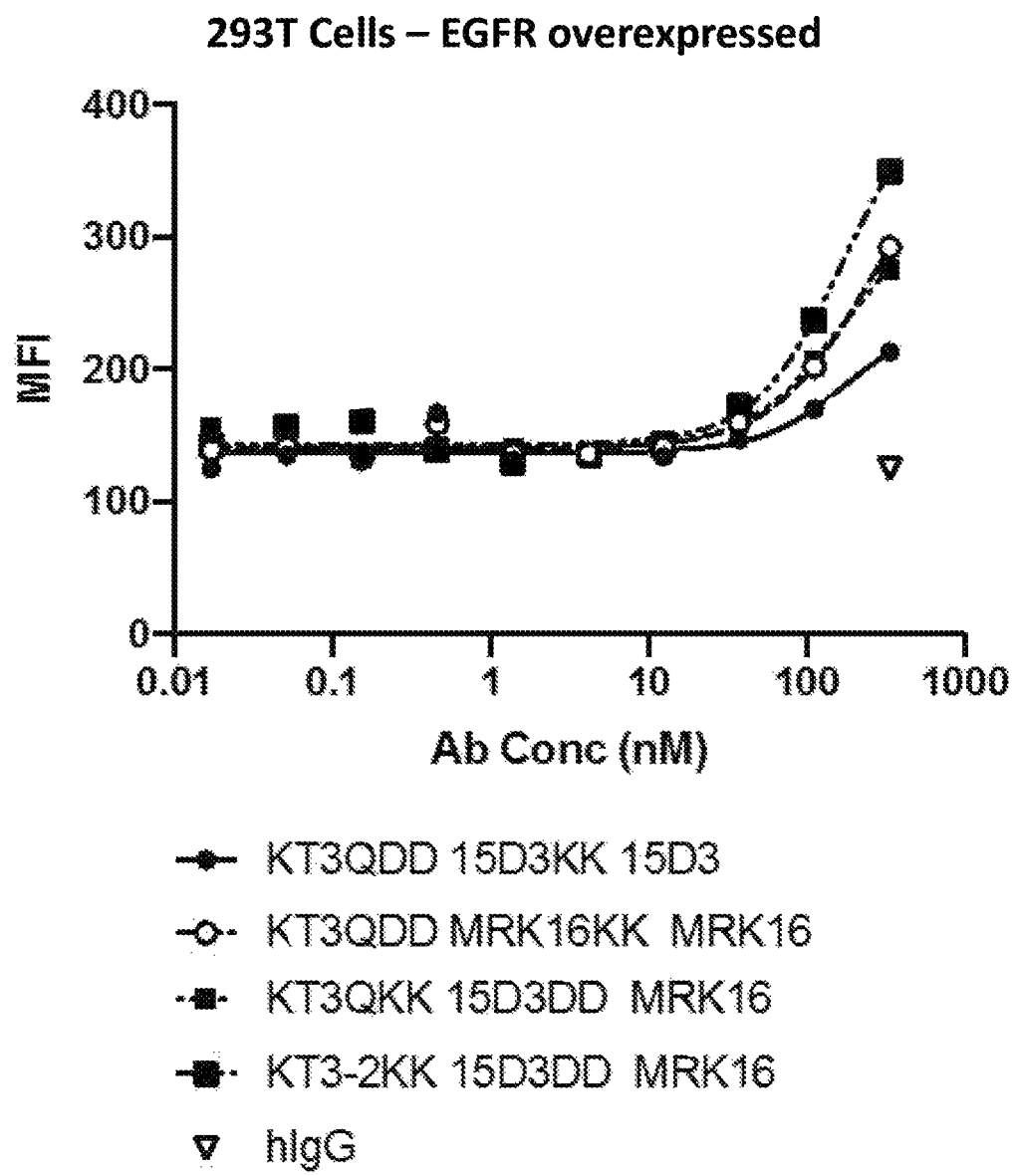
FIG. 32C shows MFI for the listed antibodies measured using 293T cells overexpressing EGFR for a subset of antibodies show in FIG. 32B.

FIGS. 32A-32C show MFI measurement for the listed antibodies:
  Human IgG1 antibody ("hIgG"),
  anti-EGFR antibody necitumumab ("KT3-2"),
  anti-EGFR anti-MDR1 bispecific antibodies:
    15D3 KK HC::cetuximab DD HC: 15D3 LC ("KT3QDD 15D3KK 15D3");
    MRK16 KK HC::cetuximab DD HC::MRK16 LC ("KT3QDD MRK16KK MRK16");
    15D3 DD HC::cetuximab KK HC::MRK16 LC ("KT3QKK 15D3DD MRK16");
    15D3 DD HC::necitumumab KK HC::MRK16 LC ("KT3-2KK 15D3DD 1MRK16")

FIG. 32A shows that each of the bispecific antibodies bound to 293T cells overexpressing MDR1. The anti-EGFR antibody necitumumab indicated in the graph as KT3-2 did not show significant binding to these cells, similar to the negative control human IgG1 antibody.

FIG. 32B shows that each of the bispecific antibodies bound to 293T cells overexpressing EGFR with an affinity significantly less that the anti-EGFR antibody necitumumab "KT3-2". FIG. 32C shows the binding data for the bispecific antibodies shown in FIG. 32B with a Y-axis showing MFI in range of ≤400. The 293T cells do not express EGFR (see FIG. 32A). The 293T cells overexpressing EGFR express EGFR to a detectable level however, the EGFR expression is relatively low which accounts for the low affinity of the bispecific antibodies for these cells. In contrast, the expression level of MDR1 in 293T cells overexpressing MDR1 is quite high which accounts for the binding of the bispecific antibodies even in absence of expression of EGFR.

A summary of the EC50 measured for the bispecific antibodies is provided below in Tables 6-7. In these 293 cell-based FACS assays the EC50 is the concentration of antibody that generates half of the maximum response (OD450):

TABLE 6

Anti-MDR1 Anti-EGFR Bispecific Ab binding to 293T-B1OX cells

| Ab | EC50 (nM) |
|---|---|
| 15D3DD: necitumumab KK:MRK16 | 33.1 |
| 15D3DD: cetuximab KK:MRK16 | 53 |
| 15D3KK:cetuximab DD:15D3 | 76.8 |
| MRK16KK: cetuximab DD:MRK16 | 144.7 |
| 15D3 | 25.1 |
| MRK16 | 58.8 |
| hIgG1 | NB |

TABLE 7

Anti-MDR1 Anti-EGFR Bispecific Ab binding to 293T-EGFR OX cells

| Ab | EC50 (nM) |
|---|---|
| 15D3DD: necitumumab KK:MRK16 | 110.2 |
| 15D3DD: cetuximab KK:MRK16 | 85.3 |
| 15D3KK: cetuximab DD:15D3 | ND |
| MRK16KK: cetuximab DD:MRK16 | 112.1 |
| necitumumab | 0.13 |
| 15D3 | ND |
| MRK16 | ND |
| hIgG1 | NB |

NB = No Binding
ND = Not Done

Example 13: Generation of Bispecific Anti-MDR1 Anti-CD47 Antibody with Humanized 5F9 VH Region In order to select human antibody frameworks (FR) to be used as templates for CDR-grafting, the mouse 5F9 VH region was compared with those of human germline sequences. The FRs from human VH5-51 and VH7-4 and VH3-23 were ultimately selected as the starting point for designing humanized 5F9 VH.

Next, humanized 15D3 HC::5F9 HC::MRK16 LC bispecific constructs were produced and examined by flow cytometry analysis with 293T cells and 293T-CD47 KO cells. Both 5F9.huVH5 and 5F9.huVH3 HCs in pair with humanized MRK16 LC can bind to CD47 (data not shown).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112 (f) or 35 U.S.C. § 112 (6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112 (6) is not invoked.

What is claimed is:

1. A bispecific antibody molecule that binds multidrug resistance protein 1 (MDR1) and CD47, the antibody molecule comprising two identical variable light (VL) chains, a first variable heavy (VH) chain, and a second VH chain,
   wherein the VL chains each comprise an antigen-binding site for MDR1, the first VH chain comprises an antigen-binding site for MDR1, and the second VH chain comprises an antigen-binding site for CD47, and wherein the second VH chain binds CD47 when paired with one of the VL chains,
   wherein the antigen binding site of the first VH chain comprises heavy chain CDRs 1-3 (HCDRs 1-3) of a VH chain having the sequence:
   EVKVVESGGVLVRPGGSLKLSCAASGFTFSRYTM-SWVRQTPEKRLEWVATISSGGGX$^2$TYYPD SVKGRFTVSRDNAMSSLYLQMSSLRSEDTALYY-CARYGAGDAWFAYWGQGTLVTVSS (SEQ ID NO: 9), wherein X$^2$ is N, Q or S, and
   wherein the antigen binding site of the second VH chain comprises HCDRs 1-3 of a VH chain having the sequence:

```
                                              (SEQ ID NO: 17)
   QVQLVQSGAEVKKPGASVKVSCKASGYTFTNYNMHWVRQAPGQRLE

WMGTIYPGNDDTSYNQKFKDRVTITADTSASTAYMELSSLRSEDTA

VYYCARGGYRAMDYWGQGTLVTVSS.
   ``` wherein the bispecific antibody binds to cancer cells expressing both MDR1 and CD47 while showing reduced binding to non-cancer cells expressing MDR1 and/or CD47,
   wherein the antigen-binding site of the two VL chains comprises light chain CDRs 1-3 (LCDRs 1-3) of a VL chain having the sequence:
   DVLMTQTPVSLSVSLGDQASISCRSSQSIVHSTGX$^1$ TYLEWYLQKPGQSPKLLIYKISNRFSGV PDRFSGSGSGTDFTLKISRVEAEDLGVYYCFQ-ASHFPRTFGGGTKLEIK (SEQ ID NO:1), wherein X$^1$ is N, Q or S.

2. The bispecific antibody molecule according to claim 1, wherein the two VL chains are humanized and/or comprise the amino acid sequence:

```
                                              (SEQ ID NO: 8)
   DIVMTQTPLSSPVTLGQPASISCRSSQSIVHSTGNTYLEWYQ

QRPGQPPRLLIYKISNRFSGVPDRFSGSGAGTDFTLKISRVE

AEDVGVYYCFQASHFPRTFGGGTKLEIK;

(SEQ ID NO: 3)
   DIVMTQTPLSSPVTLGQPASISCRSSQSIVHSTGQTYLEWYQ

QRPGQPPRLLIYKISNRFSGVPDRFSGSGAGTDFTLKISRVE

AEDVGVYYCFQASHFPRTFGQGTKLEIK;

or (SEQ ID NO: 4)
   DIVMTQTPLSSPVTLGQPASISCRSSQSIVHSTGSTYLEWYQ

QRPGQPPRLLIYKISNRFSGVPDRFSGSGAGTDFTLKISRVE

AEDVGVYYCFQASHFPRTFGQGTKLEIK.
   ```

3. The bispecific antibody molecule according to claim 1, wherein the first VH chain is humanized and/or comprises the amino acid sequence:

```
                                            (SEQ ID NO: 16)
EVQLVESGGVVVQPGGSLRLSCAASGFTFSRYTMSWVRQAPG

KGLEWVATISSGGGNTYYPDSVKGRFTVSRDNSKNSLYLQMN

SLRTEDTALYYCARYGAGDAWFAYWGQGTLVTVSS;

(SEQ ID NO: 11)
EVQLVESGGVVVQPGGSLRLSCAASGFTFSRYTMSWVRQAPG

KGLEWVATISSGGGQTYYPDSVKGRFTVSRDNSKNSLYLQMN

SLRTEDTALYYCARYGAGDAWFAYWGQGTLVTVSS; or (SEQ ID NO: 12)
EVQLVESGGVVVQPGGSLRLSCAASGFTFSRYTMSWVRQAPG

KGLEWVATISSGGGSTYYPDSVKGRFTVSRDNSKNSLYLQMN

SLRTEDTALYYCARYGAGDAWFAYWGQGTLVTVSS.
```

4. The bispecific antibody molecule according to claim 1, wherein the second VH chain is humanized and/or comprises the amino acid sequence:

```
                                            (SEQ ID NO: 17)
QVQLVQSGAEVKKPGASVKVSCKASGYTFTNYNMHWVRQAPGQRLE

WMGTIYPGNDDTSYNQKFKDRVTITADTSASTAYMELSSLRSEDTA

VYYCARGGYRAMDYWGQGTLVTVSS, (SEQ ID NO: 21)
EVQLVESGGGLVQPGGSLRLSCAASGYTFTNYNMHWVRQAPGKGLE

WMGTIYPGNDDTSYNQKFKDRVTISRDNSKNTLYLQMNSLRAEDTA

VYYCARGGYRAMDYWGQGTLVTVSS, (SEQ ID NO: 22)
EVQLVQSGAEVKKPGESLKISCKGSGYTFTNYNMHWVRQMPGKGLE

WMGTIYPGNDDTSYNQKFKDQVTISADKSISTAYLQWSSLKASDTA

MYYCARGGYRAMDYWGQGTTVTVSS, or (SEQ ID NO: 23)
QVQLVQSGSELKKPGASVKVSCKASGYTFTNYNMHWVRQAPGQGLE

WMGTIYPGNDDTSYNQKFKDRFVFSLDTSVSTAYLQISSLKAEDTA

VYYCARGGYRAMDYWGQGTTVTVSS.
```

5. A bispecific antibody molecule that binds multidrug resistance protein 1 (MDR1) and PD-L1, the antibody molecule comprising two identical variable light (VL) chains, a first variable heavy (VH) chain, and a second VH chain,
wherein the VL chains each comprise an antigen-binding site for MDR1, the first VH chain comprises an antigen-binding site for MDR1, and the second VH chain comprises an antigen-binding site for PD-L1, and wherein the second VH chain binds PD-L1 when paired with one of the VL chains,
wherein the antigen binding site of the first VH chain comprises heavy chain CDRs 1-3 (HCDRs 1-3) of a VH chain having the sequence:
EVKVVESGGVLVRPGGSLKLSCAASGFTFSRYTM-SWVRQTPEKRLEWVATISSGGGX$^2$TYYPD SVKGRFTVSRDNAMSSLYLQMSSLRSEDTALYY-CARYGAGDAWFAYWGQGTLVTVSS (SEQ ID NO: 9), wherein X$^2$ is N, Q or S,
wherein the antigen-binding site of the second VH chain comprises the HCDRs 1-3 of a VH chain comprising the amino acid sequence:

```
                                            (SEQ ID NO: 32)
EVQLVESGGGLVQPGGSLRLSCAASGFTFSDSWIHWVRQAPGKGLEWV

AWISPYGGSTYYADSVKGRFTISADTSKNTAYLQMNSLRAEDTAVYYC

ARRHWPGGFDYWGQGTLVTVSS.
``` and
wherein the antigen-binding site of the two VL chains comprises light chain CDRs 1-3 (LCDRs 1-3) of a VL chain having the sequence:
DVLMTQTPVSLSVSLGDQASISCRSSQSIVHSTGX$^1$ TYLEWYLQKPGQSPKLLIYKISN RFSGVPDRFS-GSGSGTDFTLKISRVEAEDLGVYYCFQASHF-PRTFGGGTKLEIK (SEQ ID NO: 1), wherein X$^1$ is N, Q or S.

6. A bispecific antibody molecule that binds multidrug resistance protein 1 (MDR1) and EGFR, the antibody molecule comprising two identical variable light (VL) chains, a first variable heavy (VH) chain, and a second VH chain,
wherein the VL chains each comprise an antigen-binding site for MDR1, the first VH chain comprises an antigen-binding site for MDR1, and the second VH chain comprises an antigen-binding site for EGFR, and wherein the second VH chain binds EGFR when paired with one of the VL chains,
wherein the antigen binding site of the first VH chain comprises heavy chain CDRs 1-3 (HCDRs 1-3) of a VH chain having the sequence:
EVKVVESGGVLVRPGGSLKLSCAASGFTFSRYTM-SWVRQTPEKRLEWVATISSGGGX$^2$TYYPD SVKGRFTVSRDNAMSSLYLQMSSLRSEDTALYY-CARYGAGDAWFAYWGQGTLVTVSS (SEQ ID NO: 9), wherein X$^2$ is N, Q or S,
wherein the antigen-binding site of the second VH chain comprises the HCDRs 1-3 of a VH chain comprising the amino acid sequence:

```
                                            (SEQ ID NO: 36)
QVQLQESGPGLVKPSQTLSLTCTVSGGSISSGDYYWSWIRQPPGKGLEWI

GYIYYSGSTDYNPSLKSRVTMSVDTSKNQFSLKVNSVTAADTAVYYCARV

SIFGVGTFDYWGQGTLVTVSS.
``` wherein the antigen-binding site of the two VL chains comprises light chain CDRs 1-3 (LCDRs 1-3) of a VL chain having the sequence:
DVLMTQTPVSLSVSLGDQASISCRSSQSIVHSTGX$^1$ TYLEWYLQKPGQSPKLLIYKISNRFSGV PDRFSGSGSGTDFTLKISRVEAEDLGVYYCF-QASHFPRTFGGGTKLEIK (SEQ ID NO:1), wherein X$^1$ is N, Q or S.

7. The bispecific antibody molecule according to claim 1, wherein the antibody comprises a Fc domain that has been modified to reduce or abrogate binding of the antibody to one or more Fcγ receptors.

8. A method of treating a subject for a cancer, the method comprising administering to the subject a therapeutically effective amount of the bispecific antibody molecule according to claim 1.

9. The method according to claim 8, wherein the method comprises administering the bispecific antibody molecule in combination with at least one additional active agent, wherein the at least one additional active agent comprises a chemotherapeutic agent, an inhibitor of a multidrug resistance transporter, an immunotherapy agent, or a combination thereof.

10. The method according to claim 9, wherein the at least one additional active agent is a chemotherapeutic agent, optionally wherein the chemotherapeutic agent is a taxol, a *vinca* alkaloid, or an anthracycline.

11. The method according to claim 10, wherein the subject being treated has a cancer that has been determined to be resistant to treatment with the chemotherapeutic agent, wherein optionally the chemotherapeutic agent comprises paclitaxel, Colchicine, Verapamil, Vinblastine, Topotecan, Doxorubicin, Daunorubicin, Etoposide, or Nilotinib.

12. The antibody according to claim 1, wherein a first VH chain is fused to a first Fc domain and a second VH chain is fused to a second Fc domain, optionally wherein the Fc domains comprise modified CH3 domains that preferentially form heterodimers comprising the first and second VH chains, and optionally wherein the first and second Fc domains are human immunoglobulin G1 (IgG1) Fc domains.

13. A pharmaceutical composition comprising:
   the antibody of claim 1; and
   a pharmaceutically acceptable excipient.

14. One or more nucleic acids comprising one or more sequences encoding the antibody according to claim 1.

15. A mammalian cell genetically modified with the one or more nucleic acids according to claim 14.

16. The cell according to claim 15, wherein the cell is an immune cell.

17. A kit comprising:
   the antibody or a nucleic acid encoding the antibody, according to claim 1; and
   at least one additional active agent.

18. The method according to claim 8, wherein the cancer is drug resistant or multidrug resistant.

\* \* \* \* \*

SEQUENCE LISTING

```
<160> NUMBER OF SEQ ID NOS: 105

<210> SEQ ID NO 1
<211> LENGTH: 112
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (35)..(35)
<223> OTHER INFORMATION: The amino acid at position 35 is Asn, Gln or
      Ser

<400> SEQUENCE: 1

Asp Val Leu Met Thr Gln Thr Pro Val Ser Leu Ser Val Ser Leu Gly
1               5                   10                  15

Asp Gln Ala Ser Ile Ser Cys Arg Ser Ser Gln Ser Ile Val His Ser
            20                  25                  30

Thr Gly Xaa Thr Tyr Leu Glu Trp Tyr Leu Gln Lys Pro Gly Gln Ser
        35                  40                  45

Pro Lys Leu Leu Ile Tyr Lys Ile Ser Asn Arg Phe Ser Gly Val Pro
```

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Ala
                     85                  90                  95

Ser His Phe Pro Arg Thr Phe Gly Gly Gly Thr Lys Leu Glu Ile Lys
                100                 105                 110

<210> SEQ ID NO 2
<211> LENGTH: 112
<212> TYPE: PRT
<213> ORGANISM: Artificial sequence
<220> FEATURE:
<223> OTHER INFORMATION: synthetic peptide

<400> SEQUENCE: 2

Asp Val Leu Met Thr Gln Thr Pro Val Ser Leu Ser Val Ser Leu Gly
 1               5                  10                  15

Asp Gln Ala Ser Ile Ser Cys Arg Ser Ser Gln Ser Ile Val His Ser
                20                  25                  30

Thr Gly Asn Thr Tyr Leu Glu Trp Tyr Leu Gln Lys Pro Gly Gln Ser
                35                  40                  45

Pro Lys Leu Leu Ile Tyr Lys Ile Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Ala
                     85                  90                  95

Ser His Phe Pro Arg Thr Phe Gly Gly Gly Thr Lys Leu Glu Ile Lys
                100                 105                 110

<210> SEQ ID NO 3
<211> LENGTH: 112
<212> TYPE: PRT
<213> ORGANISM: Artificial sequence
<220> FEATURE:
<223> OTHER INFORMATION: synthetic peptide

<400> SEQUENCE: 3

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Ile Val His Ser
                20                  25                  30

Thr Gly Gln Thr Tyr Leu Glu Trp Tyr Gln Gln Arg Pro Gly Gln Pro
                35                  40                  45

Pro Arg Leu Leu Ile Tyr Lys Ile Ser Asn Arg Phe Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Phe Gln Ala
                     85                  90                  95

Ser His Phe Pro Arg Thr Phe Gly Gln Gly Thr Lys Leu Glu Ile Lys
                100                 105                 110

<210> SEQ ID NO 4
<211> LENGTH: 112
<212> TYPE: PRT
<213> ORGANISM: Artificial sequence
<220> FEATURE:
```

<223> OTHER INFORMATION: synthetic peptide

<400> SEQUENCE: 4

Asp Ile Val Met Thr Gln Thr Pro Leu Ser Ser Val Thr Leu Gly
1               5                   10                  15

Gln Pro Ala Ser Ile Ser Cys Arg Ser Ser Gln Ser Ile Val His Ser
            20                  25                  30

Thr Gly Ser Thr Tyr Leu Glu Trp Tyr Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Phe Pro Arg Thr Phe Gly Gln Gly Thr Lys Leu Glu Ile Lys
            100                 105                 110

<210> SEQ ID NO 5
<211> LENGTH: 16
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: The amino acid at position 12 is Asn, Gln or
      Ser

<400> SEQUENCE: 5

Arg Ser Ser Gln Ser Ile Val His Ser Thr Gly Xaa Thr Tyr Leu Glu
1               5                   10                  15

<210> SEQ ID NO 6
<211> LENGTH: 7
<212> TYPE: PRT
<213> ORGANISM: Artificial sequence
<220> FEATURE:
<223> OTHER INFORMATION: synthetic peptide

<400> SEQUENCE: 6

Lys Ile Ser Asn Arg Phe Ser
1               5

<210> SEQ ID NO 7
<211> LENGTH: 9
<212> TYPE: PRT
<213> ORGANISM: Artificial sequence
<220> FEATURE:
<223> OTHER INFORMATION: synthetic peptide

<400> SEQUENCE: 7

Phe Gln Ala Ser His Phe Pro Arg Thr
1               5

<210> SEQ ID NO 8
<211> LENGTH: 112
<212> TYPE: PRT
<213> ORGANISM: Artificial sequence
<220> FEATURE:
<223> OTHER INFORMATION: synthetic peptide

<400> SEQUENCE: 8

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Ile Val His Ser
            20                  25                  30

Thr Gly Asn Thr Tyr Leu Glu Trp Tyr Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Phe Pro Arg Thr Phe Gly Gly Gly Thr Lys Leu Glu Ile Lys
            100                 105                 110
```

<210> SEQ ID NO 9
<211> LENGTH: 119
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (57)..(57)
<223> OTHER INFORMATION: The amino acid at position 57 is Asn, Gln or
      Ser

<400> SEQUENCE: 9

```
Glu Val Lys Val Val Glu Ser Gly Gly Val Leu Val Arg Pro Gly Gly
1               5                   10                  15

Ser Leu Lys Leu Ser Cys Ala Ala Ser Gly Phe Thr Phe Ser Arg Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Gly Xaa Thr Tyr Tyr Pro Asp Ser Val
    50                  55                  60

Lys Gly Arg Phe Thr Val Ser Arg Asp Asn Ala Met Ser Ser Leu Tyr
65                  70                  75                  80

Leu Gln Met Ser Ser Leu Arg Ser Glu Asp Thr Ala Leu Tyr Tyr Cys
                85                  90                  95

Ala Arg Tyr Gly Ala Gly Asp Ala Trp Phe Ala Tyr Trp Gly Gln Gly
            100                 105                 110

Thr Leu Val Thr Val Ser Ser
        115
```

<210> SEQ ID NO 10
<211> LENGTH: 119
<212> TYPE: PRT
<213> ORGANISM: Artificial sequence
<220> FEATURE:
<223> OTHER INFORMATION: synthetic peptide

<400> SEQUENCE: 10

```
Glu Val Lys Val Val Glu Ser Gly Gly Val Leu Val Arg Pro Gly Gly
1               5                   10                  15

Ser Leu Lys Leu Ser Cys Ala Ala Ser Gly Phe Thr Phe Ser Arg Tyr
            20                  25                  30

Thr Met Ser Trp Val Arg Gln Thr Pro Glu Lys Arg Leu Glu Trp Val
        35                  40                  45
```

```
Ala Thr Ile Ser Ser Gly Gly Gly Asn Thr Tyr Tyr Pro Asp Ser Val
    50              55                  60

Lys Gly Arg Phe Thr Val Ser Arg Asp Asn Ala Met Ser Ser Leu Tyr
65              70                  75                  80

Leu Gln Met Ser Ser Leu Arg Ser Glu Asp Thr Ala Leu Tyr Tyr Cys
                85                  90                  95

Ala Arg Tyr Gly Ala Gly Asp Ala Trp Phe Ala Tyr Trp Gly Gln Gly
            100                 105                 110

Thr Leu Val Thr Val Ser Ser
            115

<210> SEQ ID NO 11
<211> LENGTH: 119
<212> TYPE: PRT
<213> ORGANISM: Artificial sequence
<220> FEATURE:
<223> OTHER INFORMATION: synthetic peptide

<400> SEQUENCE: 11

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
            35                  40                  45

Ala Thr Ile Ser Ser Gly Gly Gly Gln Thr Tyr Tyr Pro Asp Ser Val
    50              55                  60

Lys Gly Arg Phe Thr Val Ser Arg Asp Asn Lys Asn Ser Leu Tyr
65              70                  75                  80

Leu Gln Met Asn Ser Leu Arg Thr Glu Asp Thr Ala Leu Tyr Tyr Cys
                85                  90                  95

Ala Arg Tyr Gly Ala Gly Asp Ala Trp Phe Ala Tyr Trp Gly Gln Gly
            100                 105                 110

Thr Leu Val Thr Val Ser Ser
            115

<210> SEQ ID NO 12
<211> LENGTH: 119
<212> TYPE: PRT
<213> ORGANISM: Artificial sequence
<220> FEATURE:
<223> OTHER INFORMATION: synthetic peptide

<400> SEQUENCE: 12

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
            35                  40                  45

Ala Thr Ile Ser Ser Gly Gly Gly Ser Thr Tyr Tyr Pro Asp Ser Val
    50              55                  60

Lys Gly Arg Phe Thr Val Ser Arg Asp Asn Ser Lys Asn Ser Leu Tyr
65              70                  75                  80

Leu Gln Met Asn Ser Leu Arg Thr Glu Asp Thr Ala Leu Tyr Tyr Cys
                85                  90                  95

Ala Arg Tyr Gly Ala Gly Asp Ala Trp Phe Ala Tyr Trp Gly Gln Gly
            100                 105                 110
```

Thr Leu Val Thr Val Ser Ser
        115

<210> SEQ ID NO 13
<211> LENGTH: 5
<212> TYPE: PRT
<213> ORGANISM: Artificial sequence
<220> FEATURE:
<223> OTHER INFORMATION: synthetic peptide

<400> SEQUENCE: 13

Arg Tyr Thr Met Ser
1               5

<210> SEQ ID NO 14
<211> LENGTH: 17
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: The amino acid at position 8 is Asn, Gln or Ser

<400> SEQUENCE: 14

Thr Ile Ser Ser Gly Gly Gly Xaa Thr Tyr Tyr Pro Asp Ser Val Lys
1               5                   10                  15

Gly

<210> SEQ ID NO 15
<211> LENGTH: 10
<212> TYPE: PRT
<213> ORGANISM: Artificial sequence
<220> FEATURE:
<223> OTHER INFORMATION: synthetic peptide

<400> SEQUENCE: 15

Tyr Gly Ala Gly Asp Ala Trp Phe Ala Tyr
1               5                   10

<210> SEQ ID NO 16
<211> LENGTH: 119
<212> TYPE: PRT
<213> ORGANISM: Artificial sequence
<220> FEATURE:
<223> OTHER INFORMATION: synthetic peptide

<400> SEQUENCE: 16

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Ser Gly Gly Gly Asn Thr Tyr Tyr Pro Asp Ser Val
    50                  55                  60

Lys Gly Arg Phe Thr Val Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Arg Tyr Gly Ala Gly Asp Ala Trp Phe Ala Tyr Trp Gly Gln Gly
            100                 105                 110

```
Thr Leu Val Thr Val Ser Ser
        115

<210> SEQ ID NO 17
<211> LENGTH: 117
<212> TYPE: PRT
<213> ORGANISM: Artificial sequence
<220> FEATURE:
<223> OTHER INFORMATION: synthetic peptide

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser
        115

<210> SEQ ID NO 18
<211> LENGTH: 5
<212> TYPE: PRT
<213> ORGANISM: Artificial sequence
<220> FEATURE:
<223> OTHER INFORMATION: synthetic peptide

<400> SEQUENCE: 18

Asn Tyr Asn Met His
1               5

<210> SEQ ID NO 19
<211> LENGTH: 17
<212> TYPE: PRT
<213> ORGANISM: Artificial sequence
<220> FEATURE:
<223> OTHER INFORMATION: synthetic peptide

<400> SEQUENCE: 19

Thr Ile Tyr Pro Gly Asn Asp Asp Thr Ser Tyr Asn Gln Lys Phe Lys
1               5                   10                  15

Asp

<210> SEQ ID NO 20
<211> LENGTH: 8
<212> TYPE: PRT
<213> ORGANISM: Artificial sequence
<220> FEATURE:
<223> OTHER INFORMATION: synthetic peptide

<400> SEQUENCE: 20

Gly Gly Tyr Arg Ala Met Asp Tyr
1               5
```

<210> SEQ ID NO 21
<211> LENGTH: 117
<212> TYPE: PRT
<213> ORGANISM: Artificial sequence
<220> FEATURE:
<223> OTHER INFORMATION: synthetic peptide

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Asn Met His Trp Val Arg Gln Ala Pro Gly Lys Gly Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser
        115
```

<210> SEQ ID NO 22
<211> LENGTH: 117
<212> TYPE: PRT
<213> ORGANISM: Artificial sequence
<220> FEATURE:
<223> OTHER INFORMATION: synthetic peptide

<400> SEQUENCE: 22

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30

Asn Met His Trp Val Arg Gln Met Pro Gly Lys Gly Leu Glu Trp Met
        35                  40                  45

Gly Thr Ile Tyr Pro Gly Asn Asp Asp Thr Ser Tyr Asn Gln Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Arg Ala Met Asp Tyr Trp Gly Gln Gly Thr Thr
            100                 105                 110

Val Thr Val Ser Ser
        115
```

<210> SEQ ID NO 23
<211> LENGTH: 117
<212> TYPE: PRT
<213> ORGANISM: Artificial sequence
<220> FEATURE:
<223> OTHER INFORMATION: synthetic peptide

<400> SEQUENCE: 23

```
Gln Val Gln Leu Val Gln Ser Gly Ser Glu Leu Lys Lys Pro Gly Ala
```

```
1               5                   10                  15
Ser Val Lys Val Ser Cys Lys Ala Ser Gly Tyr Thr Phe Thr Asn Tyr
                20                  25                  30

Asn Met His Trp Val Arg Gln Ala Pro Gly Gln Gly Leu Glu Trp Met
            35                  40                  45

Gly Thr Ile Tyr Pro Gly Asn Asp Thr Ser Tyr Asn Gln Lys Phe
        50                  55                  60

Lys Asp Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                85                  90                  95

Ala Arg Gly Gly Tyr Arg Ala Met Asp Tyr Trp Gly Gln Gly Thr Thr
                100                 105                 110

Val Thr Val Ser Ser
            115
```

<210> SEQ ID NO 24
<211> LENGTH: 119
<212> TYPE: PRT
<213> ORGANISM: Artificial sequence
<220> FEATURE:
<223> OTHER INFORMATION: synthetic peptide

<400> SEQUENCE: 24

```
Glu Val Lys Val Val Glu Ser Gly Gly Val Leu Val Arg Pro Gly Gly
 1               5                   10                  15

Ser Leu Lys Leu Ser Cys Ala Ala Ser Gly Phe Thr Phe Ser Arg Tyr
                20                  25                  30

Thr Met Ser Trp Val Arg Gln Thr Pro Glu Lys Arg Leu Glu Trp Val
            35                  40                  45

Ala Thr Ile Ser Ser Gly Gly Gly Asn Thr Tyr Tyr Pro Asp Ser Val
        50                  55                  60

Lys Gly Arg Phe Thr Val Ser Arg Asp Asn Ala Met Ser Ser Leu Tyr
 65                  70                  75                  80

Leu Gln Met Ser Ser Leu Arg Ser Glu Asp Thr Ala Leu Tyr Tyr Cys
                85                  90                  95

Ala Arg Tyr Gly Ala Gly Asp Ala Trp Phe Ala Tyr Trp Gly Gln Gly
                100                 105                 110

Thr Leu Val Thr Val Ser Ala
            115
```

<210> SEQ ID NO 25
<211> LENGTH: 112
<212> TYPE: PRT
<213> ORGANISM: Artificial sequence
<220> FEATURE:
<223> OTHER INFORMATION: synthetic peptide

<400> SEQUENCE: 25

```
Asp Val Leu Met Thr Gln Thr Pro Leu Ser Leu Pro Val Ser Leu Gly
 1               5                   10                  15

Asp Gln Ala Ser Ile Ser Cys Arg Ser Ser Gln Ser Ile Val His Ser
                20                  25                  30

Thr Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60
```

```
Asp Arg Phe Ser Gly Ser Gly Ser Gly Thr Asp Phe Thr Leu Lys Ile
 65                  70                  75                  80

Ser Arg Leu Glu Ala Glu Asp Leu Gly Val Tyr Tyr Cys Phe Gln Gly
                 85                  90                  95

Ser His Phe Pro Arg Thr Phe Gly Gly Gly Thr Arg Leu Glu Ile Lys
            100                 105                 110

<210> SEQ ID NO 26
<211> LENGTH: 16
<212> TYPE: PRT
<213> ORGANISM: Artificial sequence
<220> FEATURE:
<223> OTHER INFORMATION: synthetic peptide

<400> SEQUENCE: 26

Arg Ser Ser Gln Ser Ile Val His Ser Thr Gly Asn Thr Tyr Leu Glu
1               5                   10                  15

<210> SEQ ID NO 27
<211> LENGTH: 16
<212> TYPE: PRT
<213> ORGANISM: Artificial sequence
<220> FEATURE:
<223> OTHER INFORMATION: synthetic peptide

<400> SEQUENCE: 27

Arg Ser Ser Gln Ser Ile Val His Ser Thr Gly Gln Thr Tyr Leu Glu
1               5                   10                  15

<210> SEQ ID NO 28
<211> LENGTH: 16
<212> TYPE: PRT
<213> ORGANISM: Artificial sequence
<220> FEATURE:
<223> OTHER INFORMATION: synthetic peptide

<400> SEQUENCE: 28

Arg Ser Ser Gln Ser Ile Val His Ser Thr Gly Ser Thr Tyr Leu Glu
1               5                   10                  15

<210> SEQ ID NO 29
<211> LENGTH: 17
<212> TYPE: PRT
<213> ORGANISM: Artificial sequence
<220> FEATURE:
<223> OTHER INFORMATION: synthetic peptide

<400> SEQUENCE: 29

Thr Ile Ser Ser Gly Gly Gly Asn Thr Tyr Tyr Pro Asp Ser Val Lys
1               5                   10                  15

Gly

<210> SEQ ID NO 30
<211> LENGTH: 17
<212> TYPE: PRT
<213> ORGANISM: Artificial sequence
<220> FEATURE:
<223> OTHER INFORMATION: synthetic peptide

<400> SEQUENCE: 30

Thr Ile Ser Ser Gly Gly Gly Gln Thr Tyr Tyr Pro Asp Ser Val Lys
1               5                   10                  15

Gly
```

```
<210> SEQ ID NO 31
<211> LENGTH: 17
<212> TYPE: PRT
<213> ORGANISM: Artificial sequence
<220> FEATURE:
<223> OTHER INFORMATION: synthetic peptide

<400> SEQUENCE: 31

Thr Ile Ser Ser Gly Gly Gly Ser Thr Tyr Tyr Pro Asp Ser Val Lys
1               5                   10                  15
Gly

<210> SEQ ID NO 32
<211> LENGTH: 118
<212> TYPE: PRT
<213> ORGANISM: Artificial sequence
<220> FEATURE:
<223> OTHER INFORMATION: synthetic peptide

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 33
<211> LENGTH: 5
<212> TYPE: PRT
<213> ORGANISM: Artificial sequence
<220> FEATURE:
<223> OTHER INFORMATION: synthetic peptide

<400> SEQUENCE: 33

Asp Ser Trp Ile His
1               5

<210> SEQ ID NO 34
<211> LENGTH: 17
<212> TYPE: PRT
<213> ORGANISM: Artificial sequence
<220> FEATURE:
<223> OTHER INFORMATION: synthetic peptide

<400> SEQUENCE: 34

Trp Ile Ser Pro Tyr Gly Gly Ser Thr Tyr Tyr Ala Asp Ser Val Lys
1               5                   10                  15
Gly

<210> SEQ ID NO 35
<211> LENGTH: 9
```

<212> TYPE: PRT
<213> ORGANISM: Artificial sequence
<220> FEATURE:
<223> OTHER INFORMATION: synthetic peptide

<400> SEQUENCE: 35

Arg His Trp Pro Gly Gly Phe Asp Tyr
1               5

<210> SEQ ID NO 36
<211> LENGTH: 121
<212> TYPE: PRT
<213> ORGANISM: Artificial sequence
<220> FEATURE:
<223> OTHER INFORMATION: synthetic peptide

<400> SEQUENCE: 36

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asp Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Val Asn Ser Val Thr Ala Ala Asp Thr Ala Val Tyr Tyr
                85                  90                  95

Cys Ala Arg Val Ser Ile Phe Gly Val Gly Thr Phe Asp Tyr Trp Gly
            100                 105                 110

Gln Gly Thr Leu Val Thr Val Ser Ser
        115                 120

<210> SEQ ID NO 37
<211> LENGTH: 7
<212> TYPE: PRT
<213> ORGANISM: Artificial sequence
<220> FEATURE:
<223> OTHER INFORMATION: synthetic peptide

<400> SEQUENCE: 37

Ser Gly Asp Tyr Tyr Trp Ser
1               5

<210> SEQ ID NO 38
<211> LENGTH: 16
<212> TYPE: PRT
<213> ORGANISM: Artificial sequence
<220> FEATURE:
<223> OTHER INFORMATION: synthetic peptide

<400> SEQUENCE: 38

Tyr Ile Tyr Tyr Ser Gly Ser Thr Asp Tyr Asn Pro Ser Leu Lys Ser
1               5                   10                  15

<210> SEQ ID NO 39
<211> LENGTH: 11
<212> TYPE: PRT
<213> ORGANISM: Artificial sequence
<220> FEATURE:
<223> OTHER INFORMATION: synthetic peptide

<400> SEQUENCE: 39

```
Val Ser Ile Phe Gly Val Gly Thr Phe Asp Tyr
1               5                   10

<210> SEQ ID NO 40
<211> LENGTH: 119
<212> TYPE: PRT
<213> ORGANISM: Artificial sequence
<220> FEATURE:
<223> OTHER INFORMATION: synthetic peptide

<400> SEQUENCE: 40

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 41
<211> LENGTH: 5
<212> TYPE: PRT
<213> ORGANISM: Artificial sequence
<220> FEATURE:
<223> OTHER INFORMATION: synthetic peptide

<400> SEQUENCE: 41

Asn Tyr Gly Val His
1               5

<210> SEQ ID NO 42
<211> LENGTH: 16
<212> TYPE: PRT
<213> ORGANISM: Artificial sequence
<220> FEATURE:
<223> OTHER INFORMATION: synthetic peptide

<400> SEQUENCE: 42

Val Ile Trp Ser Gly Gly Asn Thr Asp Tyr Asn Thr Pro Phe Thr Ser
1               5                   10                  15

<210> SEQ ID NO 43
<211> LENGTH: 11
<212> TYPE: PRT
<213> ORGANISM: Artificial sequence
<220> FEATURE:
<223> OTHER INFORMATION: synthetic peptide

<400> SEQUENCE: 43

Ala Leu Thr Tyr Tyr Asp Tyr Glu Phe Ala Tyr
1               5                   10

<210> SEQ ID NO 44
```

```
<211> LENGTH: 16
<212> TYPE: PRT
<213> ORGANISM: Artificial sequence
<220> FEATURE:
<223> OTHER INFORMATION: synthetic peptide

<400> SEQUENCE: 44

Arg Ser Ser Gln Ser Ile Val His Ser Thr Gly Asn Thr Tyr Leu Glu
1               5                   10                  15

<210> SEQ ID NO 45
<211> LENGTH: 7
<212> TYPE: PRT
<213> ORGANISM: Artificial sequence
<220> FEATURE:
<223> OTHER INFORMATION: synthetic peptide

<400> SEQUENCE: 45

Lys Ile Ser Arg Leu Glu Ala
1               5

<210> SEQ ID NO 46
<211> LENGTH: 9
<212> TYPE: PRT
<213> ORGANISM: Artificial sequence
<220> FEATURE:
<223> OTHER INFORMATION: synthetic peptide

<400> SEQUENCE: 46

Phe Gln Gly Ser His Phe Pro Arg Thr
1               5

<210> SEQ ID NO 47
<211> LENGTH: 119
<212> TYPE: PRT
<213> ORGANISM: Artificial sequence
<220> FEATURE:
<223> OTHER INFORMATION: synthetic peptide

<400> SEQUENCE: 47

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
                20                  25                  30

Thr Met Ser Trp Val Arg Gln Thr Pro Glu Lys Arg Leu Glu Trp Val
            35                  40                  45

Ala Thr Ile Ser Ser Gly Gly Gly Asn Thr Tyr Tyr Pro Asp Ser Val
        50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg Tyr Tyr Arg Tyr Glu Ala Trp Phe Ala Ser Trp Gly Gln Gly
                100                 105                 110

Thr Leu Val Thr Val Ser Ala
        115

<210> SEQ ID NO 48
<211> LENGTH: 5
<212> TYPE: PRT
<213> ORGANISM: Artificial sequence
<220> FEATURE:
<223> OTHER INFORMATION: synthetic peptide
```

```
<400> SEQUENCE: 48

Ser Tyr Thr Met Ser
1               5

<210> SEQ ID NO 49
<211> LENGTH: 10
<212> TYPE: PRT
<213> ORGANISM: Artificial sequence
<220> FEATURE:
<223> OTHER INFORMATION: synthetic peptide

<400> SEQUENCE: 49

Tyr Tyr Arg Tyr Glu Ala Trp Phe Ala Ser
1               5                   10

<210> SEQ ID NO 50
<211> LENGTH: 5
<212> TYPE: PRT
<213> ORGANISM: Artificial sequence
<220> FEATURE:
<223> OTHER INFORMATION: synthetic peptide

<400> SEQUENCE: 50

Gly Ser Gly Gly Ser
1               5

<210> SEQ ID NO 51
<211> LENGTH: 4
<212> TYPE: PRT
<213> ORGANISM: Artificial sequence
<220> FEATURE:
<223> OTHER INFORMATION: synthetic peptide

<400> SEQUENCE: 51

Gly Gly Gly Ser
1

<210> SEQ ID NO 52
<211> LENGTH: 4
<212> TYPE: PRT
<213> ORGANISM: Artificial sequence
<220> FEATURE:
<223> OTHER INFORMATION: synthetic peptide

<400> SEQUENCE: 52

Gly Gly Ser Gly
1

<210> SEQ ID NO 53
<211> LENGTH: 5
<212> TYPE: PRT
<213> ORGANISM: Artificial sequence
<220> FEATURE:
<223> OTHER INFORMATION: synthetic peptide

<400> SEQUENCE: 53

Gly Gly Ser Gly Gly
1               5

<210> SEQ ID NO 54
<211> LENGTH: 5
<212> TYPE: PRT
<213> ORGANISM: Artificial sequence
<220> FEATURE:
<223> OTHER INFORMATION: synthetic peptide

<400> SEQUENCE: 54
```

```
Gly Ser Gly Ser Gly
1               5

<210> SEQ ID NO 55
<211> LENGTH: 5
<212> TYPE: PRT
<213> ORGANISM: Artificial sequence
<220> FEATURE:
<223> OTHER INFORMATION: synthetic peptide

<400> SEQUENCE: 55

Gly Ser Gly Gly Gly
1               5

<210> SEQ ID NO 56
<211> LENGTH: 5
<212> TYPE: PRT
<213> ORGANISM: Artificial sequence
<220> FEATURE:
<223> OTHER INFORMATION: synthetic peptide

<400> SEQUENCE: 56

Gly Gly Gly Ser Gly
1               5

<210> SEQ ID NO 57
<211> LENGTH: 5
<212> TYPE: PRT
<213> ORGANISM: Artificial sequence
<220> FEATURE:
<223> OTHER INFORMATION: synthetic peptide

<400> SEQUENCE: 57

Gly Ser Ser Ser Gly
1               5

<210> SEQ ID NO 58
<211> LENGTH: 448
<212> TYPE: PRT
<213> ORGANISM: Artificial sequence
<220> FEATURE:
<223> OTHER INFORMATION: synthetic peptide

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 59
<211> LENGTH: 451
<212> TYPE: PRT
<213> ORGANISM: Artificial sequence
<220> FEATURE:
<223> OTHER INFORMATION: synthetic peptide

<400> SEQUENCE: 59

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asp Tyr Asn Pro Ser
50                  55                  60

```
Leu Lys Ser Arg Val Thr Met Ser Val Asp Thr Ser Lys Asn Gln Phe
 65                  70                  75                  80

Ser Leu Lys Val Asn Ser Val Thr Ala Ala Asp Thr Ala Val Tyr Tyr
                 85                  90                  95

Cys Ala Arg Val Ser Ile Phe Gly Val Gly Thr Phe Asp Tyr Trp Gly
            100                 105                 110

Gln Gly Thr Leu Val Thr Val Ser Ser Ala Ser Thr Lys Gly Pro Ser
        115                 120                 125

Val Leu Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
450

<210> SEQ ID NO 60
<211> LENGTH: 449
```

```
<212> TYPE: PRT
<213> ORGANISM: Artificial sequence
<220> FEATURE:
<223> OTHER INFORMATION: synthetic peptide

<400> SEQUENCE: 60
```

| | | | | | | | | | | | | | | |
|---|---|---|---|---|---|---|---|---|---|---|---|---|---|---|
| Gln | Val | Gln | Leu | Lys | Gln | Ser | Gly | Pro | Gly | Leu | Val | Gln | Pro | Ser | Gln |
| 1 | | | | 5 | | | | | 10 | | | | | 15 |
| Ser | Leu | Ser | Ile | Thr | Cys | Thr | Val | Ser | Gly | Phe | Ser | Leu | Thr | Asn | Tyr |
| | | | 20 | | | | | 25 | | | | | 30 | | |
| Gly | Val | His | Trp | Val | Arg | Gln | Ser | Pro | Gly | Lys | Gly | Leu | Glu | Trp | Leu |
| | | | 35 | | | | 40 | | | | | 45 | | | |
| Gly | Val | Ile | Trp | Ser | Gly | Gly | Asn | Thr | Asp | Tyr | Asn | Thr | Pro | Phe | Thr |
| | 50 | | | | | 55 | | | | | 60 | | | | |
| Ser | Arg | Leu | Ser | Ile | Asn | Lys | Asp | Asn | Ser | Lys | Ser | Gln | Val | Phe | Phe |
| 65 | | | | | 70 | | | | | 75 | | | | | 80 |
| Lys | Met | Asn | Ser | Leu | Gln | Ser | Asn | Asp | Thr | Ala | Ile | Tyr | Tyr | Cys | Ala |
| | | | | 85 | | | | | 90 | | | | | 95 | |
| Arg | Ala | Leu | Thr | Tyr | Tyr | Asp | Tyr | Glu | Phe | Ala | Tyr | Trp | Gly | Gln | Gly |
| | | | 100 | | | | | 105 | | | | | 110 | | |
| Thr | Leu | Val | Thr | Val | Ser | Ala | Ala | Ser | Thr | Lys | Gly | Pro | Ser | Val | Phe |
| | | | 115 | | | | | 120 | | | | | 125 | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | | 195 | | | | | 200 | | | | | 205 | | |
| Ser | Asn | Thr | Lys | Val | Asp | Lys | Lys | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | | 275 | | | | | 280 | | | | | 285 | | |
| Ala | Lys | Thr | Lys | Pro | Arg | Glu | Glu | Gln | Tyr | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Asp | Glu | Leu | Thr | Lys | Asn | Gln | Val | Ser | Leu | Thr |
| | | | 355 | | | | | 360 | | | | | 365 | | |
| Cys | Leu | Val | Lys | Gly | Phe | Tyr | Pro | Ser | Asp | Ile | Ala | Val | Glu | Trp | Glu |
| | 370 | | | | | 375 | | | | | 380 | | | | |

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 61
<211> LENGTH: 1280
<212> TYPE: PRT
<213> ORGANISM: Homo sapiens

<400> SEQUENCE: 61

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Gly Thr Leu Ala Ala Ile Ile His Gly Ala Gly
50                  55                  60

Leu Pro Leu Met Met Leu Val Phe Gly Glu Met Thr Asp Ile Phe Ala
65              70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Thr Gly Phe Ile Val Gly Phe
        195                 200                 205

Thr Arg Gly Trp Lys Leu Thr Leu Val Ile Leu Ala Ile Ser Pro Val
210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
290                 295                 300

```
Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
            325                 330                 335

Ser Val Leu Ile Gly Ala Phe Ser Val Gly Gln Ala Ser Pro Ser Ile
                340                 345                 350

Glu Ala Phe Ala Asn Ala Arg Gly Ala Ala Tyr Glu Ile Phe Lys Ile
            355                 360                 365

Ile Asp Asn Lys Pro Ser Ile Asp Ser Tyr Ser Lys Ser Gly His Lys
370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
                420                 425                 430

Lys Ser Thr Thr Val Gln Leu Met Gln Arg Leu Tyr Asp Pro Thr Glu
            435                 440                 445

Gly Met Val Ser Val Asp Gly Gln Asp Ile Arg Thr Ile Asn Val Arg
450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
            515                 520                 525

Ala Gln Leu Ser Gly Gly Gln Lys Gln Arg Ile Ala Ile Ala Arg Ala
530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
            595                 600                 605

Lys Gly Asn His Asp Glu Leu Met Lys Glu Lys Gly Ile Tyr Phe Lys
610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
            675                 680                 685

Asp Glu Ser Ile Pro Pro Val Ser Phe Trp Arg Ile Met Lys Leu Asn
            690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
```

```
                725                 730                 735
Gly Val Phe Thr Arg Ile Asp Asp Pro Glu Thr Lys Arg Gln Asn Ser
            740                 745                 750
Asn Leu Phe Ser Leu Leu Phe Leu Ala Leu Gly Ile Ile Ser Phe Ile
            755                 760                 765
Thr Phe Phe Leu Gln Gly Phe Thr Phe Gly Lys Ala Gly Glu Ile Leu
            770                 775                 780
Thr Lys Arg Leu Arg Tyr Met Val Phe Arg Ser Met Leu Arg Gln Asp
785                 790                 795                 800
Val Ser Trp Phe Asp Asp Pro Lys Asn Thr Thr Gly Ala Leu Thr Thr
                805                 810                 815
Arg Leu Ala Asn Asp Ala Ala Gln Val Lys Gly Ala Ile Gly Ser Arg
                820                 825                 830
Leu Ala Val Ile Thr Gln Asn Ile Ala Asn Leu Gly Thr Gly Ile Ile
                835                 840                 845
Ile Ser Phe Ile Tyr Gly Trp Gln Leu Thr Leu Leu Leu Leu Ala Ile
                850                 855                 860
Val Pro Ile Ile Ala Ile Ala Gly Val Val Glu Met Lys Met Leu Ser
865                 870                 875                 880
Gly Gln Ala Leu Lys Asp Lys Lys Glu Leu Glu Gly Ser Gly Lys Ile
                885                 890                 895
Ala Thr Glu Ala Ile Glu Asn Phe Arg Thr Val Val Ser Leu Thr Gln
                900                 905                 910
Glu Gln Lys Phe Glu His Met Tyr Ala Gln Ser Leu Gln Val Pro Tyr
                915                 920                 925
Arg Asn Ser Leu Arg Lys Ala His Ile Phe Gly Ile Thr Phe Ser Phe
                930                 935                 940
Thr Gln Ala Met Met Tyr Phe Ser Tyr Ala Gly Cys Phe Arg Phe Gly
945                 950                 955                 960
Ala Tyr Leu Val Ala His Lys Leu Met Ser Phe Glu Asp Val Leu Leu
                965                 970                 975
Val Phe Ser Ala Val Val Phe Gly Ala Met Ala Val Gly Gln Val Ser
                980                 985                 990
Ser Phe Ala Pro Asp Tyr Ala Lys Ala Lys Ile Ser Ala Ala His Ile
                995                1000                1005
Ile Met Ile Ile Glu Lys Thr Pro Leu Ile Asp Ser Tyr Ser Thr
            1010                1015                1020
Glu Gly Leu Met Pro Asn Thr Leu Glu Gly Asn Val Thr Phe Gly
            1025                1030                1035
Glu Val Val Phe Asn Tyr Pro Thr Arg Pro Asp Ile Pro Val Leu
            1040                1045                1050
Gln Gly Leu Ser Leu Glu Val Lys Lys Gly Gln Thr Leu Ala Leu
            1055                1060                1065
Val Gly Ser Ser Gly Cys Gly Lys Ser Thr Val Val Gln Leu Leu
            1070                1075                1080
Glu Arg Phe Tyr Asp Pro Leu Ala Gly Lys Val Leu Leu Asp Gly
            1085                1090                1095
Lys Glu Ile Lys Arg Leu Asn Val Gln Trp Leu Arg Ala His Leu
            1100                1105                1110
Gly Ile Val Ser Gln Glu Pro Ile Leu Phe Asp Cys Ser Ile Ala
            1115                1120                1125
Glu Asn Ile Ala Tyr Gly Asp Asn Ser Arg Val Val Ser Gln Glu
            1130                1135                1140
```

Glu Ile Val Arg Ala Ala Lys Glu Ala Asn Ile His Ala Phe Ile
        1145                1150                1155

Glu Ser Leu Pro Asn Lys Tyr Ser Thr Lys Val Gly Asp Lys Gly
        1160                1165                1170

Thr Gln Leu Ser Gly Gly Gln Lys Gln Arg Ile Ala Ile Ala Arg
        1175                1180                1185

Ala Leu Val Arg Gln Pro His Ile Leu Leu Leu Asp Glu Ala Thr
        1190                1195                1200

Ser Ala Leu Asp Thr Glu Ser Glu Lys Val Val Gln Glu Ala Leu
        1205                1210                1215

Asp Lys Ala Arg Glu Gly Arg Thr Cys Ile Val Ile Ala His Arg
        1220                1225                1230

Leu Ser Thr Ile Gln Asn Ala Asp Leu Ile Val Val Phe Gln Asn
        1235                1240                1245

Gly Arg Val Lys Glu His Gly Thr His Gln Gln Leu Leu Ala Gln
        1250                1255                1260

Lys Gly Ile Tyr Phe Ser Met Val Ser Val Gln Ala Gly Thr Lys
        1265                1270                1275

Arg Gln
        1280

<210> SEQ ID NO 62
<211> LENGTH: 1276
<212> TYPE: PRT
<213> ORGANISM: Mus musculus

<400> SEQUENCE: 62

Met Glu Phe Glu Glu Asn Leu Lys Gly Arg Ala Asp Lys Asn Phe Ser
1               5                   10                  15

Lys Met Gly Lys Lys Ser Lys Lys Glu Lys Lys Lys Pro Ala
                20                  25                  30

Val Gly Val Phe Gly Met Phe Arg Tyr Ala Asp Trp Leu Asp Lys Leu
                35                  40                  45

Cys Met Ile Leu Gly Thr Leu Ala Ala Ile Ile His Gly Thr Leu Leu
50                  55                  60

Pro Leu Leu Met Leu Val Phe Gly Asn Met Thr Asp Ser Phe Thr Lys
65                  70                  75                  80

Ala Glu Ala Ser Ile Leu Pro Ser Ile Thr Asn Gln Ser Gly Pro Asn
                85                  90                  95

Ser Thr Leu Ile Ile Ser Asn Ser Ser Leu Glu Glu Glu Met Ala Ile
                100                 105                 110

Tyr Ala Tyr Tyr Tyr Thr Gly Ile Gly Ala Gly Val Leu Ile Val Ala
                115                 120                 125

Tyr Ile Gln Val Ser Leu Trp Cys Leu Ala Ala Gly Arg Gln Ile His
        130                 135                 140

Lys Ile Arg Gln Lys Phe Phe His Ala Ile Met Asn Gln Glu Ile Gly
145                 150                 155                 160

Trp Phe Asp Val His Asp Val Gly Glu Leu Asn Thr Arg Leu Thr Asp
                165                 170                 175

Asp Val Ser Lys Ile Asn Asp Gly Ile Gly Asp Lys Ile Gly Met Phe
                180                 185                 190

Phe Gln Ser Ile Thr Thr Phe Leu Ala Gly Phe Ile Ile Gly Phe Ile
        195                 200                 205

Ser Gly Trp Lys Leu Thr Leu Val Ile Leu Ala Val Ser Pro Leu Ile

```
              210                 215                 220
Gly Leu Ser Ser Ala Leu Trp Ala Lys Val Leu Thr Ser Phe Thr Asn
225                 230                 235                 240

Lys Glu Leu Gln Ala Tyr Ala Lys Ala Gly Ala Val Ala Glu Glu Val
                245                 250                 255

Leu Ala Ala Ile Arg Thr Val Ile Ala Phe Gly Gly Gln Gln Lys Glu
            260                 265                 270

Leu Glu Arg Tyr Asn Lys Asn Leu Glu Ala Lys Asn Val Gly Ile
        275                 280                 285

Lys Lys Ala Ile Thr Ala Ser Ile Ser Ile Gly Ile Ala Tyr Leu Leu
        290                 295                 300

Val Tyr Ala Ser Tyr Ala Leu Ala Phe Trp Tyr Gly Thr Ser Leu Val
305                 310                 315                 320

Leu Ser Asn Glu Tyr Ser Ile Gly Glu Val Leu Thr Val Phe Phe Ser
                325                 330                 335

Ile Leu Leu Gly Thr Phe Ser Ile Gly His Leu Ala Pro Asn Ile Glu
            340                 345                 350

Ala Phe Ala Asn Ala Arg Gly Ala Ala Phe Glu Ile Phe Lys Ile Ile
        355                 360                 365

Asp Asn Glu Pro Ser Ile Asp Ser Phe Ser Thr Lys Gly Tyr Lys Pro
    370                 375                 380

Asp Ser Ile Met Gly Asn Leu Glu Phe Lys Asn Val His Phe Asn Tyr
385                 390                 395                 400

Pro Ser Arg Ser Glu Val Gln Ile Leu Lys Gly Leu Asn Leu Lys Val
                405                 410                 415

Lys Ser Gly Gln Thr Val Ala Leu Val Gly Asn Ser Gly Cys Gly Lys
            420                 425                 430

Ser Thr Thr Val Gln Leu Met Gln Arg Leu Tyr Asp Pro Leu Glu Gly
        435                 440                 445

Val Val Ser Ile Asp Gly Gln Asp Ile Arg Thr Ile Asn Val Arg Tyr
        450                 455                 460

Leu Arg Glu Ile Ile Gly Val Val Ser Gln Glu Pro Val Leu Phe Ala
465                 470                 475                 480

Thr Thr Ile Ala Glu Asn Ile Arg Tyr Gly Arg Glu Asp Val Thr Met
                485                 490                 495

Asp Glu Ile Glu Lys Ala Val Lys Glu Ala Asn Ala Tyr Asp Phe Ile
            500                 505                 510

Met Lys Leu Pro His Gln Phe Asp Thr Leu Val Gly Glu Arg Gly Ala
        515                 520                 525

Gln Leu Ser Gly Gly Gln Lys Gln Arg Ile Ala Ile Ala Arg Ala Leu
        530                 535                 540

Val Arg Asn Pro Lys Ile Leu Leu Leu Asp Glu Ala Thr Ser Ala Leu
545                 550                 555                 560

Asp Thr Glu Ser Glu Ala Val Val Gln Ala Ala Leu Asp Lys Ala Arg
                565                 570                 575

Glu Gly Arg Thr Thr Ile Val Ile Ala His Arg Leu Ser Thr Val Arg
            580                 585                 590

Asn Ala Asp Val Ile Ala Gly Phe Asp Gly Gly Val Ile Val Glu Gln
        595                 600                 605

Gly Asn His Asp Glu Leu Met Arg Glu Lys Gly Ile Tyr Phe Lys Leu
        610                 615                 620

Val Met Thr Gln Thr Arg Gly Asn Glu Ile Glu Pro Gly Asn Asn Ala
625                 630                 635                 640
```

-continued

```
Tyr Gly Ser Gln Ser Asp Thr Asp Ala Ser Glu Leu Thr Ser Glu Glu
                645                 650                 655

Ser Lys Ser Pro Leu Ile Arg Arg Ser Ile Tyr Arg Ser Val His Arg
                660                 665                 670

Lys Gln Asp Gln Glu Arg Arg Leu Ser Met Lys Glu Ala Val Asp Glu
                675                 680                 685

Asp Val Pro Leu Val Ser Phe Trp Arg Ile Leu Asn Leu Asn Leu Ser
                690                 695                 700

Glu Trp Pro Tyr Leu Leu Val Gly Val Leu Cys Ala Val Ile Asn Gly
705                 710                 715                 720

Cys Ile Gln Pro Val Phe Ala Ile Val Phe Ser Arg Ile Val Gly Val
                725                 730                 735

Phe Ser Arg Asp Asp Asp His Glu Thr Lys Arg Gln Asn Cys Asn Leu
                740                 745                 750

Phe Ser Leu Phe Phe Leu Val Met Gly Leu Ile Ser Phe Val Thr Tyr
                755                 760                 765

Phe Phe Gln Gly Phe Thr Phe Gly Lys Ala Gly Glu Ile Leu Thr Lys
                770                 775                 780

Arg Val Arg Tyr Met Val Phe Lys Ser Met Leu Arg Gln Asp Ile Ser
785                 790                 795                 800

Trp Phe Asp Asp His Lys Asn Ser Thr Gly Ser Leu Thr Thr Arg Leu
                805                 810                 815

Ala Ser Asp Ala Ser Ser Val Lys Gly Ala Met Gly Ala Arg Leu Ala
                820                 825                 830

Val Val Thr Gln Asn Val Ala Asn Leu Gly Thr Gly Val Ile Leu Ser
                835                 840                 845

Leu Val Tyr Gly Trp Gln Leu Thr Leu Leu Val Val Ile Ile Pro
850                 855                 860

Leu Ile Val Leu Gly Gly Ile Ile Glu Met Lys Leu Leu Ser Gly Gln
865                 870                 875                 880

Ala Leu Lys Asp Lys Lys Gln Leu Glu Ile Ser Gly Lys Ile Ala Thr
                885                 890                 895

Glu Ala Ile Glu Asn Phe Arg Thr Ile Val Ser Leu Thr Arg Glu Gln
                900                 905                 910

Lys Phe Glu Thr Met Tyr Ala Gln Ser Leu Gln Val Pro Tyr Arg Asn
                915                 920                 925

Ala Met Lys Lys Ala His Val Phe Gly Ile Thr Phe Ser Phe Thr Gln
                930                 935                 940

Ala Met Met Tyr Phe Ser Tyr Ala Ala Cys Phe Arg Phe Gly Ala Tyr
945                 950                 955                 960

Leu Val Ala Gln Gln Leu Met Thr Phe Glu Asn Val Met Leu Val Phe
                965                 970                 975

Ser Ala Val Val Phe Gly Ala Met Ala Ala Gly Asn Thr Ser Ser Phe
                980                 985                 990

Ala Pro Asp Tyr Ala Lys Ala Lys Val Ser Ala Ser His Ile Ile Arg
                995                 1000                1005

Ile Ile Glu Lys Thr Pro Glu Ile Asp Ser Tyr Ser Thr Glu Gly
                1010                1015                1020

Leu Lys Pro Thr Leu Leu Glu Gly Asn Val Lys Phe Asn Gly Val
                1025                1030                1035

Gln Phe Asn Tyr Pro Thr Arg Pro Asn Ile Pro Val Leu Gln Gly
                1040                1045                1050
```

```
Leu Ser Leu Glu Val Lys Lys Gly Gln Thr Leu Ala Leu Val Gly
    1055                1060                1065

Ser Ser Gly Cys Gly Lys Ser Thr Val Val Gln Leu Leu Glu Arg
    1070                1075                1080

Phe Tyr Asp Pro Met Ala Gly Ser Val Phe Leu Asp Gly Lys Glu
    1085                1090                1095

Ile Lys Gln Leu Asn Val Gln Trp Leu Arg Ala His Leu Gly Ile
    1100                1105                1110

Val Ser Gln Glu Pro Ile Leu Phe Asp Cys Ser Ile Ala Glu Asn
    1115                1120                1125

Ile Ala Tyr Gly Asp Asn Ser Arg Ala Val Ser His Glu Glu Ile
    1130                1135                1140

Val Arg Ala Ala Lys Glu Ala Asn Ile His Gln Phe Ile Asp Ser
    1145                1150                1155

Leu Pro Asp Lys Tyr Asn Thr Arg Val Gly Asp Lys Gly Thr Gln
    1160                1165                1170

Leu Ser Gly Gly Gln Lys Gln Arg Ile Ala Ile Ala Arg Ala Leu
    1175                1180                1185

Val Arg Gln Pro His Ile Leu Leu Leu Asp Glu Ala Thr Ser Ala
    1190                1195                1200

Leu Asp Thr Glu Ser Glu Lys Val Val Gln Glu Ala Leu Asp Lys
    1205                1210                1215

Ala Arg Glu Gly Arg Thr Cys Ile Val Ile Ala His Arg Leu Ser
    1220                1225                1230

Thr Ile Gln Asn Ala Asp Leu Ile Val Val Ile Glu Asn Gly Lys
    1235                1240                1245

Val Lys Glu His Gly Thr His Gln Gln Leu Leu Ala Gln Lys Gly
    1250                1255                1260

Ile Tyr Phe Ser Met Val Gln Ala Gly Ala Lys Arg Ser
    1265                1270                1275

<210> SEQ ID NO 63
<211> LENGTH: 1280
<212> TYPE: PRT
<213> ORGANISM: Pan troglodytes

<400> SEQUENCE: 63

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140
```

```
His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
                260                 265                 270

Glu Leu Glu Arg Tyr Asn Lys Asn Leu Glu Glu Ala Lys Arg Ile Gly
            275                 280                 285

Ile Lys Lys Ala Ile Thr Ala Asn Ile Ser Ile Gly Ala Ala Phe Leu
290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
                355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Gln Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
                435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560
```

-continued

```
Leu Asp Thr Glu Ser Glu Ala Val Val Gln Val Ala Leu Asp Lys Ala
                565                 570                 575
Arg Lys Gly Arg Thr Thr Ile Val Ile Ala His Arg Leu Ser Thr Val
            580                 585                 590
Arg Asn Ala Asp Val Ile Ala Gly Phe Asp Asp Gly Val Ile Val Glu
        595                 600                 605
Lys Gly Asn His Asp Glu Leu Met Lys Glu Lys Gly Ile Tyr Phe Lys
    610                 615                 620
Leu Val Thr Met Gln Thr Ala Gly Asn Glu Val Leu Glu Asn Ala
625                 630                 635                 640
Ala Asp Glu Ser Lys Ser Glu Ile Asp Ala Leu Glu Met Ser Ser Asn
                645                 650                 655
Asp Ser Arg Ser Ser Leu Ile Arg Lys Arg Ser Thr Arg Arg Ser Val
            660                 665                 670
Arg Gly Ser Gln Ala Gln Asp Arg Lys Leu Ser Thr Lys Glu Ala Leu
        675                 680                 685
Asp Glu Ser Ile Pro Pro Val Ser Phe Trp Arg Ile Met Lys Leu Asn
    690                 695                 700
Leu Thr Glu Trp Pro Tyr Phe Val Val Gly Val Phe Cys Ala Ile Ile
705                 710                 715                 720
Asn Gly Gly Leu Gln Pro Ala Phe Ala Ile Ile Phe Ser Lys Ile Ile
                725                 730                 735
Gly Val Phe Thr Arg Ile Asp Asp Pro Glu Thr Lys Arg Gln Asn Ser
            740                 745                 750
Asn Leu Phe Ser Leu Leu Phe Leu Val Leu Gly Ile Ile Ser Phe Ile
        755                 760                 765
Thr Phe Phe Leu Gln Gly Phe Thr Phe Gly Lys Ala Gly Glu Ile Leu
    770                 775                 780
Thr Lys Arg Leu Arg Tyr Met Val Phe Arg Ser Met Leu Arg Gln Asp
785                 790                 795                 800
Val Ser Trp Phe Asp Asp Pro Lys Asn Thr Thr Gly Ala Leu Thr Thr
                805                 810                 815
Arg Leu Ala Asn Asp Ala Ala Gln Val Lys Gly Ala Ile Gly Ser Arg
            820                 825                 830
Leu Ala Val Ile Thr Gln Asn Ile Ala Asn Leu Gly Thr Gly Ile Ile
        835                 840                 845
Ile Ser Phe Ile Tyr Gly Trp Gln Leu Thr Leu Leu Leu Ala Ile
    850                 855                 860
Val Pro Ile Ile Ala Ile Ala Gly Val Val Glu Met Lys Met Leu Ser
865                 870                 875                 880
Gly Gln Ala Leu Lys Asp Lys Lys Glu Leu Glu Gly Ala Gly Lys Ile
                885                 890                 895
Ala Ser Glu Ala Ile Glu Asn Phe Arg Thr Val Val Ser Leu Thr Gln
            900                 905                 910
Glu Gln Lys Phe Glu His Met Tyr Ala Gln Ser Leu Gln Val Pro Tyr
        915                 920                 925
Arg Asn Ser Leu Arg Lys Ala His Ile Phe Gly Ile Thr Phe Ser Phe
    930                 935                 940
Thr Gln Ala Met Met Tyr Phe Ser Tyr Ala Gly Cys Phe Arg Phe Gly
945                 950                 955                 960
Ala Tyr Leu Val Ala His Lys Leu Met Ser Phe Glu Asp Val Leu Leu
                965                 970                 975
Val Phe Ser Ala Val Val Phe Gly Ala Met Ala Val Gly Gln Val Ser
```

-continued

```
                   980                 985                 990
Ser Phe Ala Pro Asp Tyr Ala Lys Ala Lys Ile Ser Ala Ala His Ile
            995                1000                1005

Ile Met Ile Ile Glu Lys Thr Pro Leu Ile Asp Ser Tyr Ser Thr
    1010                1015                1020

Glu Gly Leu Thr Pro Asn Thr Leu Glu Gly Asn Val Thr Phe Gly
    1025                1030                1035

Glu Val Val Phe Asn Tyr Pro Thr Arg Pro Asp Ile Pro Val Leu
    1040                1045                1050

Gln Gly Leu Ser Leu Glu Val Lys Lys Gly Gln Thr Leu Ala Leu
    1055                1060                1065

Val Gly Ser Ser Gly Cys Gly Lys Ser Thr Val Val Gln Leu Leu
    1070                1075                1080

Glu Arg Phe Tyr Asp Pro Leu Ala Gly Lys Val Leu Leu Asp Gly
    1085                1090                1095

Lys Glu Ile Lys Arg Leu Asn Val Gln Trp Leu Arg Ala His Leu
    1100                1105                1110

Gly Ile Val Ser Gln Glu Pro Ile Leu Phe Asp Cys Ser Ile Ala
    1115                1120                1125

Glu Asn Ile Ala Tyr Gly Asp Asn Ser Arg Val Val Ser Gln Glu
    1130                1135                1140

Glu Ile Val Arg Ala Ala Lys Glu Ala Asn Ile His Ala Phe Ile
    1145                1150                1155

Glu Ser Leu Pro Asn Lys Tyr Ser Thr Arg Val Gly Asp Lys Gly
    1160                1165                1170

Thr Gln Leu Ser Gly Gly Gln Lys Gln Arg Ile Ala Ile Ala Arg
    1175                1180                1185

Ala Leu Val Arg Gln Pro His Ile Leu Leu Leu Asp Glu Ala Thr
    1190                1195                1200

Ser Ala Leu Asp Thr Glu Ser Glu Lys Val Val Gln Glu Ala Leu
    1205                1210                1215

Asp Lys Ala Arg Glu Gly Arg Thr Cys Ile Val Ile Ala His Arg
    1220                1225                1230

Leu Ser Thr Ile Gln Asn Ala Asp Leu Ile Val Val Phe Gln Asn
    1235                1240                1245

Gly Arg Val Lys Glu His Gly Thr His Gln Gln Leu Leu Ala Gln
    1250                1255                1260

Lys Gly Ile Tyr Phe Ser Met Val Ser Val Gln Ala Gly Thr Lys
    1265                1270                1275

Arg Gln
    1280

<210> SEQ ID NO 64
<211> LENGTH: 1283
<212> TYPE: PRT
<213> ORGANISM: Macaca fascicularis

<400> SEQUENCE: 64

Met Asp Leu Glu Gly Asp Arg Asn Gly Gly Ala Glu Lys Lys Asn Phe
1               5                  10                  15

Phe Lys Leu Asn Asn Lys Ser Lys Lys Asp Lys Lys Glu Arg Lys Pro
            20                  25                  30

Thr Val Ser Val Phe Ser Met Phe Arg Tyr Ser Asn Trp Leu Asp Lys
        35                  40                  45
```

-continued

```
Leu Tyr Met Val Val Gly Thr Leu Ala Ala Ile Ile His Gly Ala Gly
 50                  55                  60

Leu Pro Leu Met Met Leu Val Phe Gly Asp Met Thr Asp Thr Phe Ala
 65                  70                  75                  80

Asn Ala Gly Asn Leu Gly Asp Leu Gly Ala Leu Leu Phe Asn Asn Thr
                 85                  90                  95

Asn Ser Ser Asn Ile Thr Asp Thr Val Pro Val Met Asn Leu Glu Glu
            100                 105                 110

Asp Met Thr Arg Tyr Ala Tyr Tyr Ser Gly Ile Gly Ala Gly Val
            115                 120                 125

Leu Val Ala Ala Tyr Ile Gln Val Ser Phe Trp Cys Leu Ala Ala Gly
130                 135                 140

Arg Gln Ile His Lys Ile Arg Lys Gln Phe Phe His Ala Ile Met Arg
145                 150                 155                 160

Gln Glu Ile Gly Trp Phe Asp Val His Asp Val Gly Glu Leu Asn Thr
                    165                 170                 175

Arg Leu Thr Asp Asp Val Ser Lys Ile Asn Glu Gly Ile Gly Asp Lys
                180                 185                 190

Ile Gly Met Phe Phe Gln Ser Met Ala Thr Phe Phe Thr Gly Phe Ile
            195                 200                 205

Val Gly Phe Thr Arg Gly Trp Lys Leu Thr Leu Val Ile Leu Ala Ile
210                 215                 220

Ser Pro Val Leu Gly Leu Ser Ala Ala Val Trp Ala Lys Ile Leu Ser
225                 230                 235                 240

Ser Phe Thr Asp Lys Glu Leu Leu Ala Tyr Ala Lys Ala Gly Ala Val
                    245                 250                 255

Ala Glu Glu Val Leu Ala Ala Ile Arg Thr Val Ile Ala Phe Gly Gly
                260                 265                 270

Gln Lys Lys Glu Leu Glu Arg Tyr Asn Lys Asn Leu Glu Glu Ala Lys
            275                 280                 285

Arg Ile Gly Ile Lys Lys Ala Ile Thr Ala Asn Ile Ser Ile Gly Ala
            290                 295                 300

Ala Phe Leu Leu Ile Tyr Ala Ser Tyr Ala Leu Ala Phe Trp Tyr Gly
305                 310                 315                 320

Thr Thr Leu Val Leu Ser Lys Glu Tyr Ser Ile Gly Gln Val Leu Thr
                    325                 330                 335

Val Phe Phe Ser Val Leu Ile Gly Ala Phe Ser Val Gly Gln Ala Ser
                340                 345                 350

Pro Ser Ile Glu Ala Phe Ala Asn Ala Arg Gly Ala Ala Phe Glu Ile
            355                 360                 365

Phe Lys Ile Ile Asp Asn Lys Pro Ser Ile Asp Ser Tyr Ser Lys Ser
370                 375                 380

Gly His Lys Pro Asp Asn Ile Lys Gly Asn Leu Glu Phe Arg Asn Val
385                 390                 395                 400

His Phe Ser Tyr Pro Ser Arg Lys Glu Val Lys Ile Leu Lys Gly Leu
                    405                 410                 415

Asn Leu Lys Val Gln Ser Gly Gln Thr Val Ala Leu Val Gly Asn Ser
                420                 425                 430

Gly Cys Gly Lys Ser Thr Thr Val Gln Leu Met Gln Arg Leu Tyr Asp
            435                 440                 445

Pro Thr Glu Gly Met Val Ser Val Asp Gly Gln Asp Ile Arg Thr Ile
450                 455                 460

Asn Val Arg Phe Leu Arg Glu Ile Ile Gly Val Val Ser Gln Glu Pro
```

```
            465                 470                 475                 480
        Val Leu Phe Ala Thr Thr Ile Ala Glu Asn Ile Arg Tyr Gly Arg Glu
                        485                 490                 495
        Asp Val Thr Met Asp Glu Ile Glu Lys Ala Val Lys Glu Ala Asn Ala
                        500                 505                 510
        Tyr Asp Phe Ile Met Lys Leu Pro Gln Lys Phe Asp Thr Leu Val Gly
                        515                 520                 525
        Glu Arg Gly Ala Gln Leu Ser Gly Gly Gln Lys Gln Arg Ile Ala Ile
                        530                 535                 540
        Ala Arg Ala Leu Val Arg Asn Pro Lys Ile Leu Leu Leu Asp Glu Ala
        545                 550                 555                 560
        Thr Ser Ala Leu Asp Thr Glu Ser Glu Ala Val Val Gln Val Ala Leu
                        565                 570                 575
        Asp Lys Ala Arg Lys Gly Arg Thr Thr Ile Val Ile Ala His Arg Leu
                        580                 585                 590
        Ser Thr Val Arg Asn Ala Asp Val Ile Ala Gly Phe Asp Asp Gly Val
                        595                 600                 605
        Ile Val Glu Lys Gly Asn His Asp Glu Leu Met Lys Glu Lys Gly Ile
                        610                 615                 620
        Tyr Phe Lys Leu Val Thr Met Gln Thr Ala Gly Asn Glu Ile Glu Leu
        625                 630                 635                 640
        Glu Asn Ala Ala Asp Glu Ser Lys Ser Glu Ile Asp Thr Leu Glu Met
                        645                 650                 655
        Ser Ser His Asp Ser Gly Ser Ser Leu Ile Arg Lys Arg Ser Thr Arg
                        660                 665                 670
        Arg Ser Val Arg Gly Ser Gln Gly Gln Asp Arg Lys Leu Ser Thr Lys
                        675                 680                 685
        Glu Ala Leu Asp Glu Ser Ile Pro Pro Val Ser Phe Trp Arg Ile Met
                        690                 695                 700
        Lys Leu Asn Leu Thr Glu Trp Pro Tyr Phe Val Val Gly Val Phe Cys
        705                 710                 715                 720
        Ala Ile Ile Asn Gly Gly Leu Gln Pro Ala Phe Ala Val Ile Phe Ser
                        725                 730                 735
        Lys Ile Ile Gly Ile Phe Thr Arg Asn Asp Asp Ala Glu Thr Lys Arg
                        740                 745                 750
        Gln Asn Ser Asn Leu Phe Ser Leu Leu Phe Leu Val Leu Gly Ile Val
                        755                 760                 765
        Ser Phe Ile Thr Phe Phe Leu Gln Gly Phe Thr Phe Gly Lys Ala Gly
                        770                 775                 780
        Glu Ile Leu Thr Lys Arg Leu Arg Tyr Met Val Phe Arg Ser Met Leu
        785                 790                 795                 800
        Arg Gln Asp Val Ser Trp Phe Asp Asp Pro Lys Asn Thr Thr Gly Ala
                        805                 810                 815
        Leu Thr Thr Arg Leu Ala Asn Asp Ala Ala Gln Val Lys Gly Ala Ile
                        820                 825                 830
        Gly Ser Arg Leu Ala Ile Ile Thr Gln Asn Ile Ala Asn Leu Gly Thr
                        835                 840                 845
        Gly Ile Ile Ile Ser Leu Ile Tyr Gly Trp Gln Leu Thr Leu Leu Leu
                        850                 855                 860
        Leu Ala Ile Val Pro Ile Ile Ala Ile Ala Gly Val Val Glu Met Lys
        865                 870                 875                 880
        Met Leu Ser Gly Gln Ala Leu Lys Asp Lys Lys Glu Leu Glu Gly Ala
                        885                 890                 895
```

```
Gly Lys Ile Ala Thr Glu Ala Ile Glu Asn Phe Arg Thr Val Val Ser
        900                 905                 910

Leu Thr Gln Glu Gln Lys Phe Glu His Met Tyr Asp Gln Ser Leu Gln
        915                 920                 925

Val Pro Tyr Arg Asn Ser Leu Arg Lys Ala His Ile Phe Gly Ile Thr
        930                 935                 940

Phe Ser Phe Thr Gln Ala Met Met Tyr Phe Ser Tyr Ala Gly Cys Phe
945                 950                 955                 960

Arg Phe Gly Ala Tyr Leu Val Ala His Ser Leu Met Ser Phe Glu Asp
                965                 970                 975

Val Leu Leu Val Phe Ser Ala Val Val Phe Gly Ala Met Ala Val Gly
                980                 985                 990

Gln Val Ser Ser Phe Ala Pro Asp Tyr Ala Lys Ala Lys Val Ser Ala
            995                 1000                1005

Ala His Ile Ile Met Ile Ile Glu Lys Thr Pro Leu Ile Asp Ser
    1010                1015                1020

Tyr Ser Thr Glu Gly Leu Lys Pro Asn Thr Leu Glu Gly Asn Val
    1025                1030                1035

Thr Phe Asn Glu Val Val Phe Asn Tyr Pro Thr Arg Leu Asp Ile
    1040                1045                1050

Pro Val Leu Gln Gly Leu Ser Leu Glu Val Lys Lys Gly Gln Thr
    1055                1060                1065

Leu Ala Leu Val Gly Ser Ser Gly Cys Gly Lys Ser Thr Val Val
    1070                1075                1080

Gln Leu Leu Glu Arg Phe Tyr Asp Pro Leu Ala Gly Lys Val Leu
    1085                1090                1095

Leu Asp Gly Lys Glu Ile Lys Gln Leu Asn Val Gln Trp Leu Arg
    1100                1105                1110

Ala His Leu Gly Ile Val Ser Gln Glu Pro Ile Leu Phe Asp Cys
    1115                1120                1125

Ser Ile Ser Glu Asn Ile Ala Tyr Gly Asp Asn Ser Arg Val Val
    1130                1135                1140

Ser Gln Glu Glu Ile Val Arg Ala Ala Lys Glu Ala Asn Ile His
    1145                1150                1155

Ala Phe Ile Glu Ser Leu Pro Asn Lys Tyr Ser Thr Arg Val Gly
    1160                1165                1170

Asp Lys Gly Thr Gln Leu Ser Gly Gly Gln Lys Gln Arg Ile Ala
    1175                1180                1185

Ile Ala Arg Ala Leu Val Arg Gln Pro His Ile Leu Leu Leu Asp
    1190                1195                1200

Glu Ala Thr Ser Ala Leu Asp Thr Glu Ser Glu Lys Val Val Gln
    1205                1210                1215

Glu Ala Leu Asp Lys Ala Arg Glu Gly Arg Thr Cys Ile Val Ile
    1220                1225                1230

Ala His Arg Leu Ser Thr Ile Gln Asn Ala Asp Leu Ile Val Val
    1235                1240                1245

Phe Gln Asn Gly Arg Val Lys Glu His Gly Thr His Gln Gln Leu
    1250                1255                1260

Leu Ala Gln Lys Gly Ile Tyr Phe Ser Met Val Ser Val Gln Ala
    1265                1270                1275

Gly Ala Lys Arg Gln
    1280
```

```
<210> SEQ ID NO 65
<211> LENGTH: 119
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (57)..(57)
<223> OTHER INFORMATION: The amino acid at position 57 is Asn, Gln or
      Ser.

<400> SEQUENCE: 65

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Arg Tyr
                20                  25                  30

Thr Met Ser Trp Val Arg Gln Ala Pro Gly Lys Gly Leu Glu Trp Val
            35                  40                  45

Ala Thr Ile Ser Ser Gly Gly Xaa Thr Tyr Tyr Pro Asp Ser Val
        50                  55                  60

Lys Gly Arg Phe Thr Val Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Arg Tyr Gly Ala Gly Asp Ala Trp Phe Ala Tyr Trp Gly Gln Gly
                100                 105                 110

Thr Leu Val Thr Val Ser Ser
        115

<210> SEQ ID NO 66
<211> LENGTH: 323
<212> TYPE: PRT
<213> ORGANISM: Homo sapiens

<400> SEQUENCE: 66

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
        130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175
```

```
Ile Ala Leu Leu Val Ala Gly Leu Val Ile Thr Val Ile Val
                180                 185                 190

Gly Ala Ile Leu Phe Val Pro Gly Glu Tyr Ser Leu Lys Asn Ala Thr
            195                 200                 205

Gly Leu Gly Leu Ile Val Thr Ser Thr Gly Ile Leu Ile Leu His
        210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu

<210> SEQ ID NO 67
<211> LENGTH: 303
<212> TYPE: PRT
<213> ORGANISM: Mus musculus

<400> SEQUENCE: 67

Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Val Ser Trp Phe Ser Pro Asn Glu Lys Ile Leu Ile Val
    130                 135                 140

Ile Phe Pro Ile Leu Ala Ile Leu Leu Phe Trp Gly Lys Phe Gly Ile
145                 150                 155                 160

Leu Thr Leu Lys Tyr Lys Ser Ser His Thr Asn Lys Arg Ile Ile Leu
                165                 170                 175

Leu Leu Val Ala Gly Leu Val Leu Thr Val Ile Val Val Gly Ala
            180                 185                 190

Ile Leu Leu Ile Pro Gly Glu Lys Pro Val Lys Asn Ala Ser Gly Leu
        195                 200                 205

Gly Leu Ile Val Ile Ser Thr Gly Ile Leu Ile Leu Leu Gln Tyr Asn
    210                 215                 220
```

Val Phe Met Thr Ala Phe Gly Met Thr Ser Phe Thr Ile Ala Ile Leu
225                 230                 235                 240

Ile Thr Gln Val Leu Gly Tyr Val Leu Ala Leu Val Gly Leu Cys Leu
            245                 250                 255

Cys Ile Met Ala Cys Glu Pro Val His Gly Pro Leu Leu Ile Ser Gly
            260                 265                 270

Leu Gly Ile Ile Ala Leu Ala Glu Leu Leu Gly Leu Val Tyr Met Lys
            275                 280                 285

Phe Val Ala Ser Asn Gln Arg Thr Ile Gln Pro Pro Arg Asn Arg
            290                 295                 300

<210> SEQ ID NO 68
<211> LENGTH: 323
<212> TYPE: PRT
<213> ORGANISM: Pongo abelii

<400> SEQUENCE: 68

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
            85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
            130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
            165                 170                 175

Ile Ala Leu Leu Val Ala Gly Leu Ile Ile Thr Val Ile Val Ile Val
            180                 185                 190

Gly Ala Ile Leu Phe Val Pro Gly Glu Tyr Ser Leu Lys Asn Ala Thr
            195                 200                 205

Gly Leu Gly Leu Ile Val Thr Ser Thr Gly Ile Leu Ile Leu Leu His
            210                 215                 220

Tyr Tyr Val Phe Ser Thr Ala Ile Gly Leu Asn Ser Phe Val Ile Ala
225                 230                 235                 240

Ile Leu Val Ile Gln Val Ile Ala Tyr Ile Leu Ala Val Val Gly Leu
            245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
            275                 280                 285

Met Lys Phe Val Ala Ser Asn Gln Lys Thr Ile Gln Pro Pro Arg Lys

```
                   290                 295                 300
Ala Val Glu Glu Pro Leu Asn Ala Phe Lys Glu Ser Lys Gly Met Met
305                 310                 315                 320

Asn Asp Glu

<210> SEQ ID NO 69
<211> LENGTH: 323
<212> TYPE: PRT
<213> ORGANISM: Macaca mulatta

<400> SEQUENCE: 69

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Ala Pro Ala Asn
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Met Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
290                 295                 300

Ala Val Glu Glu Pro Leu Asn Ala Phe Lys Glu Ser Lys Gly Met Met
305                 310                 315                 320

Asn Asp Glu

<210> SEQ ID NO 70
```

```
<211> LENGTH: 112
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (35)..(35)
<223> OTHER INFORMATION: The amino acid at position 35 is Asn, Gln or
      Ser

<400> SEQUENCE: 70

Asp Ile Val Met Thr Gln Thr Pro Leu Ser Ser Pro Val Thr Leu Gly
1               5                  10                  15

Gln Pro Ala Ser Ile Ser Cys Arg Ser Ser Gln Ser Ile Val His Ser
            20                  25                  30

Thr Gly Xaa Thr Tyr Leu Glu Trp Tyr Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Phe Pro Arg Thr Phe Gly Gly Gly Thr Lys Leu Glu Ile Lys
            100                 105                 110

<210> SEQ ID NO 71
<211> LENGTH: 17
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: The amino acid at position 12 is Asn, Gln or
      Ser

<400> SEQUENCE: 71

Arg Ser Ser Gln Ser Ile Val His Ser Thr Gly Xaa Thr Tyr Leu Glu
1               5                  10                  15

Trp

<210> SEQ ID NO 72
<211> LENGTH: 8
<212> TYPE: PRT
<213> ORGANISM: Artificial sequence
<220> FEATURE:
<223> OTHER INFORMATION: synthetic peptide

<400> SEQUENCE: 72

Lys Ile Ser Asn Arg Phe Ser Gly
1               5

<210> SEQ ID NO 73
<211> LENGTH: 10
<212> TYPE: PRT
<213> ORGANISM: Artificial sequence
<220> FEATURE:
<223> OTHER INFORMATION: synthetic peptide

<400> SEQUENCE: 73

Phe Gln Ala Ser His Phe Pro Arg Thr Phe
1               5                  10
```

```
<210> SEQ ID NO 74
<211> LENGTH: 17
<212> TYPE: PRT
<213> ORGANISM: Artificial sequence
<220> FEATURE:
<223> OTHER INFORMATION: synthetic peptide

<400> SEQUENCE: 74

Arg Ser Ser Gln Ser Leu Leu His Ser Asp Gly Phe Asp Tyr Leu Asn
1               5                   10                  15

Trp

<210> SEQ ID NO 75
<211> LENGTH: 8
<212> TYPE: PRT
<213> ORGANISM: Artificial sequence
<220> FEATURE:
<223> OTHER INFORMATION: synthetic peptide

<400> SEQUENCE: 75

Ala Leu Ser Asn Arg Ala Ser Gly
1               5

<210> SEQ ID NO 76
<211> LENGTH: 10
<212> TYPE: PRT
<213> ORGANISM: Artificial sequence
<220> FEATURE:
<223> OTHER INFORMATION: synthetic peptide

<400> SEQUENCE: 76

Met Glx Ala Leu Gln Ala Pro Ile Thr Phe
1               5                   10

<210> SEQ ID NO 77
<211> LENGTH: 17
<212> TYPE: PRT
<213> ORGANISM: Artificial sequence
<220> FEATURE:
<223> OTHER INFORMATION: synthetic peptide

<400> SEQUENCE: 77

Arg Ser Ser Gln Ser Ile Val His Ser Thr Gly Asn Thr Tyr Leu Glu
1               5                   10                  15

Trp

<210> SEQ ID NO 78
<211> LENGTH: 448
<212> TYPE: PRT
<213> ORGANISM: Artificial sequence
<220> FEATURE:
<223> OTHER INFORMATION: synthetic peptide

<400> SEQUENCE: 78

Glu Val Lys Val Val Glu Ser Gly Gly Val Leu Val Arg Pro Gly Gly
1               5                   10                  15

Ser Leu Lys Leu Ser Cys Ala Ala Ser Gly Phe Thr Phe Ser Arg Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Gly Asn Thr Tyr Tyr Pro Asp Ser Val
    50                  55                  60
```

```
Lys Gly Arg Phe Thr Val Ser Arg Asp Asn Ala Met Ser Ser Leu Tyr
 65                  70                  75                  80

Leu Gln Met Ser Ser Leu Arg Ser Glu Asp Thr Ala Leu Tyr Tyr Cys
                 85                  90                  95

Ala Arg Tyr Gly Ala Gly Asp Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Lys Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 79
<211> LENGTH: 446
<212> TYPE: PRT
<213> ORGANISM: Artificial sequence
<220> FEATURE:
<223> OTHER INFORMATION: synthetic peptide

<400> SEQUENCE: 79

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Lys Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Lys Ser
385                 390                 395                 400

Asp Gly Ser Phe Phe Leu Tyr Ser Lys Leu Thr Val Asp Lys Ser Arg
```

```
                        405                 410                 415
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 80
<211> LENGTH: 219
<212> TYPE: PRT
<213> ORGANISM: Artificial sequence
<220> FEATURE:
<223> OTHER INFORMATION: synthetic peptide

<400> SEQUENCE: 80

Asp Val Leu Met Thr Gln Thr Pro Val Ser Leu Ser Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ala
                85                  90                  95

Ser His Phe Pro Arg Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 81
<211> LENGTH: 1280
<212> TYPE: PRT
<213> ORGANISM: Artificial sequence
<220> FEATURE:
<223> OTHER INFORMATION: synthetic peptide

<400> SEQUENCE: 81

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Glu Lys Lys Pro
            20                  25                  30

Thr Val Ser Val Phe Ser Met Phe Arg Tyr Ser Asn Trp Leu Asp Lys
        35                  40                  45
```

-continued

```
Leu Tyr Met Val Val Gly Thr Leu Ala Ala Ile Ile His Gly Ala Gly
 50                  55                  60

Leu Pro Leu Met Met Leu Val Phe Gly Glu Met Thr Asp Ile Phe Ala
 65                  70                  75                  80

Asn Ala Gly Asn Leu Glu Asp Leu Met Ser Asn Ile Thr Asn Arg Ser
                 85                  90                  95

Asp Ile Asn Asp Thr Gly Phe Phe Met Asn Leu Glu Glu Asp Met Thr
                100                 105                 110

Arg Tyr Ala Tyr Tyr Ser Gly Ile Gly Ala Gly Val Leu Val Ala
                115                 120                 125

Ala Tyr Ile Gln Val Ser Phe Trp Cys Leu Ala Ala Gly Arg Gln Ile
130                 135                 140

His Lys Ile Arg Lys Gln Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
                180                 185                 190

Phe Phe Gln Ser Met Ala Thr Phe Phe Thr Gly Phe Ile Val Gly Phe
                195                 200                 205

Thr Arg Gly Trp Lys Leu Thr Leu Val Ile Leu Ala Ile Ser Pro Val
210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
                260                 265                 270

Glu Leu Glu Arg Tyr Asn Lys Asn Leu Glu Glu Ala Lys Arg Ile Gly
                275                 280                 285

Ile Lys Lys Ala Ile Thr Ala Asn Ile Ser Ile Gly Ala Ala Phe Leu
                290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
                340                 345                 350

Glu Ala Phe Ala Asn Ala Arg Gly Ala Ala Tyr Glu Ile Phe Lys Ile
                355                 360                 365

Ile Asp Asn Lys Pro Ser Ile Asp Ser Tyr Ser Lys Ser Gly His Lys
                370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
                420                 425                 430

Lys Ser Thr Thr Val Gln Leu Met Gln Arg Leu Tyr Asp Pro Thr Glu
                435                 440                 445

Gly Met Val Ser Val Asp Gly Gln Asp Ile Arg Thr Ile Asn Val Arg
450                 455                 460

Phe Leu Arg Glu Ile Ile Gly Val Val Ser Gln Glu Pro Val Leu Phe
```

```
               465                 470                 475                 480
           Ala Thr Thr Ile Ala Glu Asn Ile Arg Tyr Gly Arg Glu Asn Val Thr
                           485                 490                 495

Met Asp Glu Ile Glu Lys Ala Val Lys Glu Asn Ala Tyr Asp Phe
                           500                 505                 510

Ile Met Lys Leu Pro His Lys Phe Asp Thr Leu Val Gly Glu Arg Gly
                           515                 520                 525

Ala Gln Leu Ser Gly Gly Gln Lys Gln Arg Ile Ala Ile Ala Arg Ala
                           530                 535                 540

Leu Val Arg Asn Pro Lys Ile Leu Leu Leu Asp Glu Ala Thr Ser Ala
           545                 550                 555                 560

Leu Asp Thr Glu Ser Glu Ala Val Val Gln Val Ala Leu Asp Lys Ala
                               565                 570                 575

Arg Lys Gly Arg Thr Thr Ile Val Ile Ala His Arg Leu Ser Thr Val
                           580                 585                 590

Arg Asn Ala Asp Val Ile Ala Gly Phe Asp Asp Gly Val Ile Val Glu
                           595                 600                 605

Lys Gly Asn His Asp Glu Leu Met Lys Glu Lys Gly Ile Tyr Phe Lys
                           610                 615                 620

Leu Val Thr Met Gln Thr Ala Gly Asn Glu Val Glu Leu Glu Asn Ala
           625                 630                 635                 640

Ala Asp Glu Ser Lys Ser Glu Ile Asp Ala Leu Glu Met Ser Ser Asn
                               645                 650                 655

Asp Ser Arg Ser Ser Leu Ile Arg Lys Arg Ser Thr Arg Arg Ser Val
                               660                 665                 670

Arg Gly Ser Gln Ala Gln Asp Arg Lys Leu Ser Thr Lys Glu Ala Leu
                           675                 680                 685

Asp Glu Ser Ile Pro Pro Val Ser Phe Trp Arg Ile Met Arg Leu Asn
                           690                 695                 700

Leu Thr Glu Trp Pro Tyr Phe Val Val Gly Val Phe Cys Ala Ile Ile
           705                 710                 715                 720

Asn Gly Gly Leu Gln Pro Ala Phe Ala Ile Ile Phe Ser Lys Ile Ile
                               725                 730                 735

Gly Val Phe Thr Arg Ile Asp Asp Pro Glu Thr Lys Arg Gln Asn Ser
                           740                 745                 750

Asn Leu Phe Ser Leu Leu Phe Leu Ala Leu Gly Ile Ile Ser Phe Ile
                           755                 760                 765

Thr Phe Phe Leu Gln Gly Phe Thr Phe Gly Lys Ala Gly Glu Ile Leu
                           770                 775                 780

Thr Lys Arg Leu Arg Tyr Met Val Phe Arg Ser Met Leu Arg Gln Asp
           785                 790                 795                 800

Val Ser Trp Phe Asp Asp Pro Lys Asn Thr Thr Gly Ala Leu Thr Thr
                               805                 810                 815

Arg Leu Ala Asn Asp Ala Ala Gln Val Lys Gly Ala Ile Gly Ser Arg
                           820                 825                 830

Leu Ala Val Ile Thr Gln Asn Ile Ala Asn Leu Gly Thr Gly Ile Ile
                           835                 840                 845

Ile Ser Phe Ile Tyr Gly Trp Gln Leu Thr Leu Leu Leu Leu Ala Ile
                           850                 855                 860

Val Pro Ile Ile Ala Ile Ala Gly Val Val Glu Met Lys Met Leu Ser
           865                 870                 875                 880

Gly Gln Ala Leu Lys Asp Lys Lys Glu Leu Glu Gly Ser Gly Lys Ile
                               885                 890                 895
```

```
Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
        915                 920                 925

Arg Asn Ser Leu Arg Lys Ala His Ile Phe Gly Ile Thr Phe Ser Phe
    930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
            980                 985                 990

Ser Phe Ala Pro Asp Tyr Ala Lys Ala Lys Ile Ser Ala Ala His Ile
        995                 1000                1005

Ile Met Ile Ile Glu Lys Thr Pro Leu Ile Asp Ser Tyr Ser Thr
    1010                1015                1020

Glu Gly Leu Met Pro Asn Thr Leu Glu Gly Asn Val Thr Phe Gly
    1025                1030                1035

Glu Val Val Phe Asn Tyr Pro Thr Arg Pro Asp Ile Pro Val Leu
    1040                1045                1050

Gln Gly Leu Ser Leu Glu Val Lys Lys Gly Gln Thr Leu Ala Leu
    1055                1060                1065

Val Gly Ser Ser Gly Cys Gly Lys Ser Thr Val Gln Leu Leu
    1070                1075                1080

Glu Arg Phe Tyr Asp Pro Leu Ala Gly Lys Val Leu Leu Asp Gly
    1085                1090                1095

Lys Glu Ile Lys Arg Leu Asn Val Gln Trp Leu Arg Ala His Leu
    1100                1105                1110

Gly Ile Val Ser Gln Glu Pro Ile Leu Phe Asp Cys Ser Ile Ala
    1115                1120                1125

Glu Asn Ile Ala Tyr Gly Asp Asn Ser Arg Val Val Ser Gln Glu
    1130                1135                1140

Glu Ile Val Arg Ala Ala Thr Glu Ala Asn Ile His Ala Phe Ile
    1145                1150                1155

Glu Ser Leu Pro Asn Lys Tyr Ser Thr Lys Val Gly Asp Lys Gly
    1160                1165                1170

Thr Gln Leu Ser Gly Gly Gln Lys Gln Arg Ile Ala Ile Ala Arg
    1175                1180                1185

Ala Leu Val Arg Gln Pro His Ile Leu Leu Leu Asp Glu Ala Thr
    1190                1195                1200

Ser Ala Leu Asp Thr Glu Ser Glu Lys Val Val Gln Glu Ala Leu
    1205                1210                1215

Asp Lys Ala Arg Glu Gly Arg Thr Cys Ile Val Ile Ala His Arg
    1220                1225                1230

Leu Ser Thr Ile Gln Asn Ala Asp Leu Ile Val Val Phe Gln Asn
    1235                1240                1245

Gly Arg Val Lys Glu His Gly Thr His Gln Gln Leu Leu Ala Gln
    1250                1255                1260

Lys Gly Ile Tyr Phe Ser Met Val Ser Val Gln Ala Gly Thr Lys
    1265                1270                1275

Arg Gln
    1280
```

```
<210> SEQ ID NO 82
<211> LENGTH: 111
<212> TYPE: PRT
<213> ORGANISM: Artificial sequence
<220> FEATURE:
<223> OTHER INFORMATION: synthetic peptide

<400> SEQUENCE: 82

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Val Gly Val Tyr Tyr Cys Phe Gln Gly Ser
                85                  90                  95

His Val Pro Tyr Thr Phe Gly Gln Gly Thr Lys Leu Glu Ile Lys
            100                 105                 110

<210> SEQ ID NO 83
<211> LENGTH: 113
<212> TYPE: PRT
<213> ORGANISM: Artificial sequence
<220> FEATURE:
<223> OTHER INFORMATION: synthetic peptide

<400> SEQUENCE: 83

Asp Val Val Met Thr Gln Thr Pro Arg Ser Leu Pro Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Pro Trp Thr Phe Gly Gly Gly Thr Lys Leu Asp Ile
            100                 105                 110

Lys

<210> SEQ ID NO 84
<211> LENGTH: 122
<212> TYPE: PRT
<213> ORGANISM: Artificial sequence
<220> FEATURE:
<223> OTHER INFORMATION: synthetic peptide

<400> SEQUENCE: 84

Ala Val Gln Leu Gln Gln Ser Gly Pro Glu Leu Val Lys Thr Gly Ala
1               5                   10                  15

Ser Val Lys Ile Ser Cys Lys Ala Ser Gly Tyr Ser Phe Ser Asn Tyr
            20                  25                  30
```

```
Tyr Ile His Trp Val Lys Gln Ser His Gly Lys Ser Leu Glu Trp Ile
        35                  40                  45

Gly Phe Ile Ser Cys Tyr Asn Gly Ala Thr Phe Tyr Asn Gln Lys Phe
    50                  55                  60

Lys Gly Lys Ala Thr Phe Thr Val Asp Thr Ser Ser Ser Thr Ala Tyr
65                  70                  75                  80

Met Lys Phe Asn Ser Leu Thr Phe Glu Asp Ser Ala Val Tyr Tyr Cys
                85                  90                  95

Ala Arg Leu Pro Ile Gln Phe Gly Asn Phe Tyr Pro Met Asp Tyr Trp
                100                 105                 110

Gly Gln Gly Thr Ser Val Thr Val Ser Ser
            115                 120
```

<210> SEQ ID NO 85
<211> LENGTH: 112
<212> TYPE: PRT
<213> ORGANISM: Artificial sequence
<220> FEATURE:
<223> OTHER INFORMATION: synthetic peptide

<400> SEQUENCE: 85

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Arg
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                100                 105                 110
```

<210> SEQ ID NO 86
<211> LENGTH: 120
<212> TYPE: PRT
<213> ORGANISM: Artificial sequence
<220> FEATURE:
<223> OTHER INFORMATION: synthetic peptide

<400> SEQUENCE: 86

```
Glu Val Lys Leu Val Glu Ser Gly Gly Gly Leu Val Lys Phe Gly Gly
1               5                   10                  15

Ser Leu Lys Leu Ser Cys Ala Ala Ser Gly Phe Thr Leu Ser Ser Tyr
            20                  25                  30

Tyr Met Ser Trp Val Arg Gln Ser Pro Glu Lys Arg Leu Glu Leu Val
        35                  40                  45

Ala Val Ile Asn Ser Asn Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Ala Arg Pro Phe Tyr Tyr Ser Asn Ser Pro Phe Ala Tyr Trp Gly Gln
```

Gly Thr Leu Val Thr Val Ser Ser
        115                 120

<210> SEQ ID NO 87
<211> LENGTH: 121
<212> TYPE: PRT
<213> ORGANISM: Artificial sequence
<220> FEATURE:
<223> OTHER INFORMATION: synthetic peptide

<400> SEQUENCE: 87

Gln Val Gln Leu Gln Glu Ser Gly Gly Asp Leu Val Lys Pro Gly Gly
1               5                   10                  15

Ser Leu Lys Leu Ser Cys Ala Ala Ser Gly Phe Thr Phe Ser Arg Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Phe Pro Asp Ser Val
    50                  55                  60

Lys Gly Arg Phe Thr Ile Ser Arg Asp Asn Ala Lys Asn Thr Leu Tyr
65                  70                  75                  80

Leu Gln Val Ser Ser Leu Lys Ser Glu Asp Thr Ala Met Tyr Tyr Cys
                85                  90                  95

Ala Arg Pro Ala Glu Phe Arg Gly Tyr Ser Trp Phe Ala Tyr Trp Gly
            100                 105                 110

Gln Gly Thr Thr Val Thr Val Ser Ser
        115                 120

<210> SEQ ID NO 88
<211> LENGTH: 108
<212> TYPE: PRT
<213> ORGANISM: Artificial sequence
<220> FEATURE:
<223> OTHER INFORMATION: synthetic peptide

<400> SEQUENCE: 88

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Gly Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Ser Tyr Phe Cys Gln Gln Thr Asn Thr Phe Pro
                85                  90                  95

Leu Thr Phe Gly Gly Gly Thr Lys Val Glu Ile Lys
            100                 105

<210> SEQ ID NO 89
<211> LENGTH: 114
<212> TYPE: PRT
<213> ORGANISM: Artificial sequence
<220> FEATURE:
<223> OTHER INFORMATION: synthetic peptide

<400> SEQUENCE: 89

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Asp Pro Gly Lys Gly Leu Met Trp Val
            35                  40                  45

Ser Ser Ile Ser Thr Asp Gly Ser Ala Thr Lys Tyr Ala Asp Ser Val
50                  55                  60

Lys Gly Arg Phe Thr Ile Ser Arg Asp Asn Ala Lys Asn Thr Val Ser
65                  70                  75                  80

Leu Gln Met Asn Ser Leu Arg Ala Glu Asp Thr Ala Val Tyr Tyr Cys
                85                  90                  95

Val Gly Gly Phe Leu Gly Trp Trp Gly Gln Gly Thr Leu Val Thr Val
            100                 105                 110

Ser Ser
```

<210> SEQ ID NO 90
<211> LENGTH: 214
<212> TYPE: PRT
<213> ORGANISM: Artificial sequence
<220> FEATURE:
<223> OTHER INFORMATION: synthetic peptide

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

<210> SEQ ID NO 91
<211> LENGTH: 11

<212> TYPE: PRT
<213> ORGANISM: Artificial sequence
<220> FEATURE:
<223> OTHER INFORMATION: synthetic peptide

<400> SEQUENCE: 91

Arg Ala Ser Gln Asp Val Ser Thr Ala Val Ala
1               5                   10

<210> SEQ ID NO 92
<211> LENGTH: 7
<212> TYPE: PRT
<213> ORGANISM: Artificial sequence
<220> FEATURE:
<223> OTHER INFORMATION: synthetic peptide

<400> SEQUENCE: 92

Ser Ala Ser Phe Leu Tyr Ser
1               5

<210> SEQ ID NO 93
<211> LENGTH: 9
<212> TYPE: PRT
<213> ORGANISM: Artificial sequence
<220> FEATURE:
<223> OTHER INFORMATION: synthetic peptide

<400> SEQUENCE: 93

Gln Gln Tyr Leu Tyr His Pro Ala Thr
1               5

<210> SEQ ID NO 94
<211> LENGTH: 214
<212> TYPE: PRT
<213> ORGANISM: Artificial sequence
<220> FEATURE:
<223> OTHER INFORMATION: synthetic peptide

<400> SEQUENCE: 94

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 95
<211> LENGTH: 11
<212> TYPE: PRT
<213> ORGANISM: Artificial sequence
<220> FEATURE:
<223> OTHER INFORMATION: synthetic peptide

<400> SEQUENCE: 95

Arg Ala Ser Gln Ser Ile Gly Thr Asn Ile His
1               5                   10

<210> SEQ ID NO 96
<211> LENGTH: 7
<212> TYPE: PRT
<213> ORGANISM: Artificial sequence
<220> FEATURE:
<223> OTHER INFORMATION: synthetic peptide

<400> SEQUENCE: 96

Tyr Ala Ser Glu Ser Ile Ser
1               5

<210> SEQ ID NO 97
<211> LENGTH: 9
<212> TYPE: PRT
<213> ORGANISM: Artificial sequence
<220> FEATURE:
<223> OTHER INFORMATION: synthetic peptide

<400> SEQUENCE: 97

Gln Gln Asn Asn Asn Trp Pro Thr Thr
1               5

<210> SEQ ID NO 98
<211> LENGTH: 214
<212> TYPE: PRT
<213> ORGANISM: Artificial sequence
<220> FEATURE:
<223> OTHER INFORMATION: synthetic peptide

<400> SEQUENCE: 98

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Gln Tyr Gly Ser Thr Pro Leu
                85                  90                  95

Thr Phe Gly Gly Gly Thr Lys Ala Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 99
<211> LENGTH: 11
<212> TYPE: PRT
<213> ORGANISM: Artificial sequence
<220> FEATURE:
<223> OTHER INFORMATION: synthetic peptide

<400> SEQUENCE: 99

Arg Ala Ser Gln Ser Val Ser Ser Tyr Leu Ala
1               5                   10

<210> SEQ ID NO 100
<211> LENGTH: 7
<212> TYPE: PRT
<213> ORGANISM: Artificial sequence
<220> FEATURE:
<223> OTHER INFORMATION: synthetic peptide

<400> SEQUENCE: 100

Asp Ala Ser Asn Arg Ala Thr
1               5

<210> SEQ ID NO 101
<211> LENGTH: 9
<212> TYPE: PRT
<213> ORGANISM: Artificial sequence
<220> FEATURE:
<223> OTHER INFORMATION: synthetic peptide

<400> SEQUENCE: 101

His Gln Tyr Gly Ser Thr Pro Leu Thr
1               5

<210> SEQ ID NO 102
<211> LENGTH: 113
<212> TYPE: PRT
<213> ORGANISM: Artificial sequence
<220> FEATURE:
<223> OTHER INFORMATION: synthetic peptide

<400> SEQUENCE: 102

Asp Val Leu Met Thr Gln Thr Pro Val Ser Leu Ser Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45
```

```
Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Tyr Cys Phe Gln Ala
                85                  90                  95

Ser His Phe Pro Arg Thr Phe Gly Gly Gly Thr Lys Leu Glu Ile Lys
                100                 105                 110

Arg
```

<210> SEQ ID NO 103
<211> LENGTH: 113
<212> TYPE: PRT
<213> ORGANISM: Artificial sequence
<220> FEATURE:
<223> OTHER INFORMATION: synthetic peptide

<400> SEQUENCE: 103

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Ile Val His Ser
                20                  25                  30

Thr Gly Asn Thr Tyr Leu Glu Trp Tyr Gln Gln Arg Pro Gly Gln Pro
            35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65              70                  75                  80

Ser Arg Val Glu Ala Glu Asp Val Gly Val Tyr Tyr Cys Phe Gln Ala
                85                  90                  95

Ser His Phe Pro Arg Thr Phe Gly Gly Gly Thr Lys Leu Glu Ile Lys
                100                 105                 110

Arg
```

<210> SEQ ID NO 104
<211> LENGTH: 113
<212> TYPE: PRT
<213> ORGANISM: Artificial sequence
<220> FEATURE:
<223> OTHER INFORMATION: synthetic peptide

<400> SEQUENCE: 104

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Ile Val His Ser
                20                  25                  30

Thr Gly Gln Thr Tyr Leu Glu Trp Tyr Gln Gln Arg Pro Gly Gln Pro
            35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65              70                  75                  80

Ser Arg Val Glu Ala Glu Asp Val Gly Val Tyr Tyr Cys Phe Gln Ala
                85                  90                  95

Ser His Phe Pro Arg Thr Phe Gly Gln Gly Thr Lys Leu Glu Ile Lys
                100                 105                 110

Arg
```

```
<210> SEQ ID NO 105
<211> LENGTH: 113
<212> TYPE: PRT
<213> ORGANISM: Artificial sequence
<220> FEATURE:
<223> OTHER INFORMATION: synthetic peptide

<400> SEQUENCE: 105

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Ile Val His Ser
            20                  25                  30

Thr Gly Ser Thr Tyr Leu Glu Trp Tyr Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Phe Pro Arg Thr Phe Gly Gln Gly Thr Lys Leu Glu Ile Lys
            100                 105                 110

Arg
```